United States Patent
Bailey et al.

(10) Patent No.: US 12,285,267 B2
(45) Date of Patent: Apr. 29, 2025

(54) IMPLANTABLE REPORTING PROCESSOR FOR AN ALERT IMPLANT

(71) Applicant: CANARY MEDICAL INC., Vancouver (CA)

(72) Inventors: Stephen M. Bailey, Shoreline, WA (US); Douglas Bensch, Seattle, WA (US); Douglas Brajer, Toronto (CA); Fred Cushner, New York, NY (US); Aimee L. Desaki, Shoreline, WA (US); Jeffrey M. Gross, Carlsbad, CA (US); Winslow T. Harte, Seattle, WA (US); Nicholas H. Helseth, Seattle, WA (US); David A Herrin, Seattle, WA (US); William L. Hunter, Vancouver (CA); Dermot Keenan, Toronto (CA); George A. Morales, Kirkland, WA (US); Shane Murphy, Seattle, WA (US); Stephen Raitt, Toronto (CA); Thomas Snopek, Toronto (CA); Curtis Troupe, Seattle, WA (US)

(73) Assignee: Canary Medical Inc., Vancouver (CA)

( * ) Notice: Subject to any disclaimer, the term of this patent is extended or adjusted under 35 U.S.C. 154(b) by 25 days.

(21) Appl. No.: 17/543,556

(22) Filed: Dec. 6, 2021

(65) Prior Publication Data

US 2022/0087605 A1 Mar. 24, 2022

Related U.S. Application Data

(63) Continuation of application No. 16/084,544, filed as application No. PCT/US2017/023916 on Mar. 23, 2017, now Pat. No. 11,191,479.

(Continued)

(51) Int. Cl.
*A61B 5/00* (2006.01)
*A61B 5/11* (2006.01)
(Continued)

(52) U.S. Cl.
CPC .......... *A61B 5/4851* (2013.01); *A61B 5/0002* (2013.01); *A61B 5/0024* (2013.01);
(Continued)

(58) Field of Classification Search
CPC ..... A61B 5/4851; A61B 5/686; A61B 5/0002; A61B 5/0024; A61B 5/1114;
(Continued)

(56) References Cited

U.S. PATENT DOCUMENTS 4,161,782 A 7/1979 McCracken
4,411,266 A 10/1983 Cosman
(Continued)

FOREIGN PATENT DOCUMENTS

AT 513434 B1 2/2015
CA 1212501 A 10/1986
(Continued)

OTHER PUBLICATIONS

PCT International Search Report and Written Opinion dated Jul. 7, 2014, for PCT/US2014/028381.
(Continued)

*Primary Examiner* — Daniel L Cerioni
*Assistant Examiner* — Abel Seifu Abegaz

(57) ABSTRACT

The present disclosure provides alert implants that comprise a medical device and an implantable reporting processor (IRP), where one example of such a medical device includes a component for a total knee arthroplasty (TKA) such as a tibial extension, a femoral component for hip replacements, a breast implant, a distal rod for arm or leg breakage repair, a scoliosis rod, a dynamic hip screw, a spinal interbody (Continued)

spacer, and tooling and methods that may be used to form the alert implant, and uses of such alert implants in the health maintenance of patients who receive the implant.

15 Claims, 50 Drawing Sheets

Related U.S. Application Data

(60) Provisional application No. 62/312,072, filed on Mar. 23, 2016, provisional application No. 62/312,079, filed on Mar. 23, 2016, provisional application No. 62/312,095, filed on Mar. 23, 2016, provisional application No. 62/312,108, filed on Mar. 23, 2016, provisional application No. 62/312,114, filed on Mar. 23, 2016, provisional application No. 62/312,120, filed on Mar. 23, 2016, provisional application No. 62/312,131, filed on Mar. 23, 2016, provisional application No. 62/312,180, filed on Mar. 23, 2016, provisional application No. 62/312,188, filed on Mar. 23, 2016, provisional application No. 62/312,193, filed on Mar. 23, 2016, provisional application No. 62/312,197, filed on Mar. 23, 2016, provisional application No. 62/312,205, filed on Mar. 23, 2016.

(51) Int. Cl.
*A61F 2/12* (2006.01)
*A61F 2/36* (2006.01)
*A61F 2/38* (2006.01)

(52) U.S. Cl.
CPC .............. *A61B 5/1114* (2013.01); *A61F 2/12* (2013.01); *A61F 2/3662* (2013.01); *A61F 2/389* (2013.01); *A61B 5/686* (2013.01); *A61B 2562/0219* (2013.01); *A61F 2250/0002* (2013.01)

(58) Field of Classification Search
CPC . A61B 2562/0219; A61B 5/11; A61F 2/3662; A61F 2/389; A61F 2/12; A61F 2250/0002
See application file for complete search history.

(56) References Cited

U.S. PATENT DOCUMENTS

| | | | |
|---|---|---|---|
| 4,894,728 A | 1/1990 | Goodman | |
| 5,019,794 A | 5/1991 | Letessier et al. | |
| 5,042,504 A | 8/1991 | Huberti | |
| 5,245,109 A | 9/1993 | Kaminsky et al. | |
| 5,312,216 A | 5/1994 | Hogg | |
| 5,358,202 A | 10/1994 | Tse et al. | |
| 5,383,874 A | 1/1995 | Jackson et al. | |
| 5,413,604 A | 5/1995 | Hodge | |
| 5,626,581 A | 5/1997 | Staehlin et al. | |
| 5,672,954 A | 9/1997 | Watanabe | |
| 5,716,981 A | 2/1998 | Hunter et al. | |
| 5,833,603 A | 11/1998 | Kovacs et al. | |
| H1765 H | 12/1998 | O'Phelan | |
| 5,906,643 A | 5/1999 | Walker | |
| 6,019,794 A | 2/2000 | Walker | |
| 6,139,581 A | 10/2000 | Engh et al. | |
| 6,206,835 B1 | 3/2001 | Spillman, Jr. et al. | |
| 6,245,109 B1 | 6/2001 | Mendes et al. | |
| 6,358,202 B1 | 3/2002 | Arent | |
| 6,374,097 B1 | 4/2002 | Kudou | |
| 6,447,448 B1 | 9/2002 | Ishikawa et al. | |
| 6,610,096 B2 | 8/2003 | Macdonald | |
| 6,610,101 B2 | 8/2003 | Herr et al. | |
| 6,620,168 B1 | 9/2003 | Lombardo et al. | |
| 6,706,071 B1 | 3/2004 | Wolter | |
| 6,712,778 B1 | 3/2004 | Jeffcoat et al. | |
| 6,805,667 B2 | 10/2004 | Christopherson et al. | |
| 7,009,511 B2 | 3/2006 | Mazar et al. | |
| 7,097,662 B2 | 8/2006 | Evans, III et al. | |
| 7,127,300 B2 | 10/2006 | Mazar et al. | |
| 7,130,695 B2 | 10/2006 | Czygan et al. | |
| 7,141,026 B2 | 11/2006 | Aminian et al. | |
| 7,190,273 B2 | 3/2007 | Liao et al. | |
| 7,195,645 B2 | 3/2007 | DiSilvestro et al. | |
| 7,328,131 B2 | 2/2008 | Donofrio | |
| 7,333,013 B2 | 2/2008 | Berger | |
| 7,347,874 B2 | 3/2008 | DiSilvestro et al. | |
| 7,383,071 B1 | 6/2008 | Russell et al. | |
| 7,384,403 B2 | 6/2008 | Sherman | |
| 7,450,332 B2 | 11/2008 | Pasolini et al. | |
| 7,463,997 B2 | 12/2008 | Pasolini et al. | |
| 7,553,923 B2 | 6/2009 | Williams et al. | |
| 7,559,951 B2 | 7/2009 | DiSilvestro et al. | |
| 7,603,894 B2 | 10/2009 | Breed | |
| 7,613,497 B2 | 11/2009 | Govari et al. | |
| 7,813,808 B1 | 10/2010 | Doron et al. | |
| 7,819,808 B2 | 10/2010 | Oonuki | |
| 7,874,673 B2 | 1/2011 | Shinohara et al. | |
| 7,889,070 B2 | 2/2011 | Reeves et al. | |
| 7,922,771 B2 | 4/2011 | Otto et al. | |
| 7,924,267 B2 | 4/2011 | Sirtori | |
| 8,029,566 B2 | 10/2011 | Lozier et al. | |
| 8,075,627 B2 | 12/2011 | Caylor, III et al. | |
| 8,080,064 B2 | 12/2011 | Dietz et al. | |
| 8,109,890 B2 | 2/2012 | Kamiar et al. | |
| 8,176,922 B2 | 5/2012 | Sherman et al. | |
| 8,241,296 B2 | 8/2012 | Wasielewski | |
| 8,244,368 B2 | 8/2012 | Sherman | |
| 8,245,583 B2 | 8/2012 | Stein | |
| 8,283,793 B2 | 10/2012 | Pless | |
| 8,311,632 B2 | 11/2012 | Pless et al. | |
| 8,317,869 B2 | 11/2012 | Cloutier et al. | |
| 8,372,420 B2 | 2/2013 | Hunter et al. | |
| 8,491,569 B1 | 7/2013 | Anderson | |
| 8,551,023 B2 | 10/2013 | Sherman et al. | |
| 8,556,888 B2 | 10/2013 | Nields et al. | |
| 8,634,808 B1 | 1/2014 | Zhong et al. | |
| 8,634,928 B1 | 1/2014 | O'Driscoll et al. | |
| 8,668,742 B2 | 3/2014 | Caylor, III et al. | |
| 8,721,643 B2 | 5/2014 | Morgan et al. | |
| 8,761,859 B2 | 6/2014 | Roche | |
| 8,876,739 B2 | 11/2014 | Salarian et al. | |
| 8,996,892 B1 | 3/2015 | Chu et al. | |
| 9,019,098 B2 | 4/2015 | Okano | |
| 9,307,932 B2 | 4/2016 | Mariani et al. | |
| 9,364,659 B1 | 6/2016 | Rao | |
| 9,368,105 B1 | 6/2016 | Freed et al. | |
| 9,390,724 B2 | 7/2016 | List | |
| 9,393,433 B2 | 7/2016 | Parramon et al. | |
| 9,424,840 B1 | 8/2016 | Hart et al. | |
| 9,445,930 B2 | 9/2016 | Chen et al. | |
| 9,451,919 B2 | 9/2016 | Roche | |
| 9,456,915 B2 | 10/2016 | Chen et al. | |
| 9,549,742 B2 | 1/2017 | Berend et al. | |
| 9,603,649 B2 | 3/2017 | Matyas et al. | |
| 9,629,583 B2 | 4/2017 | Gradel et al. | |
| 9,820,858 B2 | 11/2017 | Harris et al. | |
| 9,949,669 B2 | 4/2018 | DiSilvestro et al. | |
| 10,070,973 B2 | 9/2018 | Sherman et al. | |
| 10,219,699 B2 | 3/2019 | Wilder et al. | |
| 10,285,637 B1 | 5/2019 | Hnat et al. | |
| 10,492,686 B2 | 12/2019 | Hunter et al. | |
| 10,499,855 B2 | 12/2019 | Hunter | |
| 10,582,891 B2 | 3/2020 | Wiedenhoefer et al. | |
| 10,582,896 B2 | 3/2020 | Revie et al. | |
| 10,596,009 B2 | 3/2020 | Mines et al. | |
| 10,898,106 B2 | 1/2021 | Bodewes et al. | |
| 11,071,279 B2 | 7/2021 | Singh et al. | |
| 11,191,479 B2 | 12/2021 | Bailey et al. | |
| 11,684,260 B2 | 6/2023 | Wiedenhoefer et al. | |
| 2001/0032059 A1 | 10/2001 | Kelly et al. | |
| 2001/0050087 A1 | 12/2001 | Weissman et al. | |
| 2002/0024450 A1 | 2/2002 | Townsend et al. | |
| 2002/0026224 A1 | 2/2002 | Thompson et al. | |
| 2002/0107576 A1 | 8/2002 | Meyers et al. | |

(56) References Cited

U.S. PATENT DOCUMENTS

| | | |
|---|---|---|
| 2002/0113685 A1 | 8/2002 | Izaki et al. |
| 2002/0147416 A1 | 10/2002 | Zogbi et al. |
| 2003/0004403 A1 | 1/2003 | Drinan et al. |
| 2003/0069644 A1 | 4/2003 | Kovacevic et al. |
| 2003/0204267 A1 | 10/2003 | Hazebrouck et al. |
| 2004/0011137 A1 | 1/2004 | Hnat et al. |
| 2004/0019382 A1 | 1/2004 | Amirouche et al. |
| 2004/0019384 A1 | 1/2004 | Kirking et al. |
| 2004/0083003 A1 | 4/2004 | Wasielewski |
| 2004/0098060 A1 | 5/2004 | Ternes |
| 2004/0113790 A1 | 6/2004 | Hamel et al. |
| 2004/0138757 A1 | 7/2004 | Nadzadi et al. |
| 2004/0204635 A1 | 10/2004 | Scharf et al. |
| 2004/0204766 A1 | 10/2004 | Siebel |
| 2004/0211580 A1 | 10/2004 | Wang et al. |
| 2004/0243148 A1 | 12/2004 | Wasielewski |
| 2004/0243244 A1 | 12/2004 | Otto et al. |
| 2004/0249464 A1 | 12/2004 | Bindseil et al. |
| 2004/0249471 A1 | 12/2004 | Bindseil et al. |
| 2005/0010299 A1 | 1/2005 | DiSilvestro |
| 2005/0010301 A1 | 1/2005 | DiSilvestro et al. |
| 2005/0012610 A1 | 1/2005 | Liao et al. |
| 2005/0021126 A1 | 1/2005 | Machan et al. |
| 2005/0027192 A1 | 2/2005 | Govari et al. |
| 2005/0065408 A1 | 3/2005 | Benderev |
| 2005/0165317 A1 | 7/2005 | Turner et al. |
| 2005/0171594 A1 | 8/2005 | Machan et al. |
| 2005/0181005 A1 | 8/2005 | Hunter et al. |
| 2005/0181009 A1 | 8/2005 | Hunter et al. |
| 2005/0228410 A1 | 10/2005 | Berreklouw |
| 2005/0242666 A1 | 11/2005 | Huscher et al. |
| 2005/0245992 A1 | 11/2005 | Persen et al. |
| 2005/0273170 A1* | 12/2005 | Navarro ............... A61F 2/442 600/595 |
| 2005/0288563 A1 | 12/2005 | Feliss et al. |
| 2006/0009856 A1 | 1/2006 | Sherman et al. |
| 2006/0030771 A1 | 2/2006 | Levine et al. |
| 2006/0030945 A1 | 2/2006 | Wright |
| 2006/0036246 A1 | 2/2006 | Carl et al. |
| 2006/0047283 A1 | 3/2006 | Evans et al. |
| 2006/0069403 A1 | 3/2006 | Shalon et al. |
| 2006/0111777 A1 | 5/2006 | Chen |
| 2006/0116744 A1 | 6/2006 | Von Arx et al. |
| 2006/0142670 A1 | 6/2006 | DiSilvestro et al. |
| 2006/0152377 A1 | 7/2006 | Beebe et al. |
| 2006/0165317 A1 | 7/2006 | Gzybowski |
| 2006/0184067 A1 | 8/2006 | Clark et al. |
| 2006/0200121 A1 | 9/2006 | Mowery |
| 2006/0224088 A1 | 10/2006 | Roche |
| 2006/0229711 A1 | 10/2006 | Yan et al. |
| 2006/0229730 A1 | 10/2006 | Railey et al. |
| 2006/0271112 A1 | 11/2006 | Martinson et al. |
| 2006/0271199 A1 | 11/2006 | Johnson |
| 2006/0282168 A1 | 12/2006 | Sherman et al. |
| 2007/0004994 A1 | 1/2007 | Sherman |
| 2007/0005141 A1 | 1/2007 | Sherman |
| 2007/0032749 A1 | 2/2007 | Overall et al. |
| 2007/0034013 A1 | 2/2007 | Moon et al. |
| 2007/0060955 A1 | 3/2007 | Strother et al. |
| 2007/0067018 A1 | 3/2007 | Miller |
| 2007/0088442 A1 | 4/2007 | Cima et al. |
| 2007/0089518 A1 | 4/2007 | Ericson |
| 2007/0126696 A1 | 6/2007 | Boillot |
| 2007/0151884 A1 | 7/2007 | Thoes et al. |
| 2007/0161884 A1 | 7/2007 | Black et al. |
| 2007/0167809 A1 | 7/2007 | Dala-Krishna |
| 2007/0179628 A1 | 8/2007 | Rochetin |
| 2007/0179739 A1 | 8/2007 | Donofrio et al. |
| 2007/0185551 A1 | 8/2007 | Meadows et al. |
| 2007/0211022 A1 | 9/2007 | Boillot |
| 2007/0211023 A1 | 9/2007 | Boillot |
| 2007/0233065 A1 | 10/2007 | Donofrio et al. |
| 2007/0233267 A1 | 10/2007 | Amirouche et al. |
| 2007/0234819 A1 | 10/2007 | Amirouche et al. |
| 2007/0238984 A1 | 10/2007 | Maschke et al. |
| 2007/0238992 A1 | 10/2007 | Donofrio et al. |
| 2007/0239282 A1 | 10/2007 | Caylor, III et al. |
| 2007/0265662 A1 | 11/2007 | Ufford |
| 2007/0288194 A1 | 12/2007 | Boillot |
| 2008/0020012 A1 | 1/2008 | Ju et al. |
| 2008/0027679 A1 | 1/2008 | Shklarski |
| 2008/0033527 A1 | 2/2008 | Nunez et al. |
| 2008/0048878 A1 | 2/2008 | Boillot |
| 2008/0065225 A1 | 3/2008 | Wasielewski et al. |
| 2008/0076972 A1 | 3/2008 | Dorogusker et al. |
| 2008/0088436 A1 | 4/2008 | Reeves et al. |
| 2008/0114270 A1 | 5/2008 | DiSilvestro et al. |
| 2008/0139954 A1 | 6/2008 | Day et al. |
| 2008/0214903 A1 | 9/2008 | Orbach |
| 2008/0215609 A1 | 9/2008 | Cleveland et al. |
| 2008/0235621 A1 | 9/2008 | Boillot |
| 2008/0275350 A1 | 11/2008 | Liao et al. |
| 2008/0300597 A1 | 12/2008 | Morgan et al. |
| 2008/0300659 A1 | 12/2008 | Matos |
| 2008/0306325 A1 | 12/2008 | Burnett et al. |
| 2008/0309481 A1 | 12/2008 | Tanaka et al. |
| 2009/0005708 A1 | 1/2009 | Johanson et al. |
| 2009/0005876 A1 | 1/2009 | Dietz et al. |
| 2009/0012372 A1 | 1/2009 | Burnett et al. |
| 2009/0048524 A1 | 2/2009 | Wildau et al. |
| 2009/0076358 A1 | 3/2009 | Reggiardo et al. |
| 2009/0088756 A1 | 4/2009 | Anderson |
| 2009/0099570 A1 | 4/2009 | Paradis et al. |
| 2009/0119222 A1 | 5/2009 | O'Neil |
| 2009/0149964 A1 | 6/2009 | May et al. |
| 2009/0157146 A1 | 6/2009 | Linder et al. |
| 2009/0192533 A1 | 7/2009 | Dlugos, Jr. et al. |
| 2009/0253587 A1 | 10/2009 | Fernandez |
| 2009/0264894 A1 | 10/2009 | Wasielewski |
| 2009/0299228 A1 | 12/2009 | Lozier et al. |
| 2010/0014626 A1 | 1/2010 | Fennell et al. |
| 2010/0057046 A1 | 3/2010 | Stevens et al. |
| 2010/0100011 A1 | 4/2010 | Roche |
| 2010/0145337 A1 | 6/2010 | Janna et al. |
| 2010/0152621 A1 | 6/2010 | Janna et al. |
| 2010/0164705 A1 | 7/2010 | Blanchard |
| 2010/0191100 A1 | 7/2010 | Anderson et al. |
| 2010/0204551 A1 | 8/2010 | Roche |
| 2010/0204802 A1 | 8/2010 | Wilson et al. |
| 2010/0204955 A1 | 8/2010 | Roche et al. |
| 2010/0249533 A1 | 9/2010 | Pierce et al. |
| 2010/0249787 A1 | 9/2010 | Roche |
| 2010/0249790 A1 | 9/2010 | Roche |
| 2010/0250284 A1 | 9/2010 | Roche et al. |
| 2010/0262160 A1 | 10/2010 | Boyden et al. |
| 2010/0285082 A1 | 11/2010 | Fernandez |
| 2010/0287422 A1 | 11/2010 | Miyazaki |
| 2010/0312188 A1* | 12/2010 | Robertson ............. G16H 40/67 600/300 |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331738 A1 | 12/2010 | Stein et al. |
| 2010/0331894 A1 | 12/2010 | Stein |
| 2010/0331932 A1 | 12/2010 | Stevenson et al. |
| 2010/0332152 A1 | 12/2010 | Stein |
| 2011/0004076 A1 | 1/2011 | Janna et al. |
| 2011/0015693 A1 | 1/2011 | Williamson |

(56) References Cited

U.S. PATENT DOCUMENTS

| | | |
|---|---|---|
| 2011/0019595 A1 | 1/2011 | Magar et al. |
| 2011/0054272 A1 | 3/2011 | Derchak |
| 2011/0060220 A1 | 3/2011 | Roche et al. |
| 2011/0063094 A1 | 3/2011 | Meiertoberens et al. |
| 2011/0066199 A1 | 3/2011 | Linder et al. |
| 2011/0077736 A1 | 3/2011 | Rofougaran |
| 2011/0077865 A1 | 3/2011 | Chen et al. |
| 2011/0087306 A1 | 4/2011 | Goossen |
| 2011/0092860 A1 | 4/2011 | Salarian et al. |
| 2011/0092948 A1 | 4/2011 | Shachar et al. |
| 2011/0098576 A1 | 4/2011 | Hollstien |
| 2011/0158206 A1* | 6/2011 | Shrestha ............... G01D 21/00 370/336 |
| 2011/0160572 A1 | 6/2011 | McIntosh et al. |
| 2011/0160583 A1 | 6/2011 | Roche et al. |
| 2011/0160616 A1 | 6/2011 | Stein et al. |
| 2011/0184740 A1 | 7/2011 | Gruenstein et al. |
| 2011/0196501 A1 | 8/2011 | Michelson |
| 2011/0200052 A1 | 8/2011 | Mungo et al. |
| 2011/0208444 A1 | 8/2011 | Solinsky |
| 2011/0213221 A1 | 9/2011 | Roche |
| 2011/0213413 A1 | 9/2011 | Brown et al. |
| 2011/0224564 A1 | 9/2011 | Moon et al. |
| 2011/0251694 A1 | 10/2011 | Wasielewski |
| 2011/0288436 A1 | 11/2011 | Stone |
| 2011/0288805 A1 | 11/2011 | Dejnabadi et al. |
| 2011/0319755 A1 | 12/2011 | Stein et al. |
| 2012/0029316 A1 | 2/2012 | Raptis et al. |
| 2012/0035868 A1 | 2/2012 | Roche et al. |
| 2012/0095526 A1 | 4/2012 | Roche |
| 2012/0116310 A1 | 5/2012 | Forsell |
| 2012/0123498 A1 | 5/2012 | Gross |
| 2012/0123716 A1 | 5/2012 | Clark |
| 2012/0130687 A1 | 5/2012 | Otto et al. |
| 2012/0152017 A1 | 6/2012 | Stein et al. |
| 2012/0157839 A1 | 6/2012 | Stein |
| 2012/0157884 A1 | 6/2012 | Stein et al. |
| 2012/0166680 A1 | 6/2012 | Masoud et al. |
| 2012/0190940 A1 | 7/2012 | Stein et al. |
| 2012/0191206 A1 | 7/2012 | Stein et al. |
| 2012/0216611 A1 | 8/2012 | Stein et al. |
| 2012/0220839 A1 | 8/2012 | Stein et al. |
| 2012/0226360 A1 | 9/2012 | Stein et al. |
| 2012/0226364 A1 | 9/2012 | Kampas et al. |
| 2012/0232834 A1 | 9/2012 | Roche et al. |
| 2012/0283600 A1 | 11/2012 | Stein |
| 2012/0313760 A1* | 12/2012 | Okano ............... G16H 40/67 340/10.1 |
| 2012/0323333 A1 | 12/2012 | Metzger |
| 2012/0330367 A1 | 12/2012 | Roche et al. |
| 2013/0011008 A1 | 1/2013 | Ikezoye et al. |
| 2013/0023794 A1 | 1/2013 | Stein et al. |
| 2013/0023795 A1 | 1/2013 | Stein et al. |
| 2013/0027186 A1 | 1/2013 | Cinbis et al. |
| 2013/0079668 A1 | 3/2013 | Stein et al. |
| 2013/0079669 A1 | 3/2013 | Stein et al. |
| 2013/0079670 A1 | 3/2013 | Stein et al. |
| 2013/0079671 A1 | 3/2013 | Stein et al. |
| 2013/0079672 A1 | 3/2013 | Stein et al. |
| 2013/0079674 A1 | 3/2013 | Stein et al. |
| 2013/0079675 A1 | 3/2013 | Stein et al. |
| 2013/0079679 A1 | 3/2013 | Roche et al. |
| 2013/0079790 A1 | 3/2013 | Stein et al. |
| 2013/0079884 A1 | 3/2013 | Stein et al. |
| 2013/0109998 A1 | 5/2013 | Swoboda et al. |
| 2013/0110008 A1 | 5/2013 | Bourget et al. |
| 2013/0123684 A1 | 5/2013 | Giuffrida et al. |
| 2013/0144379 A1 | 6/2013 | Najafi et al. |
| 2013/0179110 A1 | 7/2013 | Lee |
| 2013/0197656 A1 | 8/2013 | Conrad |
| 2013/0215979 A1 | 8/2013 | Yakovlev et al. |
| 2013/0225949 A1 | 8/2013 | Roche |
| 2013/0225982 A1 | 8/2013 | Mcintosh et al. |
| 2013/0226034 A1 | 8/2013 | Stein et al. |
| 2013/0226035 A1 | 8/2013 | Stein et al. |
| 2013/0252610 A1 | 9/2013 | Kim et al. |
| 2013/0261450 A1 | 10/2013 | Stein et al. |
| 2013/0268081 A1 | 10/2013 | Stein et al. |
| 2013/0281839 A1 | 10/2013 | Yan et al. |
| 2013/0317367 A1 | 11/2013 | Shuler |
| 2013/0325019 A1 | 12/2013 | Thomas et al. |
| 2013/0338455 A1 | 12/2013 | Gradel et al. |
| 2013/0338770 A1 | 12/2013 | Boyden et al. |
| 2014/0009262 A1* | 1/2014 | Robertson ............... A61B 5/117 340/5.82 |
| 2014/0025338 A1 | 1/2014 | Blount et al. |
| 2014/0031063 A1 | 1/2014 | Park et al. |
| 2014/0058289 A1 | 2/2014 | Panken |
| 2014/0085102 A1 | 3/2014 | McCormick |
| 2014/0094715 A1 | 4/2014 | Stein et al. |
| 2014/0107796 A1 | 4/2014 | Stein et al. |
| 2014/0135589 A1 | 5/2014 | Osorio |
| 2014/0135616 A1 | 5/2014 | Stein et al. |
| 2014/0135624 A1 | 5/2014 | Stein et al. |
| 2014/0135655 A1 | 5/2014 | Stein et al. |
| 2014/0135773 A1 | 5/2014 | Stein et al. |
| 2014/0136143 A1 | 5/2014 | Stein et al. |
| 2014/0148676 A1 | 5/2014 | Stein et al. |
| 2014/0163645 A1 | 6/2014 | Dinsmoor et al. |
| 2014/0171754 A1 | 6/2014 | Stein et al. |
| 2014/0180697 A1 | 6/2014 | Torok et al. |
| 2014/0188007 A1 | 7/2014 | Stein et al. |
| 2014/0194707 A1 | 7/2014 | Stein et al. |
| 2014/0200584 A1 | 7/2014 | Stein et al. |
| 2014/0213867 A1 | 7/2014 | Pletcher et al. |
| 2014/0256324 A1 | 9/2014 | Mohanty et al. |
| 2014/0257047 A1 | 9/2014 | Sillay |
| 2014/0275815 A1 | 9/2014 | Stein et al. |
| 2014/0275849 A1 | 9/2014 | Acquista |
| 2014/0275861 A1 | 9/2014 | Kroh et al. |
| 2014/0276240 A1 | 9/2014 | Stein et al. |
| 2014/0276241 A1 | 9/2014 | Stein et al. |
| 2014/0276885 A1 | 9/2014 | Stein et al. |
| 2014/0276887 A1 | 9/2014 | Stein et al. |
| 2014/0277542 A1 | 9/2014 | Stein et al. |
| 2014/0288464 A1 | 9/2014 | Stein |
| 2014/0296663 A1 | 10/2014 | Boyden et al. |
| 2014/0303739 A1 | 10/2014 | Mentink |
| 2014/0322935 A1 | 10/2014 | Filman |
| 2014/0328253 A1 | 11/2014 | Lee et al. |
| 2014/0330105 A1 | 11/2014 | Roche |
| 2014/0378872 A1 | 12/2014 | Hong et al. |
| 2014/0379090 A1 | 12/2014 | Diomidis et al. |
| 2015/0032215 A1 | 1/2015 | Slamin et al. |
| 2015/0032217 A1 | 1/2015 | Bojarski et al. |
| 2015/0039093 A1 | 2/2015 | McTighe et al. |
| 2015/0057775 A1 | 2/2015 | Dong |
| 2015/0057967 A1* | 2/2015 | Albinali ............... A61B 5/1118 702/150 |
| 2015/0080901 A1 | 3/2015 | Stein |
| 2015/0088253 A1 | 3/2015 | Doll et al. |
| 2015/0124675 A1 | 5/2015 | Farmer et al. |
| 2015/0164401 A1 | 6/2015 | Toth et al. |
| 2015/0202494 A1 | 7/2015 | Hollenbach et al. |
| 2015/0238304 A1 | 8/2015 | Lamraoui |
| 2015/0238691 A1 | 8/2015 | Boyden et al. |
| 2015/0335290 A1 | 11/2015 | Hunter |
| 2016/0025978 A1 | 1/2016 | Mallinson |
| 2016/0029952 A1 | 2/2016 | Hunter |
| 2016/0029998 A1 | 2/2016 | Brister et al. |
| 2016/0038087 A1 | 2/2016 | Hunter |
| 2016/0051823 A1 | 2/2016 | Maile et al. |
| 2016/0058582 A1 | 3/2016 | Lenzi et al. |
| 2016/0081762 A1 | 3/2016 | Stein et al. |
| 2016/0101281 A1 | 4/2016 | Chen |
| 2016/0106533 A1 | 4/2016 | Galstian et al. |
| 2016/0128573 A1 | 5/2016 | Wilder et al. |
| 2016/0166201 A1 | 6/2016 | Stein et al. |
| 2016/0192878 A1 | 7/2016 | Hunter |
| 2016/0199658 A1 | 7/2016 | Nassif et al. |
| 2016/0232322 A1 | 8/2016 | Mensinger et al. |
| 2016/0258779 A1 | 9/2016 | Hol et al. |
| 2016/0302721 A1 | 10/2016 | Wiedenhoefer et al. |
| 2016/0310066 A1 | 10/2016 | Wiedenhoefer et al. |

(56) References Cited

U.S. PATENT DOCUMENTS

| | | |
|---|---|---|
| 2016/0310077 A1 | 10/2016 | Hunter et al. |
| 2016/0338644 A1* | 11/2016 | Connor ............... A61B 5/1126 |
| 2016/0340177 A1 | 11/2016 | Takada |
| 2016/0374566 A1 | 12/2016 | Fung et al. |
| 2017/0035593 A1 | 2/2017 | Chen et al. |
| 2017/0049963 A1 | 2/2017 | Varsavsky et al. |
| 2017/0053764 A1 | 2/2017 | Mori et al. |
| 2017/0056722 A1* | 3/2017 | Singh .................... A61B 5/1118 |
| 2017/0065429 A1 | 3/2017 | Behzadi et al. |
| 2017/0119316 A1 | 5/2017 | Herrmann et al. |
| 2017/0119472 A1 | 5/2017 | Herrmann et al. |
| 2017/0119566 A1 | 5/2017 | Chen et al. |
| 2017/0138986 A1 | 5/2017 | Kern |
| 2017/0156288 A1 | 6/2017 | Singh |
| 2017/0156632 A1 | 6/2017 | Swiston et al. |
| 2017/0181825 A1 | 6/2017 | Hunter |
| 2017/0189553 A1 | 7/2017 | Hunter |
| 2017/0189752 A1 | 7/2017 | Mohrman et al. |
| 2017/0196478 A1 | 7/2017 | Hunter |
| 2017/0196499 A1 | 7/2017 | Hunter |
| 2017/0196507 A1 | 7/2017 | Singh et al. |
| 2017/0196508 A1 | 7/2017 | Hunter |
| 2017/0196509 A1 | 7/2017 | Hunter |
| 2017/0252187 A1 | 9/2017 | Chapman et al. |
| 2017/0294949 A1* | 10/2017 | Zhang ................... H04W 52/46 |
| 2017/0328931 A1 | 11/2017 | Zhang et al. |
| 2017/0333080 A1 | 11/2017 | Roschak et al. |
| 2018/0000380 A1 | 1/2018 | Stein et al. |
| 2018/0028824 A1 | 2/2018 | Pivonka et al. |
| 2018/0055443 A1 | 3/2018 | Stein et al. |
| 2018/0064335 A1 | 3/2018 | Rutschman et al. |
| 2018/0125365 A1 | 5/2018 | Hunter et al. |
| 2018/0177607 A1 | 6/2018 | Trabish et al. |
| 2018/0177611 A1 | 6/2018 | Trabish et al. |
| 2018/0177612 A1 | 6/2018 | Trabish et al. |
| 2018/0228428 A1 | 8/2018 | Anker et al. |
| 2018/0235546 A1 | 8/2018 | Hunter |
| 2019/0038361 A1 | 2/2019 | Wasielewski |
| 2019/0038425 A1 | 2/2019 | Otto et al. |
| 2019/0076033 A1 | 3/2019 | Sweeney et al. |
| 2019/0076273 A1 | 3/2019 | Goodchild et al. |
| 2019/0192072 A1 | 6/2019 | Bailey et al. |
| 2019/0231555 A1 | 8/2019 | Neubardt |
| 2019/0247197 A1 | 8/2019 | Jagannathan et al. |
| 2019/0290451 A1 | 9/2019 | Trabish et al. |
| 2019/0350518 A1 | 11/2019 | Bailey et al. |
| 2019/0350519 A1 | 11/2019 | Bailey et al. |
| 2019/0350520 A1 | 11/2019 | Bailey et al. |
| 2019/0350521 A1 | 11/2019 | Bailey et al. |
| 2019/0350522 A1 | 11/2019 | Bailey et al. |
| 2019/0350523 A1 | 11/2019 | Bailey et al. |
| 2020/0054215 A1 | 2/2020 | Roche |
| 2020/0093430 A1 | 3/2020 | Bailey et al. |
| 2020/0093431 A1 | 3/2020 | Bailey et al. |
| 2020/0155327 A1 | 5/2020 | Suh et al. |
| 2021/0077241 A1 | 3/2021 | Hunter |
| 2022/0387186 A1 | 12/2022 | Golemon, Jr. et al. |
| 2023/0301802 A1 | 9/2023 | Trousdale et al. |
| 2024/0156396 A1 | 5/2024 | Amiot et al. |

FOREIGN PATENT DOCUMENTS

| | | |
|---|---|---|
| CA | 2620247 A1 | 3/2007 |
| CA | 3017932 A1 | 9/2017 |
| CN | 2580920 Y | 10/2003 |
| CN | 1806776 A | 7/2006 |
| CN | 1899222 A | 1/2007 |
| CN | 101060815 A | 10/2007 |
| CN | 101254103 A | 9/2008 |
| CN | 101257860 A | 9/2008 |
| CN | 101287408 A | 10/2008 |
| CN | 101296673 A | 10/2008 |
| CN | 101426453 A | 5/2009 |
| CN | 101484085 A | 7/2009 |
| CN | 101495025 A | 7/2009 |
| CN | 101536938 A | 9/2009 |
| CN | 101573085 A | 11/2009 |
| CN | 101773387 A | 7/2010 |
| CN | 101849865 A | 10/2010 |
| CN | 202036215 | 11/2011 |
| CN | 101773387 | 12/2011 |
| CN | 102688097 A | 9/2012 |
| CN | 102740803 A | 10/2012 |
| CN | 102885626 A | 1/2013 |
| CN | 102905649 A | 1/2013 |
| CN | 103313661 A | 9/2013 |
| CN | 103458830 A | 12/2013 |
| CN | 103735303 A | 4/2014 |
| CN | 103957992 A | 7/2014 |
| CN | 105283150 A | 1/2016 |
| CN | 109310324 A | 2/2019 |
| DE | 4322619 C1 | 9/1994 |
| DE | 19924676 A1 | 11/2000 |
| DE | 10342823 A1 | 4/2005 |
| EP | 1528902 B1 | 11/2006 |
| EP | 2018825 | 1/2009 |
| EP | 1814471 | 3/2010 |
| EP | 2967879 B1 | 1/2022 |
| IN | 101273925 A | 10/2008 |
| JP | 2001046411 A | 2/2001 |
| JP | 2003527926 A | 9/2003 |
| JP | 2005520630 A | 7/2005 |
| JP | 2005288172 A | 10/2005 |
| JP | 2006055629 A | 3/2006 |
| JP | 2006102498 A | 4/2006 |
| JP | 2007083019 A | 4/2007 |
| JP | 2007535372 A | 12/2007 |
| JP | 2008501488 A | 1/2008 |
| JP | 2008510584 A | 4/2008 |
| JP | 2011514812 A | 5/2011 |
| JP | 2013039444 A | 2/2013 |
| JP | 2016525389 A | 8/2016 |
| JP | 2017023436 A | 2/2017 |
| JP | 2017510307 A | 4/2017 |
| JP | 2022128381 A | 9/2022 |
| KR | 101274641 B1 | 6/2013 |
| KR | 20140133419 A | 11/2014 |
| WO | 1997033513 A1 | 9/1997 |
| WO | 02064019 A2 | 8/2002 |
| WO | 2004016204 A1 | 2/2004 |
| WO | 2004091419 A2 | 10/2004 |
| WO | 2005120203 A2 | 12/2005 |
| WO | 2006089069 A2 | 8/2006 |
| WO | 2006105098 A2 | 10/2006 |
| WO | 2006108065 A2 | 10/2006 |
| WO | 2006113394 A2 | 10/2006 |
| WO | 2008032316 A2 | 3/2008 |
| WO | 2008035089 A1 | 3/2008 |
| WO | 2008103181 A1 | 8/2008 |
| WO | 2008152549 A2 | 12/2008 |
| WO | 2009145633 A1 | 12/2009 |
| WO | 2009148847 A2 | 12/2009 |
| WO | 2012103549 | 8/2010 |
| WO | 2010111678 A2 | 9/2010 |
| WO | 2012006066 | 1/2012 |
| WO | 2012061825 A2 | 5/2012 |
| WO | 2012095784 A1 | 7/2012 |
| WO | 2013022890 A1 | 2/2013 |
| WO | 2013044117 A1 | 3/2013 |
| WO | 2013044127 A1 | 3/2013 |
| WO | 2013044157 A1 | 3/2013 |
| WO | 2013044160 A2 | 3/2013 |
| WO | 2013044165 A2 | 3/2013 |
| WO | 2013044174 A2 | 3/2013 |
| WO | 2013044165 A3 | 5/2013 |
| WO | 2014053956 A1 | 4/2014 |
| WO | 2014100795 A1 | 6/2014 |
| WO | 2014144070 A1 | 9/2014 |
| WO | 2014144107 A1 | 9/2014 |
| WO | 2014144707 A1 | 9/2014 |
| WO | 2014209916 A1 | 12/2014 |
| WO | 2015021807 A1 | 2/2015 |
| WO | 2015038979 A1 | 3/2015 |
| WO | 2015092747 A2 | 6/2015 |

(56) References Cited

FOREIGN PATENT DOCUMENTS

| | | |
|---|---|---|
| WO | 2015188867 A1 | 12/2015 |
| WO | 2015200704 A1 | 12/2015 |
| WO | 2015200707 A1 | 12/2015 |
| WO | 2015200718 A1 | 12/2015 |
| WO | 2015200720 A2 | 12/2015 |
| WO | 2015200722 A2 | 12/2015 |
| WO | 2015200723 A1 | 12/2015 |
| WO | 2016044651 A1 | 3/2016 |
| WO | 2016065205 A1 | 4/2016 |
| WO | 2016174612 A1 | 11/2016 |
| WO | 2016180653 A1 | 11/2016 |
| WO | 2016180654 A1 | 11/2016 |
| WO | 2017152153 A1 | 9/2017 |
| WO | 2017165717 A1 | 9/2017 |
| WO | 2018119360 A1 | 6/2018 |
| WO | 2020206373 A1 | 10/2020 |

OTHER PUBLICATIONS

PCT International Search Report and Written Opinion dated Oct. 15, 2014, for PCT/US2014/043736.
PCT International Search Report and Written Opinion dated Feb. 1, 2016, for PCT/US2015/050789.
PCT International Search Report and Written Opinion dated Aug. 2, 2017, for PCT/US2017/023916.
PCT International Search Report and Written Opinion dated Oct. 30, 2020, for PCT/US2020/036516.
European Extended Search Report dated Mar. 17, 2017, for 14762650.1.
European Partial Search Report dated Jun. 13, 2017, for 14817352.9.
European Partial Search Report dated Oct. 16, 2018 for 15842678.3.
European Full Extended Search Report dated Nov. 12, 2018 for 15812631.8.
European Extended Search Report dated Feb. 5, 2019 for 15842678.3.
European Supplementary Search Report dated Feb. 28, 2020 for 17771204.9.
Arami, Arash et al., "Instrumented Prosthesis for Knee Implant Monitoring", 2011 IEEE International Conference on Automation Science and Engineering, Trieste, Italy, Aug. 24-27, 2011, pp. 828-835.
Arami, Arash et al., "Accurate Measurement of Concurrent Flexion-Extension and Internal-External Rotations in Smart Knee Prostheses", IEEE Transactions on BioMedical Engineering, v. 60, No. 9, Sep. 2013, pp. 2504-2510.
Bosch Sensortec Data Sheet for BMI160 Small, low power inertial measurement unit, Doc Rev 0.8, Release Date Feb. 10, 2015, No. BST-BMI160-DS000-07, 110 pp.
Bosch for BMI160 Small, low power inertial measurement unit, Jan. 15, 2015, , 2 pp.
Bosch Press Release, "Bosch Sensortec launches first IMU with sub 1mA current consumption", Jun. 25, 2014, 3 pp.
Ebrahim, A. F., et al., "The use of fiber Bragg grating sensors in biomechanics and rehabilitation applications: The state-of-the-art and ongoing research topics", Sensors, 2012, v 12, No. 10, pp. 12890-12929.
Forchelet, David et al. "Enclosed Electronic System for Force Measurements in Knee Implants", Sensors 2014, vol. 14, pp. 15009-15021.
Graichen, F., et al., "Hip endoprosthesis for in vivo measurement of joint force and termperative", Journal of Biomechanics, 1999, v 32, No. 10, pp. 1113-1117.
Heinlein, Bernd et al., "Design, calibration and pre-clinical testing of an instrumented tibial tray", Journal of Biomechanics, vol. 40, 2007, pp. S4-S10.
Jacq, Caroline et al., "Investigation of Polymer Thick-Film Piezoresistors for Medical Wrist Rehabilitation and Artificial Knee Load Sensors", Procedia Engineering, vol. 87, 2014, pp. 1194-1197.
Kroft, Steve, "The Data Brokers: Selling your Personal Information" pp. 1-8, extracted from Google on Sep. 4, 2014 is a script from "The Data Brokers" aired on Mar. 9, 2014 on 60 Minutes CBS.
Li, Yiming et al., "Wireless Sensor Networks in Healthcare", Chinese Journal of Medical Instrumentation, v. 37, No. 5, Dec. 31, 2013, pp. 351-354.
Park, Min-Ho, MD et al., "Using a Tibial Short Extension Stem Reduces Tibial Component Loosening After Primary Total Knee Arthroplasty in Severely Varus Knees: Long-term Survival Analysis with Propensity Score Matching," The Journal of Arthroplasty, vol. 33, 2018, pp. 2512-2517.
Ries, Michael D., "Endosteal Referencing in Revision Total Knee Arthroplasty," The Journal of Arthroplasty, vol. 13, No. 1, pp. 85-91. (1998).
Simoncini, Matteo; "Design and integration of an instrumented knee prosthesis", Thesis No. 6379 (2014), École Polytechnique Fédérale de Lausanne.
Xie, Xiang et al., "A Review of the Implantable Electronic Devices in Biology and Medicine", ACTA Electronica Sinica, vol. 32, No. 3, Mar. 2004, pp. 462-467.
Zimmer® NexGen® RH Knee Brochure 8 pp.
Almouahed S., et al., "New Trends in Instrumented Knee Prostheses," International Conference on Information and Communication Technologies: From Theory to Applications, Apr. 7-11, 2008, 6 Pages.
Angers-Goulet M., et al., "Up to Seven Years' Follow-up of Short Cemented Stems in Complex Primary Total Knee Arthroplasty: a Prospective Study," The Knee, Accepted on May 13, 2017, vol. 24, pp. 1166-1174.
Chandrakasan A.P., et al., "Next Generation Micro-Power Systems," Symposium on VLSI Circuits Digest of Technical Papers, 2008, pp. 1-5, 04 pages.
Christian R., MD., et al., "Short-keeled Cemented Tibial Components Show an Increased Risk for Aseptic Loosening," Clinical Orthopaedics and Related Research, Mar. 2013, vol. 471, No. 3, pp. 1008-1013.
Cushner F., MD., et al., "Feasibility and Compliance of Monitoring Post-Operative Activity Levels in TKA Patients Using Wireless Technology," Lenox Hill Hospital, Northwell Health, PPT Presentation, 1 Page.
D'Apuzzo M.R., et al., "Morbid Obesity Independently Impacts Complications, Mortality, and Resource Use After TKA," Clinical Orthopaedics and Related Research, Jan. 2015, Published Online on May 13, 2014, vol. 473, No. 01, pp. 57-63.
Extended European Search Report for European Application No. 14762269.0, mailed Oct. 24, 2016, 08 Pages.
Extended European Search Report for European Application No. 14762650.1, mailed Jul. 21, 2017, 10 Pages.
Extended European Search Report for European Application No. 20214094.3, mailed May 28, 2021, 07 Pages.
Extended European Search Report for European Application No. 22153300.3, mailed Jul. 18, 2022, 07 Pages.
International Preliminary Report on Patentability for International Application No. PCT/US2014/028381, mailed Sep. 24, 2015, 13 Pages.
International Preliminary Report on Patentability for International Application No. PCT/US2014/043736, mailed Jan. 7, 2016, 11 Pages.
International Preliminary Report on Patentability for International Application No. PCT/US2015/050789, mailed Mar. 30, 2017, 07 Pages.
International Preliminary Report on Patentability for International Application No. PCT/US2017/023916, mailed Oct. 4, 2018, 20 Pages.
International Preliminary Report on Patentability for International Application No. PCT/US2020/036516, mailed Dec. 16, 2021, 10 Pages.
Loh N.C., et al., "Sub-10 cm3 Interferometric Accelerometer with Nano-g Resolution," Journal of Microelectromechanical Systems, vol. 11, No. 3, Jun. 2002, pp. 182-187.
Malin A.S., MD., et al., "Routine Surveillance of Modular PFC TKA Shows Increasing Failures after 10 Years," Clinical Orthopaedics and Related Research, Sep. 2010, vol. 468, No. 9, pp. 2469-2476.

(56) References Cited

OTHER PUBLICATIONS

Old A.B., et al., "Revision of Total Knee Arthroplasties Performed in Young, Active Patients with Posttraumatic Arthritis and Osteoarthritis," J. Knee Surg, Nov. 2017, vol. 30, No. 9, pp. 905-908, 1 Page.

Parratte S., MD., et al., "Do Stemmed Tibial Components in Total Knee Arthroplasty Improve Outcomes in Patients with Obesity?," Clinical Orthopaedics and Related Research, Jan. 2017, vol. 475, No. 1, pp. 137-145.

Partial Supplementary European Search Report for European Application No. 14762650.1, mailed Apr. 13, 2017, 08 Pages.

Partial Supplementary European Search Report for European Application No. 14817352.9, mailed Feb. 14, 2017, 09 Pages.

Patil S., MD., et al., "How Do Knee Implants Perform Past the Second Decade? Nineteen- to 25-year Followup of he Press-fit Condylar Design TKA," Clinical Orthopaedics and Related Research, Jan. 2015, vol. 473, No. 1, pp. 135-140.

Polla D.L., et al., "Microdevices in Medicine," Annual Review of Biomedical Engineering, 2000, vol. 02, pp. 551-576.

Singh U.K., et al., "Piezoelectric Power Scavenging of Mechanical Vibration Energy," Australian Mining Technology Conference, Oct. 2-4, 2007, pp. 111-118.

Yeh R., et al., "Single Mask, Large Force, and Large Displacement Electrostatic Linear Inchworm Motors," Journal of Microelectromechanical Systems, Aug. 4, 2002, vol. 11, No. 4, pp. 330-336, XP011064780.

Yoon C., MD., et al., "Medial Tibial Periprosthetic Bone Resorption and Its Effect on Clinical Outcomes after Total Knee Arthroplasty: Cobalt-Chromium versus Titanium Implants," The Journal of Arthroplasty, Accepted Manuscript on Apr. 16, 2018, 43 Pages.

Yun K-S., et al., "A Surface-Tension Driven Micropump for Low-voltage and Low-Power Operations", Journal of Microelectromechanical Systems, Oct. 5, 2002, vol. 11, No. 5, pp. 454-461, DOI:10.1109/JMEMS.2002.803286, XP001192816.

Zimmer: "Persona The Personalized Knee Systems," Brochure, 2014, 12 Pages.

European Search Report in European Patent Application No. 23177756.6, dated Nov. 8, 2023, 8 Pages.

Laqua D., "Intelligent Power Management Enables Autonomous Power Supply of Sensor Systems for Modern Prostheses", Journal of Biomedical Engineering / Biomedizinische Technik, Published by Walter de Gruyter, Sep. 6, 2012, vol. 57, Supp. 1, pp. 247-250.

Bergmann G., et al., "Standardized Loads Acting in Knee Implants", PLoS ONE, Public Library of Science, vol. 9, No. 1: e86035, Jan. 23, 2014, pp. 1-12.

* cited by examiner

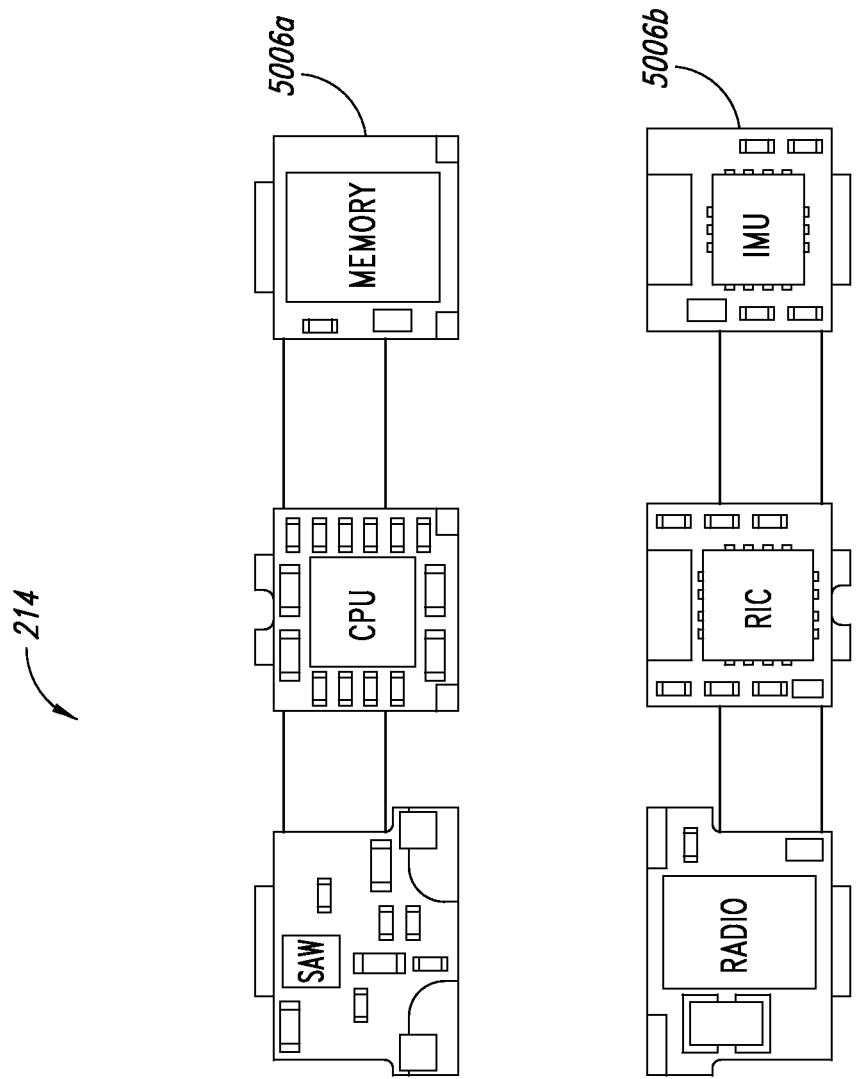
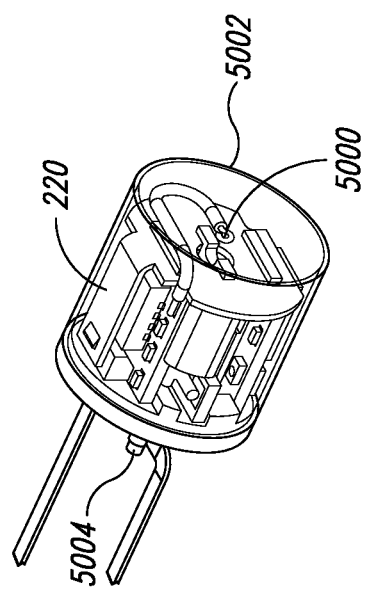
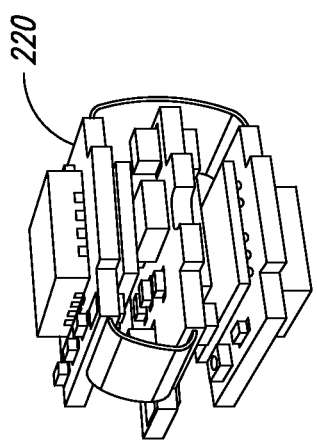
*FIG. 5C*
*FIG. 5A*
*FIG. 5B*

IMPLANTABLE REPORTING PROCESSOR FOR AN ALERT IMPLANT

CROSS-REFERENCE TO RELATED APPLICATIONS

This application is a Continuation of U.S. application Ser. No. 16/084,544, filed Sep. 12, 2018, which is a national phase under 35 U.S.C. § 371 of International Application No. PCT/US2017/023916, filed Mar. 23, 2017, which claims the benefit under 35 U.S.C. § 119(e) of U.S. Provisional Patent Application No. 62/312,072 filed Mar. 23, 2016, and U.S. Provisional Patent Application No. 62/312,079 filed Mar. 23, 2016, and U.S. Provisional Patent Application No. 62/312,095 filed Mar. 23, 2016, and U.S. Provisional Patent Application No. 62/312,108 filed Mar. 23, 2016, and U.S. Provisional Patent Application No. 62/312,114 filed Mar. 23, 2016, and U.S. Provisional Patent Application No. 62/312,120 filed Mar. 23, 2016, and U.S. Provisional Patent Application No. 62/312,131 filed Mar. 23, 2016, and U.S. Provisional Patent Application No. 62/312,180 filed Mar. 23, 2016, and U.S. Provisional Patent Application No. 62/312,188 filed Mar. 23, 2016, and U.S. Provisional Patent Application No. 62/312,193 filed Mar. 23, 2016, and U.S. Provisional Patent Application No. 62/312,197 filed Mar. 23, 2016, and U.S. Provisional Patent Application No. 62/312,205 filed Mar. 23, 2016, which applications are incorporated herein by reference in their entireties.

FIELD OF THE INVENTION

The present invention relates generally to in vivo implants, and more specifically to alert implants with implantable reporting processors that may, e.g., monitor host activity, store measurements and output data, as well as features of alert implants including space-efficient circuit assemblies therefor, enhanced transmitting antenna configurations therefor, and implants that can transfer the data to an external recipient via a wireless communication link.

BACKGROUND

Medical devices and implants have become commonplace in modern medicine. Typically, medical devices and implants are manufactured to replace, support, or enhance an anatomical or biological structure. When the medical device is located on the surface of the patient, the device is readily viewable by the patient and the attending health care professional. However, when the medical device is designed to be implanted in a patient, i.e., is an implantable medical device or a medical implant, it is typically not readily viewable.

Examples of medical implants include orthopedic implants such as hip and knee prosthesis; spinal implants and hardware (spinal cages, screws, plates, pins, rods and artificial discs); intrauterine devices; orthopedic hardware used to repair fractures and soft tissue injuries (casts, braces, tensor bandages, plates, screws, pins and plates); cochlear implants; aesthetic implants (breast implants, fillers); and dental implants.

Unfortunately, various complications may arise during insertion of the medical implant (whether it is an open surgical procedure or a minimally invasive procedure). For example, a surgeon may wish to confirm correct anatomical alignment and placement of the implant within surrounding tissues and structures. This can however be difficult to do during the procedure itself, making corrective adjustments difficult.

In addition, a patient may experience a number of complications post-procedure. Such complications include neurological symptoms, pain, malfunction (blockage, loosening, etc.) and/or wear of the implant, movement or breakage of the implant, inflammation and/or infection. While some of these problems can be addressed with pharmaceutical products and/or further surgery, they are difficult to predict and prevent; often early identification of complications and side effects is difficult or impossible.

The present invention discloses novel medical devices, including medical implants, which can overcome difficulties and limitations found with previous medical devices and implants, methods for constructing and monitoring these novel medical devices and implants, and further provides other related advantages.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

Briefly stated, and in various embodiments, the present disclosure provides implantable devices which may be utilized to monitor and report the post-surgical activities and progress of the patient involved, as well as features thereof. The present disclosure provides an alert implant that achieves the benefit of a medical implant, e.g., the benefit afforded by a prosthesis which replaces or supplements a natural function of a patient, while also achieving the benefit of monitoring and reporting, which provides insight into the function and/or condition of the device and/or the patient who has received the implanted device. In one embodiment, the implantable device is an in-vivo implantable prosthesis that can be implanted into the body of a living host (also referred to as a patient), for example, to improve the function of, or to replace, a biological structure or organ of the patient's body.

Thus, the present disclosure provides a reporting processor that is intended to be implanted with a medical device, e.g., a prosthesis, where the reporting processor monitors the state of the device after implantation. This reporting processor is also referred to as an implantable reporting processor or IRP. As discussed herein, the state of the device may include the integrity of the device, the movement of the device, the forces exerted on the device and other information relevant to the implanted device. The present disclosure also provides medical devices having a structure such that they can be readily fitted with an IRP. An implantable medical device that has been fitted with an IRP is referred to herein as an alert implant, in recognition that the implant is monitoring its own state or condition to thereby obtain data, where that data is stored in the implant and then as needed, that data is transmitted to a separate device for review by, e.g., a physician.

For example, an alert implantable device of the present disclosure having suitable internal electronic components can be utilized to monitor and measure the movements of a surgical patient's synthetic joint (prosthesis) implanted via a total knee arthroplasty (TKA), store the measurement data and unique identification information of the prosthetic components, and transfer the data to an external recipient (e.g., doctor, clinician, medical assistant, etc.) as required. The IRP will include one or more sensors, such as gyroscopes, accelerometers, and temperature and pressure sensors, and these sensors may be located anywhere within the IRP outer casing, e.g., they may all be located on the PC board. In one embodiment, e.g., when the alert implant is a joint prosthesis, the IRP makes kinematic measurements, and in another embodiment the IRP makes only kinematic measurements. Thus, an alert joint implant may include sensors for kinematic measurements, to determine the movements experienced by the implanted prosthesis.

As another example, an alert implantable device with suitable internal electronic components can be utilized to monitor and measure the status of a surgical patient's synthetic breast implant which is implanted via breast reconstruction surgery, where exemplary measurements include measuring pressure—in which case the outside surface of the IRP includes a communication window or port, e.g., a membrane through which pressure may be measured, and/or a gyroscope to provide a measure of implant orientation. With such measurements, it can be determined whether the breast implant is stiffening and/or leaking fluid. The IRP of a breast implant will store the measurement data and unique identification information of the implant, and transfer the data to an external recipient (e.g., doctor, clinician, medical assistant, etc.) as required.

Other examples of alert medical devices include a component for a total or partial joint replacement, such as occurs during a total knee arthroplasty (TKA) where the IRP may be a component of, or attached to, a tibial extension; or such as occurs during a hip replacement, where the IRP may be a component of or attached to the femoral component for hip replacements. Other examples of a medical device that may be combined with an IRP to provide an alert implant include a breast implant, a lumbar interbody cage, and a leg intramedullary rod.

The IRP and the medical device are each intended to be implanted into a living subject, e.g., a mammal, e.g., a human, horse, dog, etc. Accordingly, in one embodiment the IRP is sterile, e.g., is treated with sterilizing radiation or is treated with ethylene oxide. In another embodiment, the alert implant comprising the IRP and the medical device is sterile, again optionally by treatment with sterilizing radiation or ethylene oxide, as two examples. In order to be protected from the in vivo environment, in one embodiment the IRP is hermetically sealed, so that fluids cannot enter into the IRP.

The implantable device needs to be sturdy as well as small or space-efficient because of the limited space within the body and/or within the prosthetic implant to place such devices. Challenges to the commercial success of an implantable device with internal electronic components and either internal or external transmitting antennae are that the devices and/or the transmitting antennae should not be unsuitably large, their power consumption should allow them to operate for a suitably long period of time, i.e., not for limited durations, and they should not be adversely affected by their local biologic environment. An IRP may have suitable internal or external space-efficient and/or power-efficient antennae.

The alert implant will optionally have a power source needed to run the electronics inside the IRP that measures, records and transmits data concerning the state of the implant. Some medical implants already have a power supply. An example of an in-vivo implantable prosthesis that can improve the function of an organ and which has a power supply is an implantable atrial defibrillator, which detects when a heart enters into an abnormal rhythm commonly known as "atrial fibrillation," and which generates one or more electrical pulses to restore the heart to a normal sinus rhythm. Typically, this power supply is in the form of a battery.

Because the electrical charge on the battery may last a relatively short period of time, the prosthesis is typically located in a region of the body from which it is practical to remove the prosthesis to replace the battery, or to recharge the battery. For example, an atrial defibrillator is typically implanted just under the skin of a patient's chest. To replace the battery, a surgeon makes an incision, removes the old defibrillator, implants a new defibrillator containing a new battery, and closes the incision. Or, the patient or a physician, such as a cardiologist, recharges the battery, without removing the defibrillator from the subject, by placing, over the implanted defibrillator, a device that recharges the battery via inductive (sometimes called magnetic) coupling.

Unfortunately, removing a prosthesis to replace a battery is often undesirable, at least because it involves an invasive procedure that can be relatively expensive and that can have adverse side effects, such as infection and soreness. Although inductively recharging an implanted battery is non-invasive, it may be impractical or impossible to locate the prosthesis such that the battery may be inductively recharged. Additionally, the size of the coils necessary to transfer power are large relative to the device, and this can pose a problem in the limited space available within the body. The time for recharging can be excessive, lack of coil alignment can cause excess heat generation, which potentially can damage surrounding tissue, and the inductive battery configuration can render the implant incompatible with MRI use. Additionally, battery chemistries that are compatible with recharging (i.e., secondary cell) generally have a significantly reduced energy-storage capacity in comparison to batteries of similar size constructed using non-rechargeable chemistries (i.e., primary cell).

An alternative that can overcome this latter problem is to implant the battery remotely from the implanted prosthesis in a location in which it is practical to inductively recharge the battery. An advantage of implanting the battery remotely from the implanted prosthesis is that the battery can be made larger, and thus longer lasting, than it would be if it were located inside of the prosthesis. But implanting the battery remotely from the implanted prosthesis can have several disadvantages. For example, even though the battery is suitably located for inductive recharging, the recharging equipment can be too expensive or too complex for home use, the patient may forget to recharge the device, and periodically visiting the doctor to recharge the battery may be inconvenient and expensive for the patient. Furthermore, it can be difficult to implant the wires used to couple the battery to the remote (from the battery) implanted prosthesis or if powering the implant sensors wirelessly from the rechargeable battery, the sensors may be limited in measurement capability. Moreover, because the battery is typically implanted just below the skin to heighten the inductive-coupling coefficient, it can be visible, and thus embarrassing, to the patient, and it can make the patient physically uncomfortable.

Thus, the IRP may contain a power source (e.g., a battery) as well as mechanisms to manage the power output of an implanted power source, so that the power source will provide power for a sufficient period of time regardless of the location of the power source within a body of a patient. The IRP may contain the only power source present in the alert implant.

An example of a battery suitable for use with an implantable reporter processor includes a container sized to fit inside of bone of a living patient, and has a lifetime, such as years, that is sufficient to power the electronic circuitry within the implantable reporter processor for a period of time that is suitable for a prosthesis in which the implantable reporter processor is installed. The battery can be configured for disposal directly in the bone, or can be configured for disposal in a portion of the implantable reporting processor that is disposed in the bone. Or, the battery can be configured for disposal in a region of a living body other than a bone where it is impractical to recharge the battery, and where it is impractical to replace the battery before replacing a prosthesis or other device with which the battery is associated.

The IRP comprises an outer casing that encloses a plurality of components. Exemplary suitable IRP components include a signal portal, an electronics assembly, and a power source. In one embodiment, the IRP does include each of a signal portal, an electronics assembly and a power source. The signal portal functions to receive and transmit wireless signals, and may contain, for example, an antenna for transmitting the wireless signals. The electronics assembly includes a circuit assembly which may comprise, e.g., a PC board and electrical components formed on one or more integrated circuits (ICs) or chips, such as a radio transmitter chip, a real-time clock chip, one or more sensor components, e.g., an Inertial Measurement Unit (IMU) chip, temperature sensor, pressure sensor, pedometer, a memory chip, and the like. In addition, the electronics assembly includes a header assembly which provides a communication interface between the circuit assembly and the signal portal (e.g., antenna). The power source provides the energy needed to operate the IRP, and may be, for example, a battery. The IRP will also include one or more sensors, such as gyroscopes, accelerometers, pedometers, and temperature and pressure sensors, and these sensors may be located anywhere within the IRP outer casing, e.g., they may all be located on the PC board. More precisely, an embodiment of the present invention is directed to space-efficient, printed-circuit assemblies (PCAs) for an implantable reporting processor (IRP). The implantable reporting processor may also include a plurality of transmitting antennae structured in different configurations. As such, an embodiment of the present invention is directed to a plurality of enhanced space-efficient and power-efficient antenna configurations for an implantable reporting processor, such as an IRP.

An example of an implantable reporting processor includes an outer casing, or housing, sized to fit in, or to form a part of, a prosthesis that has at least a portion designed to fit in a bone of a living patient. Electronic circuitry is disposed in the housing and is configured to provide, to a destination outside of a patient's body, information related to the prosthesis. The battery is also disposed in the housing and is coupled to the electronic circuitry.

An example of a prosthesis includes a receptacle for receiving the implantable reporting processor, which can be designed to fit into a cavity formed in a bone of a living patient. For example, the implantable reporting processor can be disposed in, or form part of, a tibial extension of a knee prosthesis, where the tibial extension is designed to fit into a cavity formed in the tibia of the living patient.

The power profile of the electronic circuitry of the implantable reporting processor can be configured so that the battery has a desired anticipated lifetime suitable for the type of prosthesis (or other device) with which the battery is associated. For example, such a desired anticipated lifetime may range from 1 to 15+ years, e.g., 10 years. An embodiment of such circuitry includes a supply node configured to be coupled to a battery, at least one peripheral circuit, a processing circuit coupled to the supply node and configured to couple the at least one peripheral circuit to the supply node, and a timing circuit coupled to the supply node and configured to activate the processing circuit at a set time or set times.

A base station may be provided to facilitate communications with the implantable reporting processor, and to act as an interface between the reporting processor and another computing system, such as a database or remote server on "the cloud," before and after the implantable reporting processor is implanted in the body of a patient as part of a prosthesis. The base station can have different configurations. For example, the base station can be configured for use by a surgeon or other professional before the prosthesis is implanted. The base station also can be configured for use in the residence of the patient. For example, the base station can be configured to poll the implantable reporting processor, periodically and automatically (for example, while the patient is sleeping), for information that the processor obtains or generates regarding the prosthesis, and to provide this information to the other computing system for storage or analysis via a wireless internet connection. And the base station can be configured for use in a doctor's office while the doctor is checking the operation of the prosthesis and the patient's health as it relates to the prosthesis. Furthermore, the network to which the base station belongs can include a voice-command device (e.g., Amazon Echo®, Amazon Dot®, Google Home®) that is configured to interact with the base station.

In a further embodiment, the present disclosure provides a tool that may be used to bring two pieces together under force. More specifically, the tool is used to exert force on a first piece, where the first piece is adjacent to a second piece, and the second piece is held stationary. The force exerted on the tool is transmitted to the first piece, whereupon the first piece is pressed against the stationary second piece. The tool is intended for the situation where the first and second pieces have complementary mating surfaces, such that when the first and second pieces are forced against one another at the location of the mating surfaces, and under force generated through the tool of the present disclosure, the mating surfaces hold together, at least in part by frictional forces. In this way, two separate (first and second) pieces are combined to form a joined piece. The tool of the present disclosure is particularly advantageous in the situation where the first piece has both fragile and non-fragile regions, and the tool contacts the first piece at non-fragile regions only. In this way, a first piece having fragile regions can be pressed into a second piece, leaving the fragile regions unharmed. The tool is useful, for example, in assembling an alert implant of the present disclosure.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIG. 5A-5C are detailed views of an exemplary electronics assembly including a three-board folded printed circuit assembly that can be utilized to implement the electronics assembly depicted in FIG. 4.

DETAILED DESCRIPTION OF THE INVENTION

Figure 1:
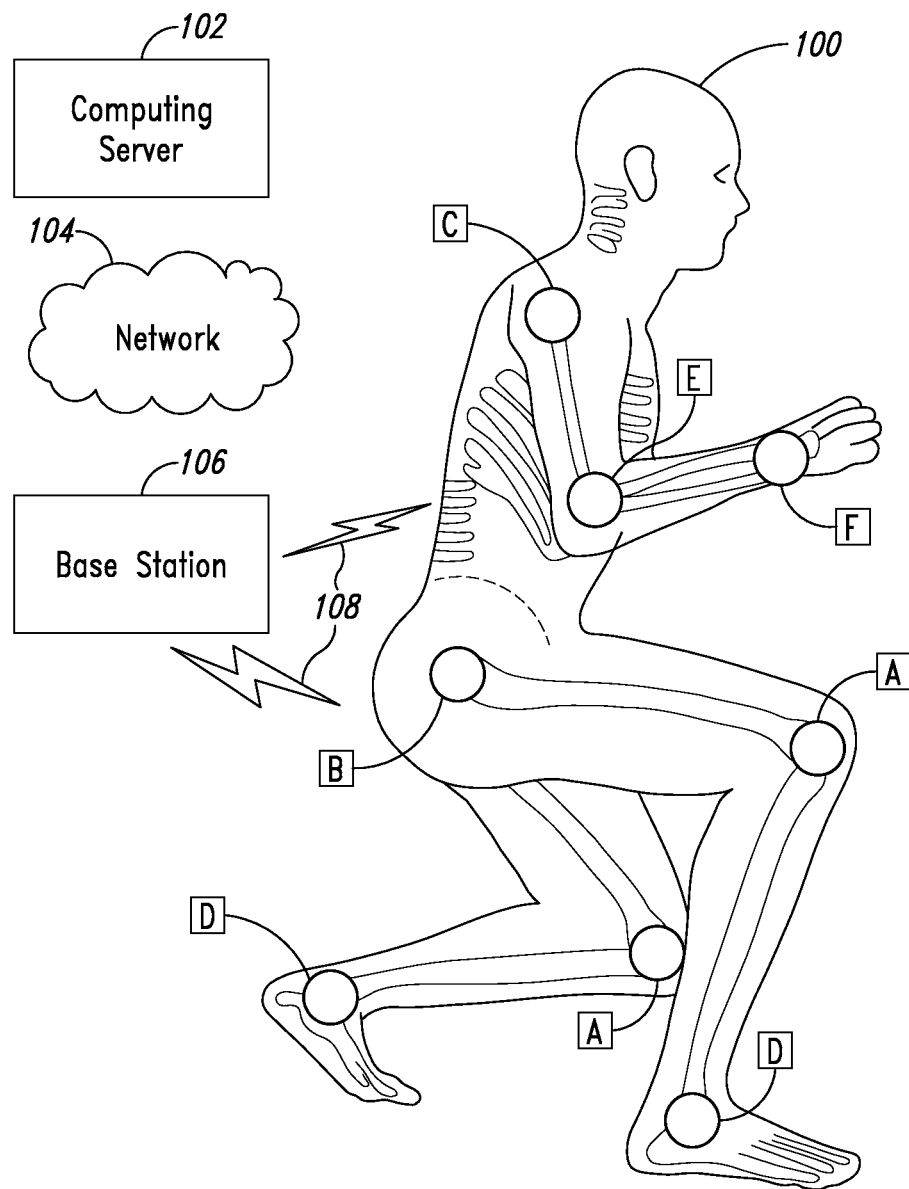
FIG. 1 is a schematic view of a subject who is fitted with an alert joint prosthesis at optional locations, where a prosthesis communicates with an external data storage medium.

The present invention may be understood more readily by reference to the following detailed description of preferred embodiments of the invention included herein. Prior to setting forth this disclosure in more detail, it may be helpful to an understanding thereof to provide definitions of certain terms to be used herein. Additional definitions are set forth throughout this disclosure.

The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, or embodiments combining software and hardware aspects.

Certain words and phrases used in the specification are set forth as follows. The terms "include" and "comprise," as well as derivatives thereof, mean inclusion without limitation. The term "or," is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation, such a device may be implemented in hardware (e.g., electronic circuitry), firmware, or software, or some combination of at least two of the same. The functionality associated with any particular controller may be centralized or distributed, whether locally or remotely. Other definitions of certain words and phrases may be provided within this patent document. Those of ordinary skill in the art will understand that in many, if not most instances, such definitions apply to prior as well as future uses of such defined words and phrases.

An "alert prosthesis," as used in the present disclosure, is an implantable or implanted medical device that desirably replaces or functionally supplements a subject's natural body part. As used herein, the term "alert prosthesis" is interchangeably referred to as an "alert implant," a "smart implant," a "smart medical device," or by another like term. When the alert prosthesis makes kinematic measurements, it may be referred to as a "kinematic medical device," or a "kinematic implantable device". In describing the present invention, reference may be made to a kinematic implantable device, however it should be understood that this is exemplary only of the alert prostheses which may be employed in the present invention. Whether or not the alert prosthesis makes kinematic, or makes other or additional measurements, the prosthesis will comprise an implantable reporting processor (IRP). The alert prosthesis is an implanted or implantable medical device having an implantable reporting processor arranged to perform the functions as described herein. The alert prosthesis may perform one or more of the following exemplary actions in order to characterize the post-implantation status of the alert prosthesis: identifying the alert prosthesis or a portion of the alert prosthesis, e.g., by recognizing one or more unique identification codes for the alert prosthesis or a portion of the alert prosthesis; detecting, sensing and/or measuring parameters, which may collectively be referred to as monitoring parameters, in order to collect operational, kinematic, or other data about the alert prosthesis or a portion of the alert prosthesis and wherein such data may optionally be collected as a function of time; storing the collected data within the alert prosthesis or a portion of the alert prosthesis; and communicating the collected data and/or the stored data by a wireless means from the alert prosthesis or a portion of the alert prosthesis to an external computing device. The external computing device may have or otherwise have access to at least one data storage location such as found on a personal computer, a base station, a computer network, a cloud-based storage system, or another computing device that has access to such storage. Non-limiting and non-exhaustive list of embodiments of alert prostheses include total joint arthroplasty such as total knee arthroplasty (TKA), a tibial extension, a femoral component for hip replacements, a breast implant, a distal rod for arm or leg breakage repair, a scoliosis rod, a dynamic hip screw, a spinal interbody spacer, an annuloplasty ring, a heart valve, and a vascular stent graft.

"Kinematic data," as used herein, individually or collectively includes some or all data associated with a particular kinematic implantable device and available for communication outside of the particular kinematic implantable device. For example, kinematic data may include raw data from one or more sensors of a kinematic implantable device, wherein the one or more sensors include such as gyroscopes, accelerometers, pedometers, strain gauges, and the like that produce data associated with motion, force, tension, velocity, or other mechanical forces. Kinematic data may also include processed data from one or more sensors, status data, operational data, control data, fault data, time data, scheduled data, event data, log data, and the like associated with the particular kinematic implantable device. In some cases, high resolution kinematic data includes kinematic data from one, many, or all of the sensors of the kinematic implantable device that is collected in higher quantities, resolution, from more sensors, more frequently, or the like.

In one embodiment, kinematics refers to the measurement of the positions, angles, velocities, and accelerations of body segments and joints during motion. Body segments are considered to be rigid bodies for the purposes of describing the motion of the body. They include the foot, shank (leg), thigh, pelvis, thorax, hand, forearm, upper-arm and head. Joints between adjacent segments include the ankle (talocrural plus subtalar joints), knee, hip, wrist, elbow and shoulder. Position describes the location of a body segment or joint in space, measured in terms of distance, e.g., in meters. A related measurement called displacement refers to the position with respect to a starting position. In two dimensions, the position is given in Cartesian co-ordinates, with horizontal followed by vertical position. In one embodiment, a kinematic implant or alert kinematic implants obtains kinematic data, and optionally only obtains only kinematic data.

FIG. 1 is a schematic view of a subject 100 who has been fitted with at least one alert joint prosthesis selected from a knee prosthesis (A), a hip prosthesis (B), a shoulder prosthesis (C), an ankle prosthesis (D), an elbow prosthesis (E) and a wrist prosthesis (F). The alert prosthesis monitors and transmits data concerning the prosthesis and its status to at least one of a computing server 102, a network 104, and a base station 106, where the transmission may occur by wireless signal transmission 108. The data may be transmitted by wireless signals 108 to a base station 106, and then from base station 106 to either or both of a network cloud 104, e.g., the internet, and a remote computing device 102.

Figure 2:
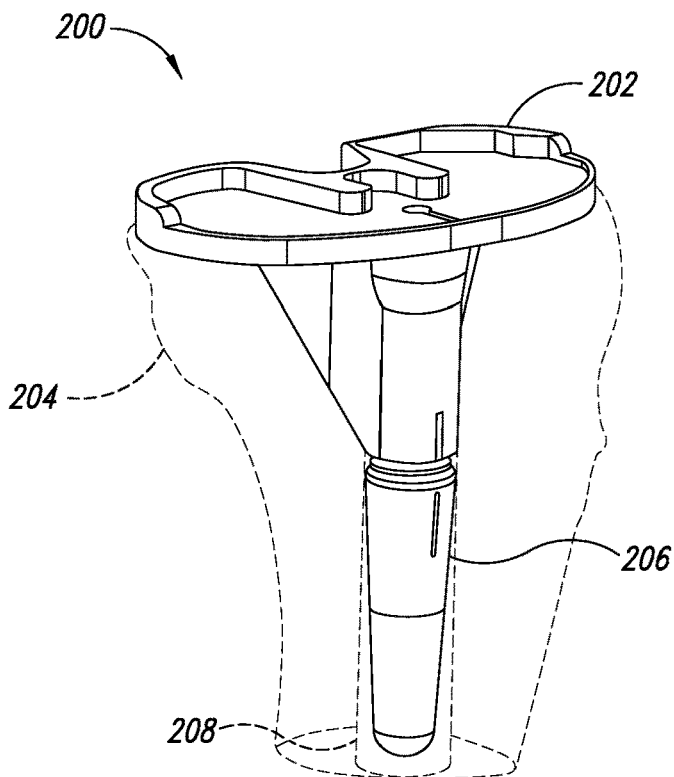
FIG. 2 is a perspective view of a tibial component that can be utilized to implement one exemplary embodiment of the present invention.

FIG. 2 is a perspective view of a tibial component 200 that can be utilized to implement one exemplary embodiment of the present invention. For example, the tibial component 200 shown in FIG. 2 can include an implanted medical device for a TKA, such as a tibial extension and the like. Referring to the exemplary embodiment shown in FIG. 2, the tibial component 200 includes a tibial plate 202 physically attached to an upper surface of a tibia 204. For example, the tibial plate 202 can be a base plate section of an artificial knee joint (prosthesis) that can be implanted during a surgical procedure, such as a TKA. During the surgical procedure, an implantable reporting processor 206 can be physically attached to the tibial plate 202 and also implanted into the tibia 204. For the exemplary embodiment shown in FIG. 2, the tibial component 200 includes the tibial plate 202 and the reporting processor 206, which are surgically implanted to form a tibial extension 208.

Figure 3:
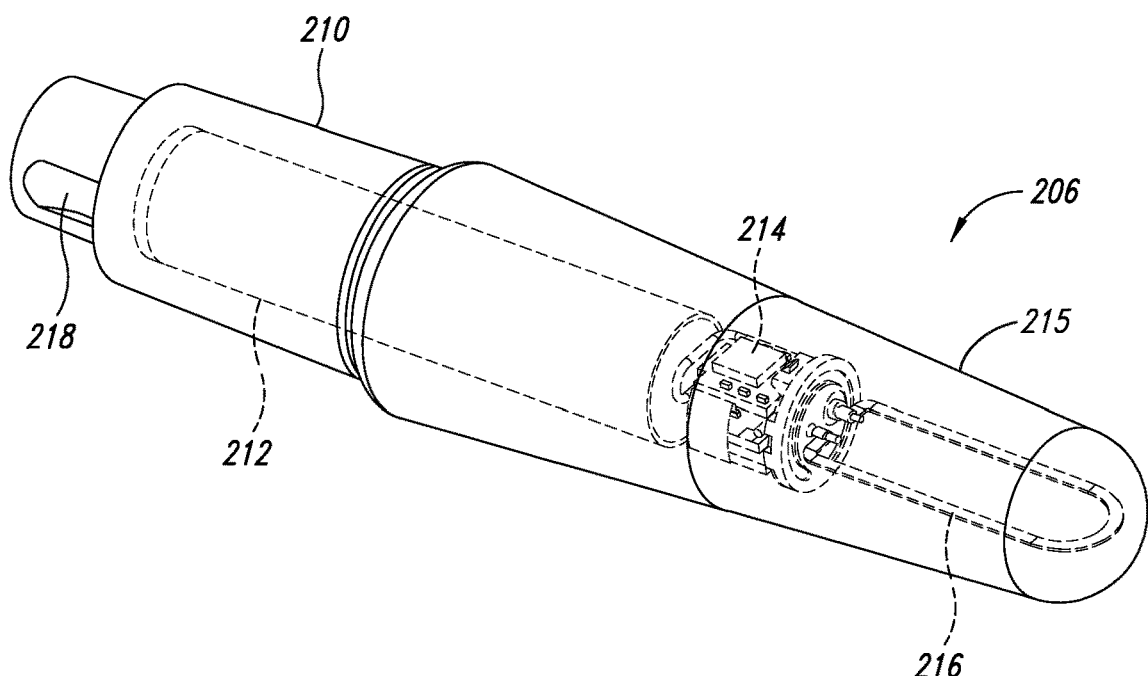
FIG. 3 is a perspective view of an exemplary embodiment of a reporting processor that can be utilized to implement the implantable reporting processor depicted in FIG. 2.

FIG. 3 is a perspective view of an exemplary embodiment of a reporting processor 206 that can be utilized to implement the implantable reporting processor 206 depicted in the exemplary embodiment shown in FIG. 2. In the embodiment shown in FIG. 3, the implantable reporting processor 206 can be implemented, for example, utilizing an IRP assembly. As such, for the exemplary embodiment shown, the implantable reporting processor 206 includes an outer casing 210 that encloses a power component (battery) 212, an electronics assembly 214, and an antenna 216. One component of the casing is the radome 215, used to cover and protect the antenna which allows the implantable reporting processor to receive and transmit information. The radome 215 can be made from any material, such as plastic or ceramic, that allows radio-frequency (RF) signals to propagate through the radome with acceptable levels of attenuation and other signal degradation.

In the embodiment shown in FIG. 3, the diameter of the power component 212 and the electronics assembly 214 is approximately 8 mm, and their combined length is approximately 43 mm. The antenna 216 is approximately 20 mm long. The outer casing 210 can include a set-screw engagement hole 218, which can be utilized to physically attach the reporting processor 206 to the tibial plate 202, as depicted in FIG. 2. It is understood that the mechanism for affixing the alert implant to the tibial plate or other implant may also include threaded fasteners as well as a variety of clips and locking mechanisms.

Figure 4:
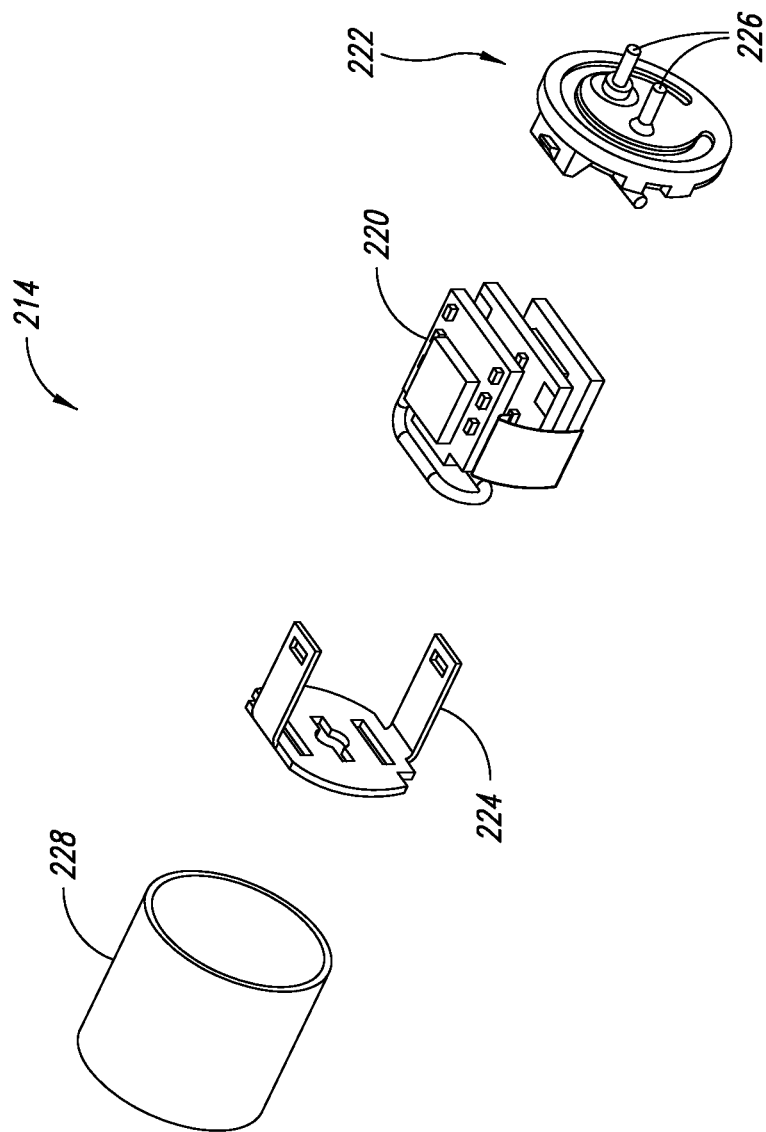
FIG. 4 is a perspective view of an exemplary electronics assembly that can be utilized to implement the electronics assembly depicted in FIG. 3.

FIG. 4 is a perspective view of an exemplary electronics assembly 214 that can be utilized to implement the electronics assembly 214 depicted in the exemplary embodiment shown in FIG. 3. Referring to FIG. 4, the electronics assembly 214 includes a printed circuit assembly (PCA) 220, which is physically attached and electrically connected to a header assembly 222. For this exemplary embodiment, the printed circuit assembly 220 includes three rigid printed circuit boards (PCBs) with electronic components (e.g., integrated circuit chips) mounted thereon and electrically interconnected utilizing flexible conductive wiring, such as, for example, flexible flat cable fabricated as an inner layer of the PCB (e.g., rigid-flex). The exemplary printed circuit assembly (220) configuration shown with three printed circuit boards, which are folded over so as to overlap each other and thus save physical space, may be characterized as a tri-fold printed circuit assembly. The exemplary electronics assembly 214 also includes a printed circuit assembly clip 224, which is utilized to physically affix the printed circuit assembly 220 to one side of the header assembly 222. The clip 224 can be made of a suitable sturdy and corrosion-resistant material, such as, for example, titanium (Ti) and the like. The other side of the header assembly 222 includes two antenna connections 226, which can be utilized as mounting points and electrical connections for an antenna. Thus, the header assembly 222 can function to electrically and physically connect an antenna to, for example, a radio transmitter circuit mounted on one of the printed circuit boards of the printed circuit assembly 220. The exemplary electronics assembly 214 also includes a case 228, which is physically affixed to the header assembly 222 and thereby utilized to enclose and hermetically seal the printed circuit assembly 220 and printed circuit assembly clip 224 within. For example, the case 228 can be made of a suitable sturdy and corrosion-resistant material, such as titanium (Ti) and the like.

FIGS. 5A, 5B and 5C provides a detailed view of an exemplary electronics assembly including a three-board folded printed circuit assembly (PCA) that can be utilized to implement the electronics assembly 214 depicted in FIG. 4. Referring to FIG. 5B, the electronics assembly 214 includes a PCA 220, which is affixed by a clip to the header assembly shown. The PCA 220 is enclosed (and hermetically sealed) by a case 5002 as shown in FIG. 5A. One antenna connection or terminal 5004 (e.g., of two antenna connections or terminals) and a battery connection or terminal 5000 are shown in FIG. 5A. Thus, the electronics assembly 214 can be coupled physically and electrically to a transmission antenna and power component (e.g., battery) at either end.

An exploded view of the PCA 220 is also shown, see FIG. 5C. Specifically, the PCA 220 depicted in the exploded view includes three rigid printed circuit board (PCB) sections coupled together physically and electrically by flexible conductive wiring, such as, for example, rigid-flex. In the exemplary embodiments shown in FIG. 4 and FIG. 5A-5C, the PCA 220 includes three PCB sections 5006, with electronic circuit components mounted on each side 5006A and 5006B. The PCB sections 5006A may include at least a central processor unit (CPU) integrated circuit or chip, a memory integrated circuit or chip, and a Surface Acoustic Wave (SAW) chip (among other circuit components). The PCB sections (on the reverse side) 5006B may include at least a radio transmitter (RADIO) integrated circuit or chip, a Real-Time Clock (RTC) integrated circuit or chip, and an Inertial Measurement Unit (IMU) integrated circuit or chip (among other circuit components). In any event, the three-board folded PCA 220 shown in FIG. 5A-5C and FIG. 4, respectively, provides a compact configuration that conserves a significant amount of physical space in the reporting processor(s) involved.

Figure 6:
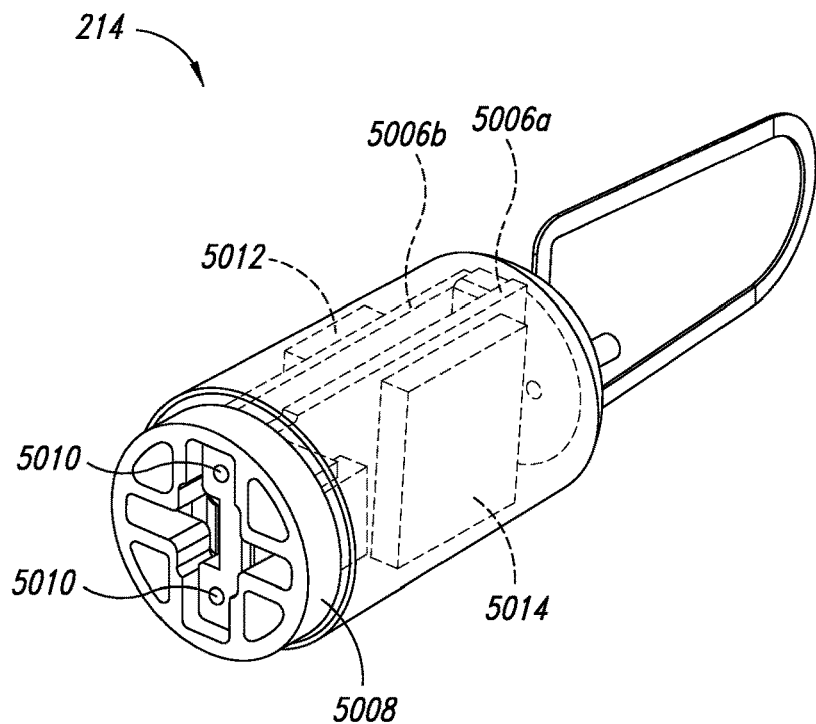
FIG. 6 is a perspective view of a second exemplary electronics assembly that can be utilized to implement the electronics assembly depicted in FIG. 3.

FIG. 6 is a perspective view of a second exemplary electronics assembly that can be utilized to implement the electronics assembly 214 depicted in FIG. 3. Referring to FIG. 6, the exemplary electronics assembly 214 includes a two-board folded PCA. Specifically, a first rigid PCB 5006A and a second rigid PCB 5006B are configured in parallel and physically affixed to a base 5008. At least one circuit component (e.g., RADIO integrated circuit or chip) 5012 is mounted on one surface of the second rigid PCB 5006B, and at least one additional circuit component (e.g., CPU integrated circuit or chip) 5014 is mounted on one surface of the first rigid PCB 5006A. For example, in one embodiment, a MEMORY integrated circuit and a SAW chip can be mounted with the CPU integrated circuit on the one surface (or the opposite surface) of the first rigid PCB 5006A, and an RTC integrated circuit and an IMU integrated circuit can be mounted with the RADIO integrated circuit on the one surface (or the opposite surface) of the second rigid PCB 5006B. The electronic circuits mounted on the base 5008 are electrically coupled to a power component (battery) via the battery connections 5010. In any event, the electronic assembly with the two-board folded PCA shown in FIG. 6 also provides a compact configuration that conserves a significant amount of physical space in the reporting processor(s) involved.

Figure 7:
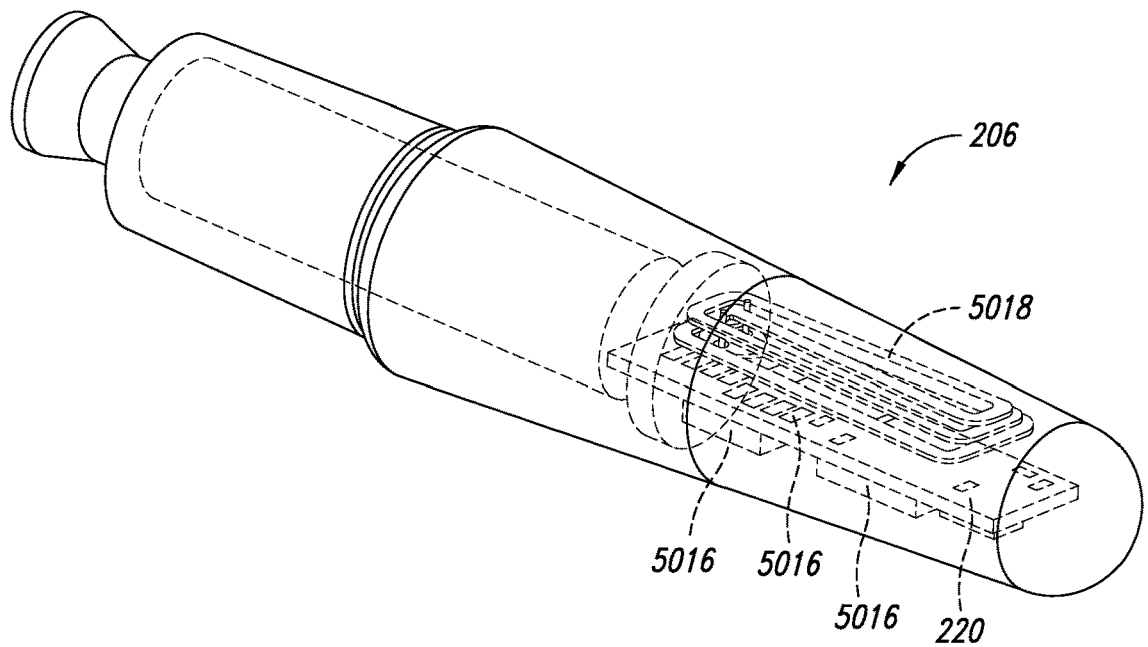
FIG. 7 is a perspective view of a second reporting processor including an electronics assembly that can be utilized to implement the electronics assembly depicted in FIG. 3.

FIG. 7 is a perspective view of an exemplary reporting processor 206 including an electronics assembly that can be utilized to implement the electronics assembly 214 depicted in FIG. 3. Referring to FIG. 7, the exemplary reporting processor 206 includes a half-lap PCA 220. The term "half-lap" is used herein to indicate that a single PCB (as opposed to the multiple PCB configurations described above) is utilized to mount the electronic integrated circuits involved. The half-lap PCA configuration depicted in FIG. 7 is preferably a single board design that is intended for those antenna configurations that overlap the electronic circuits involved. Referring to FIG. 7, the reporting processor 206 includes a PCA 220, which in this embodiment is a single PCB. A plurality of electronic (integrated) circuits 5016 can be mounted on one or both sides of the PCA/PCB 220. An antenna 5018 is disposed over (and thus overlaps) the electronic circuits 5016.

Figure 8A:
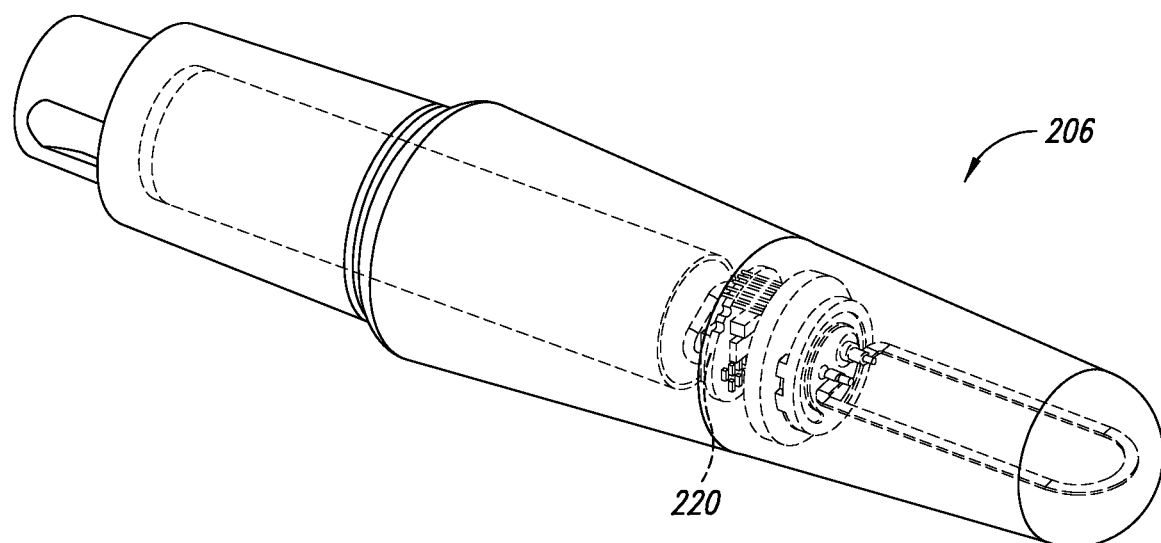
FIG. 8A-8E are perspective views of a reporting processor with circular-stacked printed circuit assembly that can be utilized to implement exemplary embodiments of the present invention.
Figure 8C:
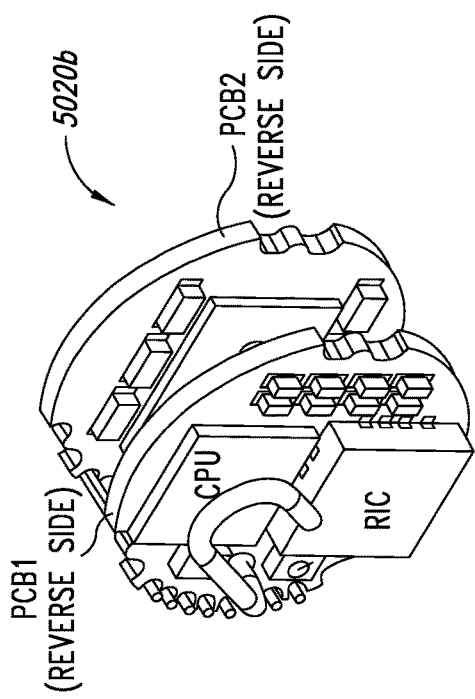
Figure 8E:
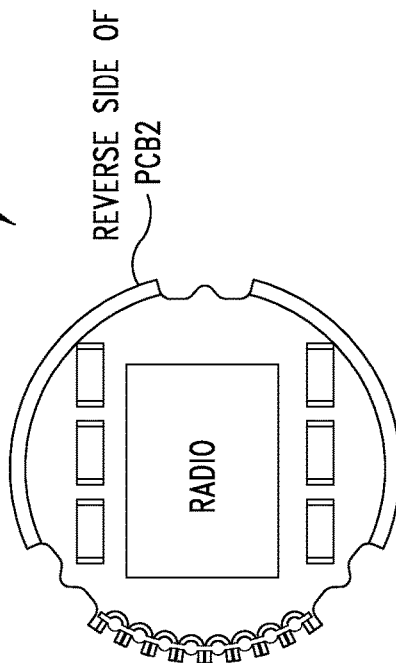
Figure 8B:
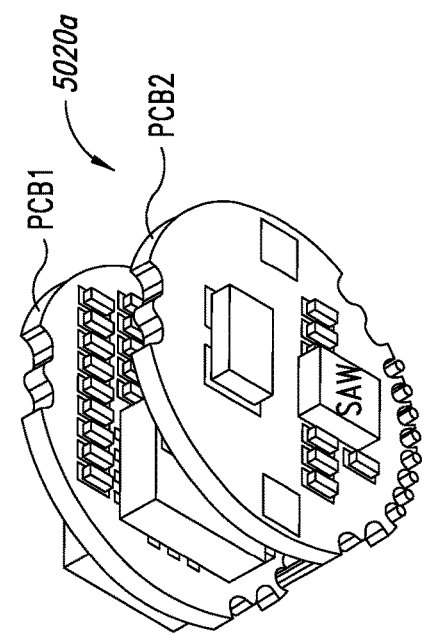
Figure 8D:
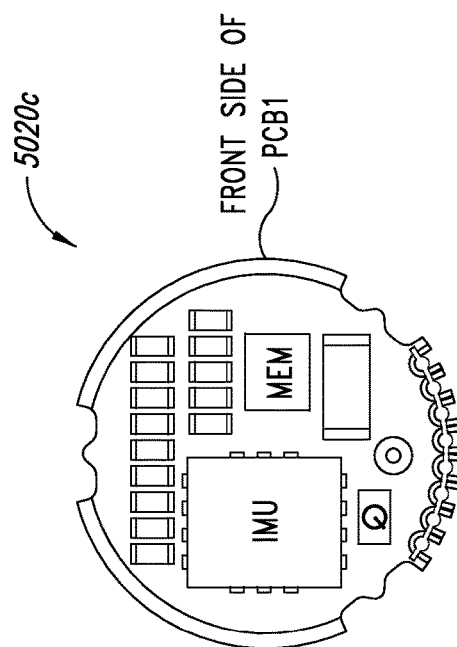

FIG. 8A is a perspective view of an IRP that includes a reporting processor with a circular-stacked (COIN) PCA that can be utilized to implement an exemplary embodiment of the present invention. Referring to FIG. 8A, a reporting processor (e.g., IRP) 206 is shown with a circular-stacked PCA 220. In other words, as depicted in FIG. 8B and FIG. 8C, for this exemplary embodiment, the PCA 220 includes two circular-shaped (coin-shaped) circuit boards PCB1 and PCB2 that are fixedly mounted parallel to each other (e.g., stacked). For this exemplary embodiment, the front side or surface of PCB1 (FIG. 8D) has an IMU integrated circuit or chip and a MEMORY integrated circuit or chip mounted thereon (along with other integrated circuits or chips), and the reverse side or surface of PCB1 (FIG. 8C) has a CPU integrated circuit or chip and an RTC integrated circuit or chip mounted thereon (along with other integrated circuits or chips). Also, the front side or surface of PCB2 (FIG. 8B) has a SAW chip and a quartz crystal integrated circuit or chip (e.g., CX-16 chip in one embodiment) mounted thereon (along with other integrated circuits or chips), and the reverse side or surface of PCB2 (FIG. 8E) has a RADIO integrated circuit or chip mounted thereon (along with other integrated circuits or chips). As such, the reporting processor 206 with the circular-stacked PCA 220 and 8B through 8E as shown in FIG. 8A provides a compact configuration that conserves a significant amount of physical space in the reporting processor(s) involved.

Figure 9A:
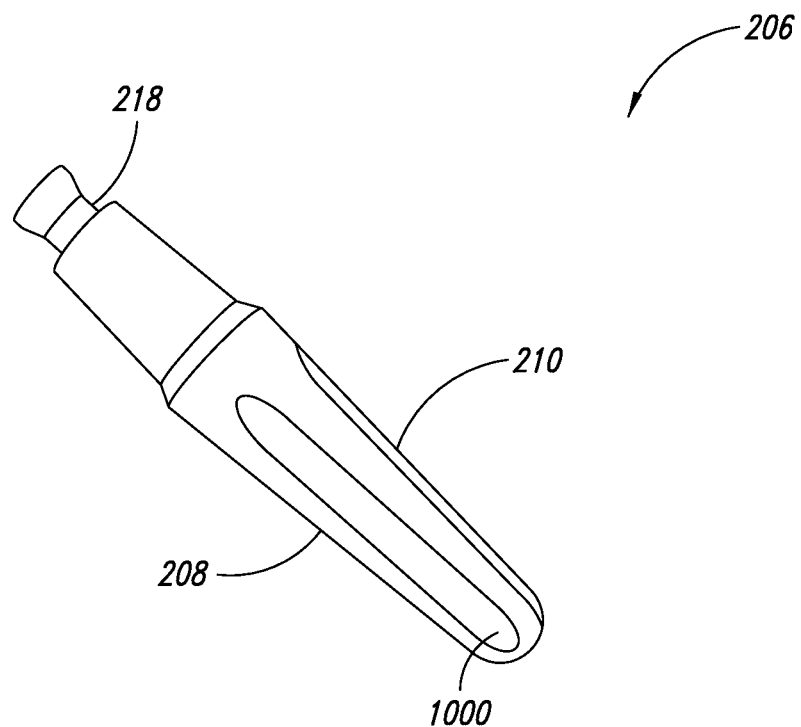
FIG. 9A is a perspective view of an exemplary reporting processor with an enhanced antenna configuration that can be utilized to implement the reporting processor depicted in FIG. 2.

FIG. 9A is a perspective view of an exemplary reporting processor that can be utilized to implement the reporting processor 206 depicted in FIG. 2. Referring to FIG. 2 and FIG. 9A, the implantable reporting processor 206 (e.g., IRP) shown in FIG. 9A can be physically attached to the tibial plate 202 utilizing the set-screw engagement hole (218) and implanted into the tibia 204. For the exemplary embodiment shown in FIG. 9A, the tibial plate 202 and the reporting processor 206 are thus surgically implanted into the tibia 204 to form the tibial extension 208. For this embodiment, the outer casing 210 and thus the tibial extension 208 are preferably made of a suitable polymer material. The surface of the outer casing 210 at the distal end of the tibial extension 208 includes suitable ribbing 1000 that is utilized to enhance the engagement of the tibial extension 208 with the bone material of the tibia 204. In one embodiment, the outer casing 210 of the reporting processor 206 can be hermetically sealed to enhance the useful life of the reporting processor 206.

Figure 9B:
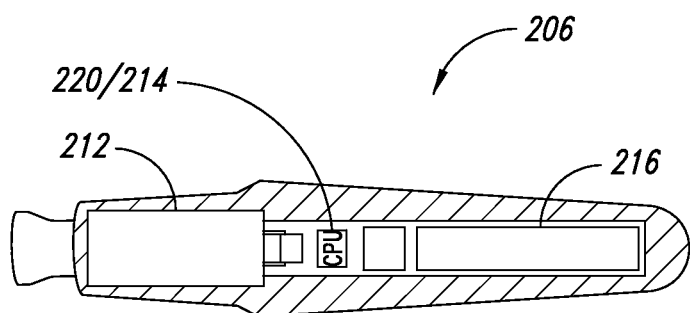
FIG. 9B is a detailed view of exemplary internal components that can be utilized to implement the reporting processor depicted in FIG. 9A.

FIG. 9B is a detailed view of exemplary internal components that can be utilized to implement the reporting processor 206 depicted in FIG. 9A. Referring to FIG. 9B, the reporting processor 206 shown includes a power component 212 (e.g., battery) that is physically attached and electrically connected to a printed circuit assembly (PCA) 220, which is a component of an electronics assembly 214. For the exemplary embodiment depicted in FIG. 9A and FIG. 9B, a ceramic chip antenna 216 is mounted directly to an extended portion of a PCB in the PCA 220 shown. Notably, the reliability and interference problems typically associated with antennae being in close proximity to human tissue and electronic components are greatly reduced with ceramic chip antennas, such as the ceramic chip antenna 216 shown in FIG. 9B. In other words, close proximity to human tissue and other components does not cause as severe a detuning as with other (e.g., trace) antennas. As such, for the exemplary embodiment depicted in FIG. 9B, the operating center frequency of the antenna 216 utilized, for example, in an industrial/medical process can be 2.45 GHz, the operating frequency can be approximately between 2,400 to 2,488 MHz, and the antenna 216 is linearly polarized. The transmitted radiation pattern of the ceramic chip antenna 216 is generally perpendicular to the ground plane of the chip. So, the ceramic chip antenna 216 can be oriented during surgery so that the transmitted radiation pattern can be directed outward from the tibia 204. Additionally, the ceramic chip antenna 216 can be flexibly tuned and readily tested pre- and post-manufacture. In any event, the ceramic chip antenna 216 is an ultra-compact antenna configuration that is relatively easy to implement (e.g., mounted by hand or machine process) on a PCB.

Figure 10A:
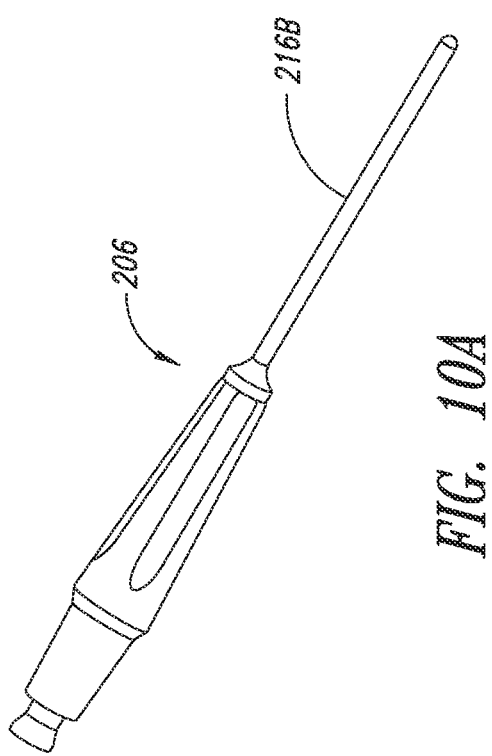
FIG. 10A is a perspective view of a second exemplary reporting processor that can be utilized to implement the reporting processor depicted in FIG. 2.

FIG. 10A is a perspective view of a second exemplary reporting processor that can be utilized to implement the reporting processor 206 depicted in FIG. 2. Referring to FIG. 10A, the reporting processor 206 includes a whip antenna 216 that transmits an omni-directional radiation pattern (e.g., radiates equal power in all azimuthal directions). For example, the whip antenna 216 can be a straight metal "whip" or rod (or electrically conductive wire or other suitable material configured to form a metal "whip" or rod) that is attached through the bottom of the tibial extension 208 to the terminals of a radio transmitter in the electronics assembly 214. Also, for example, the whip antenna 216 can be utilized for additional structural stability (e.g., in a TKA) as a metal extension of the tibial extension 208.

Figure 10B:
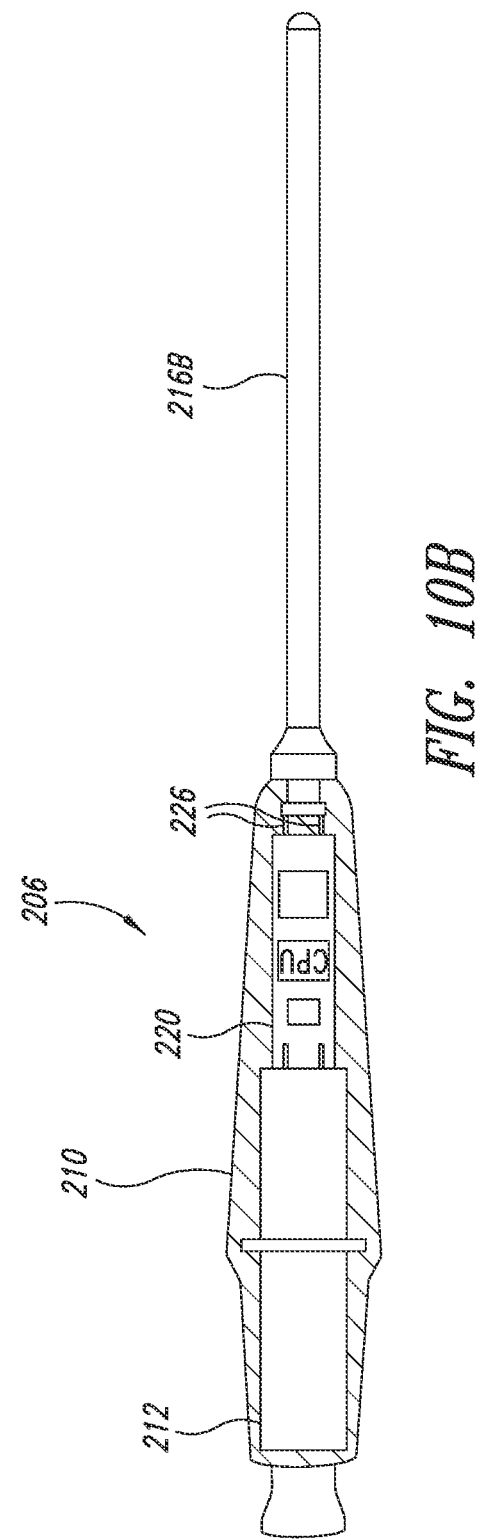
FIG. 10B is a detailed view of exemplary components that can be utilized to implement the reporting processor depicted in FIG. 10A.

FIG. 10B is a detailed view of exemplary components that can be utilized to implement the reporting processor 206 depicted in FIG. 10A. Referring to FIG. 10B, the reporting processor 206 shown includes a power component 212 (e.g., battery) that is physically attached and electrically connected to a printed circuit assembly (PCA) 220. For the exemplary embodiment depicted in FIG. 10A and FIG. 10B, a whip antenna 216 is physically attached and electrically connected via the antenna connections 226 to the PCA 220 through the outer casing 210 as shown. Thus, by mounting the whip antenna 216 externally to the outer casing 210, the size and capacity of the power component 212 can be significantly increased, and/or the number or size of the electronic circuits in the PCA 220 can be significantly increased. As such, the external whip antenna 216 can be utilized to conserve a significant amount of space within the outer casing 210.

Figure 11A:
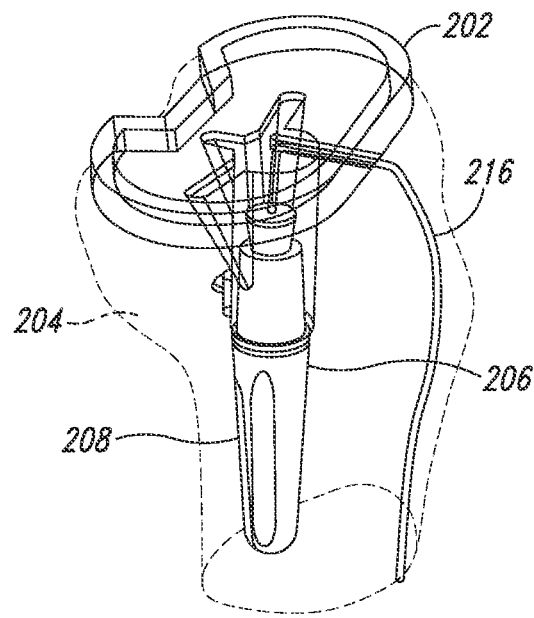
FIG. 11A is a perspective view of a third exemplary reporting processor that can be utilized to implement the reporting processor depicted in FIG. 2.

FIG. 11A is a perspective view of a third exemplary reporting processor that can be utilized to implement the reporting processor 206 depicted in FIG. 2. Referring to FIG. 11A, the reporting processor 206 includes an in-muscle (lead) whip antenna 216 that transmits an omni-directional radiation pattern (e.g., radiates equal power in all azimuthal directions). For example, the whip antenna 216 can be a flexible, electrically conductive lead or wire that is configured to exit through the top of the tibial extension 208. The flexible whip antenna or lead 216 is then fed through the tibial plate 202, and routed to and fixedly attached to the patient's muscle tissue outside the tibia 204.

Figure 11B:
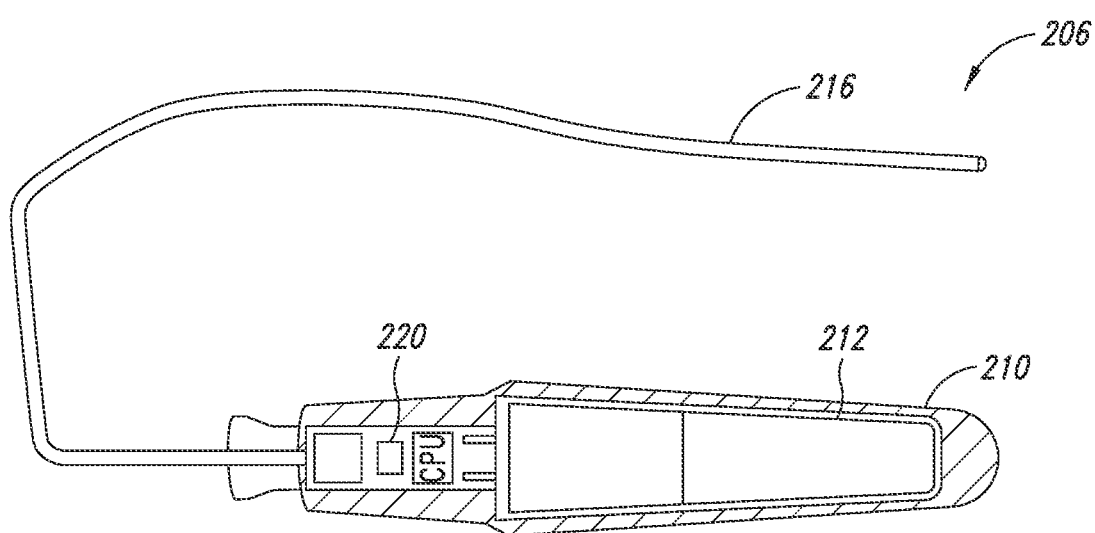
FIG. 11B is a detailed view of exemplary components that can be utilized to implement the reporting processor depicted in FIG. 11A.

FIG. 11B is a detailed view of exemplary components that can be utilized to implement the reporting processor 206 depicted in FIG. 11A. Referring to FIG. 11B, the reporting processor 206 shown includes a power component 212 (e.g., prismatic battery or cell) that is physically attached and electrically connected to a printed circuit assembly (PCA) 220. Notably, the utilization of a prismatic battery or cell for the power component 212 satisfies the requirement for thinner and thus smaller, space-conserving component sizes. For the exemplary embodiment depicted in FIG. 11A and FIG. 11B, a flexible whip or lead antenna 216 is physically attached and electrically connected to the PCA 220 through the outer casing 210 of the reporting processor 206 as shown. Thus, by mounting the whip antenna 216 externally to the outer casing 210, the size and capacity of the power component 212 can be significantly increased, and/or the number or size of the electronic circuits in the PCA 220 can be significantly increased. As such, the external whip antenna 216 can be utilized to conserve a significant amount of space within the outer casing 210. Also, by attaching the antenna 216 to the patient's muscle tissue outside of the tibia 204 (e.g., outside the bone), less radiation power is required, and thus the useful life of the power component 212 can be significantly increased. Notably, the configuration of the flexible whip antenna 216 is compatible with that of a tibial extension (e.g., 208) having a metal extension and thus enhances the stability of the prosthesis involved.

Figure 12A:
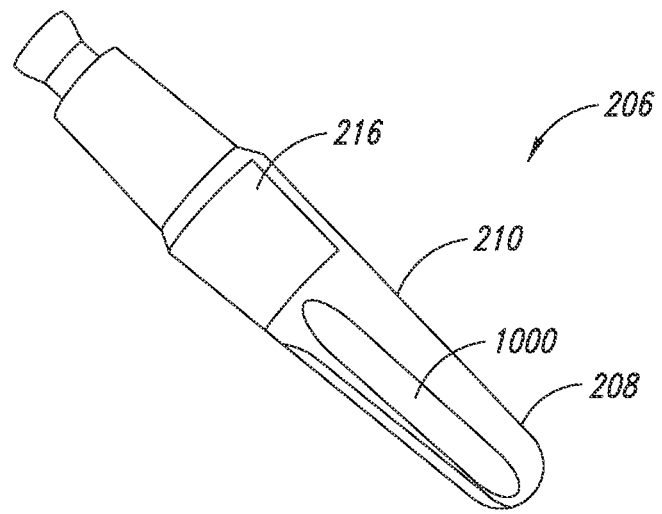
FIG. 12A is a perspective view of a fourth exemplary reporting processor that can be utilized to implement the reporting processor depicted in FIG. 2.

FIG. 12A is a perspective view of a fourth exemplary reporting processor that can be utilized to implement the reporting processor 206 depicted in FIG. 2. Referring to FIG. 2 and FIG. 12A, the implantable reporting processor 206 (e.g., IRP) shown in FIG. 12A can be physically attached to the tibial plate 202 utilizing the set-screw engagement hole (218) and implanted into the tibia 204. For the exemplary embodiment shown in FIG. 12A, the tibial plate 202 and the reporting processor 206 are thus surgically implanted into the tibia 204 to form the tibial extension 208. For this embodiment, the outer casing 210 and thus the tibial extension 208 are preferably made of a suitable polymer material. The surface of the outer casing 210 at the distal end of the tibial extension 208 includes suitable ribbing 1000 that is utilized to enhance the engagement of the tibial extension 208 with the bone material of the tibia 204. In one embodiment, the outer casing 210 of the reporting processor 206 can be hermetically sealed to enhance the useful life of the reporting processor 206. Notably, for this embodiment, the reporting processor 206 has a patch antenna 216 affixed to the external surface of the outer casing 210.

Figure 12B:
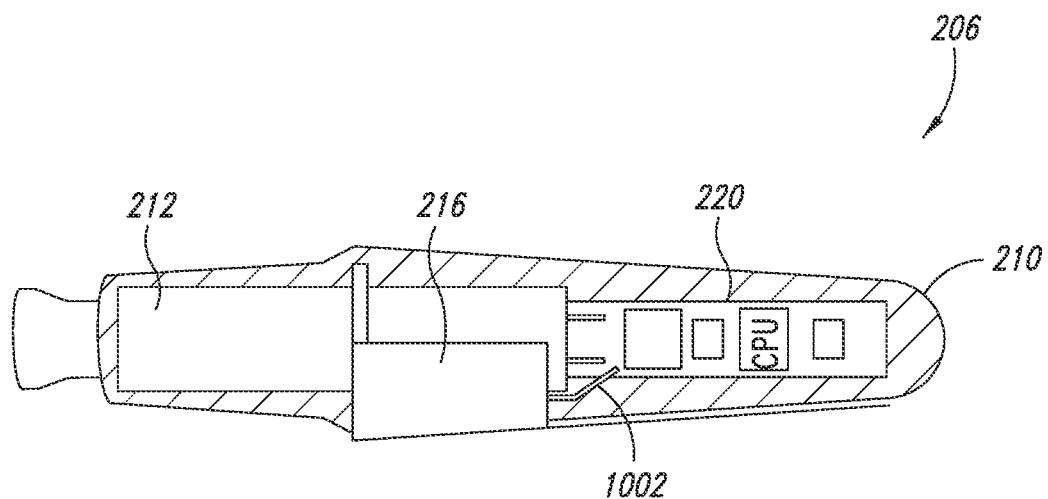
FIG. 12B is a detailed view of exemplary components that can be utilized to implement the reporting processor depicted in FIG. 12A.

FIG. 12B is a detailed view of exemplary components that can be utilized to implement the reporting processor 206 depicted in FIG. 12A. Referring to FIG. 12B, the reporting processor 206 shown includes a power component 212 (e.g., battery) that is physically attached and electrically connected to a printed circuit assembly (PCA) 220. For the exemplary embodiment depicted in FIG. 12A and FIG. 12B, a (e.g., microstrip) patch antenna 216 is fixedly attached to the external surface of the outer casing 210, and electrically connected to the PCA 220 utilizing an electrically conductive lead or wire 1002 (e.g., micro-coaxial cable in one embodiment) that extends into the reporting processor 206 through the outer casing 210 as shown. Notably, the patch antenna 216 is a low profile component that is readily conformable to the non-planar surface of the outer casing 210, and also inexpensive, easily fabricated and tested, and mechanically robust. The transmitted radiation pattern of the patch antenna 216 is bipolar and generally perpendicular to its ground plane. So, the transmitted radiation pattern of the patch antenna 216 can be directed outward from the tibia 204 (FIG. 2). Notably, the reliability and interference problems typically associated with antennae being in close proximity to human tissue and electronic components are greatly reduced with patch antennas, such as the patch antenna 216 shown in FIG. 12B. In other words, close proximity to human tissue and other components does not cause as severe a detuning as with other types of (e.g., trace) antennas. As such, for the exemplary embodiment depicted in FIG. 12B, the operating center frequency of the patch antenna 216 utilized, for example, in an industrial/medical process can be 2.4 GHz to 2.5 GHz. In any event, the patch antenna 216 is a low profile, ultra-compact antenna configuration that is relatively easy to implement (e.g., mounted by hand or machine process) on the outer casing 210 of the reporting processor 206. Also, the relatively low power consumption of a radio transmitter utilizing the patch antenna 216 significantly enhances the useful life of the power component 212, which can also be enhanced further by utilizing a relatively larger power component 212 due to the increased space available inside the outer casing 210 with an external patch antenna 216.

Figure 13A:
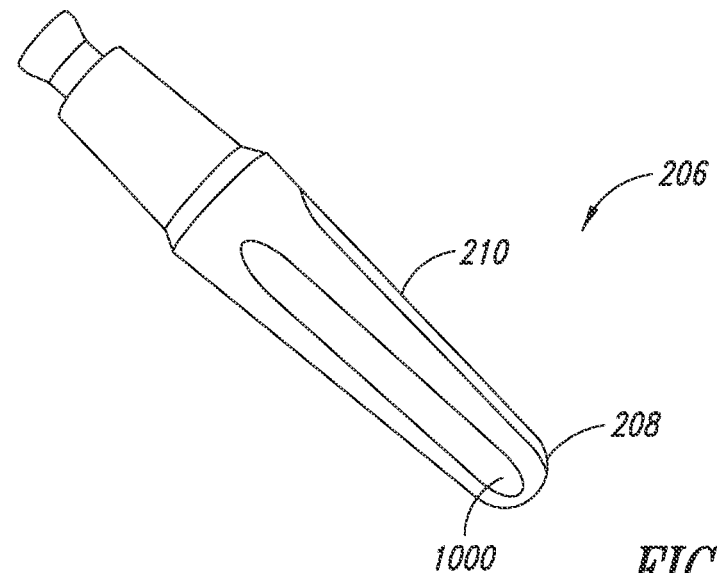
FIG. 13A is a perspective view of a fifth exemplary reporting processor that can be utilized to implement the reporting processor depicted in FIG. 2.

FIG. 13A is a perspective view of a fifth exemplary reporting processor that can be utilized to implement the reporting processor 206 depicted in FIG. 2. Referring to FIG. 2 and FIG. 13A, the implantable reporting processor 206 (e.g., IRP) shown in FIG. 13A can be physically attached to the tibial plate 202 utilizing the set-screw engagement hole (218) and implanted into the tibia 204. For the exemplary embodiment shown in FIG. 13A, the tibial plate 202 and the reporting processor 206 are thus surgically implanted into the tibia 204 to form the tibial extension 208. For this embodiment, the outer casing 210 and thus the tibial extension 208 are preferably made of a suitable polymer material. The surface of the outer casing 210 at the distal end of the tibial extension 208 includes suitable ribbing 1000 that is utilized to enhance the engagement of the tibial extension 208 with the bone material of the tibia 204. In one embodiment, the outer casing 210 of the reporting processor 206 can be hermetically sealed to enhance the useful life of the reporting processor 206. Notably, for this embodiment, the reporting processor 206 has a (e.g., custom made) patch antenna 216 installed inside the outer casing 210 of the tibial extension 208.

Figure 13B:
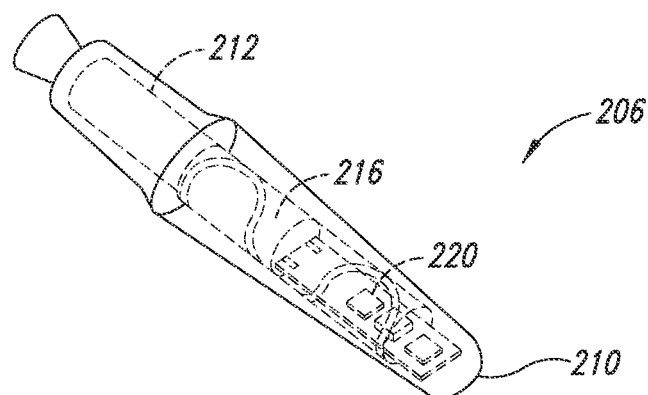
FIG. 13B is a first detailed view of exemplary components that can be utilized to implement the reporting processor depicted in FIG. 13A.
Figure 13C:
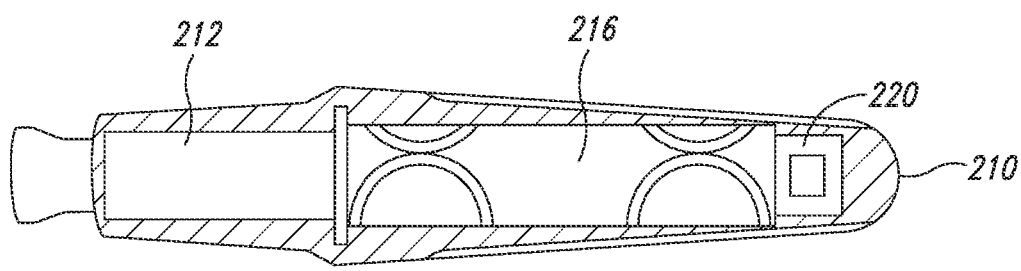
FIG. 13C is a second detailed view of the exemplary components that can be utilized to implement the reporting processor depicted in FIG. 13A.

FIG. 13B is a first detailed view of exemplary components that can be utilized to implement the reporting processor 206 depicted in FIG. 13A. Referring to FIG. 13B, the reporting processor 206 shown includes a power component 212 (e.g., battery) that is physically attached and electrically connected to a printed circuit assembly (PCA) 220. For the exemplary embodiment depicted in FIG. 13A and FIG. 13B, a (e.g., microstrip) patch antenna 216 is fixedly attached to the internal surface of the outer casing 210 (or, alternatively, fixedly attached to one or more support braces that partially enclose the PCA 220), and electrically connected to the PCA 220 utilizing an electrically conductive lead or wire (e.g., micro-coaxial cable in one embodiment) that is physically attached and electrically connected to the PCA 220 shown. Thus, the internal patch antenna 216 has all of the enhancements and/or benefits of the external patch antenna described above with respect to FIG. 12A and FIG. 12B. However, the internal patch antenna 216 in FIG. 13A and FIG. 13B is further enhanced, because as shown in the second detailed view in FIG. 13C, the internal patch antenna 216 can be configured with a significant amount of additional surface area than that of the external patch antenna, which enhances the radio transmission distance and directional capabilities of the internal patch antenna 216 over those of the external patch antenna described above. Also, compared to the external patch antenna, the internal patch antenna 216 is better protected from the corrosive effects of the surrounding tissue and environment, because the internal patch antenna 216 is enclosed within the outer casing 210 and thus can be hermetically sealed (e.g., along with the other components inside the outer casing 210).

Figure 14A:
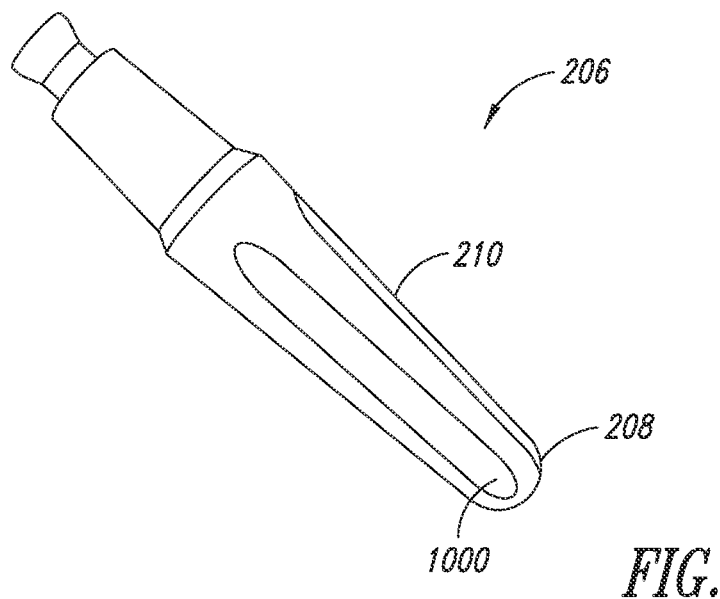
FIG. 14A is a perspective view of a sixth exemplary reporting processor that can be utilized to implement the reporting processor depicted in FIG. 2.

FIG. 14A is a perspective view of a sixth exemplary reporting processor that can be utilized to implement the reporting processor 206 depicted in FIG. 2. Referring to FIG. 2 and FIG. 14A, the implantable reporting processor 206 (e.g., IRP) shown in FIG. 14A can be physically attached to the tibial plate 202 utilizing the set-screw engagement hole (218) and implanted into the tibia 204. For the exemplary embodiment shown in FIG. 14A, the tibial plate 202 and the reporting processor 206 are thus surgically implanted into the tibia 204 to form the tibial extension 208. For this embodiment, the outer casing 210 and thus the tibial extension 208 are preferably made of a suitable polymer material. The surface of the outer casing 210 at the distal end of the tibial extension 208 includes suitable ribbing 1000 that is utilized to enhance the engagement of the tibial extension 208 with the bone material of the tibia 204. In one embodiment, the outer casing 210 of the reporting processor 206 can be hermetically sealed to enhance the useful life of the reporting processor 206. Notably, for this embodiment, the reporting processor 206 has a Near Field Communications (NFC) coil antenna 216 installed inside the outer casing 210 of the tibial extension 208.

Figure 14B:
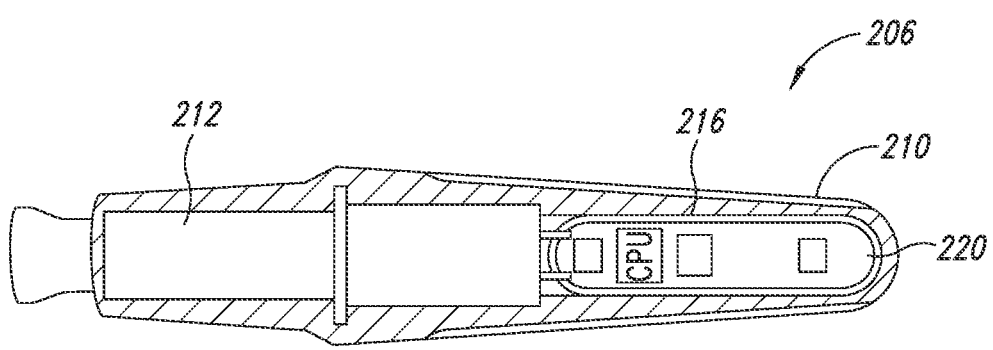
FIG. 14B is a detailed view of exemplary components that can be utilized to implement the reporting processor depicted in FIG. 14A.

FIG. 14B is a detailed view of exemplary components that can be utilized to implement the reporting processor 206 depicted in FIG. 14A. Referring to FIG. 14B, the reporting processor 206 shown includes a power component 212 (e.g., battery) that is physically attached and electrically connected to a printed circuit assembly (PCA) 220. For the exemplary embodiment depicted in FIG. 14A and FIG. 14B, a NFC coil antenna 216 is fixedly attached to and thereby installed onto the PCB and its support components on the PCA 220 inside the outer casing 210. Thus, for this exemplary embodiment, no RADIO transmitter integrated circuit or chip is required for the PCA 220, which significantly decreases the power draw or consumption of the power component 212. For example, since the antenna 216 is implemented with a NFC coil, adequate communication power can be supplied by electromagnetic induction to the NFC coil antenna 216 by the radiation from an external radio transmitter, such as, for example, a portable base station transmitter located nearby the NFC coil antenna 216. For example, such a portable base station can be attached to a custom knee brace worn by a patient recovering from a surgical procedure such as a TKA.

Figure 15A:
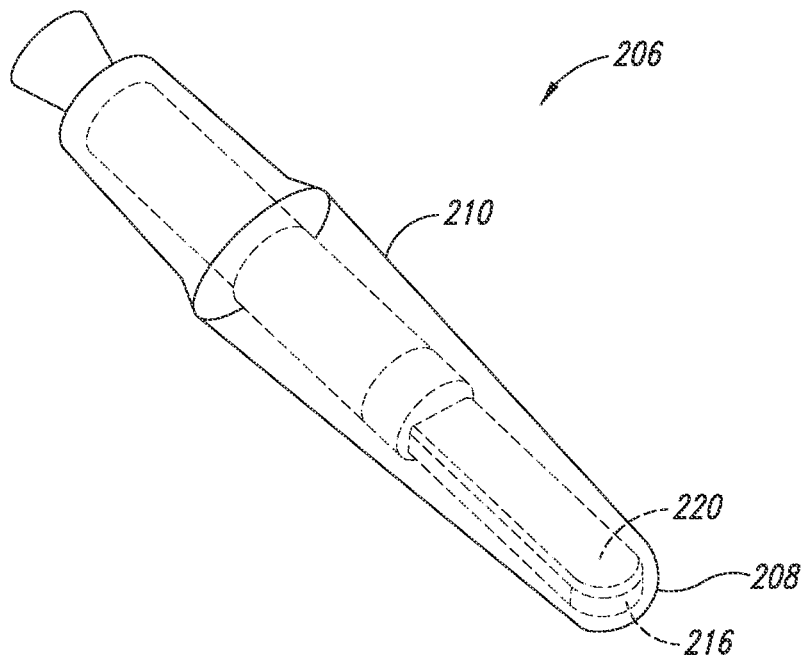
FIG. 15A is a perspective view of a seventh exemplary reporting processor that can be utilized to implement the reporting processor depicted in FIG. 2.

FIG. 15A is a perspective view of a seventh exemplary reporting processor that can be utilized to implement the reporting processor 206 depicted in FIG. 2. Referring to FIG. 2 and FIG. 15A, the implantable reporting processor 206 (e.g., IRP) shown in FIG. 15A can be physically attached to the tibial plate 202 utilizing the set-screw engagement hole (218) and implanted into the tibia 204. For the exemplary embodiment shown in FIG. 15A, the tibial plate 202 and the reporting processor 206 are thus surgically implanted into the tibia 204 to form the tibial extension 208. For this embodiment, the outer casing 210 and thus the tibial extension 208 are preferably made of a suitable polymer material. The surface of the outer casing 210 at the distal end of the tibial extension 208 includes suitable ribbing that is utilized to enhance the engagement of the tibial extension 208 with the bone material of the tibia 204. In one embodiment, the outer casing 210 of the reporting processor 206 can be hermetically sealed to enhance the useful life of the reporting processor 206. Notably, for this embodiment, the reporting processor 206 utilizes a metal drawn case that encloses the PCA 220 as the antenna 216 inside the outer casing 210 of the tibial extension 208.

Figure 15B:
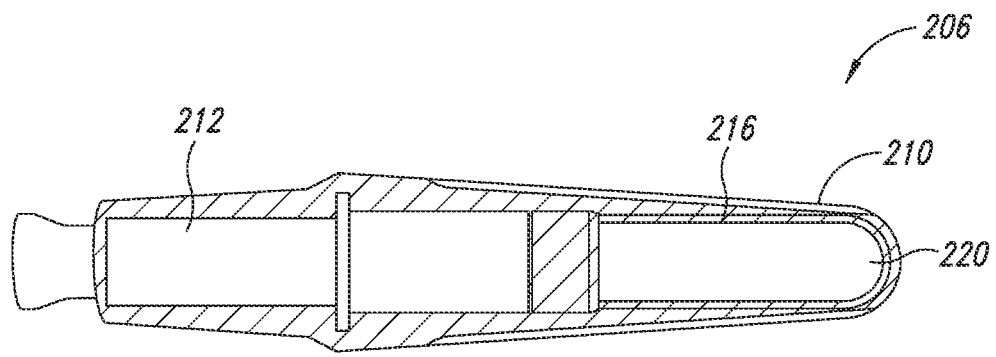
FIG. 15B is a detailed view of exemplary components that can be utilized to implement the reporting processor depicted in FIG. 15A.

FIG. 15B is a detailed view of exemplary components that can be utilized to implement the reporting processor 206 depicted in FIG. 15A. Referring to FIG. 15B, the reporting processor 206 shown includes a power component 212 (e.g., battery) that is physically attached and electrically connected to a printed circuit assembly (PCA) 220. For the exemplary embodiment depicted in FIG. 15A and FIG. 15B, a metal drawn case is utilized as the transmitting antenna 216. The metal drawn case (216) is also utilized to enclose the components of the PCA 220 inside the outer casing 210.

In this embodiment, the case antenna 216 is electrically connected to a RADIO transmitter integrated circuit or chip mounted on the PCB of the PCA 220. One benefit of the case antenna 216 is that provides a very inexpensive integrated solution to those design problems associated with the pressing requirements to limit both space and power consumption of the reporting processor(s) 206 involved.

Figure 16A:
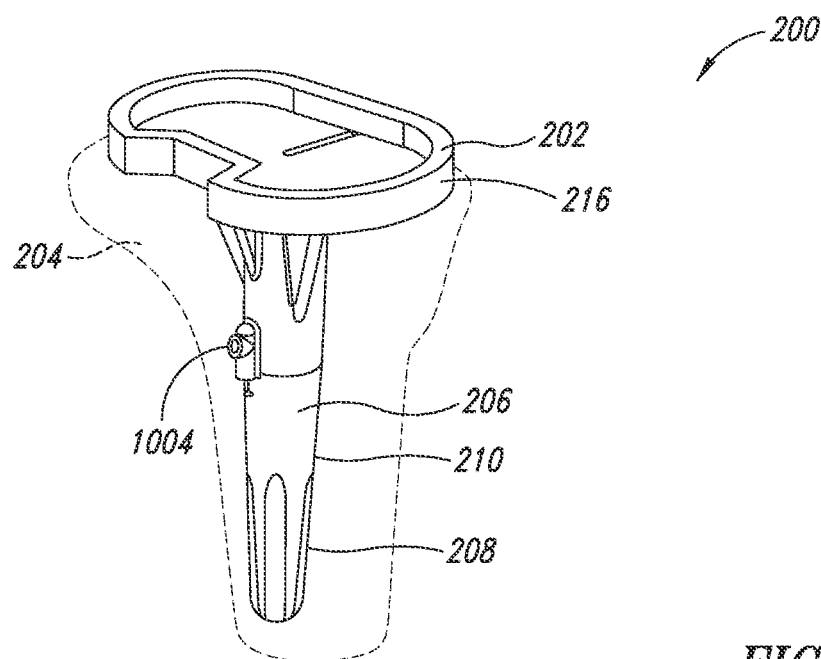
FIG. 16A is a perspective view of a tibial component that can be utilized to implement the tibial component depicted in FIG. 2.

FIG. 16A is a perspective view of a tibial component that can be utilized to implement the tibial component 200 depicted in FIG. 2. Referring to FIG. 2 and FIG. 16A, the tibial component 200 includes the implantable reporting processor 206 (e.g., IRP) shown in FIG. 16A that can be physically attached to the tibial plate 202 utilizing the set-screw engagement hole (218) and implanted into the tibia 204. For the exemplary embodiment shown in FIG. 16A, the tibial plate 202 and the reporting processor 206 are thus surgically implanted into the tibia 204 to form the tibial extension 208. For this embodiment, the outer casing 210 and thus the tibial extension 208 are preferably made of a suitable polymer material. The surface of the outer casing 210 at the distal end of the tibial extension 208 includes suitable ribbing that is utilized to enhance the engagement of the tibial extension 208 with the bone material of the tibia 204. In one embodiment, the outer casing 210 of the reporting processor 206 can be hermetically sealed to enhance the useful life of the reporting processor 206. Notably, for this embodiment, the reporting processor 206 is electrically connected to an antenna connection 1004 that is fixedly attached to the base of the tibial plate 202, and the metal material of the tibial plate 202 is thereby utilized as the antenna 216.

Figure 16B:
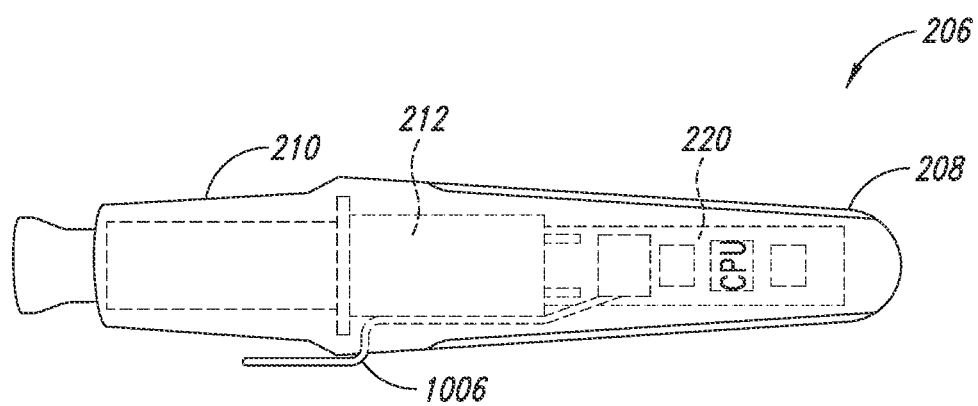
FIG. 16B is a detailed view of exemplary components that can be utilized to implement the reporting processor and tibial plate antenna depicted in FIG. 16A.

FIG. 16B is a detailed view of exemplary components that can be utilized to implement the reporting processor 206 and tibial plate antenna 216 depicted in FIG. 16A. Referring to FIG. 16B, the reporting processor 206 shown includes a power component 212 (e.g., battery) that is physically attached and electrically connected to a printed circuit assembly (PCA) 220. For the exemplary embodiment depicted in FIG. 16A and FIG. 16B, an antenna connecting lead 1006 (e.g., an electrically conductive, insulated lead or wire such as coaxial cable) is physically attached and electrically connected to (e.g., a RADIO integrated circuit or chip on) the PCA 220 shown inside the outer casing 210 of the tibial extension 208. The antenna connecting lead 1006 is also routed through the outer casing 210 and connected to the antenna connection 1004. Thus, the metal material of the tibial plate 202 can be utilized as the transmitting antenna 216. In one embodiment, the tibial plate is electrically insulated (e.g., utilizing a suitable insulation material) from the human tissue. Alternatively, if the surgical environment requires that the tibial plate 202 is not utilized as the antenna 216, then a separate antenna can be introduced during the surgical procedure and electrically connected to the reporting processor 206 at that time. The major benefits of utilizing the tibial plate antenna 216 are that there is an economical advantage and also enhanced performance that accompanies the utilization of the existing structure of the tibial plate 202 outside the bone. Also, since the reporting processor 206 is physically separated from the antenna 216, more system design flexibility is available. Furthermore, if a metal extension is affixed to the distal end of the tibial extension 208, the tibial plate antenna 216 will not interfere with the metal extension involved.

Figure 17:
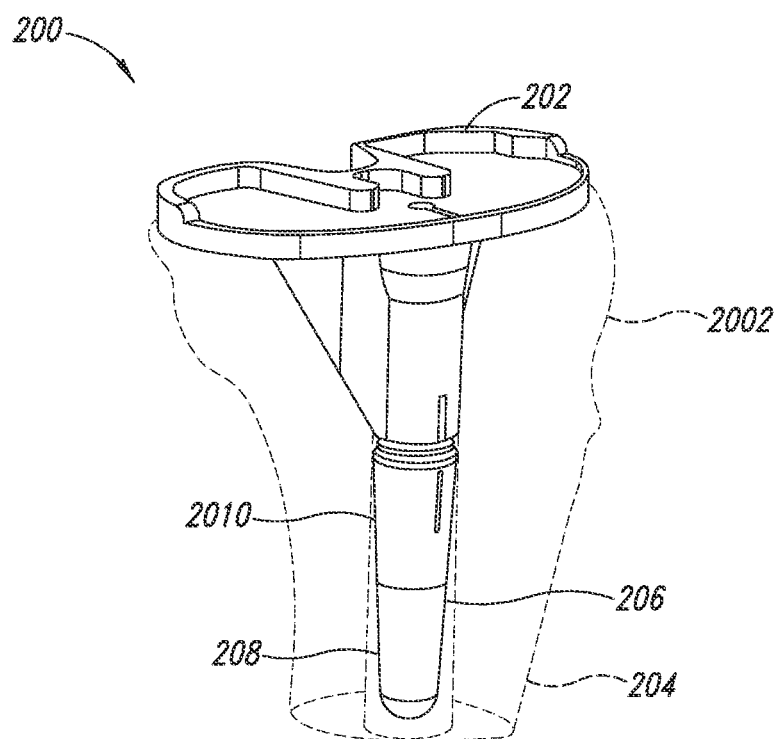
FIG. 17 is a perspective view of a tibial component of an implanted knee prosthesis that includes an implantable reporting processor, according to an embodiment.

FIG. 17 is a perspective view of a tibial component 200 of a knee prosthesis that is implanted in a leg 2002 of a living patient (e.g., a human subject), and that includes an implantable reporting processor 206, according to an embodiment.

The tibial component 200 of the implanted knee prosthesis includes a tibial plate 202, which engages with an upper portion (not shown in FIG. 17) of the knee prosthesis, and includes a tibial extension 208, which includes the implantable reporting processor 206 and which extends into a cavity 2010 formed in a tibia 204 of a living subject, such as a human subject. That is, the implantable reporting processor 206 forms part of the tibial extension 208. But the implantable reporting processor 206 is sized such that the tibial extension 208 is within the size range of tibial extensions used within conventional knee prostheses.

Still referring to FIG. 17, alternate embodiments of the tibial component 200 of the knee prosthesis are contemplated. For example, instead of forming a part of the tibial extension 208, the implantable reporting processor 206 may be disposed in a hollow portion of the tibial extension. Furthermore, the implantable reporting processor 206 may form part of, or may be disposed inside of, a prosthesis other than a knee prosthesis. For example, the implantable reporting processor 206 may form part of, or be disposed inside of, a hip prosthesis, shoulder prosthesis, elbow prosthesis, intramedullary rod, dynamic hip screw, spinal interbody spacer, or a breast implant.

Figure 18B:
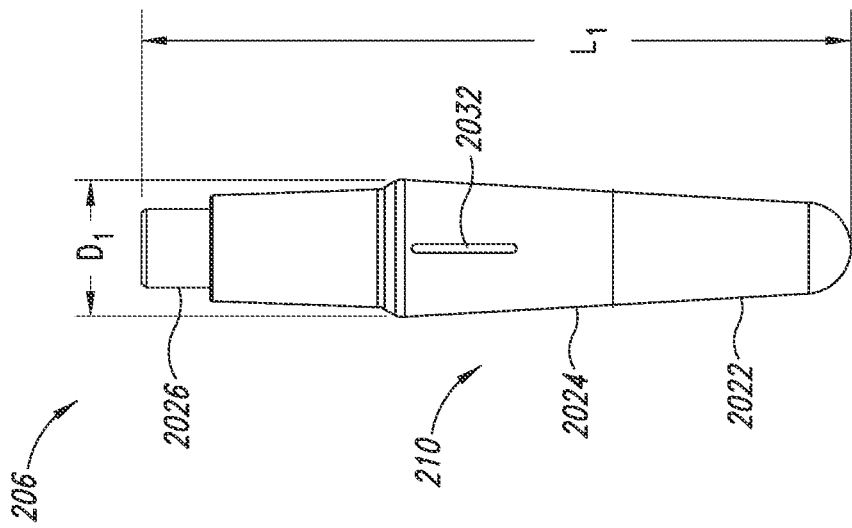
FIG. 18B is a side view the implantable reporting processor of FIGS. 17 and 18A, according to an embodiment.
Figure 18A:
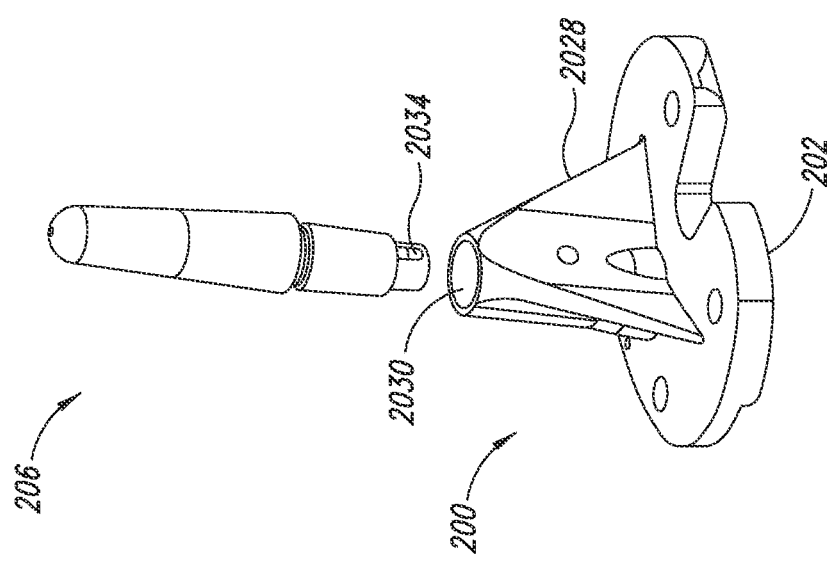
FIG. 18A is an exploded view of the tibial component of the knee prosthesis of FIG. 17, according to an embodiment.

FIG. 18A is an exploded view of the tibial component 200 of the knee prosthesis of FIG. 17, according to an embodiment.

FIG. 18B is a side view of the implantable reporting processor 206 of FIG. 17, according to an embodiment.

Referring to FIGS. 18A-18B, the implantable reporting processor 206 includes a generally cylindrical outer casing, hereinafter housing, 210, which includes a radome 2022, a central section 2024, and a coupling section 2026. The housing 210 has a length $L_1$ of about 73 millimeters (mm), and has a diameter $D_1$ of about 14 mm at its widest cross section. In various embodiments, an IRP of the present disclosure may have a length $L_1$ selected from 70 mm, or 71 mm, or 72 mm, or 73 mm, or 74 mm, or 75 mm, or 76 mm, or 77 mm, or 78 mm, or 79 mm, or 80 mm, or 85 mm, or 90 mm, or 95 mm, or 100 mm, and a range provided by selecting any two of these $L_1$ values. In various embodiments, an IRP of the present disclosure may have a diameter $D_1$ at its widest cross-section of 12 mm, or 13 mm, or 14 mm, or 15 mm, or 16 mm, or 17 mm, or 18 mm, or 19 mm, or 20 mm, or 22 mm, or 24 mm, or 26 mm, or 28 mm, or 30 mm, and range provided by selecting any two of the $D_1$ values. It should be noted that the term diameter is used in a broad sense to refer to a maximum cross-sectional distance, where that cross-section need not be an exact circle, but may be other shapes such as oval, elliptical, or even 4-, 5- or 6-sided.

The tibial plate 202 includes a support structure 2028, which includes a receptacle 2030 configured to receive the implantable reporting processor 206 as described below.

The radome 2022 covers and protects an antenna (not shown in FIGS. 18A-18B), which allows the implantable reporting processor 206 to receive and transmit data/information (hereinafter "information"). The radome 2022 can be made from any material, such as plastic or ceramic, which allows radio-frequency (RF) signals to propagate through the radome with acceptable levels of attenuation and other signal degradation.

The central and coupling sections 2024 and 2026, which are integral with one another, cover and protect electronic circuitry and a battery (not shown in FIGS. 18A-18B), and can be made from any suitable material, such as metal, plastic, or ceramic.

Furthermore, the central section 2024 includes an alignment mark 2032, which is configured to align with a corresponding alignment mark (not shown in FIGS. 18A-18B) on the outside of the receptacle 2030. Aligning the mark 2032 with the mark on the receptacle 2030 when the tibial component 200 of the knee prosthesis is implanted ensures that the implantable reporting processor 206 is in a desired orientation relative to the support structure 2028.

The coupling section 2026 is sized and otherwise configured to fit into the receptacle 2030. The fit may be snug enough so that no securing mechanism (e.g., adhesive, set-screw) is needed, or the coupling section can include a securing mechanism, such as threads, clips, and/or a set-screw (not shown in FIGS. 18A-18B) and a set-screw engagement hole 218, for attaching and securing the implantable reporting processor 206 to the tibial plate 202 via the support structure 2028.

Still referring to FIGS. 18A-18B, alternate embodiments of the implantable reporting processor 206 and the tibial component 200 of the knee prosthesis are contemplated. For example, the implantable reporting processor 206 can have any suitable configuration and shape other than that described above. Furthermore, the support structure 2028 of the tibial component 200 can include a hollow extension (not shown in FIGS. 18A-18B) for holding the implantable reporting processor 206.

Figures 19A, 19B:
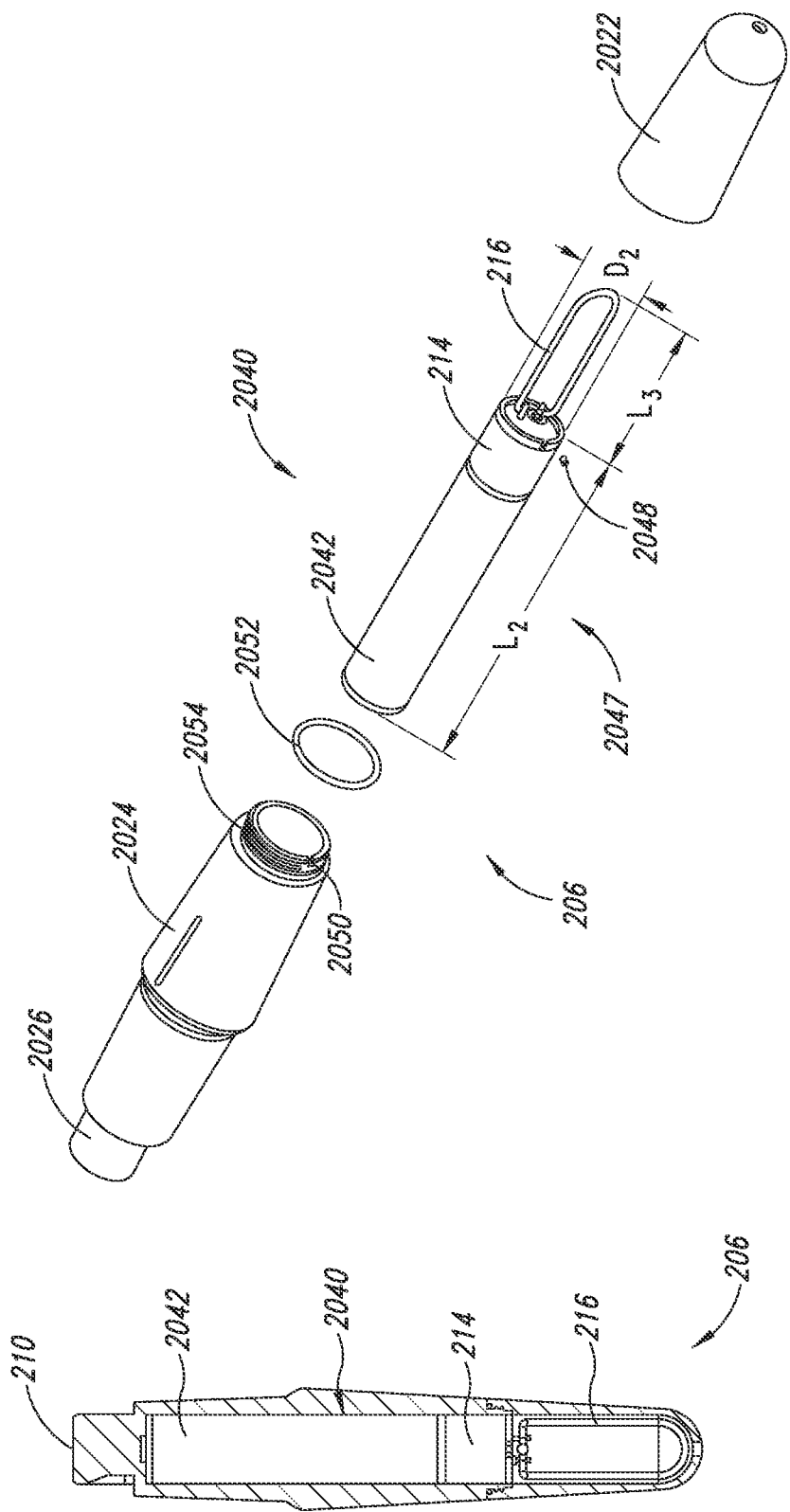
FIG. 19A is a side view, with portions broken away, of the implantable reporting processor of FIGS. 17-18B, according to an embodiment.
FIG. 19B is an exploded view of the implantable reporting processor of FIGS. 17-19A, according to an embodiment.

FIG. 19A is a view, with portions broken away, of the implantable reporting processor 206 of FIGS. 18A-18B, according to an embodiment.

FIG. 19B is an exploded view of the implantable reporting processor 206 of FIG. 19A, according to an embodiment.

Referring to FIGS. 19A-19B, the implantable reporting processor 206 includes, inside of the housing 210, a battery-circuit-antenna assembly 2039, which includes a battery 2042, an electronic-circuit assembly 214, and an antenna 216, each of which may include a respective alignment structure (not shown in FIGS. 19A-19B) and securing mechanism such that each of these components is suitably attached to, and aligned relative to, the other components. A battery-circuit subassembly 2047 of the assembly 2040, which subassembly excludes the antenna 216, has a length $L_2$ of about 43 mm and a diameter $D_2$ of about 8 mm, and the antenna has a length $L_3$ of about 20 mm.

As further described below, the battery 2042 is configured to power electronic circuitry within the electronic-circuit assembly 214 over a significant portion (e.g., 1-15+ years, e.g., 10 years, or 15 years), or the entirety (e.g., 18+ years), of the anticipated lifetime of the prosthesis in which the implantable reporting processor 206 is installed.

The electronic circuitry within the electronic-circuit assembly 214 is configured to gather, from sensors (not shown in FIGS. 19A-19B), information relating to the state and functioning of the knee prosthesis, to process this information, and to send the processed information, via the antenna 216, to a base station (base station not shown in FIGS. 19A-19B), and to a cloud-based information repository and analyzer (repository and analyzer not shown in FIGS. 19A-19B) for use, e.g., by a doctor treating a subject in which the knee prosthesis is implanted. The communication of information from the base station to the cloud-based repository may use a variety of pathways for Internet access including, but not limited to, wireless, Ethernet, and cable-modem access modalities. And as further described below, a power profile of the electronic circuitry within the electronic-circuitry assembly 214 can also be configured so as to impart a desired lifetime to the battery 2042.

The antenna 216 is designed to transmit, to a remote destination outside of the body of a subject in which the knee prosthesis is implanted, information generated by the electronic circuitry within the electronic-circuit assembly 214, to receive, from a remote source outside of the subject's body, information from a remote source, and to provide the received information to the electronic circuitry for processing.

Still referring to FIGS. 19A-19B, in a first step of assembling the implantable reporting processor 206, the battery 2042 is secured to one end of the electronic-circuit assembly 214, and the antenna 216 is secured to the other end of the electronic-circuit assembly, to form the battery-circuit-antenna assembly 2040. The battery 2042, circuitry 214, and antenna 216 can include respective alignment marks or structures (alignment marks and structures not shown in FIGS. 19A-19B) to insure proper alignment of the battery, circuit assembly, and antenna relative to one another, and can include respective securing mechanisms (not shown in FIGS. 19A-19B) to insure that the battery, circuit assembly, and antenna are properly secured to one another. Or, the battery 2042 can be welded to the corresponding end of the electronic-circuit assembly 214, and the antenna 216 can be welded to the other end of the electronic-circuit assembly. No matter the method of attachment, the battery 2042, the electronic-circuit assembly 214, and the antenna 216 form a hermetical seal to insure safety of the implantable reporting processor 2040 from ingress of biologic materials that could cause the implant to fail.

Next, the battery-circuit-antenna assembly 2040 is inserted into the central and coupling sections 2024 and 2026 of the housing 210. To insure proper alignment of the assembly 2040 relative to the sections 2024 and 2026, an alignment pin 2048 on the electronic-circuit assembly 214 is aligned with an alignment notch 2050 in the central section 2024 before the battery-circuit-antenna assembly is fully inserted into the central and coupling sections of the implantable-reporting-processor housing 210.

Then, an O-ring 2052 is slipped over a threaded portion 2054 of the central section 2026, and the radome 2022 is screwed onto the threads of the threaded portion such that the battery-circuitry-antenna assembly 2040 is secured within the housing 210 in a fixed orientation relative to the housing, and such that the O-ring forms, between the central section and the radome, a seal that is impervious to bodily fluids and tissues (e.g., blood, bone marrow) to which the implantable reporting processor 206 may be exposed. Other compressible gasket materials capable of performing the same sealing function as the O-ring may also replace the O-ring. Additional material (e.g., a biological sealant) may be applied to the threads of the threaded portion 2054 to gain greater protection against biological-fluid ingress into the radome 2022. For example, using a fill port (not shown in FIGS. 19A-19B) located at the distal end of the radome 2022, an inert flowable and biocompatible material such as silicone can be dispensed into the radome 2022, with air allowed to escape through a bleed valve (not shown in FIGS. 19A-19B) in the radome, until the radome is completely, or nearly completely, void of air. Filling the radome 2022 with such a material makes potential ingress of biologic fluid and material more difficult as it would have to displace the fill material. The two ports (fill port and bleed-valve port) are then sealed using ultrasonic welding or one or more other conventional technique to permanently plug the fill port and bleed-valve port of the radome 2022.

Still referring to FIGS. 19A-19B, alternate embodiments of the implantable reporting processor 206 are contemplated. For example, the housing 210, battery 2042, electronic-circuit assembly 214, and antenna 216 may have any suitable sizes and shapes.

Figure 20:
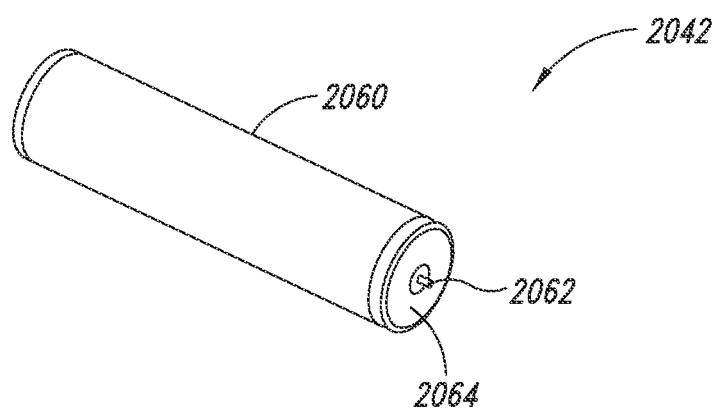
FIG. 20 is a perspective view of the battery of FIGS. 19A-19B, according to an embodiment.

FIG. 20 is an isometric view of the battery 2042 of FIGS. 19A-19B, according to an embodiment.

The battery 2042 has a lithium-carbon-monofluoride (LiCFx) chemistry, a cylindrical housing, hereinafter a cylindrical container, 2060, a cathode terminal 2062, and an anode terminal 2064, which is a plate that surrounds the cathode terminal. LiCFx is a non-rechargeable (primary) chemistry, which is advantageous for maximizing the battery-energy storage capacity. The cathode terminal 2062 makes conductive contact with an internal cathode electrode (not show in FIG. 20) and couples to the cylindrical container using a hermetic feed-through insulating material of glass or ceramic. The use of the hermetic feed through prevents leakage of internal battery materials or reactive products to the exterior battery surface. Furthermore, the glass or ceramic feed-through material electrically insulates the cathode terminal 2062 from the cylindrical container 2060, which makes conductive contact with the internal anode electrode (not shown in FIG. 20). The anode terminal is welded to the cylindrical container 2060. By locating the cathode and anode terminals 2062 and 2064 on the same end of the battery 2042, both terminals can be coupled to the electronic-circuit assembly 214 (FIGS. 19A-19B) without having to run a lead, or other conductor, to the opposite end of the battery.

The container 2060 can be formed from any suitable material, such as titanium or stainless steel, and can have any configuration suitable to limit expansion of the battery 2042 as the battery heats during use; because the battery 2042 is inside of the housing 210, if the battery were to expand too much, it could crack the container 2060 or the housing 210 (FIGS. 19A-19B), or irritate the subject's tibia or other bodily tissue.

The battery 2042 also includes, inside of the container 2060, a carbon monofluoride cathode coupled to the cathode terminal 2062, and a lithium anode coupled to the anode terminal 2064 (neither the cathode nor the anode is shown in FIG. 20). The structure and arrangement of the carbon monofluoride cathode and the lithium anode within the container 2060 can be conventional.

With its LiCFx chemistry, the battery 2042 can provide, over its lifetime, about 360 milliampere-hours (mAh) at 3.7 volts (V), although one can increase this output by about 36 mAh for each 5 mm of length added to the battery (similarly, one can decrease this output by about 36 mAh for each 5 mm of length subtracted from the battery). It is understood that other battery chemistries can be used if they can achieve the appropriate power requirements for a given application subject to the size and longevity requirements of the application. Some additional potential battery chemistries include, but are not limited to, Lithium ion (Li-ion), Lithium Manganese dioxide (Li—MnO2), silver vanadium oxide (SVO), Lithium Thionyl Chloride (Li—SOCl2), Lithium iodine, and hybrid types consisting of combinations of the above chemistries such as CFx-SVO.

Still referring to FIG. 20, alternate embodiments of the battery 2042 are contemplated. For example, although the cylindrical shape of the battery 2042 is suitable for disposing the battery in the housing 210 of the implantable reporting processor 206, the battery shape is also suitable for disposing the battery in other locations. For example, the battery 2042 can be implanted remotely from the knee prosthesis and directly inside of a subject's tibia or other bone (not shown in FIG. 20), or at some other location within the subject's body (not shown in FIG. 20). Because the battery 2042 has a relatively long lifetime, it can be disposed in a location of a subject's body (either directly or as part of a prosthesis) where it is impractical to replace the battery before replacing the associated prosthesis, and where it is impractical or impossible to recharge the battery using inductive coupling or any other recharging technique. Furthermore, to allow the battery to be implanted directly in a bodily location, the container 2060 can be configured to prevent leakage of substances (e.g., lithium, carbon monofluoride, and any byproducts) from inside of the container, and to be non-reactive to bodily substances, so that the battery 2042 does not irritate, injure, or destroy tissue in which the battery is implanted, and does not initiate a rejection response from the subject's body. Moreover, although described as being disposed in, and being associated with, a knee prosthesis, the battery 2042 can be disposed in, or associated with, a prosthesis other than a knee prosthesis. In addition, although shown with the cathode and anode terminals 2062 and 2064 on a same end of the battery 2042, the cathode and anode terminals can be disposed on opposite ends of the battery, or anywhere along the length of the battery. Furthermore, although, as described above, one can increase the length of the battery 2042 to increase the mAh output of the battery, one can also increase the diameter/width of the battery to increase the mAh output of the battery. Moreover, the implantable reporting processor 206 (FIGS. 19A-19B) can include a kinematic assembly that is configured to convert kinetic energy caused by movement of the subject's body into an electrical current for recharging the battery 2042. For example, such a kinematic assembly can be part of the electronic-circuit assembly 214, or can be a section of the implantable reporting processor 206 that is separate from, and in addition to, the battery 2042, the electronic-circuit assembly, and the antenna 216. An example of a kinematic assembly suitable for inclusion in an implantable prosthesis includes a conventional kinematic assembly included with a watch to recharge the watch's battery. In addition, the implantable reporting processor 206 can include an inductive assembly, or other assembly, that is configured to recharge the battery 2042, e.g., in response to an external charging source (not shown in FIG. 20). Furthermore, the battery 2042 can possess any of the features described in this paragraph even if the battery is disposed in the housing 210 as described above.

Figure 21A:
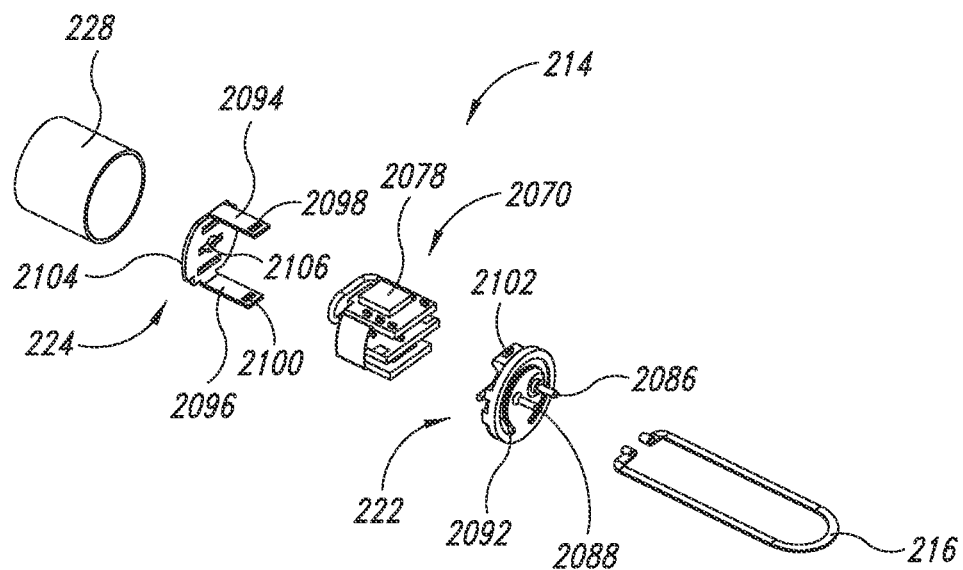
FIG. 21A is an exploded view of the electronic-circuit assembly of FIGS. 19A-19B, according to an embodiment.

FIG. 21A is an exploded isometric view of the electronic-circuit assembly 214 and the antenna 216 of FIGS. 19A-19B, according to an embodiment.

Figure 21B:
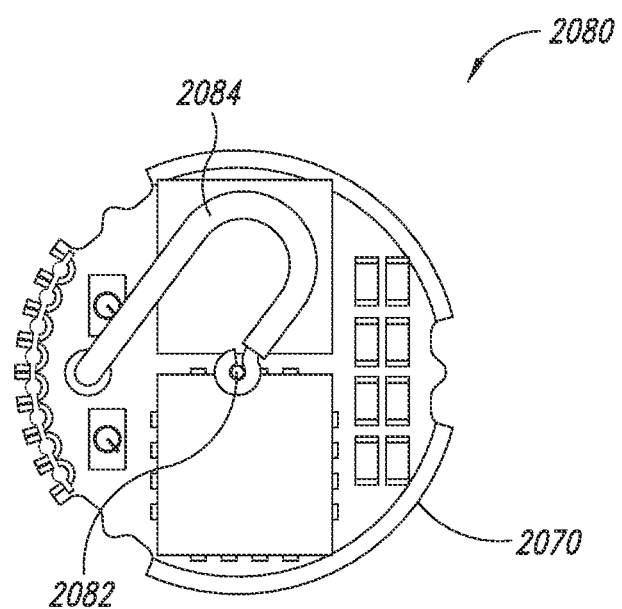
FIG. 21B is an end view of the electronic-circuit module of FIG. 21A, according to an embodiment.

FIG. 21B is an end view of the electronic-circuit module 2070 of FIG. 21A, according to an embodiment.

Referring to FIGS. 21A and 21B, in addition to the electronic-circuit module 2070, the electronic-circuit assembly 214 includes a header assembly 222, a clip 224, and a case 228.

As described above in conjunction with FIGS. 19A-19B, the electronic-circuitry module 2070 includes electronic circuitry 2078, which is configured to receive, from one or more sensors (not shown in FIGS. 21A-21B), information relating to the state and functioning of the knee prosthesis (FIG. 17), to process this information, and to send the processed information, via the antenna 216, to a base station (base station not shown in FIGS. 21A-21B), and to a cloud-based information repository and analyzer (repository and analyzer not shown in FIGS. 21A-21B) for use, e.g., by a doctor treating a subject in which the knee prosthesis is implanted. The communication from the base station to the cloud-based repository may use a variety of pathways for Internet access including, but not limited to, wireless, Ethernet, and cable-modem access modalities. The electronic circuitry 2078 is further described below, and the one or more sensors can include, e.g., accelerometers, gyroscopes, pedometers, temperature sensors, pressure sensors, and moisture sensors, can be disposed on the electronic-circuit module 2070, elsewhere in or on the knee prosthesis, or remote from the knee prosthesis, and can communicate with the electronic circuitry 2078 via conductors or wirelessly. The electronic-circuit module 2070 also includes a battery-connector 2080, which includes an inner conductor 2082 configured to contact the cathode terminal 2062 of the battery 2042 (FIG. 20), and which includes an outer conductor 2084 disposed around the inner conductor and configured to be coupled to the anode terminal 2064 of the battery via the clip 224 as described below. An electrical insulator is disposed between the inner conductor 2082 and outer conductor 2084 to prevent a short circuit of the battery 2042.

The header assembly 222 has one end configured to couple to the antenna 216, and another end configured to couple to the electronic-circuit module 2070. The header assembly 222 includes pins 2086 and 2088 (referred to as antenna connections 226 in FIG. 4), which feed through the header assembly to couple the antenna 216 electrically to the electronic circuitry 2078, and which may include, or pass through, respective hermetic seals 2090 and 2092 to prevent bodily fluids and other substances from leaking into the electronic-circuit assembly 214. In addition to coupling the antenna 216 to the electronic-circuit module 2070, the header assembly 222 forms a hermetic seal with the case 228 to prevent bodily fluids and other substances from leaking into the electronic-circuit assembly 214. Furthermore, the header assembly 222 and the electronic-circuit module 2070 can include alignment structures configured to cause the header assembly to have a desired alignment with the electronic-circuit module.

The clip 224 is configured to secure the electronic-circuit module 2070 to the header assembly 222, and to promote the electrical coupling of the battery 2042 to the electronic-circuit module. The clip 224 includes arms 2094 and 2096 having protrusions 2098 and 2100, which respectively engage a recess 2102 and a recess opposite to the recess 2102 but not shown in FIGS. 21A-21B. The clip 224 also includes a plate 2104 having an opening 2106. The plate 2104 is conductive and contacts the outer connector 2084 of the electronic-circuit module 2070, and the opening 2106 is aligned with the inner connector 2082 of the electronic-circuit module.

And the case 228 covers and protects the electronic-circuit module 2070 and portions of the header assembly 222 and clip 224. In addition to forming a seal with the header assembly 222, the case 228 forms a seal, such as a hermetic seal, with the clip 224. The case 228 can be formed from any suitable material; for example, the case 228 can be formed from the same material as the material from which the battery container 2060 (FIG. 20) is formed.

Referring to FIGS. 19A-19B, when the battery-circuit-antenna assembly 2040 is assembled, the cathode terminal 2062 of the battery 2042 extends through the opening 2106 in the clip plate 2104 and contacts the inner conductor 2082 of the electronic-circuit module 2070, and the anode terminal 2064 of the battery is electrically coupled to the outer conductor 2084 of the electronic-circuit module because the anode terminal contacts the clip plate, which contacts the outer conductor. That is, the clip plate 2104 is sandwiched between, and electrically contacts, the battery's anode terminal 2064 and the outer conductor 2084 of the electronic-circuit module 2070.

Referring to FIGS. 21A-21B, alternate embodiments of the electronic-circuit assembly 214 are contemplated. For example, although described as having an inner conductor 2082 and an outer conductor 2084 for electrically coupling the electronic circuitry 2078 to the battery 2042 (FIG. 20), the electronic-circuit module 2070 can include any other suitable structure for electrically coupling the electronic circuitry to the battery.

Figure 22:
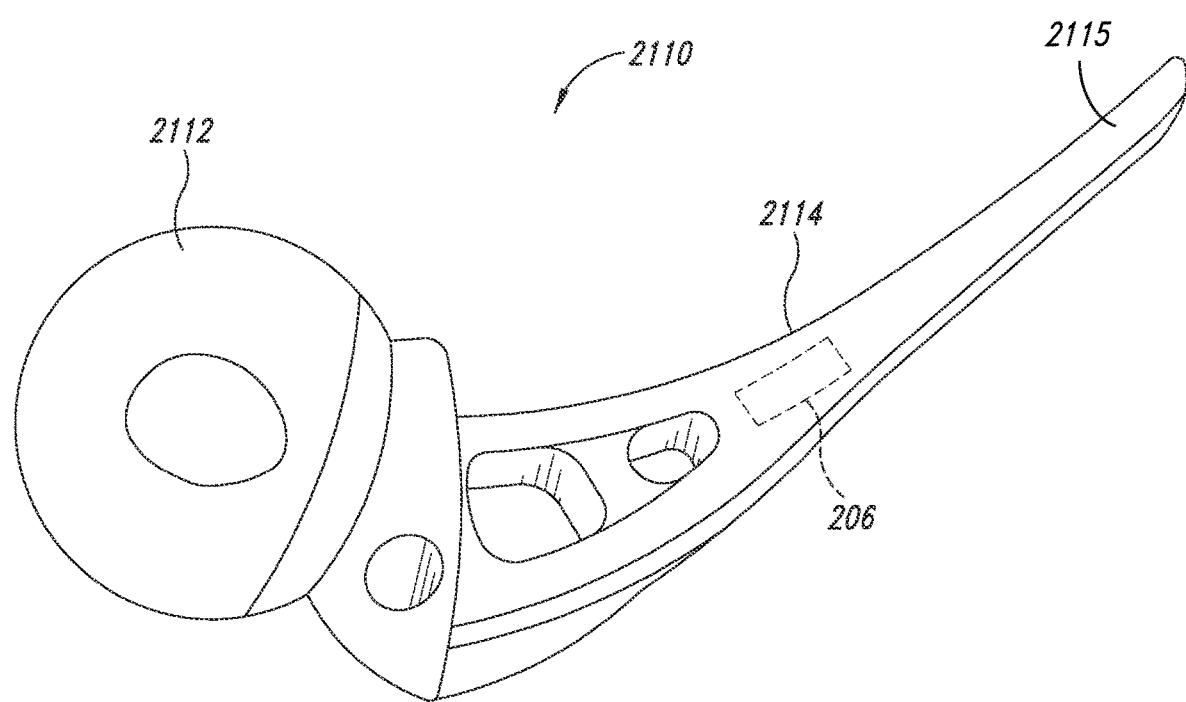
FIG. 22 is a side view of an implantable hip prosthesis that includes an implantable reporting processor, according to an embodiment.

FIG. 22 is a perspective view of a hip prosthesis 2110, which is implantable to replace a hip joint of a living subject (e.g., a human subject) and that includes the implantable reporting processor 206 of FIGS. 17-21B, according to an embodiment.

The hip prosthesis 2110 of the hip prosthesis includes a femoral head 2112, which engages with a socket portion (not shown in FIG. 22) of the hip prosthesis, and includes a femoral stem 2114, which is configured to extend into a cavity formed in a femur (not shown in FIG. 22) of the subject.

The implantable reporting processor 206 is disposed in a hollow portion within the femoral stem 2114, or forms part of the femoral stem.

The implantable reporting processor 206 being configured to fit inside of, or to from part of, the hip prosthesis reduces the space occupied by the prosthesis as compared to a hip prosthesis having any portion, or all, of the implantable reporting processor being disposed outside of and apart from the hip prosthesis. Furthermore, the implantable reporting processor 206 is sized such that the femoral stem 2114 need be no longer or wider, in cross section, than a femoral stem of a conventional hip prosthesis.

Still referring to FIG. 22, alternate embodiments of the hip prosthesis 2110 are contemplated. For example, the implantable reporting processor 206 may be disposed in the femoral head 2112. As another example, the implant may be integrated into the distal tip 2115 of the femoral stem 2114 without changing the length or diameter of the femoral stem 2114.

Figure 23:
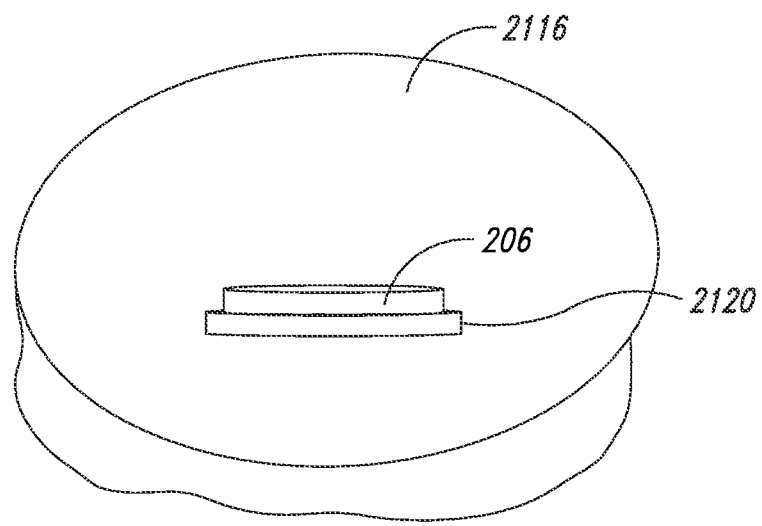
FIG. 23 is a perspective view of a breast implant that includes an implantable reporting processor, according to an embodiment.

FIG. 23 is a perspective view of a breast implant or prosthesis 2116, which is used for aesthetic purposes or aesthetic reconstructive surgery subsequent to removal of breast tissue for, e.g., oncologic reasons, and which includes one or more sensors (not shown in FIG. 23) and an implantable reporting processor 206 similar to that described in FIGS. 17-21B, but with some differences, according to an embodiment. For example, the implantable reporting processor 206 can have a different shape from the processors described above in conjunction with FIGS. 17-21. Furthermore, where at least one of the one or more sensors is a pressure sensor, the implantable reporting processor 206 can be configured to monitor pressure, and other parameters, within the breast implant. Moreover, the implantable reporting processor 206 can be configured to determine, in response to the monitored parameters, whether the breast implant's contents are leaking into the surrounding tissue. In addition, the implantable reporting processor 206 can be configured to detect, in response to the monitored parameters, whether the implant has failed, and/or to assess for the presence of capsular contraction through variation in the monitored.

The breast prosthesis 2116 may have a single compartment, or a variety of fluid-filled compartments. The fluid may be saline or liquid silicone. The compartments may be isolated or communicate with one another via fluidic pathways.

Figure 24:
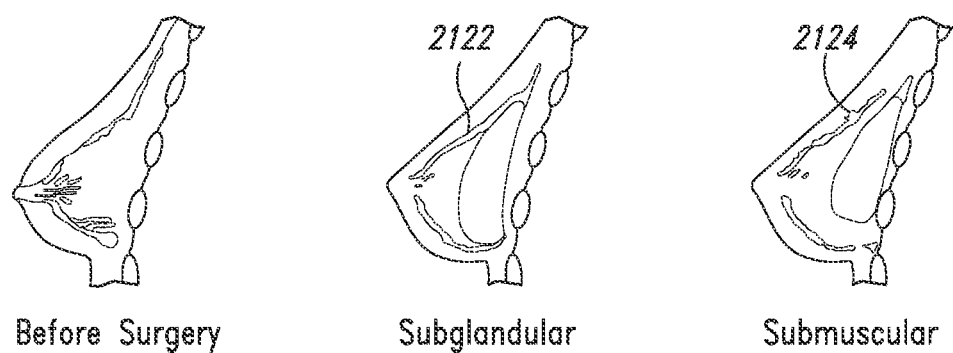
FIG. 24 is a side view of human breast anatomy showing placement of the breast implant of FIG. 23 subglandular and submuscular, according to an embodiment

FIG. 24 depicts subglandular 2122 and submuscular 2124 insertion of the breast prosthesis 2116 within the female breast of a living subject, according to an embodiment.

The implantable reporting processor 206 is disposed in a retaining structure 2120 integral to the posterior wall of the breast implant.

It is understood that in the case of a breast implant with multiple compartments (not shown), a respective reporting processor 2118 can be located in each compartment.

The implantable reporting processor 206 is configured to fit inside the breast implant 2116 such that the patient does not feel its presence, yet the implantable reporting processor is held securely such that it cannot migrate within the implant.

Referring to FIGS. 23 and 24, alternate embodiments of the prosthesis 2116 and the implantable reporting processor 206 are contemplated.

Figure 25:
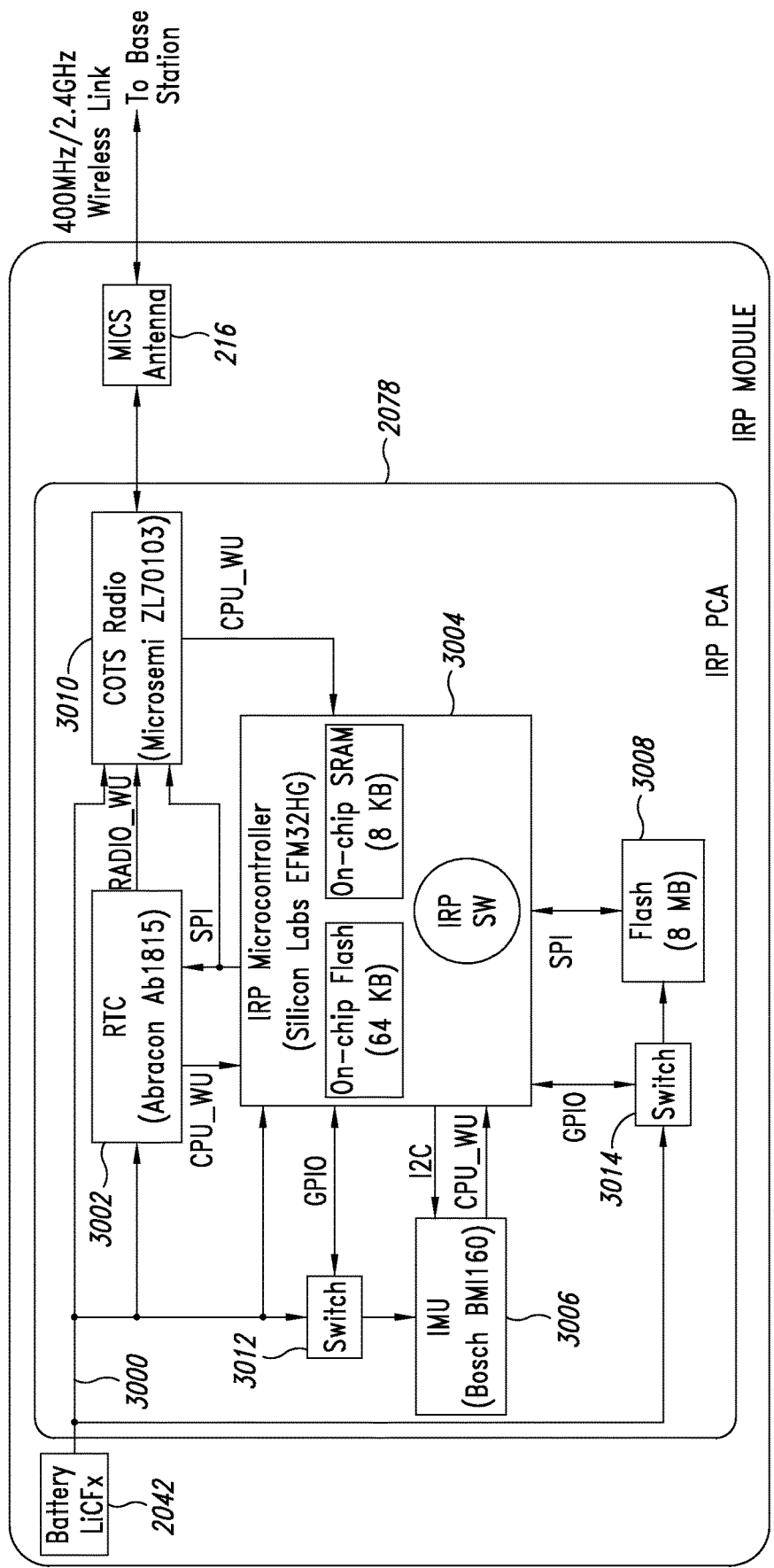
FIG. 25 is a schematic block diagram of the battery of FIG. 20, and the antenna and the electronic circuitry of FIG. 21A, according to an embodiment.

FIG. 25 is a block diagram of the battery 2042 of FIG. 20, and the antenna 216 and the electronic circuitry 2078 of FIG. 21A, according to an embodiment. As described below, the electronic circuitry 2078 can be configured to limit the power drawn from the battery 2042 so that the battery has a predictable lifetime that is at least as long as the lifetime of the prosthesis with which the battery is associated. Furthermore, one or more of the circuit components described above in conjunction with FIGS. 5A-5C and 6-8E may form part of the electronic circuitry 2078, although components in FIG. 25 corresponding to components in FIGS. 5A-5C and 6-8E may have different reference numbers.

The electronic circuitry 2078 includes the following circuit components: a supply node 3000, a timing circuit 3002, a processing circuit 3004, an inertial measurement unit (hereinafter "inertial measurement circuit") 3006, a memory circuit 3008, a radio circuit 3010, and electronically controllable switches 3012 and 3014. At least the inertial measurement circuit 3006 and the memory circuit 3008 can be considered to be peripheral circuits to the processing circuit 3004.

The supply node 3000 is configured to receive a current and a voltage from the battery 2042 (FIG. 20), and to provide this current and voltage to the timing circuit 3002, processing circuit 3004, radio circuit 3010, and switches 3012 and 3014. For example, the battery 2042 can provide, to the supply node 3000, a voltage in a range of about 2.3 V-3.3 V.

The timing circuit 3002 is configured, e.g., by software, firmware, or other configuring means, to awaken the processing circuit 3004 and the radio circuit 3010 from respective "sleep," i.e., lower-power, states at respective set times. By awakening the processing circuit 3004 and the radio circuit 3010 only at respective times, e.g., one time, or a few times, per day, the timing circuit 3002 conserves power drawn from the battery 2042 (FIG. 20) as compared to allowing the processing circuit and radio circuit to stay perpetually "awake," i.e., in a higher-power state. For example, the timing circuit 3002 can be a real-time clock circuit such as an Abracon® AB1815 real-time-clock (RTC) integrated circuit (IC).

The processing circuit 3004 is programmable to open and close the switches 3012 and 3014 to selectively couple the inertial measurement circuit 3006 and the memory circuit 3008 to the supply node 300 at set respective times while the processing circuit 3004 is in a higher-power operational state. By powering the inertial measurement circuit 3006 and memory circuit 3008 only at respective times, e.g., a few times per day, the processing circuit 3004 further conserves power drawn from the battery 2042 (FIG. 20) as compared to providing power to the inertial measurement circuit and memory circuit perpetually. Even if the inertial measurement circuit 3006 and memory circuit 3008 are configurable to enter respective lower-power states, they would still draw at least some power in these respective states. Therefore, by disconnecting the inertial measurement circuit 3006 and memory circuit 3008 from the supply node 3000, via the switches 3012 and 3014, respectively, while the measurement circuit and memory circuit are not being used, the processing circuit 3004 conserves even more power than by putting the measurement circuit and memory circuit in a lower-power state while they are not being used.

The processing circuit 3004 can also program, configure, or otherwise control the timing circuit 3002, the inertial measurement circuit 3006, the memory circuit 3008, and the radio circuit 3010. For example, the processing circuit 3004 can reconfigure the timing circuit 3002, in response to instructions received from a remote source via antenna 216 and radio circuit 3010, to change the set times at which the timing circuit "wakes up" the processing circuit and radio circuit 3010.

Furthermore, the processing circuit 3004 can include, or be electrically coupled to, peripheral circuits in addition to the inertial measurement circuit 3006 and the memory 3008. Examples of such additional peripheral circuits include pressure sensors, temperature sensors, pedometers, on-board volatile memory (e.g., random-access memory (RAM), dynamic RAM (DRAM), or static RAM (SRAM)) and nonvolatile memory (e.g., read-only memory (ROM), programmable ROM (PROM, electrically programmable ROM (EPROM), and electrically erasable and programmable ROM (EEPROM)). The electronic circuitry 2078 can include switches in addition to the switches 3012 and 3014 to couple these additional peripheral circuits to the supply node 3000. If the additional peripheral circuits are on-board the processing circuit 3004, then the processing circuit may employ power-island technology to selectively provide power to these peripheral circuits.

Moreover, the processing circuit 3004 can be a microcontroller, a microprocessor, or any other computing circuit, such as a Silicon Labs® EFM32HG microcontroller IC.

The inertial measurement circuit 3006 includes one or more sensors (not shown in FIG. 25) for acquiring data related to the motion of a prosthesis (not shown in FIG. 25) in which the electronic circuitry 2078 is located, or with which the electronic circuitry 2078 is otherwise associated. For example, the inertial measurement circuit 3006 can include one or more accelerometers, gyroscopes, pedometers, and magnetometers that are respectively configured to sense and measure linear and rotational accelerations, step counts, and magnetic fields that the prosthesis experiences or to which the prosthesis is exposed. In an embodiment, the inertial measurement circuit 3006 includes three accelerometers and three gyroscopes, one accelerometer and gyroscope for each dimension of linear (X, Y, Z) and rotational (rotation about X axis, rotation about Y axis, rotation about Z axis) freedom, respectively, that the implanted prosthesis possesses, or is configured to possess. By analyzing the information generated by these sensors while a patient, or other subject, in which the prosthesis is implanted, is moving, one can determine whether the prosthesis is functioning properly, and can predict when the prosthesis should be replaced. For example, the inertial measurement circuit 3006 can be a Bosch® BMI160 integrated inertial-measurement-unit (IMU) IC. Furthermore, the processing circuit 3004 can include, or can be electrically coupled to, peripheral circuits in addition to the inertial measurement circuit 3006. Examples of such additional peripheral circuits include pedometers, pressure sensors, and temperature sensors.

The memory circuit 3008 is a nonvolatile memory that can be configured to store programming and configuration data for the processing circuit 3004, and data generated by the processing circuit 3004 for transmission to a destination (e.g., a cloud-based monitor and analyzer) via the radio circuit 3010 during a period while the radio circuit is awake. Because the memory circuit 3008 is nonvolatile, it can store data even while the switch 3014 is open and the memory circuit receives no power. The memory 3008 can be any type of nonvolatile memory such as NOR or NAND flash, magnetic RAM (MRAM), and EEPROM.

The radio circuit 3010 can be configured to receive, from a source external to the prosthesis with which the electronic circuitry 2078 is associated, signals carrying information, to recover the information from the signals (e.g., by decoding and demodulation), and to provide the recovered information to the processor circuit 3004. For example, this received information can include programming (e.g., software instructions) or configuration (e.g., firmware) data for one or more of the timing circuit 3002, processing circuit 3004, inertial measurement circuit 3006, memory circuit 3008, radio circuit 3010, and switches 3012 and 3014, or can include a request for the processing circuit to transmit, to the external source, information specified in the request.

The radio circuit 3010 can also be configured to transmit, to a destination external to the prosthesis with which the electronic circuitry 2078 is associated, signals carrying information. For example, the radio circuit 3010 can receive information from the processing circuit 3004, code (e.g., for error correction and compression) the information, modulate a carrier signal with the coded information, and drive the antenna 216 with the modulated carrier signal. The processing circuit 3004 could have generated the information, for example, in response to processing sensing measurements made by the inertial measuring circuit 3006, stored the information in the memory circuit 3008, retrieved the information from the memory circuit, and provided the information to the radio circuit 3010. Alternatively, the information could be status information that the processing circuit 3004 collects from the circuits coupled to it and provides to the radio circuit for transmission in the manner described above. For example, status information from the inertial measurement circuit 3006 can include the voltage across the battery 2042, and status information from the timing circuit 3002 can include the current times or intervals at which it is scheduled to activate the processing circuit 3004 and the radio circuit 3010.

The switches 3012 and 3014 can include any suitable conventional switches, such as NMOS or PMOS switching transistors, which can be opened and closed electronically, in response to a signal from the processing circuit 3004.

Still referring to FIG. 25, operation of the electronic circuitry 2078 is described, according to an embodiment.

The timing circuit 3002 is programmed to activate the processing circuit 3004 and the radio circuit 3010 at programmed times, for example, once per day. These times may be fixed (e.g., noon each day), varied (e.g., start at noon and increase by one hour each day), random (e.g., once per day at a time randomly determined each day), or in response to an event (e.g., movement of the subject in which the electronic circuitry 2078 is implanted). Furthermore, these times can be the same for both of the processing circuit 3004 and the radio circuit 3010, or different. For example, the timing circuit 3002 can activate the processing circuitry 3004 three times per day to analyze and record sensor measurements, and can activate the radio circuit 3010 only once per day to transmit the recorded sensor measurements to a remote destination (not shown in FIG. 25). Moreover, the processing circuit 3004 can program the timing circuit 3002 in response to commands or instructions that the processing circuit receives from a source (not shown in FIG. 25) via the antenna 216 and the radio circuit 3010.

Next, in response to being activated by the timing circuit 3002, the processing circuit 3004 closes the switches 3010 and 3012 to power the inertial measurement circuit 3006 and the memory circuit 3008. Furthermore, the processing circuit 3004 can close other switches to power other peripheral circuits that form part of the electronic circuitry 2078.

Then, in response to receiving power, the inertial measurement circuit 3006, the memory circuit 3008, and any other powered-up peripheral circuits, execute respective power-up routines if they are configured to do so.

Next, the processing circuit 3004 controls the inertial measurement circuit 3006, memory circuit 3008, and radio circuit 3010 to operate according to a programmed routine (examples of such routines are further described below). The processing circuit 3004 can also reprogram or reconfigure the timing circuit 3002, inertial memory circuit 3006, and memory circuit 3008 according to the programmed routine, or according to instructions received from a remote source (not shown in FIG. 25). Furthermore, the processing circuit 3004 can store, in the memory circuit 3008, data generated by the processing circuit or other component of the electronic circuitry 2078 during the routine. The processing circuit 3004 also can transmit such data to a remote destination (not shown in FIG. 25) via the radio circuit 3010 and antenna 216.

Then, after the routine is complete, the processing circuitry 3004 instructs the inertial measurement circuit 3006 and the memory circuit 3008 to execute respective power-down routines if applicable, opens the switches 3012 and 3024 to disconnect power from the inertial measurement circuit and memory circuit, causes the radio circuit 3010 to enter a lower-power (e.g., sleep) state, informs the timing circuit 3002 that the routine is complete, and enters into a lower-power (e.g., sleep) state.

At the next set time, the timing circuit 3002 activates the processing circuit 3002 and, if needed, the radio circuit 3010 to start a repeat the above routine or to start another routine.

Still referring to FIG. 25, alternate embodiments of the electronic circuitry 2078 are contemplated. For example, the electronic circuitry 2078 can include circuits other than those described above, and can include additional switches to provide power to these other circuits as controlled by the processing circuit 3004; examples of such other circuits include volatile memory such as random-access memory (RAM), and one or more additional sensor circuits such as a pedometer, temperature sensor, or pressure sensor. Furthermore, the electronic circuitry 2078 can include one or more circuits or mechanisms for recharging the battery 2042; examples of such circuits and mechanisms include a kinetic or biochemical recharging mechanism, an inductive recharging circuit, and a highly resonant wireless-power-transfer recharging circuit. Moreover, some or all of the component circuits of the electronic circuitry 2078 can be disposed on one or more integrated circuits, or can be discrete-component circuits (e.g., circuits formed form one or more discrete components). In addition, the processing circuit 3004 can execute any suitable routine in any manner to conserve power such that the battery 2042 has an anticipated lifetime, such as more than one year, ten or more years, even up to twenty or more years; so conserving power can dramatically increase the chances that the battery will not need not be replaced at least until its associated prosthesis is replaced.

Referring to Tables I and II, configuration and operation of the electronic circuitry 2078 of FIG. 21A over a desired lifetime of the battery 2042 (FIG. 20) is described, according to an embodiment.

TABLE I

| Energy Consumption | Period |
| --- | --- |
| EC1 | P1 |
| EC2 | P2 |
| EC3 | P3 |

Referring to FIG. 21A and Table I, the electronic circuitry 2078 can be configured to control its energy consumption so that the battery 2042 (FIG. 20) lasts for its anticipated lifetime. In more detail, the timing circuit 3002 can be configured to activate the processing circuit 3004 and the radio circuit 3010 at set times, and the activated processing circuit can be configured to activate, to configure, and to process data from, the inertial measurement circuit 3006, and to control when data is sent and received via the radio circuit, so as to control the energy consumption of the electronic circuitry 2078. For example, it may be desirable for the battery 2042 to last until a corresponding implanted prosthesis is replaced, or at least until it is anticipated that operation of the electronic circuitry 2078 will no longer be needed.

The designed-for lifetime of the battery 2042 (FIG. 20) can be divided into multiple periods P of respective energy consumptions EC; as long as these energy consumptions EC sum to no more than the total energy that the battery 2042 can provide to the electronic circuitry 2078, the battery will last until the end of the last period P (assuming no failure of, or other unanticipated problem with, the battery or of the electronic circuitry). For example, if the battery 2042 can store energy equivalent to 360 mAh, and it is desired that the electronic circuitry 2078 be designed such that the battery lasts for at least ten years, then as long as the sum of energies EC anticipated to be consumed during the energy-consumption periods P is no greater than an energy equivalent to 360 mAh, then, barring an error in, or malfunction with, the battery or the electronic circuitry, the battery will be able to power the electronic circuitry for at least ten years. Further to this example, suppose that a first energy-consumption period P1 is four months, and that it is anticipated that the electronic circuitry 2078 will consume a maximum energy EC1 equivalent to 72 mAh during P1. Similarly, assume that a second energy-consumption period P2 is the eight months immediately following P1, and that the maximum anticipated energy consumption EC2 during P2 is equivalent to 36 mAh. And further assume that a third energy-consumption period P3 is the nine years immediately following P2 and that the maximum anticipated energy consumption EC3 during P3 is equivalent to 240 mAh. Therefore, at the end of P1+P2+P3=ten years, the total energy consumption EC1+EC2+EC3 of the electronic circuitry 2078 is equivalent to 348 mAh, which leaves a margin for error of 12 mAh (i.e., 360 mAh−348 mAh=12 mAh).

Referring to FIG. 21A and Table II, in an embodiment for controlling the energy that the electronic circuitry 2078 consumes during a period P, the electronic circuitry is configured to operate according to defined modes of operation.

For example, the electronic circuitry 2078 can be configured to operate in a lower-power mode LPM for a first portion of the corresponding period P, and in a higher-power mode HPM for a second portion of the corresponding period P. While operating in a particular mode, the processing circuit 3004 receives and processes data from the inertial measurement circuit 3006. By controlling parameters such as what portions of the inertial measurement circuit 3006 are active, what data the inertial measurement circuit generates, how long the inertial measurement circuit is active, at what speed and resolution the processing circuit samples this data, and how often the processing circuit sends data to an external destination via the radio 3010, the electronic circuitry 2078 can control how much energy it consumes, and, therefore, draws from the battery 2042, during each period.

TABLE II

| Energy-Consumption Rate (ECR) | Period (P) | Lower-Power Mode (LPM) | Higher-Power Mode (HPM) |
| --- | --- | --- | --- |
| ECR1 | P1 | LPM1 | HPM1 |
| ECR2 | P2 | LPM2 | HPM2 |
| ECR3 | P3 | LPM3 | HPM3 |

Figure 26:
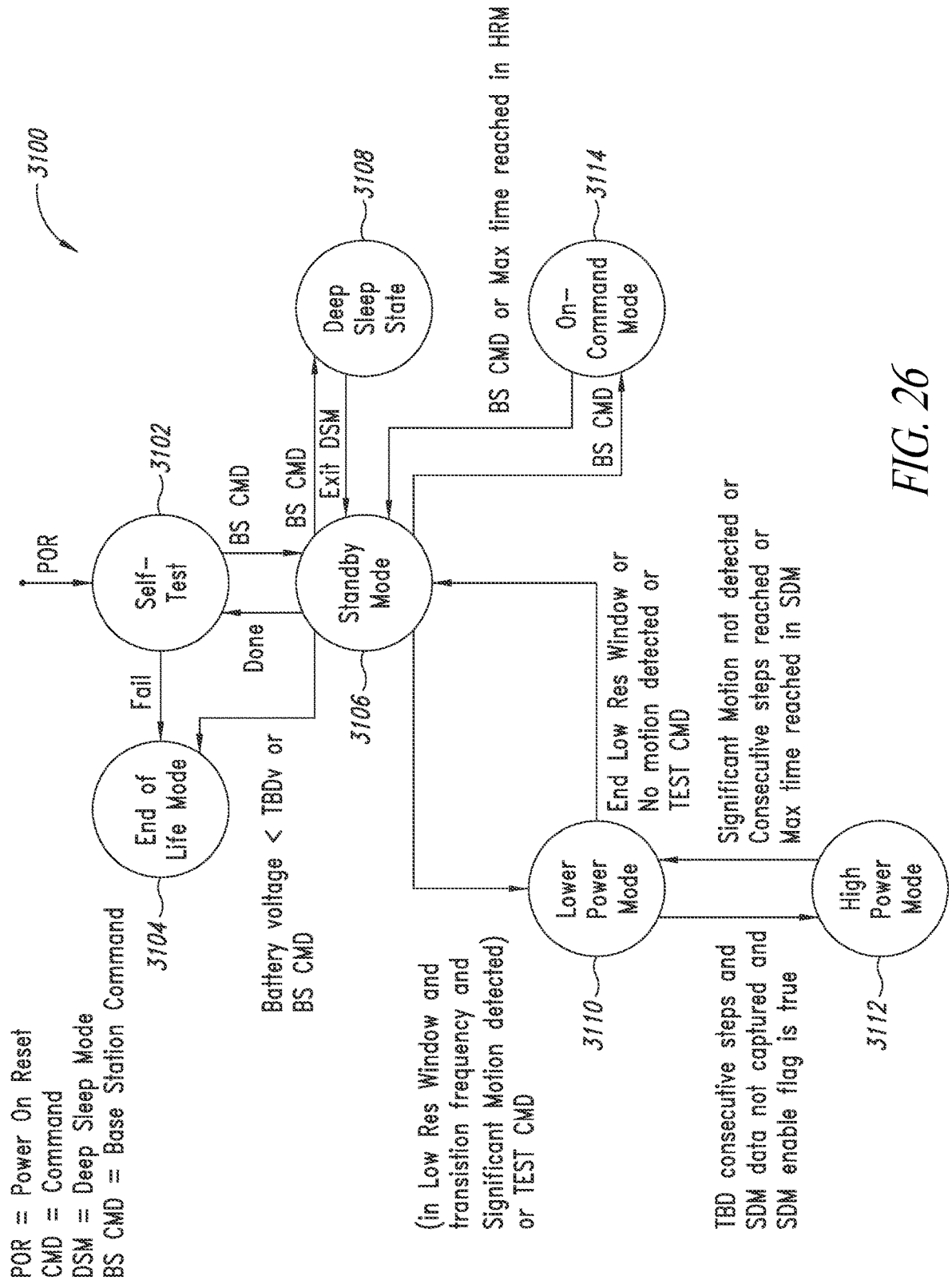
FIG. 26 is a state diagram of the operation of the electronic circuitry of FIG. 21A over the lifetime of the battery of FIG. 20, according to an embodiment.

FIG. 26 is a state diagram 3100 of the operation of the electronic circuitry 2078 (FIG. 21A) over the lifetime of the battery 2042 (FIG. 20), according to an embodiment in which the prosthesis with which the electronic circuitry is associated is a knee prosthesis.

In the following example, in all lower-power modes LPM (i.e., LPM1, LPM2, LPM3), the processing circuit 3004 configures the inertial measuring circuit 3006 so that only two accelerometers (for example, walking dimension X and vertical dimension Z) are active, and the processing circuit samples the signals generated by these active accelerometers at 50 samples/second and at a resolution of 8 bits, generates a total step count from these signals, and saves, in the memory 3008, the accumulated step count at the end of the lower-power mode. Furthermore, the durations and frequencies of the low-power modes are as follows: LPM1=8 hours/day, 7 days/week; LPM2=6 hours/day, 2 days/week, and LPM3=4 hours/day, 1 day/week. For LPM2 and LPM3, the timing circuit 3002 can be configured to select the same day(s) each week, to rotate the day(s) each week, or to randomly select the day(s) each week (or the processing circuit 3004 can configure the timing in this manner while the processing circuit is active). Alternatively, instead of continually sampling the signals from the two accelerometers, the processing circuit 3004 can sample the signals only when the inertial measurement unit 3006 senses that the subject is walking such that the processing circuit is not consuming power for sampling when the subject is not walking. It is also to be understood that sampling of accelerometers as described may be accomplished with a single accelerometer.

Further in the following example, in all higher-power modes p (i.e., HPM1, HPM2, and HPM3), the processing circuit 3004 configures the inertial measuring circuit 3006 so that at least three accelerometers and at least three gyroscopes are active, and the processing circuit samples each of the signals generated by these active accelerometers and gyroscopes at 400 samples/second and at a resolution of 16 bits, performs a preconfigured/preprogrammed analysis of these signals, and saves, in the memory 3008, the result of the analysis at the end of the higher-power mode. The processing circuit 3004 enters a higher-power mode HPM (e.g., activates at least three accelerometers and at least three gyroscopes) from a lower-power mode LPM after the processing circuit has detected that the subject has taken at least three steps (because at least three accelerometers and at least three gyroscopes are activated, a higher-power mode can also be called a six-degrees-of-freedom mode). The processing circuit 3004 stays in the higher-power mode for a total of ten steps more than the initial three steps. If the processing circuit 3004 does not detect an additional ten steps, then it exits the higher-power mode and returns to the lower-power mode, and repeats this procedure until it is able to detect ten steps while in the higher-power mode, until it has entered a higher-power mode a threshold number of times, or until it is time to end the lower-power mode. After detecting ten steps and receiving and sampling the signals generated by the three accelerometers and three gyroscopes in the inertial measurement circuit 3006, the processing circuit 3004 processes these sampled signals and stores the results in the memory 3008; furthermore, the processing circuit does not enter a higher-power mode again until the next lower-power mode. The frequencies at which the processing circuit 3004 at least attempts to complete a higher-power mode are as follows: HPM1=7 days/week; HPM2=2 days/week (same days as LPM2), and HPM3=1 day/week (same day as LPM3).

Moreover in the following example, a test, or doctor's office, mode can be the same as the above-described higher-power modes except that it is initiated by, e.g., a doctor at a doctor's office so that the doctor can put the subject through a battery of tests (e.g., knee bends, bending range, stopping and starting), receive processed data from the processing circuit 3004, and analyze this data to determine, e.g., whether the implanted knee prosthesis is functioning properly. To prevent doctor's office modes from causing the battery 2042 to have a lifetime less than the designed-for lifetime, the processing circuit 3004 can be configured to limit the duration or number of doctor's office modes. For example, the processing circuit 3004 can limit each doctor's office mode to three minutes, but where the doctor can enter and exit the mode such that the three minutes can be broken up and spread over more than three consecutive minutes; and the processing circuit 3004 can limit the number of doctor's office modes to a total number distributed among the periods P1-P3 (e.g., a limit of ten doctor's office modes in each of P1 and P2, a limit of five doctor's office modes in P3, and a total of five "floating" doctor's office modes that can be used in any of P1-P3 for a total of thirty permitted doctor's office modes). It is also understood that the doctor's office mode initiated by a doctor in their office environment may be interchanged with another healthcare professional, such as a physical therapist, and the test can be conducted as part of a patient's physical therapy in an appropriate setting.

Referring to FIGS. 25 and 26, before surgery to implant the knee prosthesis (not shown in FIGS. 25-26), the electronic circuitry 2078 is activated with a power-on-reset (POR) signal (e.g., via a base station as described below), and proceeds to a self-test state 3102. During this state, the processing circuit 3004 executes one or more test routines, the results of which indicate whether the battery 2042, antenna 2048, and electronic circuitry 2078 are functioning properly. For example, such test routines can measure the voltage across the battery 2042, measure output signals from the inertial measurement circuit 3006, and check the functioning of the memory 3008, the radio circuit 3010, and the switches 3012 and 3014.

If the electronic circuitry 2078 fails any of the test routines, then the processing circuitry 3004 proceeds to a state 3104, and enters itself, and the other circuits that form the electronic circuitry, into an end-of-life mode. For example, in this mode, the processing circuit 3004 can broadcast, via the radio circuit 3010 and antenna 2048, that the battery 2042, antennal 216, or electronic circuitry 2078 is not functioning properly and that the implantable reporting processor 206 (FIGS. 19A and 19B) should be replaced before the knee prosthesis is implanted. Alternatively, if it is the battery 2042, antenna 2048, or radio circuit 3010 that is malfunctioning such that the processing circuit 3004 cannot send a broadcast, then the lack of a broadcast indicating that the battery, antenna, and electronic circuitry are functioning properly can serve as an indication to an external device (e.g., a base station) that the implantable reporting processor 206 should be replaced.

If, however, the battery 2042, antenna 216, and electronic circuitry 2078 pass all of the test routines at step 3102, then the processing circuit 3004 proceeds to a state 3106 and enters a standby mode.

From the standby mode, the processing circuit 3004 proceeds to a state 3108 and enters itself and the radio circuit 3010 into respective low-power states, collectively called a deep-sleep state in this example. Before entering the deep-sleep state, the processing circuit 3004 instructs the inertial measurement circuit 3006, the memory 3008, and any other peripheral circuits to execute respective power-down routines if applicable, and then, after the last power-down routine is completed, opens the switches 3112 and 3114 and any other switches corresponding to other peripheral circuits.

During the deep-sleep state at step 3108, the timing circuit 3002 remains active, and keeps track of when to enter the next low-power mode LPM. For example, for the period P1, the next LPM can be LPM1 the day after the knee prosthesis is implanted.

When it is time to enter the next low-power mode LPM, the timing circuit 3002 activates (e.g., "wakes up") the processing circuit 3004.

The activated processing circuit 3004 proceeds to the standby state 3106, and then closes the switches 3012 and 3014, and any other such switches, and activates the inertial measurement circuit 3006, memory 3008, and any other peripheral circuits that need to be activated. The processing circuit 3004 also configures the inertial measurement circuit 3006 for low-power operation, such as, for example, instructing the inertial measurement circuit to activate only one or two accelerometers and no other sensors.

Then after activating and configuring the peripheral circuits such as the inertial measurement circuit 3006, the processing circuit 3004 proceeds to a state 3110, where it enters into a low-power mode LPM of operation as described above.

If, during the low-power mode LPM at state 3110, the inertial measurement circuit 3006 detects that the subject in which the knee prosthesis is implanted has taken at least three steps, then the processing circuit 3004 enters into a scheduled higher-power mode HPM at a state 3112 by activating at least three accelerometers (one for each dimension of linear movement) and three gyroscopes (one for each dimension of rotational movement) of the inertial measurement circuit 3006, and begins to sample the signals from these accelerometers and gyroscopes at a higher frequency and higher resolution (e.g., 400 samples per second and sixteen bits vs. 50 samples per second and eight bits in the lower-power mode).

In response to either sampling the accelerometers and gyroscopes over a previously set minimum number (e.g., ten) steps of the subject, or in response to the subject taking fewer than the minimum number of steps within a set time (e.g., three minutes) from entering the higher-power mode HPM, the processing circuitry 3004 returns to the low-power mode LPM at the state 3110. Before returning to the lower-power mode LPM, however, the processing circuit 3004 deactivates the gyroscopes and all but two of the accelerometers of the inertial measurement circuit 3006. If, during the higher-power mode HPM, the inertial measurement circuit 3006 was able to generate data over at least ten steps (exclusive of the initial three steps detected to enter the higher-power mode HPM), then the processing circuit 3004 indicates, e.g., by setting a flag, that it need not enter any more higher-power modes until the next lower-power mode. For example, during period P1, the processing circuit 3004 indicates that it need not enter any more higher-power modes until the next day. But if, during the higher-power mode, the inertial measurement circuit 3006 was unable to generate data over at least ten steps (exclusive of the initial three steps detected to enter the higher-power mode), then the processing circuit 3004 indicates, e.g., by not setting the flag, that it will enter the higher-power mode again upon detection of three steps of the subject by the inertial measuring circuit 3006.

Back at state 3110, the processing circuit 3004 can take one of a number of actions. As described above, if, at step 3112, the processing circuit 3004 was unsuccessful in receiving data for ten steps of the subject, then the processing circuit continues to wait for the subject to take a previously set minimum number (e.g., three), of steps so that it can proceed again to the higher-power mode at state 3112. But if, at state 3112, the processing circuit 3004 was successful in receiving data for ten steps of the subject, then the processing circuit remains at state 3110 until the end of the lower-power mode (e.g., eight hours total), at which point the processing circuit returns to the standby mode at state 3106, and then to the deep-sleep state at state 3108. Or, the processing circuit 3004 can return to states 3108 and 3106 virtually immediately in response to a successful completion of the higher-power mode at state 3112; that is, the processing circuit 3004 may maintain the electronic circuitry 2078 in the lower-power mode only until it is able to successfully obtain data from the inertial measurement circuit 3006 for ten steps of the subject, or until a set maximum time (e.g., eight hours) of the lower-power mode.

During the standby state 3106 before entering the deep-sleep state 3108, the processing circuit 3004 can activate the radio circuit 3010 and transmit the data corresponding to the higher-power mode, and, optionally, a step count, to an external destination.

The processing circuit 3004 (and all the other circuits of the electronic circuitry 2078 but for the timing circuit 3002) remains at state 3106 until the timing circuit activates the processing circuit for the next lower-power mode LPM.

Still referring to FIGS. 25-26, by entering a command via a base station (described below), a doctor or other medical professional can cause the electronic circuitry 2078 to enter an on-command mode, such as a doctor's office mode as described above, even while the electronic circuitry is otherwise scheduled to be inactive. For example, the command may be received by the timing circuit 3002, and may cause the timing circuit to activate the processing circuit 3004, which, therefore, exits the deep-sleep state 3108 and proceeds to state 3106 in a manner similar to that described above. Next, the processing circuit 3004 enters the on-command mode at state 3114, such as the doctor's office mode, in which, for example, the processing circuit activates at least three accelerometers and at least three gyroscopes of the inertial measurement circuit 3006 so that, e.g., a doctor, can put a subject through a battery of tests and analyze the performance of the knee prosthesis. As described above, to preserve the charge on the battery 2042 (FIG. 20), the processing circuit 3004 can limit the length of the on-command mode, the number of times per period P, or the total number of times, that one can cause the electronic circuitry 2078 to operate in an on-command mode.

Still referring to FIGS. 25-26 and Tables I and II, alternate embodiments of the above-described power-savings routines are contemplated. For example, although Tables I and II include three periods P over the anticipated lifetime of the battery 2042, the anticipated lifetime of the battery can include more or fewer than three periods P. Furthermore, although Table II shows only one lower-power mode LPM and one higher-power mode HPM per period P, there may be more or fewer than one lower-power mode, or more or fewer than one higher-power mode, per period P. Moreover, the operational modes can be designed for any suitable level of energy consumption by setting any configurable parameters (e.g., number of sensors of the inertial measurement circuit 3006 activated, sampling rates and sampling resolution of sensor outputs, and the time that the processing circuitry 3004 and various peripheral circuits are active) to any suitable values. In addition, the programming/configuration of one or more components (e.g., timer 3002, processing circuit 3004) of the electronic circuitry 2078 can be changed via a base station (described below) that can communicate with the electronic circuitry via the antenna 216 and the radio 3010. Furthermore, if the electronic circuitry 2078, or other portion of the implantable reporting processor 206 (FIGS. 19A-19B), includes a battery-recharging mechanism or circuit, then the routines described above can be modified to take recharging into account. Moreover, instead of activating two linear accelerators of the inertial measurement unit 3006 during a lower-power mode LPM, the processing circuit 3004 can activate a pedometer that is part of, or that is separate from, the inertial measurement unit. In addition, the routines described above can include additional steps not described, can omit one or more described steps, or can change the order in which the described steps are performed.

Figure 27:
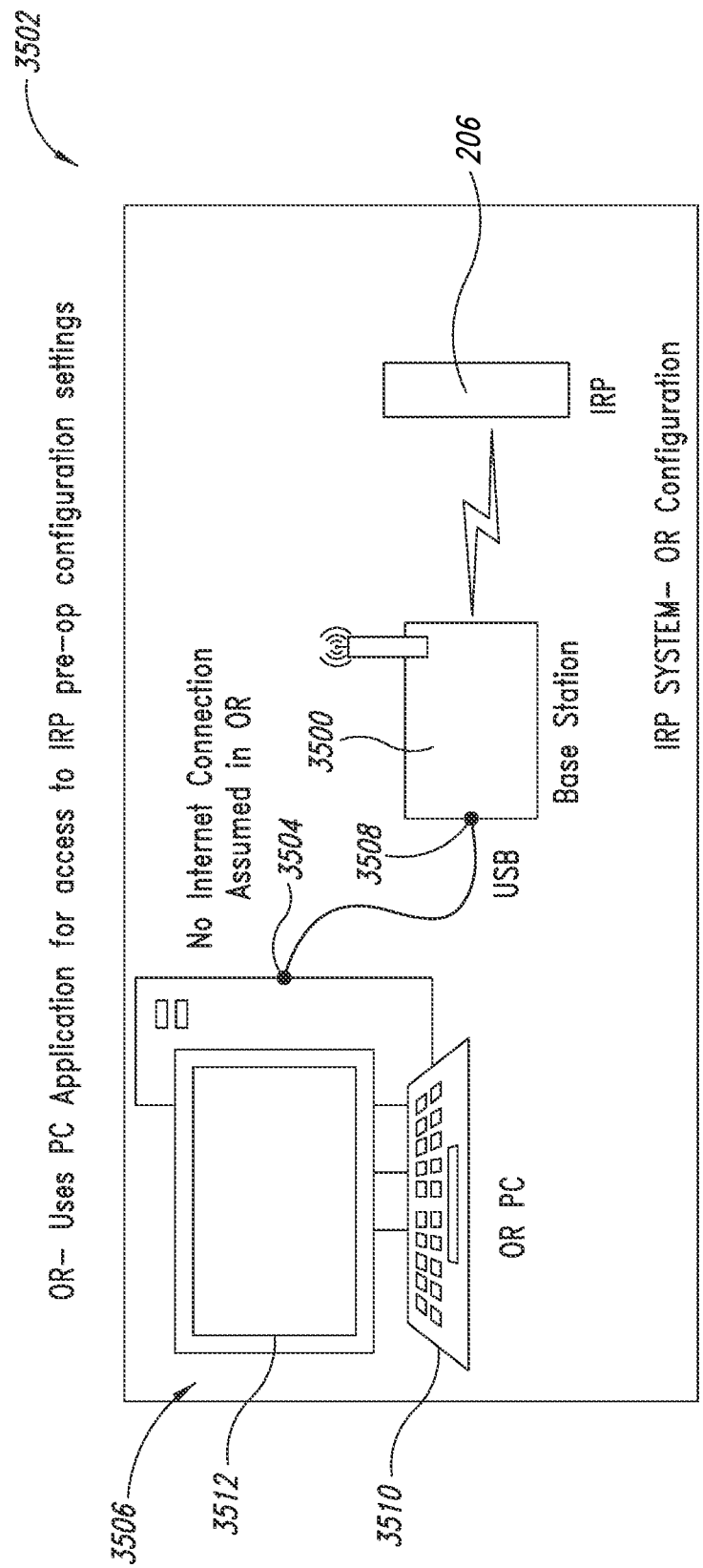
FIG. 27 is a diagram of a base station for facilitating communications with the implantable reporting processor prior to, during, and after a prosthesis with which the implantable reporting processor is associated is implanted in a subject, according to an embodiment.

FIG. 27 is a diagram of a base station 3500 configured to facilitate communications with the implantable reporting processor 206 of FIGS. 19A-19B prior to implantation of a prosthesis, according to an embodiment.

In an operating room 3502 before an operation to surgically implant, into a patient, a prosthesis, such as a knee prosthesis, that is related to (e.g., that includes) the implantable reporting processor 206, one connects a universal-serial-bus (USB) port 3504 of a computing system 3506 to a USB port 3508 of the base station 3500. The computing system 3506 can be a personal computer, a laptop, a smart phone, a tablet computer, or the like. The computing system 3506 can include a keyboard 3510 or other input device to allow a doctor or technician to enter commands to the implantable reporting processor 206, and may generate on a display 3512 a graphical user interface (GUI) corresponding to the implantable reporting processor.

There are two procedures to link the patient with his/her implantable reporting processor 206.

According to a first procedure, prior to surgery, the patient receives a base station from his/her clinician for home installation. At home, the patient installs the base station 3500 and configures it for connecting it to the internet by connecting the power cord, powering on the base station, and connecting the base station to his/her home internet directly (e.g., via a wireless router) or via a supplied wireless range extender 3532 (if present in the configuration) using conventional wireless technology, examples of which include WiFi®, Bluetooth®, or Bluetooth Low Energy®. Using a home computer, tablet, smart phone, or other internet accessing device with input capability, the patient establishes an account with the manufacturer of the implantable reporting processor 206 using methods known to those skilled in the art, and the manufacture (e.g., the manufacturer's website) assigns a unique patient identifier to the patient. The patent identifier allows a correspondence to be established between the patient and a base station 3500. Once the patient returns home after the procedure in which the prosthesis including the implantable reporting processor 206 is implanted, the installed base station 3500 transmits a query as to whether an implantable reporting processor 206 associated with the unique patient identifier is in the vicinity of the base station 3500. If so, the implantable reporting processor 206 provides its registration (e.g., its serial number) and associated contents of its non-volatile memory to the base station 3500 in response to the query, and the base station, in turn, provides this information to the internet account associated with the unique patient identifier, thereby forming a correspondence between the patient, the implantable reporting processor, and the contents of the processor's non-volatile memory.

According to a second, alternative procedure, the surgeon, nurse, other medical professional, or technician (hereinafter "technician"), registers the implantable prosthesis that includes the implantable reporting processor 206 with an online/cloud database (FIG. 28) (this alternative procedure is typically viable only if there is internet access in the operating room in which the implant surgery is to occur). The technician enters into the computing system 3506 via the keyboard 3510 and GUI a unique patient identifier. Therefore, the patient is thereafter associated with the prosthesis, and vice-versa, for example, in a cloud database administered by the implant manufacturer or an implant analyzer. Alternatively, the technician can use a barcode scanner (not shown in FIG. 27) coupled to the computing system 3506 to scan the patient identifier from a tag on the implantable reporting processor 206 (or on the prosthesis with which the implantable reporting processor is related) into the computing system 3506. In addition to the patient identifier, the technician can enter an internet-protocol (IP) address of the implantable reporting processor 206, which can then be configured, for example, as an element of an internet-of-things (IoT) network.

Next, in response to a command entered into the computing system 3506 by the technician, the base station 3500 polls the implantable reporting processor 206 to request the opening of a communication channel; the base station may use amplitude shift keying (such binary amplitude shift keying) as a modulation protocol while polling the implantable reporting processor. Typically, the implantable reporting processor 206 is in a "warehouse" mode, during which the timer 3002 (FIG. 25) enables the radio circuit 3010 (FIG. 25) to sense such a polling request only periodically, such as every ten minutes. Therefore, it may take a few minutes before the implantable reporting processor 206 responds to the base station 3500.

The implantable reporting processor 206 allows the base station 3500 to open the channel only if the base station transmits to the implantable reporting processor the patient identifier previously entered into the computing system 3506 described above; therefore, the base station 3500 stores this identifier in nonvolatile memory so that whenever it seeks to establish communication with the implantable reporting processor, it has access to the identifier. The implantable reporting processor 206 can also store the patient identifier in nonvolatile memory. In addition to providing a level of security to the channel, the identifier is useful to keep track of multiple channels in an environment where the base station 3500 is communicating with multiple implantable reporting processors 206.

In opening the channel, the base station 3500 can implement conventional security, such as conventional password protection and encryption.

After the channel is open, the base station 3500 receives, from the implantable reporting processor 206, a unique serial number of the prosthesis, and associates the serial number with the patient identifier. Thereafter, the patient is associated with the prosthesis, and vice-versa, for example, in a cloud database. Furthermore, the implantable reporting processor 206, the base station 3500, or both the implantable reporting processor and the base station, can store the serial number and the patient identifier in respective nonvolatile memory. After the channel is open, the base station 3500 receives from the computing system 3506, and transmits to the implantable reporting processor 206, configuration information, such as an energy-consumption profile as described above in conjunction with Tables I and II and FIGS. 25-26. While transmitting information to the implantable reporting processor 206, the base station 3500 can use frequency-shift-keying (FSK) modulation, and can include error-correction coding in the transmitted signal.

During and after the implanting surgery but while the patient is still in the hospital, the base station 3500 may continue to poll the implantable reporting processor 206 to verify that it is still functioning properly.

When the patient is ready to leave the hospital, he/she can take the base station 3500 with him/her for home use (described below in conjunction with FIG. 28), or the technician can configure another base station for home use, e.g., by storing on the other base station the patient identifier, and, optionally, the prosthesis serial number. In either case, the technician can cause the base station 3500 to be configured for home use before the patient takes the base station home.

Still referring to FIG. 27, alternate embodiments of the base station 3500 are contemplated. For example, the base station 3500 can include an input device and a display, and can generate a GUI on the display, such that the computing system 3506 can be omitted. Furthermore, although the base station 3500 is described as downloading the configuration information to the implantable reporting processor 206 before the prosthesis and implantable reporting processor are implanted in the patient, the base station can download the configuration information after, or during, the implantation surgery. In addition, the base station 3500 can store this configuration information in case the implantable reporting processor 206 needs to be configured or reconfigured after the subject returns home for recovery and normal activities. Furthermore, the first procedure for establishing a link between the patient and the implantable reporting processor 206 can include more or fewer steps, and can include one or more of the steps of the second, alternative procedure; similarly, the second, alternative procedure for establishing a link between the patient and the implantable reporting processor 206 can include more or fewer steps, and can include one or more of the steps of the first procedure.

Figure 28:
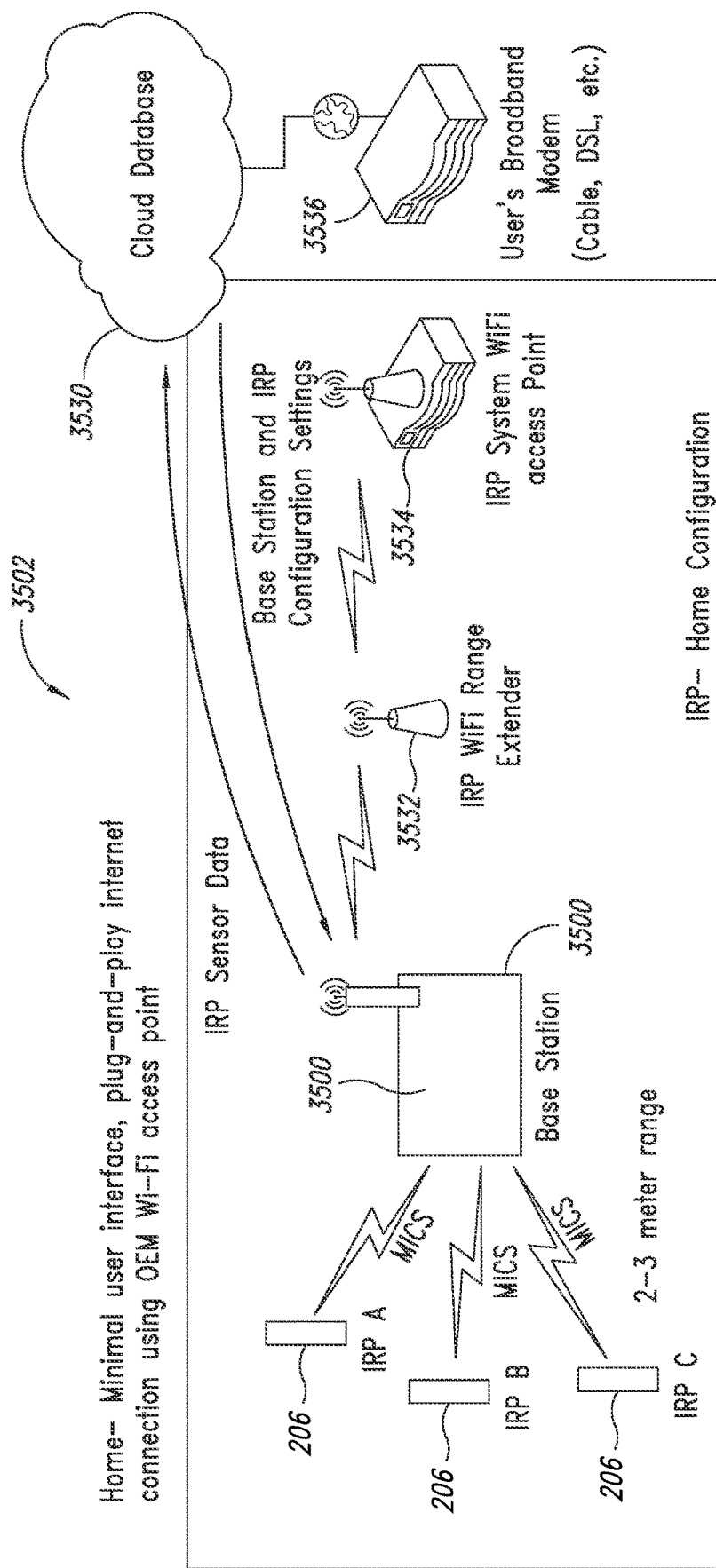
FIG. 28 is a diagram of network that includes a base station for facilitating communications with the implantable reporting processor while a subject, in which is implanted a prosthesis related to the implantable reporting processor, is away from a medical facility, according to an embodiment.

FIG. 28 is a diagram of a network 3502 including the base station 3500, which is configured to facilitate communications with the implantable reporting processor 206 while the patient, in which the implantable reporting processor is implanted, is at home, according to an embodiment.

In its home configuration, the base station 3500 interfaces the implantable reporting processor 206 with a remote server, such as a cloud server 3530, to which the implantable reporting processor uploads/pushes prosthesis-related information that the implantable reporting processor collects and generates.

The base station 3500 may not communicate directly with the cloud data base or remote server, but may do so via an optional range extender 3532, which is configured to be dedicated to the base station, a bridge/access point 3534, which is also configured, e.g., by conventional precoding, to be dedicated to the base station, and a conventional wireless router/modem 3536.

Because the range of the base station 3500 relative to the implantable reporting processor 206 is relatively short, for example, in a range of 2-10 meters (m), the base station is typically located in the patient's bedroom (e.g., on a night stand) within range of the patient's bed.

Furthermore, the base station 3500 can be configured to communicate with, and to interface to a remote server, multiple implantable reporting processors 206. For example, the patient may have multiple implanted prostheses, such as more than one implanted prosthesis selected from the following: a knee prosthesis, a hip prosthesis, a shoulder prosthesis, and a breast prosthesis. To keep track of the different prostheses of a single patient, the base station 3500 is configured to associate a single patient identifier with each prosthesis serial number such that multiple prostheses are assigned to the single patient. When the base station 3500 communicates with a prosthesis, it is configured to include, in its initial poll, both the patient identifier and the prosthesis serial number so that only the polled prosthesis responds to the poll. To keep track of the different prostheses of multiple patients, the base station 3500 is configured to associate each patient identifier with each serial number of the prosthesis (or prostheses) of that patient. When the base station 3500 communicates with a prosthesis, it is configured to include, in its initial poll, both the patient identifier and the serial number so that only the polled prosthesis responds to the poll. For example, a single base station 3500 can be used to communicate with prostheses belonging to different patients in a nursing home, rehabilitation center, or where members of the same household each have at least one prosthesis. Therefore, as described above in conjunction with FIG. 27, the base station 3500 is configured to use the unique patient identifier for each patient, and the prosthesis serial number if needed, to keep track of the implantable reporting processor 206 with which it is communicating at any given time.

Referring to FIGS. 25-28, in operation, a patient or other person uses a standard device (e.g., computer, smart phone) to open an online account on a remote server with the patient's unique patient identifier; for example, the patient can open the account when he/she returns home from the prosthesis-implantation surgery, or can do so before he/she is admitted for the implantation surgery. Thereafter, the base station 3500 sends data to the cloud database 3530 or the remote server (not shown in FIG. 28), which correlates the data with the patient by matching the patient identifier included in the data with the account associated with the identifier. The data also can include the serial number for each prosthesis implanted in the patient; therefore, the cloud database 3530 or the remote server can associate the so-identified prosthesis (or prostheses) with the patient.

Thereafter, the base station 3500 periodically polls each implantable reporting processor 206 to which it is associated at regular intervals, such as every thirty seconds. As described above in conjunction with FIGS. 25-26 and Tables I and II, to maintain energy draw on the battery 2042 (FIG. 20) at designed-for levels, the timing circuit 3002 (FIG. 25) of each implantable reporting processor 206 enables the radio circuit 3010 (FIG. 25) to receive a communication request from the base station 3500 only periodically, for example, once every ten minutes, during "listening" windows of, for example, one minute. Therefore, the frequency at which the base station 3500 polls each implantable reporting processor 206 is sufficient to ensure that the poll doesn't "miss" a listening window. Furthermore, the poll can include the identifier of the implantable reporting processor 206 being polled (this identifier can be the serial number of the prosthesis as described above).

In response to a poll from the base station 3500 during a listening window, the radio circuit 3010 (FIG. 25) causes the timing circuit 3002 to activate the processing circuit 3004, or the radio circuit activates the processing circuit 3004 directly.

After being activated, the processing circuit 3004 (FIG. 25) responds to the poll by sending, via the radio circuit 3010, information collected from, and generated in response to, e.g., the inertial measurement circuit 3006, since the last push of information. If the processing circuit 3004 has neither collected nor generated any such information since the last push (e.g., a patient with a shoulder prosthesis has his/her arm in a sling and, therefore, did not "use" the prosthesis sufficiently for the inertial measurement circuit to generate information), it responds to the poll by indicating that it has no information to send. As described above, such information can include, for example, a step count for one or more days, information collected during a higher-power mode HPM, and data that the processing circuit 3004 generated by analyzing the collected information. The processing circuit 3004 is configured to push this information by retrieving the information from the memory 3008 and coupling the retrieved information to the radio circuit 3010 for transmission to the base station 3500.

The base station 3500 then transmits the information received from the implantable reporting processor 206 to the cloud database 3530 or remote server (which can be cloud based) via the range extender 3532 (if present), access point 3534 (if present), and router 3536.

The base station 3500 is also configured to provide configuration and other information to the implantable reporting processor 206. For example, to change the configuration of the implantable reporting processor 206, a technician, doctor, or other authorized person can send configuration information to the router 3536 via the internet, and then the router can provide this information to the base station 3500 via the access port 3534 (if present) and the range extender 3532 (if present). The base station 3500 stores this information until the next poll to which the implantable reporting processor 206 responds, at which time the base station provides this configuration information to the implantable reporting processor. Or it can be the base station 3500 that stores the information in Table II, and reconfigures the implantable reporting processor 206 for a period P (e.g., P2) after the expiration of the prior period P (e.g., P1).

Still referring to FIG. 28, alternate embodiments of the network 3502 and the base station 3500, and the system of which the base station forms part, are contemplated. For example, although shown as wired connected to the router 3536, the access point 3534 can be configured for wireless connection to the router. Furthermore, the base station 3500 can be configured to communicate directly with the router 3536 either in wired or wireless fashion such that the range extender 3532 and the access point 3534 can be omitted. Moreover, the base station 3500 itself can have a unique station identifier. If the base station 3500 provides its station identifier to a remote server, and the remote server associates the base station, using its station identifier, to a patient's account, then if the remote server determines that it has not "heard from" a prosthesis of a patient for longer than a threshold period of time (e.g., 1 to 3 days), the remote server can poll the base station. If the base station 3500 responds, then the remote server "knows" that the base station is functioning, and can command the base station to perform a routine designed to determine if the implantable reporting processor 206 is malfunctioning, or merely has been out of communication range of the base station. In addition, the remote server can be configured to associate multiple base stations 3500 to a particular patient and prosthesis. For example, a patient may have one base station 3500 for his/her primary residence, another base station for his/her vacation home, and still another base station for travel. Furthermore, a base station 3500 can be configured to establish communications with any implantable reporting processor 206 of any patient within range of the base station, and to provide data from such an implantable reporting processor 206 to the cloud database 3530 or the remote server. For example, the base station 3500 in a rehabilitation facility can be configured to send out general polls in addition to prosthetic-specific polls. If a patient is checked into rehab, instead of having to manually associate a base station 3500 with the patient's prosthesis, the prosthesis can be configured to recognize such a general poll, and, in response to the general poll, to send to the base station the patient's unique identifier and prosthesis serial number so that the base station can upload data from the prosthesis to the cloud database 3530 or to the remote server, either of which can associate the data with the correct patient account.

Figure 29:
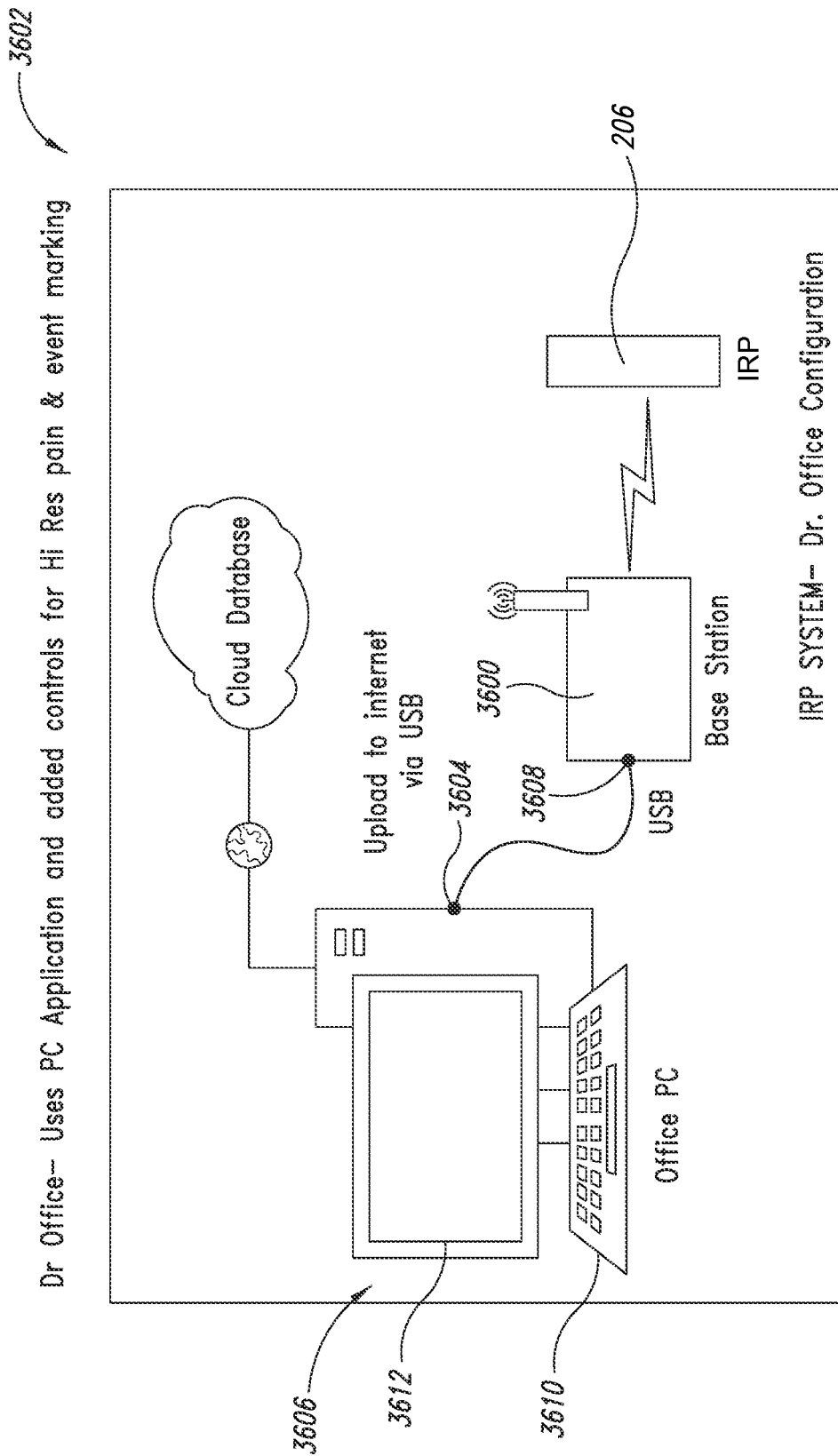
FIG. 29 is a diagram of a base station for facilitating communications with the implantable reporting processor while a subject, in which is implanted a prosthesis related to the implantable reporting processor, is at a medical facility such as a doctor's office, according to an embodiment.

FIG. 29 is a diagram of the base station 3600 configured to facilitate communications with the implantable reporting processor 206 while the patient in which the implantable reporting processor is implanted is at doctor's office or other medical facility for, e.g., a checkup, according to an embodiment. The base station 3600 can be similar to the base station 3500 of FIGS. 27-28, but the base station 3600 can also include additional circuitry and a control panel (not shown in FIG. 29) to allow a doctor or other medical professional to put the implantable reporting processor 206 into a test or other mode while the patient is in the office.

In a doctor's office (or other medical facility) 3602, before a checkup of a subject who has an implanted prosthesis, such as a knee prosthesis, that is related to (e.g., that includes) the implantable reporting processor 206, one connects a universal-serial-bus (USB) port 3604 of a computing system 3606 to a USB port 3608 of the base station 3600. The computing system 3606 can be a personal computer, a laptop, a smart phone, a tablet computer, or the like. The computing system 3606 can include a keyboard 3610 or other input device to allow a doctor or technician to enter commands to the implantable reporting processor 206, and may generate on a display 3612 a graphical user interface (GUI) corresponding to the implantable reporting processor. Alternatively, as described above, the base station 3600 can include an input device to allow the doctor/technician to enter commands to the implantable reporting processor 206, in which case the computing system 3606 can be omitted. For purposes of explanation, however, the following example assumes that an interface and display (not shown in FIG. 29) that are part of the base station 3600 are used to issue commands to, and to receive and to display information from, the implantable reporting processor 206, it being understood that the these functions could also be performed using the computing system 3606. Furthermore, although a doctor is described as performing certain actions, it is understood that a nurse, technician, or other personnel can perform these actions.

First, a doctor enters into the computing system 3606 via the keyboard 3610 and GUI an identity of the implantable reporting processor 206; the doctor may obtain the identity from medical records or from the patient.

Next, in response to a command entered into the computing system 3606 by the doctor, the base station 3600 polls the implantable reporting processor 206 to request the opening of a communication channel; the base station may use amplitude shift keying (such binary amplitude shift keying) as a modulation protocol while polling the implantable reporting processor. As discussed above, the timer 3002 (FIG. 9) enables the radio circuit 3010 (FIG. 25) to sense such a polling request only periodically, such as every ten minutes. Therefore, it may take a few minutes before the implantable reporting processor 206 responds to the base station 3600. To insure that the base station's polling falls within a listening window of the implantable reporting processor 206, the base station 3600 can poll frequently, such as once per second.

In response to the command and the identifier, the implantable reporting processor 206 allows the base station 3600 to open the channel.

In opening the channel, the base station 3600 can implement conventional security, such as conventional password protection and encryption.

After the channel is open, the doctor can issue other commands via the base station 3600.

For example, the doctor can issue a command that causes the implantable reporting processor 206 to enter a test mode, such as the HPM mode/six-degree-of-freedom mode described above in conjunction Table II and FIG. 26. Because the test mode may be time-limited (e.g., to three minutes) as described above, the doctor can start and stop the mode, by issuing commands, so that he can make maximum use of the allotted time. For example, if the subject has a knee prosthesis, then the doctor may tell the subject to start walking down a long hall, and start the test when the subject reaches a constant walking speed, and stop the test after a number of steps or elapsed time. It is noted that because the range of the base station 3600 relative to the implantable reporting processor 206 may be only 2 m-3 m, the doctor may need to carry the base station 3600 and walk with the patient so that the base station can receive all of the test data sent by the implantable reporting processor. Therefore, the base station 3600 can include a battery so that it is portable. Alternatively, so that the doctor need not walk with the subject, the processing circuit 3004 (FIG. 25) can save all of the test information in the memory 3008 (FIG. 25) for transmission to the base station 3600 after the test is complete.

The doctor can start and stop the test a number of times, as long as the total test time does not exceed the time limit described above. For example, a next step of the test may be to have the patient lie down while the doctor manipulates the prosthesis to determine, e.g., a range of motion.

If the implantable reporting processor 206 did not transmit the test data to the base station 3600 during the test, then, in response to a request form the base station, the implantable reporting processor sends, via the radio circuit 3010 (FIG. 25) the information to the base station.

The doctor can then upload this test information to a computing system, such as the computing system 3606, or to a remote server, such as a cloud-based server 3614, for analysis. In the latter case, the base station 3600 can connect to the remote server via the computing system 3606, or via, e.g., a range extender, access point, and router in a manner similar to that described above in conjunction with FIG. 28.

The doctor can then share the results of the analysis with the subject.

The doctor can also re-configure the implantable reporting processor 206 via the base station 3600, for example, by changing the parameters of the lower-power modes LPM and higher-power modes HPM that the processor 3004 (FIG. 25) executes during various periods P. The amounts by which the doctor can change these parameters may be constrained to ensure that the battery 2042 (FIG. 25) has its designed-for lifetime.

At the end of the check-up, the doctor can issue, via the base station 3600, a command that causes the implantable reporting processor 206 to return to its non-test mode of operation.

Still referring to FIG. 29, alternate embodiments of the base station 3600, and the system of which the base station forms part, are contemplated. For example, although shown having a wired USB connection to the computing system 3606, the base station 3600 can be connected to the computing system in another manner such as wirelessly. Furthermore, although described for use with an implantable reporting processor 206 that is associated with a knee prosthesis, the implantable reporting processor can be associated with any other type of prosthesis, or any other type of implantable device or structure.

Figure 30:
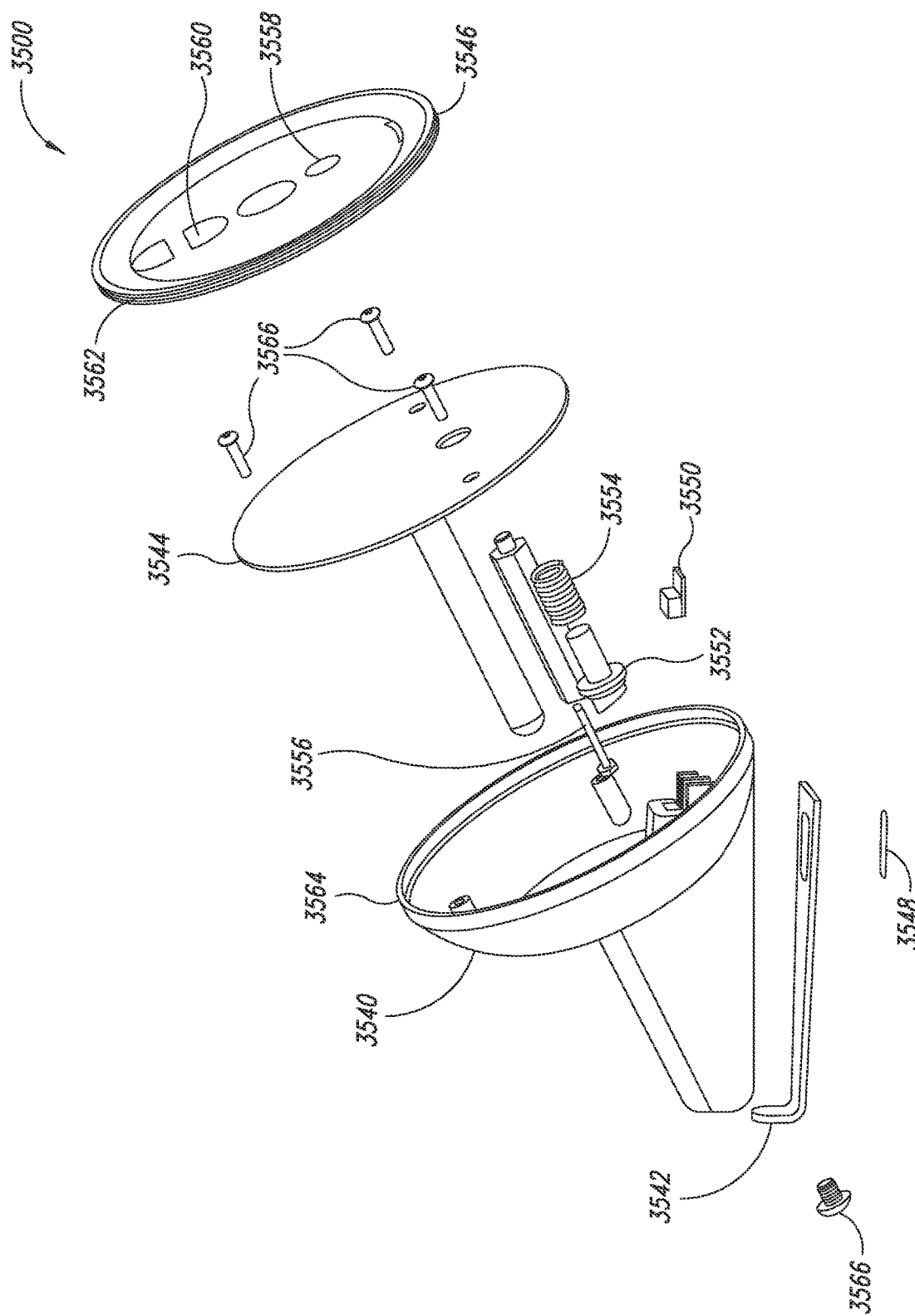
FIG. 30 is an exploded view of the base station of FIGS. 27-29, according to an embodiment.

FIG. 30 is an exploded view of the base station 3500 of FIGS. 27-28, according to an embodiment. And where the base station 3600 of FIG. 29 is the same as the base station 3500, then FIG. 30 is also an exploded view of the base station 3600.

The base station 3500 includes a housing assembly 3540, a foot 3542 configured to support the housing assembly, a printed-circuit-board assembly 3544, and a faceplate assembly 3546.

The housing assembly 3540 and foot 3542 can be formed from any suitable material such as plastic. The printed-circuit-board assembly 3544 is configured to have mounted thereon circuitry (described below in conjunction with FIG. 33A) configured to provide the functioning of the base station 3500, and an antenna (not shown in FIG. 30) configured to allow the base station to communicate with the antenna 2046 of the implantable reporting processor 206 (e.g., FIG. 19B) and with a cloud data base 3530 (FIG. 28) or a remote server via, e.g., the range extender 3532 (if present), access point 3534 (if present), and wireless router/modem 3536 (FIG. 28).

The printed-circuit-board assembly 3544 can be formed from any suitable material, such as a plastic or a resin, and can have any suitable number of electrically conducting and electrically insulating layers.

And the faceplate assembly 3546 is configured to cover and seal the interior of the housing assembly 3540, and can be formed from any suitable material such as a plastic.

A serial-number label 3548 is mounted to a bottom of the housing assembly 3540, and includes the serial number of the base station 3500.

A USB port 3550 is mounted inside of the housing assembly 3540, as is a power button/switch assembly 3552, which includes a return spring 3554 and a light assembly, and a battery light assembly 3556. The power-button light assembly is configured to generate a light to indicate that the base station 3500 is powered "on," and is configured to generate no light to indicate that the base station is "off." Similarly, the battery light assembly 3556 is configured to generate light of one color (e.g., green) to indicate that a battery or a capacitor (neither shown in FIG. 30) is fully, or nearly fully, charged, and to generate light of one or more other colors to indicate one or more other respective levels of charge on the battery or a capacitor.

The faceplate assembly 3546 includes a power-button/switch viewing portion 3558, molded elastomeric buttons 3560, which allow a user, such as a patient, to push buttons/switches (not shown in FIG. 30) mounted to the printed-circuit-board assembly 3544, and includes a gasketed edge 3562, which engages (e.g., by "snapping" into) an edge receptacle 3564 of the housing assembly 3540. The viewing portion 3558 is transparent but covered to allow viewing of the power-button light while maintaining a seal.

And screws 3566 are configured to hold together the various components (e.g., the housing assembly 3540, foot 3542, printed-circuit-board assembly 3544, and faceplate assembly 3546) of the base station 3500.

Figure 31:
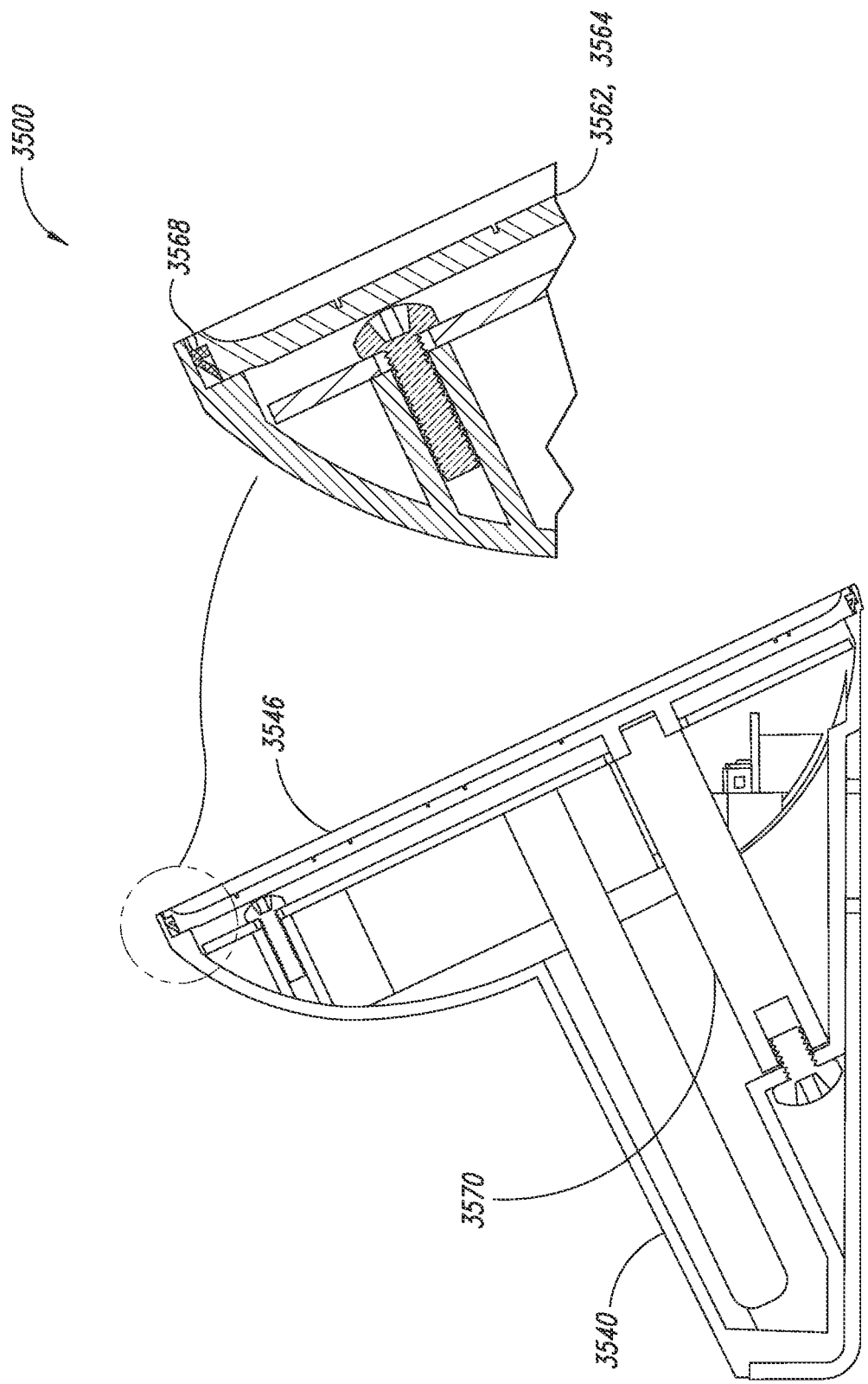
FIG. 31 is a cut-away view of a portion of the base station of FIG. 30, according to an embodiment.

FIG. 31 is a cut-away side view of a portion of the base station 3500 of FIG. 30, according to an embodiment. And where the base station 3600 of FIG. 29 is the same as the base station 3500, then FIG. 31 is also a cut-away side view of the same portion of the base station 3600. An elastomeric gasket 3568 is configured to form a seal along the gasketed edge 3562 and the edge receptacle 3564. And a standoff assembly 3570 attaches the faceplate assembly 3546 to the housing assembly 3540.

Figure 32:
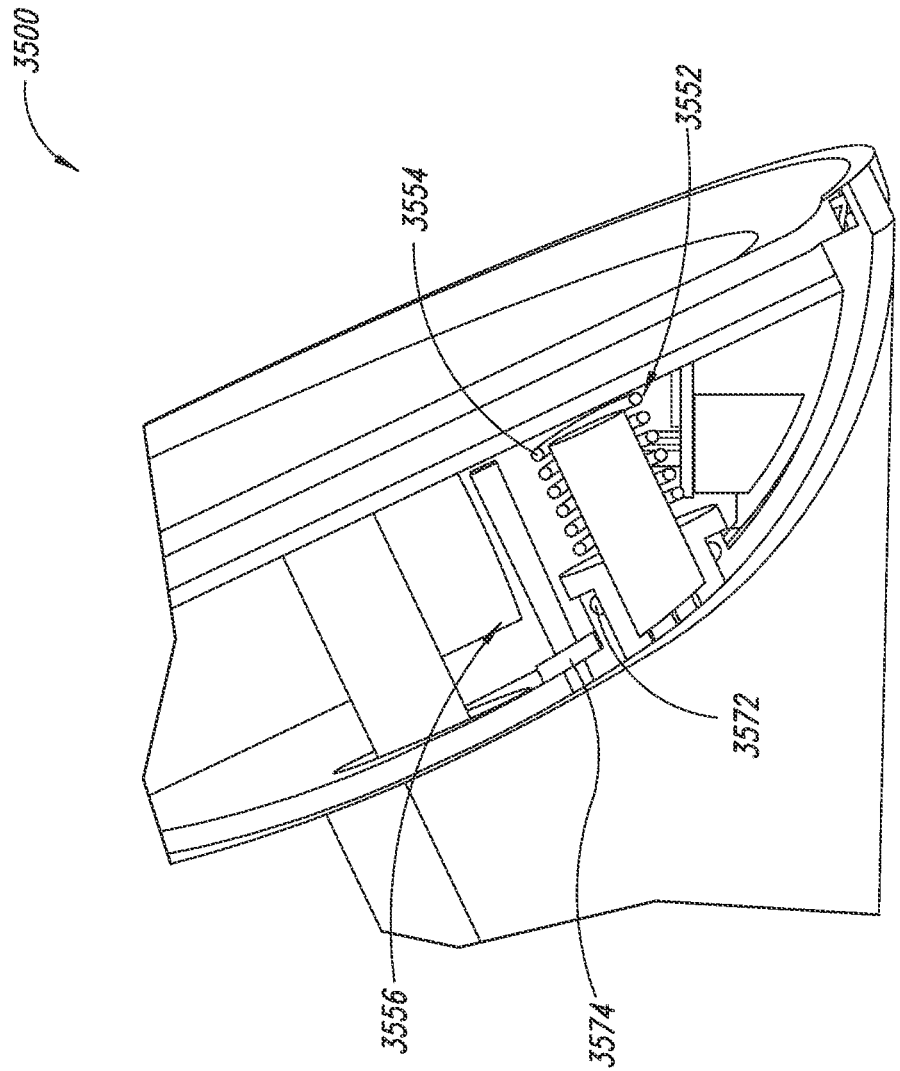
FIG. 32 is a cut-away view of another portion of the base station of FIG. 30, according to an embodiment.

FIG. 32 is a cut-away side view of another portion of the base station 3500 of FIG. 30, according to an embodiment. And where the base station 3600 of FIG. 29 is the same as the base station 3500, then FIG. 32 is also a cut-away side view of the same portion of the base station 3600. The power button/switch assembly 3552 includes an O-ring 3572 configured to form a fluid-tight seal, and a battery light pipe 3574 of the battery light assembly 3556 includes a light that is configured to show, by the color of the light, the charge level of a battery or a capacitor (neither shown in FIG. 32) in the base station 3500, where the battery or capacitor allows operation of the base station while the base station is disconnected from AC power (e.g., while a doctor is following a patient with the base station during an exam as described above). Transparent portion 3558 of the faceplate assembly 3546 allows one to see the button light while maintaining a flexible seal that still allows one to push the bottom to turn the base station 3500 "on" or "off." Similarly, another transparent portion of the faceplate assembly 3546 allows one to see the battery light while maintaining a seal (this transparent portion may not be flexible because the battery light typically is not configured to be pushed).

Figure 33A:
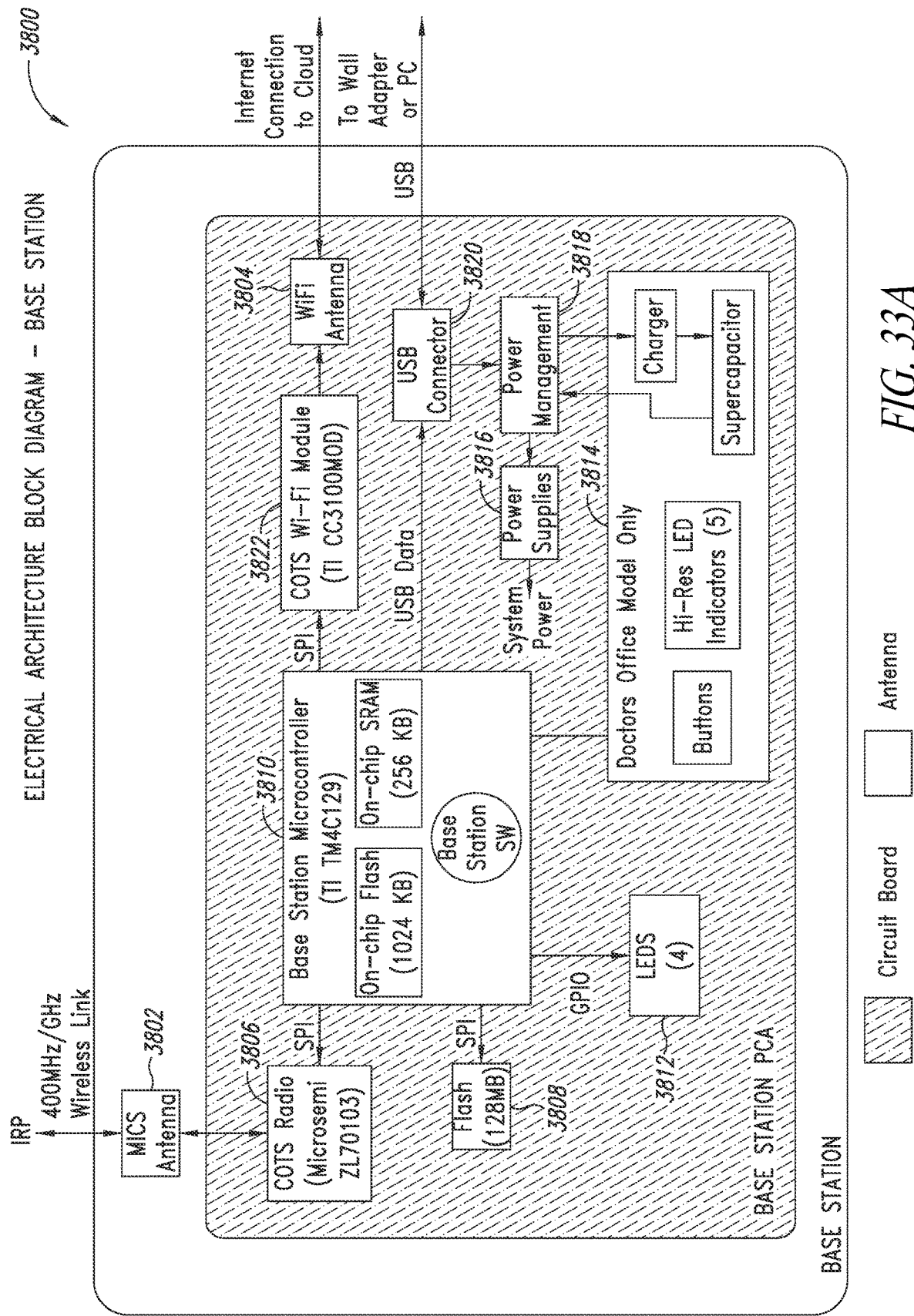
FIG. 33A is a schematic block diagram of the circuitry of the base station of FIG. 30, according to an embodiment.

FIG. 33A is a schematic block diagram of the electronic circuitry 3800 and the antennas 3802 and 3804 of the base station 3500 of FIGS. 27-28 and 30-32 and of the base station 3600 of FIGS. 29-32, according to an embodiment.

The base-station electronic circuitry 3800 includes the following circuit components: a radio circuit 3806, a memory 3808, a processing circuit 3810, light-emitting diodes (LEDs) 3812, an optional doctor-office circuitry 3814, one or more power supplies 3816, a power-management circuit 3818, a USB circuit 3820, and a radio 3822.

The antenna 3802 is for communication with the implantable reporting processor 206 of FIGS. 27-29. For example, the antenna 3802 can be designed to communicate with the implantable reporting processor 206 over a wireless link at a carrier frequency ranging from about 400 MHz-2.4 GHz.

The antenna 3804 is for communication with one or more of a WiFi range extender, an access point, and a wireless router such as described above in conjunction with FIG. 28.

The radio circuit 3806 is configured to communicate with the implantable reporting processor 206 of FIGS. 27-29 via the antenna 3802, and can be, for example, a Microsemi ZL70103 radio IC.

The memory circuit 3808 is a nonvolatile memory that can be configured to store programming and configuration data for the processing circuit 3810, and data generated or received by the processing circuit. The memory 38008 can be any type of nonvolatile memory such as ROM, PROM, EPROM, and EEPROM.

The processing circuit 3810 is configured to interact with and control the other component circuits of the base-station circuitry 3800, and can be a microcontroller, a microprocessor, or any other computing circuit, such as a Texas Instruments® TM4C129 microcontroller IC.

The LEDs 3812 are configured to be controlled to be on or off by the processing circuit 3810 for providing status or other information to an observer. For examples, two of the LEDs 3812 can be used as the power-button light and the battery light, respectively (FIGS. 30-32).

The doctor-office circuitry 3814 is included at least in the base station 3600 of FIG. 29, and provides the functionality and features (e.g., input buttons, display) of the base station 3600 that facility use of the base station in a doctor's office or other medical setting.

The one or more power supplies 3816 provide power to the other circuit components of the base-station circuitry 3800, and can include, e.g., a battery and a switching power supply.

The power-management circuit 3818 interfaces the power line of the USB circuit 3820 to the one or more power supplies 3816, and can include a protection circuit that limits the current drawn from the USB power line.

The USB circuit 3820 includes the USB connector 3508/3608 of FIGS. 27 and 29.

And the radio circuit 3822 is configured to communicate with, e.g., the internet, via the antenna 3804 and a wireless router or other component per above, and can be, for example, a Texas Instruments CC3100MOD radio IC.

Still referring to FIG. 33A, alternate embodiments of the base-station electronic circuitry 3800 are contemplated. For example, the electronic circuitry 3800 can include circuits other than those described above; examples of such other circuits include volatile memory such as random-access memory (RAM). Furthermore, some or all of the component circuits of the electronic circuitry 3800 can be disposed on one or more integrated circuits, or can be discrete component circuits. In addition, the processing circuit 3810 can execute any suitable routine in any manner to interact with and to control the other components of the electronic circuitry 3800.

Figure 33B:
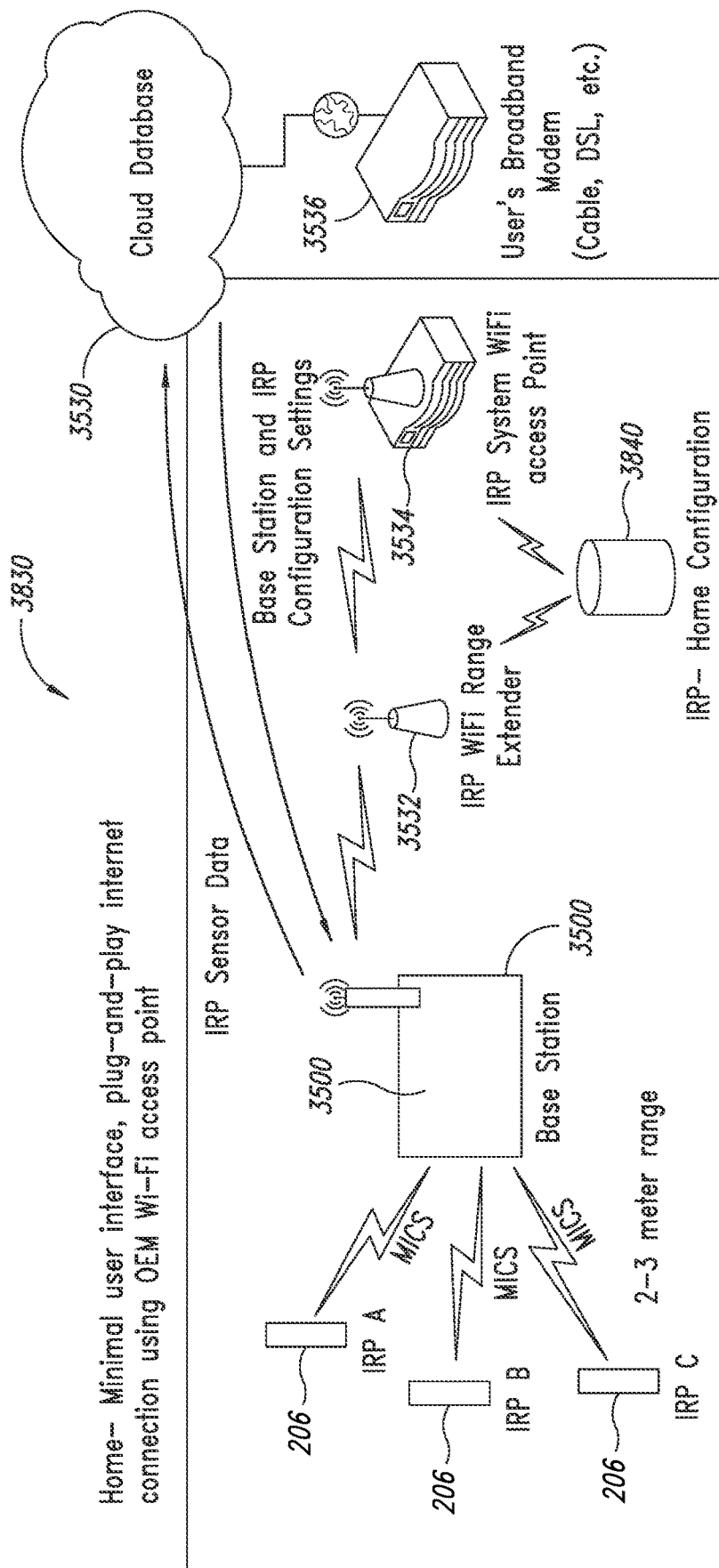
FIG. 33B is a diagram of a network that includes voice-command device and a base station for facilitating communications with the implantable reporting processor while a subject, in which is implanted a prosthesis related to the implantable reporting processor, is away from a medical facility, according to an embodiment

FIG. 33B is a diagram of a network 3830 including the base station 3500, which is configured to facilitate communications with one or more implantable reporting processors 206 while a patient (or patients) in which the implantable reporting processor(s) is(are) implanted is(are) at home, according to an embodiment. The configuration of the base station 3500 is similar to that described above in conjunction with FIG. 28, except that in the embodiment described in conjunction with FIG. 33B, the base station is configured to communicate with, and otherwise to interact with, a voice-command device 3840, examples of which include an Amazon Echo®, an Amazon Dot®, a Google Home®, a Google Glasses® or other wearable device, or a smart phone with voice-command capability. Representative examples of suitable voice-command devices (also referred to as, for example, a "voice controlled assistant") and features thereof are described in, for example, U.S. Pat. Nos. 8,855,295; 9,473,64; 9,472,206; 9,391,575; 9,368,105; 9,251,787; 9,304,736; 9,390,724; 9,424,840; and 9,418,658; and U.S. Pat. Pub. Nos. 2015/0279365; 2015/0109191; 2014/0365884; 2013/0317823; 2011/0184740; 2015/0279389; and 2014/0180697, all of which are incorporated by reference in their entirety.

Within alternative embodiments of the invention, certain critical components of the base station, e.g., the electronic circuitry 3800, may be connected directly to or contained within a voice-command device.

Within related embodiments of the invention, the voice-command device can respond to queries from a subject. For example, a statement by a subject "My knee hurts" can processed by the device, time stamped and stored with records associated with the subject. Such subjective statements made by the patient or a health care professional can be correlated with objective measurements obtained from the subject, as well as to other forms of data that may be collected from the subject or the subject's implant.

Each of the base stations as disclosed herein may incorporate the voice-command feature, or equivalently, a device having voice-command capability may be modified or supplemented to incorporate the features of the base station. In either event, a person is able to verbally communicate with a voice-command device in order to place additional information into the record that is being generated by the IRP interacting with the base station. Additionally, a person is able to verbally communicate with a voice-command device in order to obtain information from the record that is being generated by the IRP interacting with the base station. Optionally, the verbal query from the person will cause the IRP to obtain information specifically in response to the query.

The base station 3500 (or the wireless range extender 3532 if present in the configuration) includes, or is fitted with (e.g., has inserted in its USB port 3550 (FIG. 30)), a dongle (not shown in FIG. 33B) that allows the base station to communicate wirelessly with the voice-command device 3840 using conventional wireless technology, examples of which include WiFi®, Bluetooth®, or Bluetooth Low Energy®.

While configured for communicating with the voice-command device 3840, the base station 3500 can communicate with the cloud database 3530, or a remote server (not shown in FIG. 33B) via the voice-command device, or can bypass the voice-command device and communicate directly with the wireless access point 3534 (if present), with the range extender 3532 (if present), or with the modem 3536 if neither the wireless access point nor the range extender is present.

The base station 3500 communicating via the voice-command device 3840 can provide one or more advantages.

For example, the voice-command device 3840 can be configured, with software, firmware, hardware, or a combination of two of more of these items, such that in response to a command from the base station 3500, the voice-command device initiates a "conversation" with the patient. The base station 3500 or the voice-command device 3840 can be configured to provide information gleaned from the conversation, or to provide a recording of the conversation itself, to the cloud database 3530 or the remote server (not shown in FIG. 33B) for analysis. As a further example, the voice-command device 3840 can be configured to ask a patient with a knee prosthesis "how is your knee today?" The patient can respond, for example, "it is fine," or "something is wrong." In response to "it is fine," the voice-command device 3840 can be configured to stop the conversation with the patient, and to send to the base station 3500 information indicating that the patient is experiencing no problems with the prosthetic knee. In response to "something is wrong," the voice-command device 3840 can be configured to "ask" the patient one or more follow-up questions designed to help the remote server, or a doctor, determine the problem, if any, with the knee prosthesis. Alternatively, the base station 3500 can be configured to command the voice-command device 3840 to ask one or more follow-up questions. The base station 3500 can be configured to include information gleaned from the patient's response to the one or more follow-up questions in the information that the base station sends to the cloud database 3530 or the remote server. Or, either the base station 3500 or the voice-command device 3840 can be configured to include a recording (e.g., a .wav file) of the "conversation" with the information that the base station sends to the cloud database 3530 or the remote server.

Further in example, the implantable reporting processor 206, or the base station 3500, can be configured to send messages to a patient via the voice-command device 3840, which can vocalize these messages. For example, if the processor 2004 determines that there is a problem with an associated implanted prosthesis, the processor can send, via the base station 3500, a message, in response to which the voice-command device 3840 "says" "there is something wrong with your implant, please call your doctor." Or, if the processor 2004 is configured to perform a test of a knee prosthesis, the processor can send, via the base station 3500, a message, in response to which the voice-command device 3840 "says" "please walk at least ten steps without stopping."

Furthermore, the base station 3500 communicating via the voice-command device 3840 can provide additional security for the information from the implantable reporting processor 206 of the patient's prosthesis, particularly where the processor is not configured to encrypt the information that it sends to the base station, or where the base station is not configured to encrypt the information that it sends to the implantable reporting processor or to the voice-command device.

The transmission of information from the implantable reporting processor 2004 to the base station 3500 is relatively secure, even without encryption, for the following reasons. First, the transmitting range of the implantable reporting processor 206 is relatively short, e.g., ≤10 m, so a data hacker, or hacking device, would need to be very close to the prosthesis, most likely so close that the patient, or another person, would notice the hacker or device. Second, the implantable reporting processor 206 is configured to transmit the data in a non-standard, possibly proprietary, format, so that even if a hacker were to obtain the data, he/she would still have to figure out what it means, i.e., decode it. And third, the implantable reporting processor 206 is configured to transmit the data relatively infrequently (only once per day, or even less frequently, as described above to preserve battery life), so a hacker, or hacking device, would need to be "listening" at precisely the time at which the processor is transmitting data to the base station 3500.

But relaying the prosthesis data via the voice-command device 3840 can allow the base station 3500 to "piggy back" on the encryption, and to utilize other data-security features, that the voice-command device is configured to provide. For example, the patient could configure the voice-command device 3840 to operate in an encrypted mode such that the base-station dongle encrypts data that it sends to the voice-command device (via the dongle), and such that the voice-command device encrypts data that it sends to the base station 3500 and to the router 3534 (or directly to the modem 3536). This encryption can be compatible with the wireless router 3534 and the modem 3536 such that the wireless router or the modem can be configured to decrypt (and possibly re-encrypt) the data from the voice-command device 3840 before the router/modem relays the data to the cloud database 3530 or to the remote server, and can be configured to encrypt data from the cloud database or remote server before sending the data to the voice-command device.

Still referring to FIG. 33B, alternative embodiments of the configuration of the network 3830 are contemplated. For example, the base station 3500 can be made part of, or can be incorporated within, the voice-command device 3840. Furthermore, if the voice-command device 3840 is a smart phone, then the device can be configured to allow a patient to field and answer "questions" in text instead of in voice.

Figure 34:
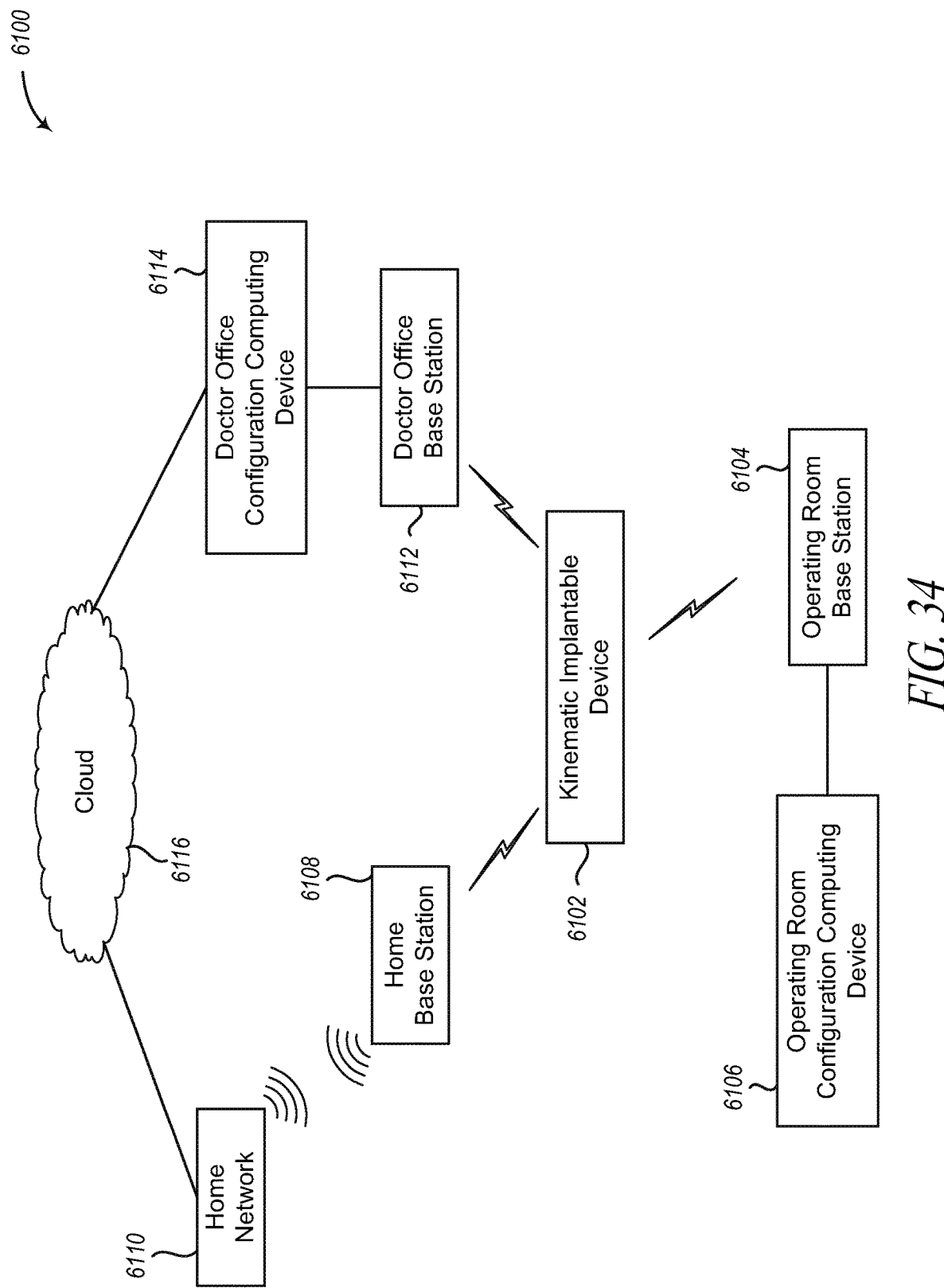
FIG. 34 illustrates a context diagram of a kinematic implantable device environment.

FIG. 34 illustrates a context diagram of a kinematic implantable device environment 6100. In the environment, a kinematic implantable device 6102 is implanted by a medical practitioner in the body of a patient. The kinematic implantable device 6102 is arranged to collect data including operational data of the device 6102 along with kinematic data associated with particular movement of the patient or particular movement of a portion of the patient's body. The kinematic implantable device 6102 communicates with one or more base stations during different stages of monitoring the patient.

For example, in association with a medical procedure, a kinematic implantable device 6102 is implanted in the patient's body. Coetaneous with the medical procedure, the kinematic implantable device 6102 communicates with an operating room base station 6104. Subsequently, after sufficient recovery from the medical procedure, the patient returns home wherein the kinematic implantable device 6102 is arranged to communicate with a home base station 6108. At other times, the kinematic implantable device 6102 is arranged to communicate with a doctor office base station 6112. The kinematic implantable device 6102 communicates with each base station via a short range network protocol, such as the medical implant communication service (MICS), the medical device radio communications service (MedRadio), or some other wireless communication protocol suitable for use with the kinematic implantable device 6102.

The kinematic implantable device 6102 is implanted into a body of a patient. The kinematic implantable device 6102 may be a standalone medical device or it may be a component in a larger medical device, such as an artificial joint (e.g., a knee replacement, a hip replacement, a vertebral device, or the like), a breast implant, a femoral rod, or some other implanted medical device that can desirably collect and provide in situ kinematic data, operational data, or other useful data.

The kinematic implantable device 6102 includes one or more sensors to collect information and kinematic data associated with the use of the body part to which the kinematic implantable device 6102 is associated. For example, the kinematic implantable device 6102 may include an inertial measurement unit that includes gyroscope(s), accelerometer(s), pedometer(s), or other kinematic sensors to collect acceleration data for the medial/lateral, anterior/posterior, and anterior/inferior axes of the associated body part; angular velocity for the sagittal, frontal, and transverse planes of the associated body part; force, stress, tension, pressure, duress, migration, vibration, flexure, rigidity, or some other measurable data.

The kinematic implantable device 6102 collects data at various different times and at various different rates during a monitoring process of the patient. In some embodiments, the kinematic implantable device 6102 may operate in a plurality of different phases over the course of monitoring the patient so that more data is collected soon after the kinematic implantable device 6102 is implanted into the patient, but less data is collected as the patient heals and thereafter.

In one non-limiting example, the monitoring process of the kinematic implantable device 6102 may include three different phases. A first phase may last for four months where kinematic data is collected once a day for one minute, every day of the week. After the first phase, the kinematic implantable device 6102 transitions to a second phase that lasts for eight months and collects kinematic data once a day for one minute, two days a week. And after the second phase, the kinematic implantable device 6102 transitions to a third phase that last for nine years and collects kinematic data one day a week for one minute for the next nine years. Of course, the time periods associated with each phase may be longer, shorter, and otherwise controllable. The type and amount of data collected may also be controllable. The added benefit of this passive monitoring process is that after the first phase of monitoring, the patient will be unaware of when data is being collected. Thus, the collected data will be protected from potential bias.

Along with the various different phases, the kinematic implantable device 6102 can operate in various modes to detect different types of movements. In this way, when a predetermined type of movement is detected, the kinematic implantable device 6102 can increase, decrease, or otherwise control the amount and type of kinematic data and other data that is collected.

In one example, the kinematic implantable device 6102 may use a pedometer to determine if the patient is walking. If the kinematic implantable device 6102 measures that a determined number of steps crosses a threshold value within a predetermined time, then the kinematic implantable device 6102 may determine that the patient is walking. In response to the determination, the amount and type of data collected can be started, stopped, increased, decreased, or otherwise suitably controlled. The kinematic implantable device 6102 may further control the data collection based on certain conditions, such as when the patient stops walking, when a selected maximum amount of data is collected for that collection session, when the kinematic implantable device 6102 times out, or based on other conditions. After data is collected in a particular session, the kinematic implantable device 6102 may stop collecting data until the next day, the next time the patient is walking, after previously collected data is offloaded (e.g., by transmitting the collected data to the home base station 6108), or in accordance with one or more other conditions.

The amount and type of data collected by a kinematic implantable device 6102 may be different from patient to patient, and the amount and type of data collected may change for a single patient. For example, a medical practitioner studying data collected by the kinematic implantable device 6102 of a particular patient may adjust or otherwise control how the kinematic implantable device 6102 collects future data.

The amount and type of data collected by a kinematic implantable device 6102 may be different for different body parts, for different types of movement, for different patient demographics, or for other differences. Alternatively, or in addition, the amount and type of data collected may change overtime based on other factors, such as how the patient is healing or feeling, how long the monitoring process is projected to last, how much battery power remains and should be conserved, the type of movement being monitored, the body part being monitored, and the like. In some cases, the collected data is supplemented with personally descriptive information provided by the patient such as subjective pain data, quality of life metric data, co-morbidities, perceptions or expectations that the patient associates with the kinematic implantable device 6102, or the like.

In some embodiments, the kinematic implantable device 6102 is implanted into a patient to monitor movement or other aspects of a particular body part. Implantation of the kinematic implantable device 6102 into the patient may occur in an operating room. As used herein, operating room includes any office, room, building, or facility where the kinematic implantable device 6102 is implanted into the patient. For example, the operating room may be a typical operating room in a hospital, an operating room in a surgical clinic or a doctor's office, or any other operating theater where the kinematic implantable device 6102 is implanted into the patient.

The operating room base station 6104 is utilized to configure and initialize the kinematic implantable device 6102 in association with the kinematic implantable device 6102 being implanted into the patient. A communicative relationship is formed between the kinematic implantable device 6102 and the operating room base station 6104, for example, based on a polling signal transmitted by the operating room base station 6104 and a response signal transmitted by the kinematic implantable device 6102.

Upon forming a communicative relationship, which will often occur prior to implantation of the kinematic implantable device 6102, the operating room base station 6104 transmits initial configuration information to the kinematic implantable device 6102. This initial configuration information may include, but is not limited to, a time stamp, a day stamp, an identification of the type and placement of the kinematic implantable device 6102, information on other implants associated with the kinematic implantable device, surgeon information, patient identification, operating room information, and the like.

In some embodiments, the initial configuration information is passed unidirectionally; in other embodiments, initial configuration is passed bidirectionally. The initial configuration information may define at least one parameter associated with the collection of kinematic data by the kinematic implantable device 6102. For example, the configuration information may identify settings for one or more sensors on the kinematic implantable device 6102 (e.g., accelerometer range, accelerometer output data rate, gyroscope range, gyroscope output data rate, and the like) for each of one or more modes of operation). The configuration information may also include other control information, such as an initial mode of operation of the kinematic implantable device 6102, a particular movement that triggers a change in the mode of operation, radio settings, data collection information (e.g., how often the kinematic implantable device 6102 wakes up to collected data, how long it collects data, how much data to collect), home base station 6108 identification information, and other control information associated with the implantation or operation of the kinematic implantable device 6102.

In some embodiments, the configuration information may be pre-stored on the operating room base station 6104 or an associated computing device. In other embodiments, a surgeon, surgical technician, or some other medical practitioner may input the control information and other parameters to the operating room base station 6104 for transmission to the kinematic implantable device 6102. In at least one such embodiment, the operating room base station 6104 may communicate with an operating room configuration computing device 6106. The operating room configuration computing device 6106 includes an application with a graphical user interface that enables the medical practitioner to input configuration information for the kinematic implantable device 6102. In various embodiments, the application executing on the operating room configuration computing device 6106 may have some of the configuration information predefined, which may or may not be adjustable by the medical practitioner.

The operating room configuration computing device 6106 communicates the configuration information to the operating room base station 6104 via a wired or wireless network connection (e.g., via a USB connection, Bluetooth connection, Wi-Fi connection, etc.), which in turn communicates it to the kinematic implantable device 6102.

The operating room configuration computing device 6106 may also display information regarding the kinematic implantable device 6102 or the operating room base station 6104 to the surgeon, surgical technician, or other medical practitioner. For example, the operating room configuration computing device 6106 may display error information if the kinematic implantable device 6102 is unable to store or access the configuration information, if the kinematic implantable device 6102 is unresponsive, if the kinematic implantable device 6102 identifies an issue with one of the sensors or radio during an initial self-test, if the operating room base station 6104 is unresponsive or malfunctions, or for other reasons.

Although the operating room base station 6104 and the operating room configuration computing device 6106 are illustrated as separate devices, embodiments are not so limited; rather, the functionality of the operating room configuration computing device 6106 and the operating room base station 6104 may be included in a single computing device or in separate devices as illustrated. In this way, the medical practitioner may be enabled in one embodiment to input the configuration information directly into the operating room base station 6104.

Once the kinematic implantable device 6102 is implanted into the patient and the patient returns home, the home base station 6108 can communicate with the kinematic implantable device 6102. The kinematic implantable device 6102 can collect kinematic data at determined rates and times, variable rates and times, or otherwise controllable rates and times. Data collection can start when the kinematic implantable device 6102 is initialized in the operating room, when directed by a medical practitioner, or at some later point in time. At least some data collected by the kinematic implantable device 6102 may be transmitted to the home base station 6108.

In various embodiments, the home base station 6108 pings the kinematic implantable device 6102 at periodic, predetermined, or other times to determine if the kinematic implantable device 6102 is within communication range of the home base station 6108. Based on a response from the kinematic implantable device 6102, the home base station 6108 determines that the kinematic implantable device 6102 is within communication range, and the kinematic implantable device 6102 can be requested, commanded, or otherwise directed to transmit the data it has collected to the home base station 6108.

The home base station 6108 may in some cases be arranged with an optional user interface. The user interface may be formed as a multimedia interface that unidirectionally or bidirectionally passes one or more types of multimedia information (e.g., video, audio, tactile, etc.). Via the user interface of a home base station, the patient 100 or an associate of the patient 100 may enter other data to supplement the kinematic data collected by the kinematic implantable device 6102. A user, for example, may enter personally descriptive information (e.g., age change, weight change, etc.), changes in medical condition, co-morbidities, pain levels, quality of life or other subjective metric data, personal messages for a medical practitioner, and the like. In these embodiments, the personally descriptive information may be entered with a keyboard, mouse, touch-screen, microphone, wired or wireless computing interface, or some other input means. In cases where the personally descriptive information is collected, the personally descriptive information may include or otherwise be associated with one or more identifiers that associate the information with unique identifier of the kinematic implantable device 6102, the patient, an associated medical practitioner, an associated medical facility, or the like.

In some of these cases, an optional user interface of the home base station 6108 may also be arranged to deliver information associated with the kinematic implantable device 6102 to the user from, for example, a medical practitioner. In these cases, the information delivered to the user may be delivered via a video screen, an audio output device, a tactile transducer, a wired or wireless computing interface, or some other like means.

In embodiments where the home base station 6108 is arranged with a user interface the user interface may be formed with an internal user interface arranged for communicative coupling to a patient portal device. The patent portal device may be smartphone, a tablet, a body-worn device, a weight or other health measurement device (e.g., thermometer, bathroom scale, etc.), or some other computing device capable of wired or wireless communication. In these cases, the user is able to enter the personally descriptive information, and the user may also be able to receive information associated with their implantable device 6102.

The home base station 6108 utilizes a home network 6110 of the patient to transmit the collected data (i.e., kinematic data and in some cases, personally descriptive information) to cloud 6116. The home network 6110, which may be a local area network, provides access from the home of the patient to a wide area network, such as the internet. In some embodiments, the home base station 6108 may utilize a Wi-Fi connection to connect to the home network 6110 and access the internet. In other embodiments, the home base station 6108 may be connected to a home computer (not illustrated) of the patient, such as via a USB connection, which itself is connected to the home network 6110.

Along with transmitting collected data to the cloud 6116, the home base station 6108 may also obtain data, commands, or other information from the cloud 6116 via the home network 6110. The home base station 6108 may provide some or all of the received data, commands, or other information to the kinematic implantable device 6102. Examples of such information include, but are not limited to, updated configuration information, diagnostic requests to determine if the kinematic implantable device 6102 is functioning properly, data collection requests, and other information.

The cloud 6116 may include one or more server computers or databases to aggregate data collected from the kinematic implantable device 6102, and in some cases personally descriptive information collected from a patient 100, with data collected from other kinematic implantable devices (not illustrated), and in some cases personally descriptive information collected from other patients. In this way, the cloud 6116 can create a variety of different metrics regarding collected data from each of a plurality of kinematic implantable devices that are implanted into separate patients. This information can be helpful in determining if the kinematic implantable devices are functioning properly. The collected information may also be helpful for other purposes, such as determining which specific devices may not be functioning properly, determining if a procedure or condition associated with the kinematic implantable device is helping the patient (e.g., if the knee replacement is operating properly and reducing the patient's pain), and determining other medical information.

At various times throughout the monitoring process, the patient may be requested to visit a medical practitioner for follow up appointments. This medical practitioner may be the surgeon who implanted the kinematic implantable device 6102 in the patient or a different medical practitioner that supervises the monitoring process, physical therapy, and recovery of the patient. For a variety of different reasons, the medical practitioner may want to collect real-time data from the kinematic implantable device 6102 in a controlled environment. In some cases the request to visit the medical practitioner may be delivered through an optional bidirectional user interface of the home base station 6108.

A medical practitioner utilizes the doctor office base station 6112, which communicates with the kinematic implantable device 6102, to pass additional data between the doctor office base station 6112 and the kinematic implantable device 6102. Alternatively, or in addition, the medical practitioner utilizes the doctor office base station 6112 to pass commands to the kinematic implantable device 6102. In some embodiments, the doctor office base station 6112 instructs the kinematic implantable device 6102 to enter a high-resolution mode to temporarily increase the rate or type of data that is collected for a short time. The high-resolution mode directs the kinematic implantable device 6102 to collect different (e.g., large) amounts of data during an activity where the medical practitioner is also monitoring the patient.

In some embodiments, the doctor office base station 6112 enables the medical practitioner to input event or pain markers, which can be synchronized with the high-resolution data collected by the kinematic implantable device 6102. For example, assume the kinematic implantable device 6102 is a component in a knee replacement. The medical practitioner can have the patient walk on a treadmill while the kinematic implantable device 6102 is in the high-resolution mode. As the patient walks, the patient may complain about pain in their knee. The medical practitioner can click a pain marker button on the doctor office base station 6112 to indicate the patient's discomfort. The doctor office base station 6112 records the marker and the time at which the marker was input. When the timing of this marker is synchronized with the timing of the collected high-resolution data, the medical practitioner can analyze the data to try and determine the cause of the pain.

In other embodiments, the doctor office base station 6112 may provide updated configuration information to the kinematic implantable device 6102. The kinematic implantable device 6102 can store this updated configuration information, which can be used to adjust the parameters associated with the collection of the kinematic data. For example, if the patient is doing well, the medical practitioner can direct a reduction in the frequency at which the kinematic implantable device 6102 collects data. On the contrary, if the patient is experiencing an unexpected amount of pain, the medical practitioner may direct the kinematic implantable device 6102 to collect additional data for determined period of time (e.g., a few days). The medical practitioner may use the additional data to diagnose and treat a particular problem. In some cases, the additional data may include personally descriptive information provided by the patient 100 after the patient 100 has left presence of the medical practitioner and is no longer in range of the doctor office base station 6112. In these cases, the personally descriptive information may be collected and delivered from via the home base station 6108. Firmware within the kinematic implantable device and/or the base station will provide safeguards limiting the duration of such enhanced monitoring to insure the battery retains sufficient power to last for the implant's lifecycle. Firmware within the kinematic implantable device and/or the base station will provide safeguards limiting the duration of such enhanced monitoring to insure the battery retains sufficient power to last for the implant's lifecycle.

In various embodiments, the doctor office base station 6112 may communicate with a doctor office configuration computing device 6114. The doctor office configuration computing device 6114 includes an application with a graphical user interface that enables the medical practitioner to input commands and data. Some or all of the commands, data, or other information may be later transmitted to the kinematic implantable device 6102 via the doctor office base station 6112. For example, in some embodiments, the medical practitioner can use the graphical user interface to instruct the kinematic implantable device 6102 to enter its high-resolution mode. In other embodiments, the medical practitioner can use graphical user interface to input or modify the configuration information for the kinematic implantable device 6102. The doctor office configuration computing device 6114 transmits the information (e.g., commands, data, or other information) to the doctor office base station 6112 via a wired or wireless network connection (e.g., via a USB connection, Bluetooth connection, Wi-Fi connection, etc.), which in turn transmits some or all of the information to the kinematic implantable device 6102.

The doctor office configuration computing device 6114 may also display other information regarding the kinematic implantable device 6102, regarding the patient 100 (e.g., personally descriptive information), or the doctor office base station 6112 to the medical practitioner. For example, the doctor office configuration computing device 6114 may display the high-resolution data that is collected by the kinematic implantable device 6102 and transmitted to the doctor office base station 6112. The doctor office configuration computing device 6114 may also display error information if the kinematic implantable device 6102 is unable to store or access the configuration information, if the kinematic implantable device 6102 is unresponsive, if the kinematic implantable device 6102 identifies an issue with one of the sensors or radio, if the doctor office base station 6112 is unresponsive or malfunctions, or for other reasons.

In some embodiments, doctor office configuration computing device 6114 may have access to the cloud 6116. In at least one embodiment, the medical practitioner can utilize the doctor office configuration computing device 6114 to access data stored in the cloud 6116, which was previously collected by the kinematic implantable device 6102 and transmitted to the cloud 6116 via the home base station 6108. Similarly, the doctor office configuration computing device 6114 can transmit the high-resolution data obtain from the kinematic implantable device 6102 via the doctor office base station 6112 to the cloud 6116. In some embodiments, the doctor office base station 6112 may have internet access and may be enabled to transmit the high-resolution data directly to the cloud 6116 without the use of the doctor office configuration computing device 6114.

In various embodiments, the medical practitioner may update the configuration information of the kinematic implantable device 6102 when the patient is not in the medical practitioner's office. In these cases, the medical practitioner can utilize the doctor office configuration computing device 6114 to transmit updated configuration information to the kinematic implantable device 6102 via the cloud 6116. The home base station 6108 can obtain updated configuration information from the cloud 6116 and pass updated configuration information to the cloud. This can allow the medical practitioner to remotely adjust the operation of the kinematic implantable device 6102 without needing the patient to come to the medical practitioner's office. This may also permit the medical practitioner to send messages to the patient 100 in response, for example, to personally descriptive information that was provided by the patient 100 and passed through the home base station 6108 to the doctor office base station 6112.

Although the doctor office base station 6112 and the doctor office configuration computing device 6114 are illustrated as separate devices, embodiments are not so limited; rather, the functionality of the doctor office configuration computing device 6114 and the doctor office base station 6112 may be included in a single computing device or in separate devices (as illustrated). In this way, the medical practitioner may be enabled in one embodiment to input the configuration information or markers directly into the doctor office base station 6112 and view the high-resolution data (and synchronized marker information) from a display on the doctor office base station 6112.

Figure 35:
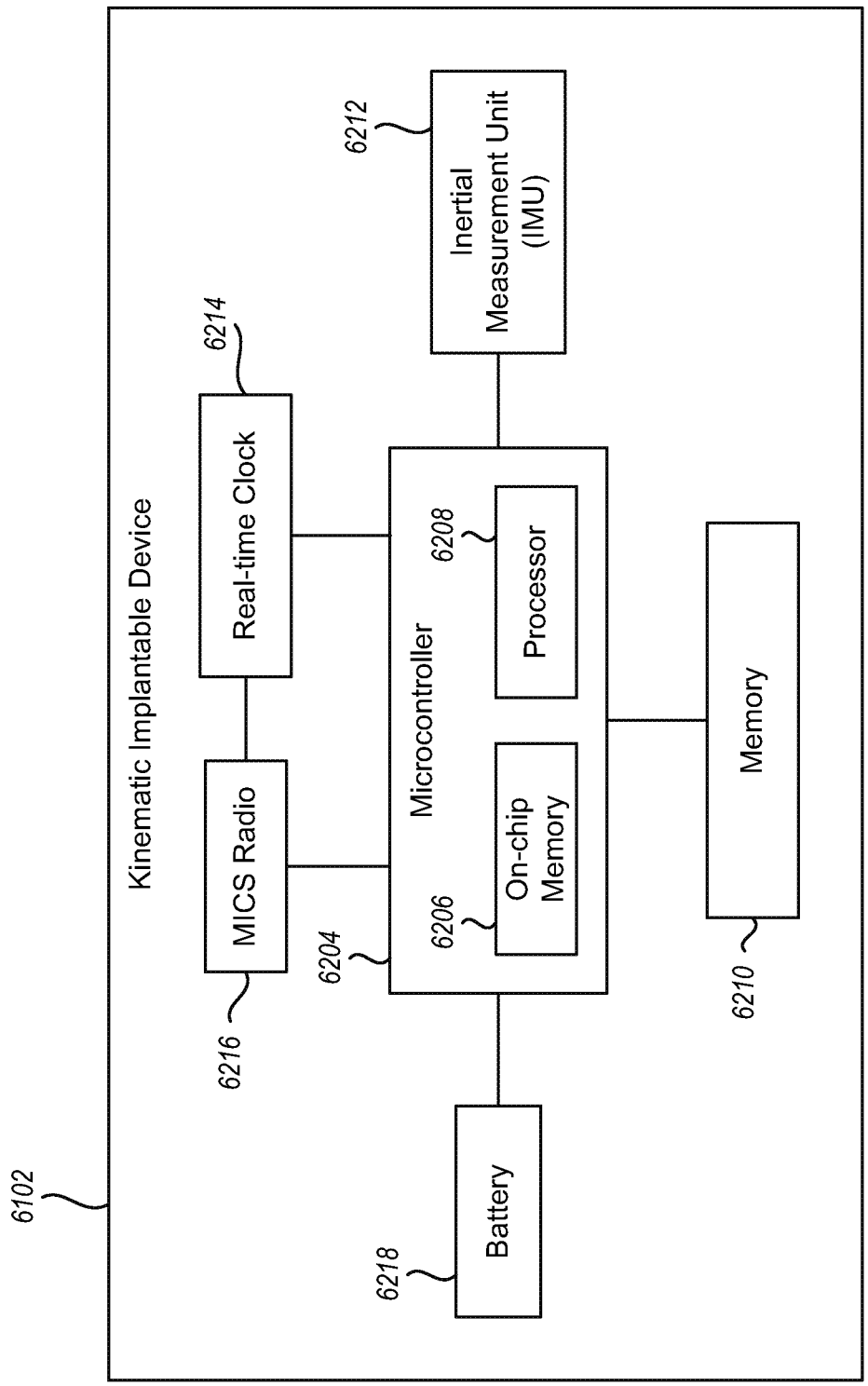
FIG. 35 is an exemplary system diagram of a kinematic implantable device in accordance with embodiments described herein.

FIG. 35 is an exemplary system diagram of a kinematic implantable device in accordance with embodiments described herein. The kinematic implantable device 6102 includes a microcontroller 204, a memory 210, a battery 218, a radio 216, a real-time clock 214, and an inertial measurement unit 212. Other logic (e.g., circuits, devices, structures, and the like) are not illustrated for simplicity.

The microcontroller 204 includes a processor 208 and on-chip memory 206. The on-chip memory 206 may store instructions that are executed by the processor 208 to perform the actions and functionality of the kinematic implantable device 6102 as described herein. In some embodiments, the on-chip memory 206 stores the configuration information to define one or more parameters associated with the collection of data by the inertial measurement unit 212.

In at least some embodiments described herein, radio 216 is a short range communication device configured to communicate with a base station (e.g., the operating room base station 6104, the home base station 6108, and the doctor office base station 6112 in FIG. 34). In various embodiments, the radio 216 communicates information between the kinematic implantable device 6102 and one or more base stations using the medical implant communication service (MICS) standards, medical device radio communications service (MedRadio), or other such protocols. In at least one embodiment, the radio 216 communicates with the one or more base stations over the 402 MHz to 405 MHz MICS band.

The real-time clock 214 is configurable by the microcontroller 204, such as through the configuration information stored in the on-chip memory 206. The real-time clock 214 may provide one or more signals to wake up the radio 216 or the microcontroller 204 at predetermined times. For example, the real-time clock 214 may wake up the radio 216 every other day at 4 am to try to communicate with a base station.

In various embodiments, the battery 218 is a non-rechargeable battery that provides power to the kinematic implantable device 6102. In at least some embodiments, the battery 218 provides power to the microcontroller 204 and other components of the kinematic implantable device 6102.

The memory 210 may be RAM, flash, or any other type of transitory or non-transitory computer readable medium. The memory 210 stores data collected from the IMU 212, configuration information and settings, log records, other kinematic implantable device data, software instructions, and other information.

The IMU 212 is a device that includes one or more sensors that detect and measure kinematic motion (e.g., linear and angular acceleration motion) when the kinematic implantable device 6102 operates (e.g., due to a movement in the body part associated with the kinematic implantable device 6102). In some embodiments, the IMU 212 includes an accelerometer, a gyroscope, a pedometer, or other kinematic sensors.

The operation of certain aspects of the disclosure will now be described with respect to FIGS. 36-38. In at least one of various embodiments, processes 6300, 6400, and 6500 described in conjunction with FIGS. 36-38, respectively, may be implemented by or executed on a kinematic implantable device, such as kinematic implantable device 6102 in FIGS. 34-35.

Figure 36:
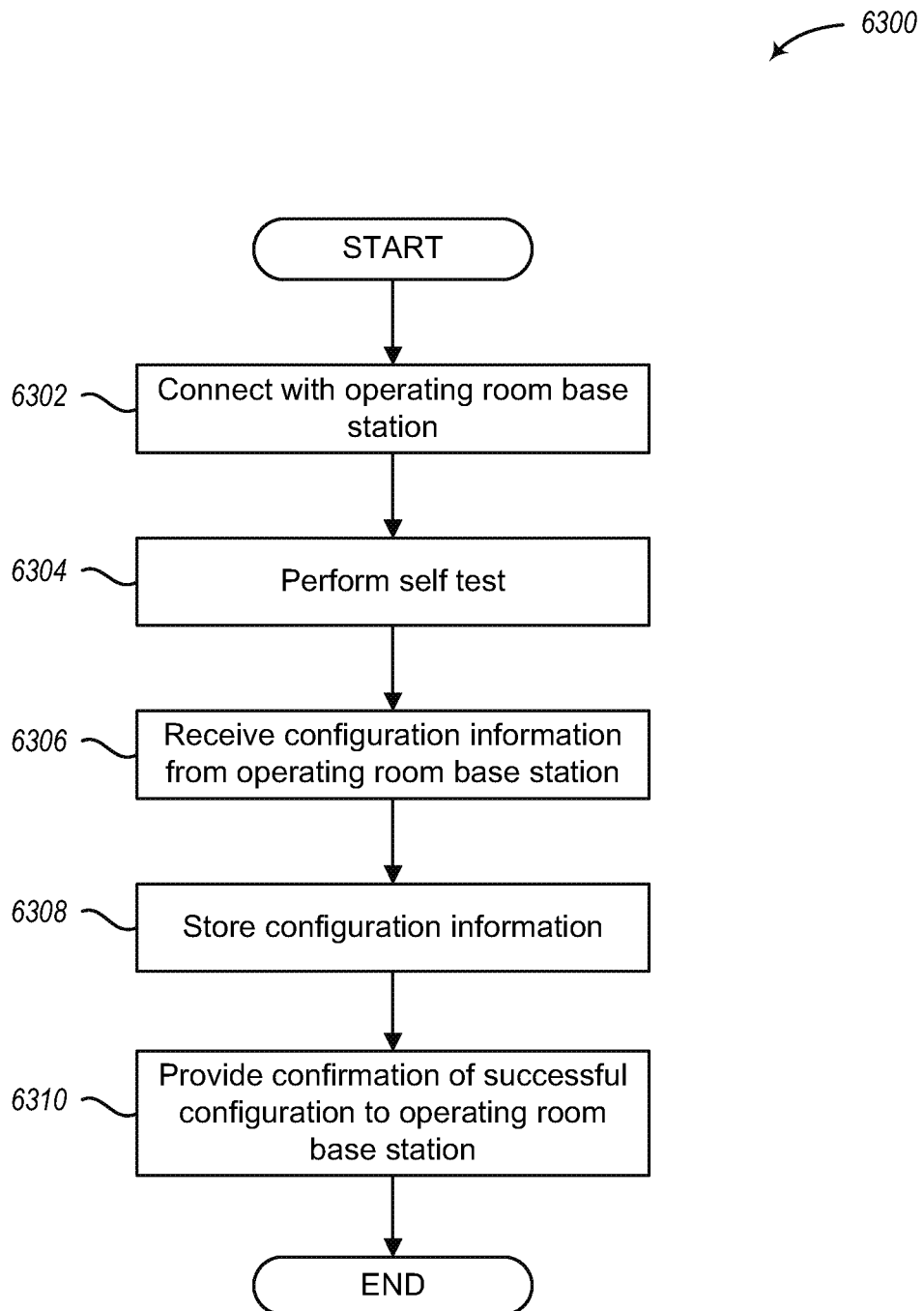
FIG. 36 is a logical flow diagram generally showing one embodiment of a process for configuring the kinematic implantable device from an operating room base station.

FIG. 36 illustrates a logical flow diagram generally showing one embodiment of a process for configuring the kinematic implantable device 6102 from an operating room base station 6104. Process 6300 begins at a start block.

At block 6302, the kinematic implantable device 6102 connects with an operating room base station (e.g., operating room base station 6104 in FIG. 34). In some embodiments, the kinematic implantable device 6102 may receive a wake-up command from the operating room base station 6104. The wake-up command may include identification information of the operating room base station 6104 so that the kinematic implantable device 6102 can establish a connection with the operating room base station 6104.

Process 6300 proceeds to block 6304, where the kinematic implantable device 6102 performs a self-test. This self-test may check the communication between the processor 6208 and the IMU 6212, calibration of the IMU 6212, communication with the real-time clock 6214, integrity of the memory 6206 and battery 6218, and other initialization checks or setup. In at least one embodiment, the kinematic implantable device 6102 may provide the results of the self-test back to the operating room base station 6104. The results may indicate that the kinematic implantable device 6102 is functioning properly or it may indicate if there was a problem with any of the components of the kinematic implantable device 6102.

Process 6300 continues at block 6306, where the kinematic implantable device 6102 receives configuration information from the operating room base station 6104. The configuration information may be identification information, information that defines one or more parameters associated with the collection of kinematic data, or some other information. Examples of configuration information include, but are not limited to, a time, date, day, identification of the body part in which the kinematic implantable device is associated, identification of associated implanted devices, medical practitioner information, patient identification (e.g., encoded or otherwise obfuscated information), operating room information, an initial mode of operation of the kinematic implantable device 6102, settings for one or more sensors on the kinematic implantable device for one or more different modes of operation, specification of a particular movement that triggers a change in the mode of operation, radio settings, data collection information, home base station identification information, and the like.

Subsequent to receiving the configuration information, process 6300 proceeds to block 6308, where the configuration information is stored in the memory 206 of the kinematic implantable device 6102. Storage of the configuration information may provide the initial parameters that define how often the kinematic implantable device 6102 will wake up and collect data.

If the storage of the configuration information is successful, process 6300 provides a confirmation of the successful configuration of the kinematic implantable device 6102 to the operating room base station 6104. If unsuccessful, the kinematic implantable device 6102 may provide an error message to the operating room base station 6104 or it will provide no response, which would be interpreted by the operating room base station 6104 as a failure to properly configure the kinematic implantable device.

After block 6310, process 6300 terminates or returns to a calling process to perform other actions.

Figure 37:
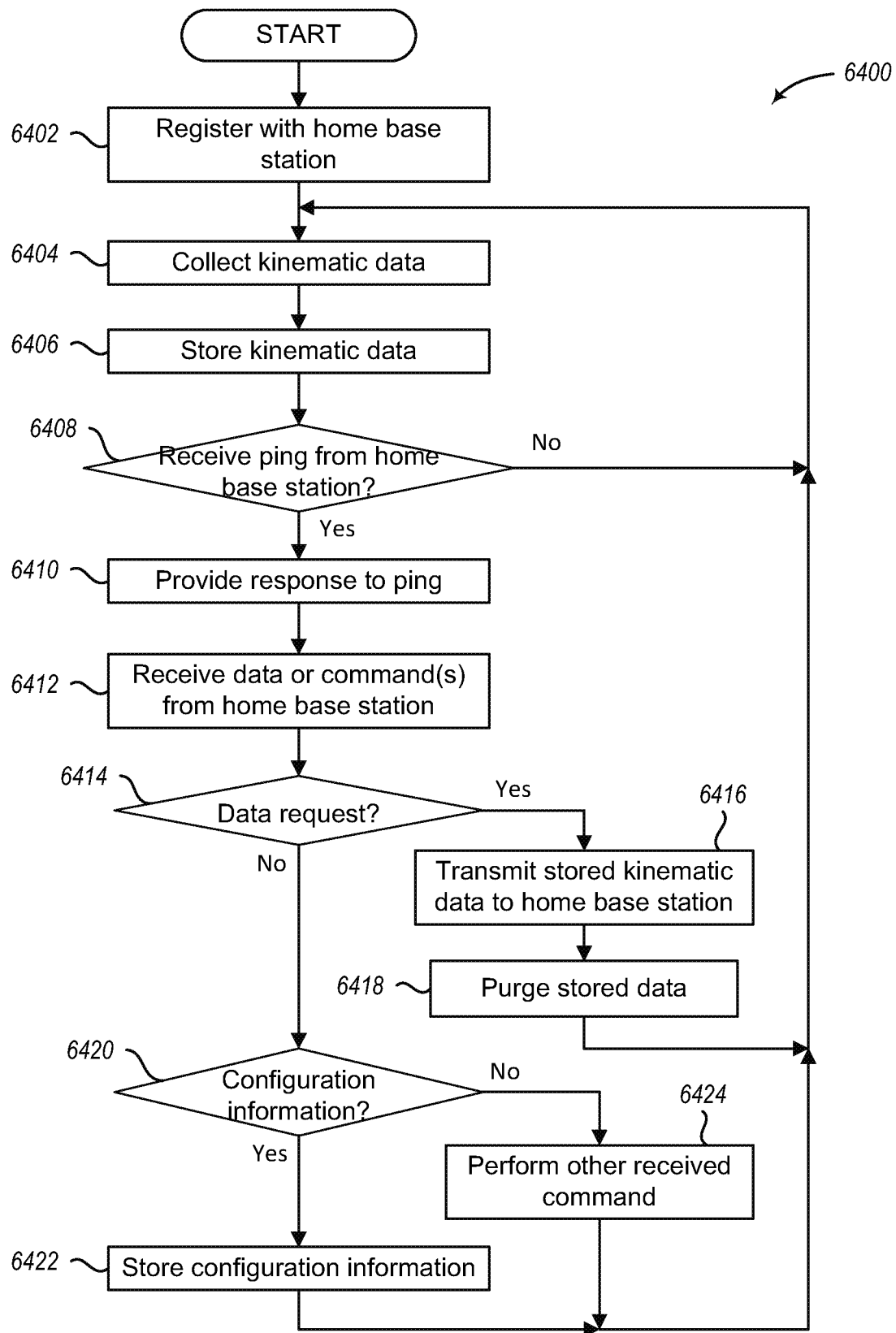
FIG. 37 is a logical flow diagram generally showing one embodiment of a kinematic data collection, storage, and data communication process.

FIG. 37 is a logical flow diagram 6400 generally showing one embodiment of a kinematic data collection, storage, and data communication process 6400 for collecting and storing kinematic data and communicating it from the kinematic implantable device 6102 to a home base station 6104. Process 6400 begins at a start block. At block 6402, the kinematic implantable device 6102 registers with a home base station (e.g., home base station 6108 in FIG. 34). In various embodiments, the kinematic implantable device 6102 may register with the home base station 6108 by responding to a ping by the home base station 6108 with an identifier of the kinematic implantable device 6102. In other embodiments, the home base station 6108 may receive the kinematic implantable device identifier from another computing device, such as from the cloud 6116, or it may be manually input by the medical practitioner of the patient.

Process 6400 proceeds to block 6404, where the kinematic implantable device 6102 collects kinematic data, operational data, and other data. As described herein, the kinematic implantable device 6102 may operate in various different modes to collect different amounts or types of data at different rates or at different times based on the mode the kinematic implantable device is currently operating in. For example, the kinematic implantable device 6102 may wake up and collected pedometer data, movement data, or other data once every minute to determine if the patient is performing a predetermined activity, such as walking. If the kinematic implantable device 6102 determines that the patient is walking or otherwise performing the predetermined activity, it can collect additional data (e.g., linear and rotational acceleration) for a determined time period (e.g., 30 seconds). Once this predetermined time period expires, the kinematic implantable device 6102 may stop collecting data and transition to a different mode, such as a lower data collection mode.

As data is being collected at block 6404, process 6400 stores the data at block 6406. In various embodiments, the kinematic implantable device may store the collected data in a buffer in memory 6206 for later communication to the home base station 6108. In some embodiments, the buffer may be a FIFO buffer such that the kinematic implantable device 6102 will continue to collect data even after the buffer is full. But in other embodiments, the kinematic implantable device 6102 may stop collecting data once the buffer is full. The kinematic implantable device 6102 can collect a maximum amount of data that is proportional to the size of the buffer and then transition into a non-data or low-data collection mode. In this way, the kinematic implantable device 6102 can conserve power by not superfluously collecting and storing data that is overwriting other previously stored data.

In some embodiments, the kinematic implantable device 6102 may store a protected/unprotected table, such that data labeled as protected will not be overwritten. In various embodiments, some types of collected data, such as collected while the kinematic implantable device 6102 is in a specific mode of operation, may be labeled as protected, while other collected data may be labeled as unprotected.

The kinematic implantable device 6102 may continue to collect and store kinematic or other data based on its current mode of operation. The current mode of operation may periodically change based on time of day, amount of data collected, determination of a particular activity, or the like. The change in the mode of operation may result in the collection and storage or more or less data.

Process 6400 proceeds to decision block 6408, where a determination is made whether the kinematic implantable device 6102 has received a ping from the home base station 6108. In various embodiments, the home base station 6108 may ping the kinematic implantable device to determine if the kinematic implantable device 6102 is within communication range of the home base station 6108. In some embodiments, the home base station 6108 may ping the kinematic implantable device 6102 in the middle of the night (e.g., 2:00 am). In this way, if the home base station 6108 is positioned in the patient's bedroom as the patient sleeps, there is a higher likelihood that in the middle of the night the kinematic implantable device 6102 will be within range of the home base station 6108. If the kinematic implantable device 6102 is within range of the home base station 6108, then it will receive the ping and process 6400 proceeds to block 6410; otherwise, process 6400 loops to block 6404 to continue to collect and store data in accordance with configuration information and modes of operation.

At block 6410, the kinematic implantable device 6102 responds to the ping by providing a confirmation message back to the home base station 6108. The home base station 6108 can utilize this response message as an indication that the kinematic implantable device 6102 is within communication range of the home base station 6108.

In response to receiving the response message, the home base station 6108 may provide data or commands to the kinematic implantable device 6102, which are received by the kinematic implantable device 6102 at block 6412. The data, commands, or other information that is received may include updated configuration information (e.g., a change in the mode of operation, a change in the timing or rate at which kinematic data is collected, the type of kinematic data that is collected), a request to transmit kinematic or other data stored by the kinematic implantable device 6102 to the home base station 6108, a request to perform a self-test or some other procedure.

Process 6400 proceeds next to decision block 6414, where a determination is made whether the received data or commands includes a request for stored collected data. This command indicates that the home base station 6108 is ready to receive stored data from the kinematic implantable device 6102. If the command is a request for data, then process 6400 flows to block 6416; otherwise, process 6400 flows to decision block 6420.

At block 6416, the kinematic implantable device 6102 communicates the stored data to the home base station 6108. The data that is transmitted may include, but is not limited to, log data, the collected and stored IMU data (e.g., step count, accelerometer data, gyroscope data, etc.), self-test results (if performed), battery voltage, and other data.

Process 6400 continues at block 6418, where the kinematic implantable device 6102 purges some or all of the stored collected data. In various embodiments, the kinematic implantable device 6102 may wait until it receives a message from the home base station 6108 confirming that home base station 6108 successfully received data before purging the stored collected data from memory 6206. In other embodiments, the kinematic implantable device 6102 may purge data as it is being transferred to the home base station 6108 without waiting for a response from the home base station 6108.

In various embodiments, purging the data may include deleting the data from the memory 6206 of the kinematic implantable device 6102. However, this process may consume too much power. So, in other embodiments, the kinematic implantable device 6102 may store a table identifying which data has been transferred to the home base station 6108 and which data has not. In at least one such embodiment, the kinematic implantable device 6102 may use the protected/unprotected table used when storing the data at block 6406. Once the protected or unprotected data is transferred to the home base station 6108, it can be labeled as unprotected and be overwritten at block 6406.

After block 6418, process 6400 loops to block 6404 to continue to collect and store data.

If, at decision block 6414, the received data or commands are not a request for the transfer of the collected data, then process 6400 flows from decision block 6414 to decision block 6420. At decision block 6420, a determination is made whether the received data or commands includes updated configuration information. If the data includes updated configuration data, then process 6400 flows to block 6422 to store the updated configuration information similar to block 6308 in FIG. 36; otherwise, process 6400 flows to block 6424 to perform other commands received from the home base station 6108. Examples, of the other commands may include a request for the kinematic implantable device 6102 to perform a self-test, reboot, or perform some other actions.

After blocks 6422 and 6424, process 6400 loops to block 6404 to continue to collect and store additional data, such as kinematic data.

Process 6400 may continue to loop until the battery of the kinematic implantable device 6102 fails or until the kinematic implantable device 6102 is put into a non-collection mode of operation, such as when the patient is no longer being monitored. In various embodiments, the kinematic implantable device 6102 may be put into a non-collection mode of operation based on an update to the configuration information or an elapse of a predetermined lifetime of the kinematic implantable device 6102.

Figure 38:
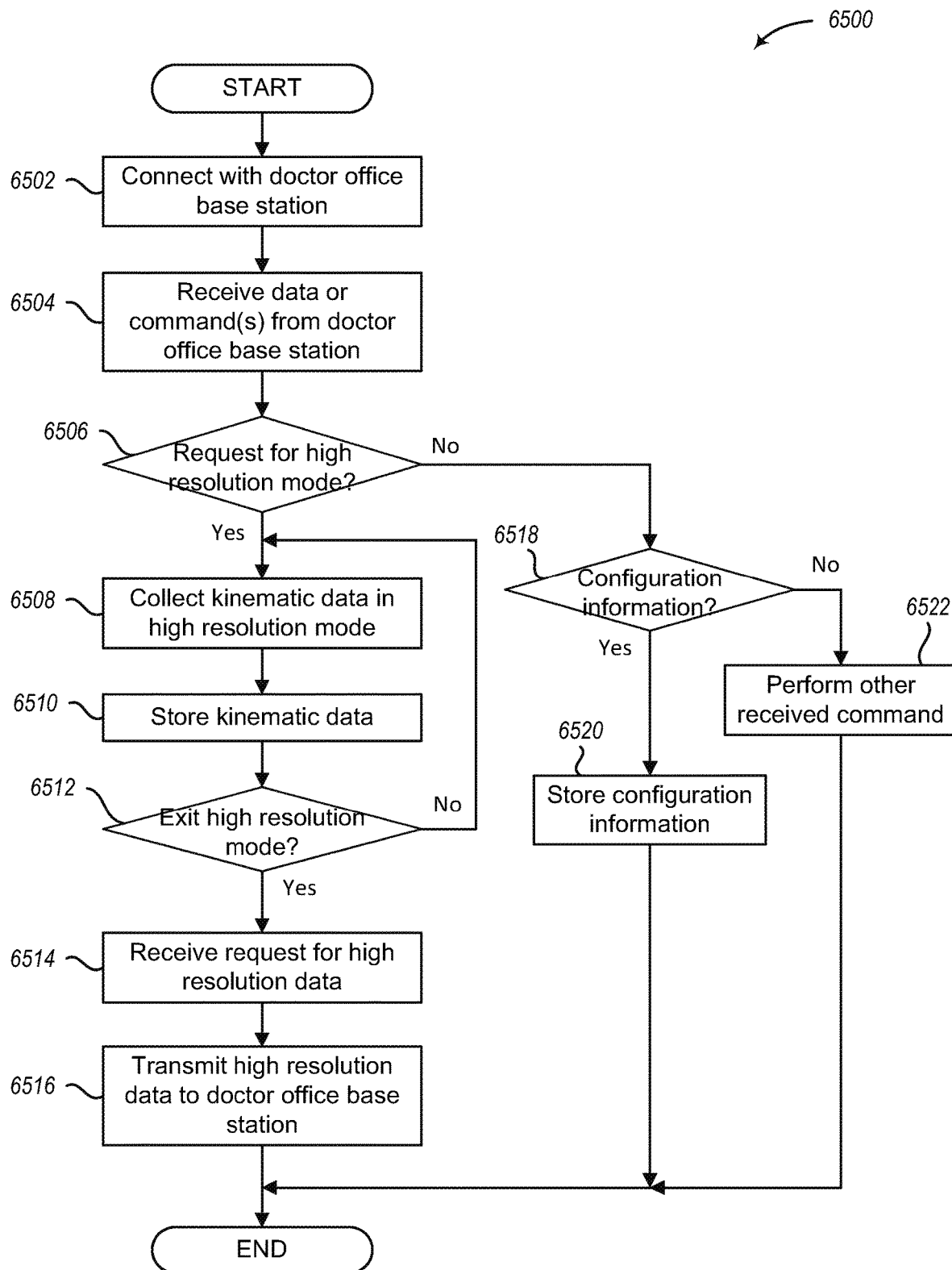
FIG. 38 illustrates a logical flow diagram generally showing one embodiment of a process for temporarily increasing an amount of data collected by the kinematic implantable device and transferring the data to a doctor office base station in accordance with embodiments described herein.

FIG. 38 is a logical flow diagram generally showing one embodiment of a process for temporarily increasing an amount of data collected by the kinematic implantable device 6102 and transferring the data to a doctor office base station 112. Process 6500 begins at a start block. At block 6502, the kinematic implantable device 6102 connects with a doctor office base station (e.g., doctor office base station 6112 in FIG. 34). In various embodiments, the kinematic implantable device 6102 may connect with the doctor office base station 6112 by responding to a connection request provided by the doctor office base station 6112.

Process 6500 proceeds next to block 6504 where the kinematic implantable device 6102 receives data, commands, or other information from the doctor office base station 6112. The data, commands, or other information may include updated configuration information (e.g., a change in the mode of operation, a change in the timing or rate at which data, such as kinematic data, is collected, the type of data that is collected), a request to enter a high-resolution mode, a request to perform a self-test, or some other procedure.

Process 6500 proceeds next to decision block 6506, where a determination is made whether the received data, commands, or other information includes a request to put the kinematic implantable device 6102 into a high-resolution mode. In some embodiments, the kinematic implantable device 6102 receives a command from the doctor office base station 6112 to put the kinematic implantable device 6102 into the high-resolution mode. In other embodiments, the kinematic implantable device 6102 receives updated configuration information, which when stored by the kinematic implantable device 6102 puts the kinematic implantable device 6102 into the high-resolution mode. If a request to put the kinematic implantable device 6102 into the high-resolution mode is received, then process 6500 flows to block 6508; otherwise, process 6500 flows to decision block 6518.

At block 6508, the kinematic implantable device 6102 collects data, such as kinematic data, in a high-resolution mode. As described herein, the high-resolution mode may be a mode of operation where the kinematic implantable device 6102 collects a large amount of data for a predetermined period of time while the medical practitioner is observing the patient perform a given movement or activity.

For example, the kinematic implantable device 6102 may collect linear and rotational acceleration data from the accelerometer and the gyroscope every second for a predetermine time period (e.g., 360 seconds). Once this predetermined time period expires, the kinematic implantable device 6102 may stop collecting data and transition to a different lower data collection mode.

As the high-resolution kinematic data is being collected at block 6508, process 6500 stores the high-resolution data at block 6510. In various embodiments, the kinematic implantable device 6102 may store the collected data in memory for later communication to the doctor office base station 6112. In some embodiments, the high-resolution data may be marked as protected so that it will not be overwritten until it is communicated to the doctor office base station 6112.

Process 6500 proceeds next to decision block 6512, where a determination is made whether to exit the high-resolution mode. In some embodiments, the medical practitioner can activate a button on the doctor office base station 6112 (or on the doctor office configuration computing device 6114) to exit the high-resolution mode. Upon activation of the button, the doctor office base station 6112 sends a command to the kinematic implantable device 6102 to halt the high-resolution mode. In some embodiments, the kinematic implantable device 6102 receives a command from the doctor office base station 6112 to exit the high-resolution mode. In other embodiments, the kinematic implantable device 6102 receives updated configuration information, which when stored by the kinematic implantable device 6102 puts the kinematic implantable device into another, non-high-resolution mode. In yet other embodiments, the high-resolution mode may time out, at which point the kinematic implantable device 6102 transitions to a non-high-resolution mode. If the high-resolution mode exits, then process 6500 flows to block 6514; otherwise, process 6500 loops to block 6508 to continue to collect and store data in the high-resolution mode until the kinematic implantable device 6102 exits the high-resolution mode.

At block 6514, the kinematic implantable device 6102 receives a request for the stored collected high-resolution data. This command indicates that the doctor office base station 6112 is ready to receive the high-resolution data from the kinematic implantable device 6102.

Process 6500 continues at block 6516, where the kinematic implantable device 6102 transmits the stored high-resolution data to the doctor office base station 6112. In various embodiments, block 6516 employs embodiments similar to those described in association with block 6416 in FIG. 37. At 6416, the stored high-resolution data is communicated to the doctor office base station 6112 rather than the home base station 6108. In various embodiments, block 6516 may also employ embodiments similar to those described in block 6418 in FIG. 37 to purge the high-resolution data from the kinematic implantable device 6102 memory 6206 after the data is transferred to the doctor office base station 6112. After block 6516, process 6500 terminates or returns to a calling process to perform other actions.

If, at decision block 6506, the received request from the doctor office base station 6112 is not a request for the kinematic implantable device 6102 to enter the high-resolution mode, then process 6500 flows from decision block 6502 to decision block 6518. At decision block 6518, a determination is made whether the data received from the doctor office base station 6112 includes updated configuration information. If the data includes updated configuration information, then process 6500 flows to block 6520 to store the updated configuration information similar to block 6308 in FIG. 36; otherwise, process 6500 flows to block 6522 to perform other commands received from the doctor office base station 6112. In various embodiments, block 6522 may employ embodiments similar to those described in conjunction with block 6424 in FIG. 37. After blocks 6520 and 6522, process 6500 terminates or returns to another process to perform other actions.

Figure 39:
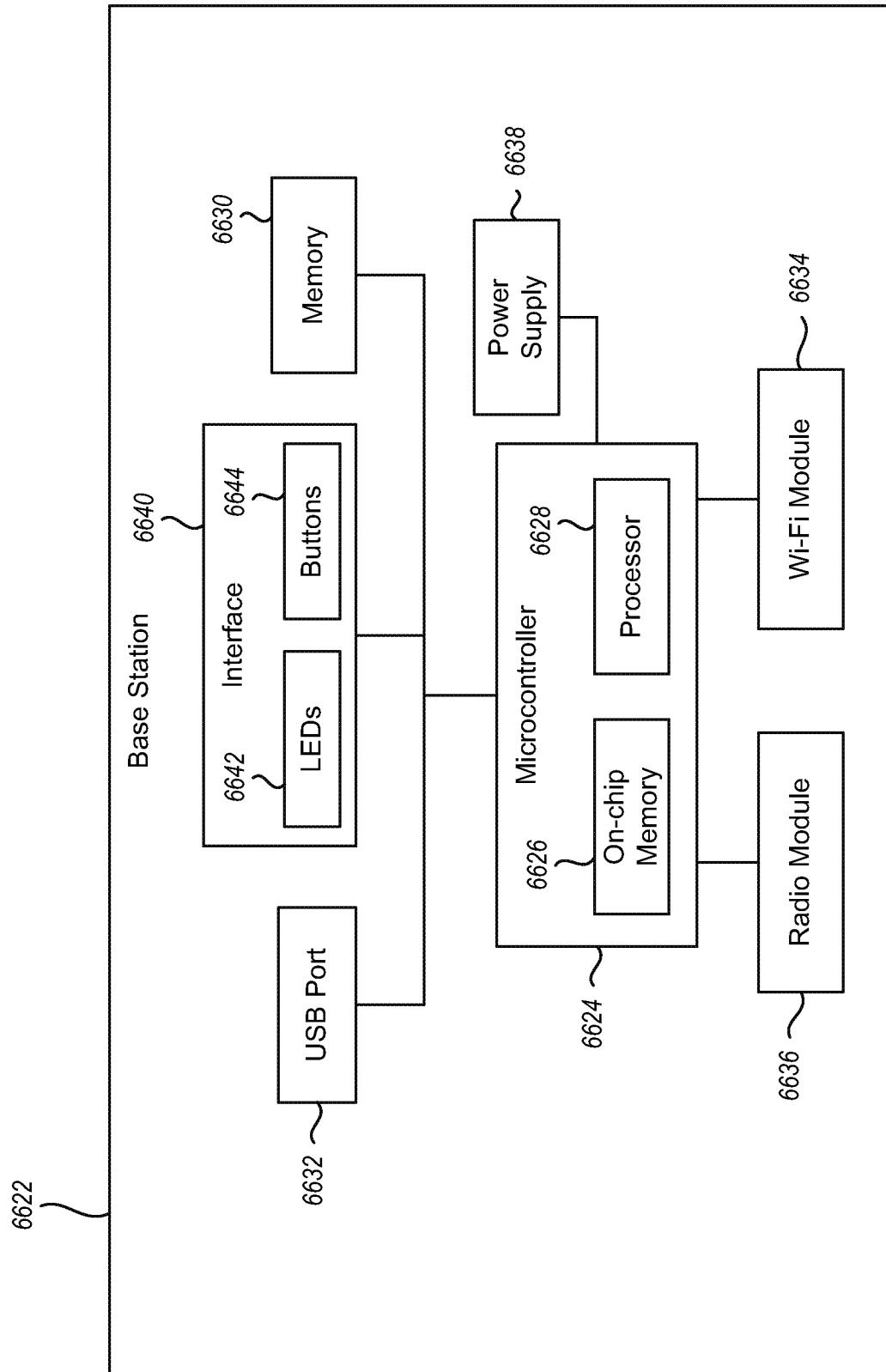
FIG. 39 is an exemplary system diagram of a base station in accordance with embodiments described herein.

FIG. 39 is an exemplary system diagram of a base station. The base station 6622 is an embodiment of the operating room base station 6604, the home base station 6608, and the doctor office base station 6612 illustrated in FIG. 34.

Although the operating room base station 6604, the home base station 6608, and the doctor office base station 6612 provide different functionality, the components of each type of base station may be similar to one another and include some or all of the components illustrated in FIG. 39.

In some embodiments, a separate base station 6622 may be configured to provide the functionality of each separate type of base station (operating room base station, home base station, and doctor office base station). For example, the operating room base station may be designed with a cleanable outer shell to meet cleanliness and sanitization standards of an operating room, and also be enabled to connect to and communicate with an operating room configuration computer. Similarly, the doctor office base station may be arranged with a cleanable outer shell, but to a lesser degree than the sanitization requirements of the operating room, and also be enabled to connect to and communicate with a doctor office configuration computer. In contrast, the home base station may be more portable, discrete, and stylish to blend into the patient's home and lifestyle. Although the appearance and functionality of each type of base station may be slightly different, the overall components of each base station are the same or similar to what is illustrated in FIG. 39.

In other embodiments, the base station 6622 may be configured to provide the functionality of multiple types of base stations. For example, in one embodiment, the functionality of the operating room base station and the doctor office base station may be provided in a single device. Since the operating room base station and the doctor office base station may include an outer shell that can be cleaned, manufacturing a single device with the functionality of both base stations may be more cost effective than manufacturing separate devices. In at least one such embodiment, the operating room configuration computer or the doctor office configuration computer can send a message to the base station 6622 to indicate which mode the base station 6622 is to be executing (as the operating room base station or the doctor office base station).

In another example embodiment, the base station 6622 is configured with the functionality of the operating room base station, the doctor office base station, and the home base station provided in a single device. In at least one such embodiment, the medical practitioner can set which of a plurality of modes the base station 6622 is to be executing— where each separate mode includes the functionality of the separate types of base stations (operating room base station, home base station, and doctor office base station). In various embodiments, the components of the base station 6622 may perform the functionality of each separate type of base station, but installed into a different shell to meet cleanliness and sanitization requirements of the operating room or medical practitioner office.

As illustrated, the base station 6622 includes a microcontroller 6624, a memory 6630, a power supply 6638, a radio module 6636, a Wi-Fi module 6634, a USB port 6632, and an interface 6640. Other logic (e.g., circuits, devices, structures, and the like) are not illustrated for simplicity.

The microcontroller 6624 includes a processor 6628 and an on-chip memory 6626. The on-chip memory 6626 stores instructions that are executed by the processor 6628 to perform the actions and functionality of the base station 6622 as described herein. In some embodiments, the on-chip memory 6626 may store the different base station modes in which the base station 6622 can operate.

In at least some embodiments described herein, radio module 6636 is a short range communication device configured to communicate with a kinematic implantable device, such as kinematic implantable device 6602 in FIG. 34. In various embodiments, the radio module 6636 communicates information between the kinematic implantable device and the base station 6622 using the medical implant communication service (MICS) standards, medical device radio communications service (MedRadio) or other such protocols. In at least one embodiment, the radio module 6636 communicates with the kinematic implantable device over the 402 MHz to 405 MHz MICS band.

The Wi-Fi module 6634 is a communication device configured to implement a Wi-Fi radio to wirelessly communicate with other computing devices. For example, the Wi-Fi module 6634 can be utilized by the base station 6622 to communicate with the operating room configuration computer 6606, the doctor office configuration computer 6614, the home network 6610, or the cloud 6616 illustrated in FIG. 34. In various embodiments, the Wi-Fi module 6634 includes support of TCP/IP (Transmission Control Protocol/Internet Protocol) and TLS (Transport Layer security) protocols to provide secure communications and secure data transfers between the base station 6622 and the other computing devices.

The power supply 6638 provides power to the base station 6622. The power supply 6638 may include an interface to receive power from an external source, such as via a power cord. In some embodiments, the power supply 6638 may include a battery to provide power in the event that the external power becomes disconnected.

In various embodiments, the USB port 6632 is configured to transmit communications between the base station 6622 and the operating room configuration computer or the doctor office configuration computer. In some embodiments, the base station 6622 may be powered through the USB port 6632.

The memory 6630 may be RAM, flash, or any other type of transitory or non-transitory computer readable medium. The memory 6630 stores data received from a kinematic implantable device, configuration information for the kinematic implantable device, log records, other base station data, software instructions, and other information.

The interface 6640 is configured to receive input from or display information to a user (e.g., the surgeon or another medical practitioner). As illustrated, the interface 6640 includes LEDs 6642 and buttons 6644. The LEDs 6642 can display a status of the base station 6622 (e.g., power on or off, connected to a kinematic implantable device, if the kinematic implantable device is operating in a high resolution mode, acknowledgement of an input of a pain or event marker, and the like). The buttons 6644 can provide interface controls to the user to select base station actions (e.g., power on or off, activate kinematic implantable device high resolution mode, input of a pain or event marker, and the like). Although interface 6640 is illustrated with LEDs and buttons, embodiments are not so limited. For example, in some embodiments where the base station 6622 is operating as an operating room base station, the interface 6640 may include a touch screen that can be used by the surgeon to configure the kinematic implantable device in the operating room, which may provide functionality similar to that of the operating room configuration computer. In other embodiments where the base station 6622 is operating as a doctor office base station, the interface 6640 may include a touch screen that can be used by the medical practitioner to modify configuration information of the kinematic implantable device or to view kinematic data received from the kinematic implantable device, which may provide functionality similar to that of the doctor office configuration computer.

The operation of certain aspects of the disclosure will now be described with respect to FIGS. 40 to 42. In at least one of various embodiments, processes 6650, 6670, and 6700 described in conjunction with FIGS. 40 to 42, respectively, may be implemented by or executed on a base station, such as base station 6622 in FIG. 39. In some embodiments, process 6650 may be implemented by or executed on the operating room base station 6604 in FIG. 34, process 6670 may be implemented by or executed on the home base station 6608 in FIG. 34, and process 6700 may be implemented by or executed on the doctor office base station 6612 in FIG. 34.

Figure 40:
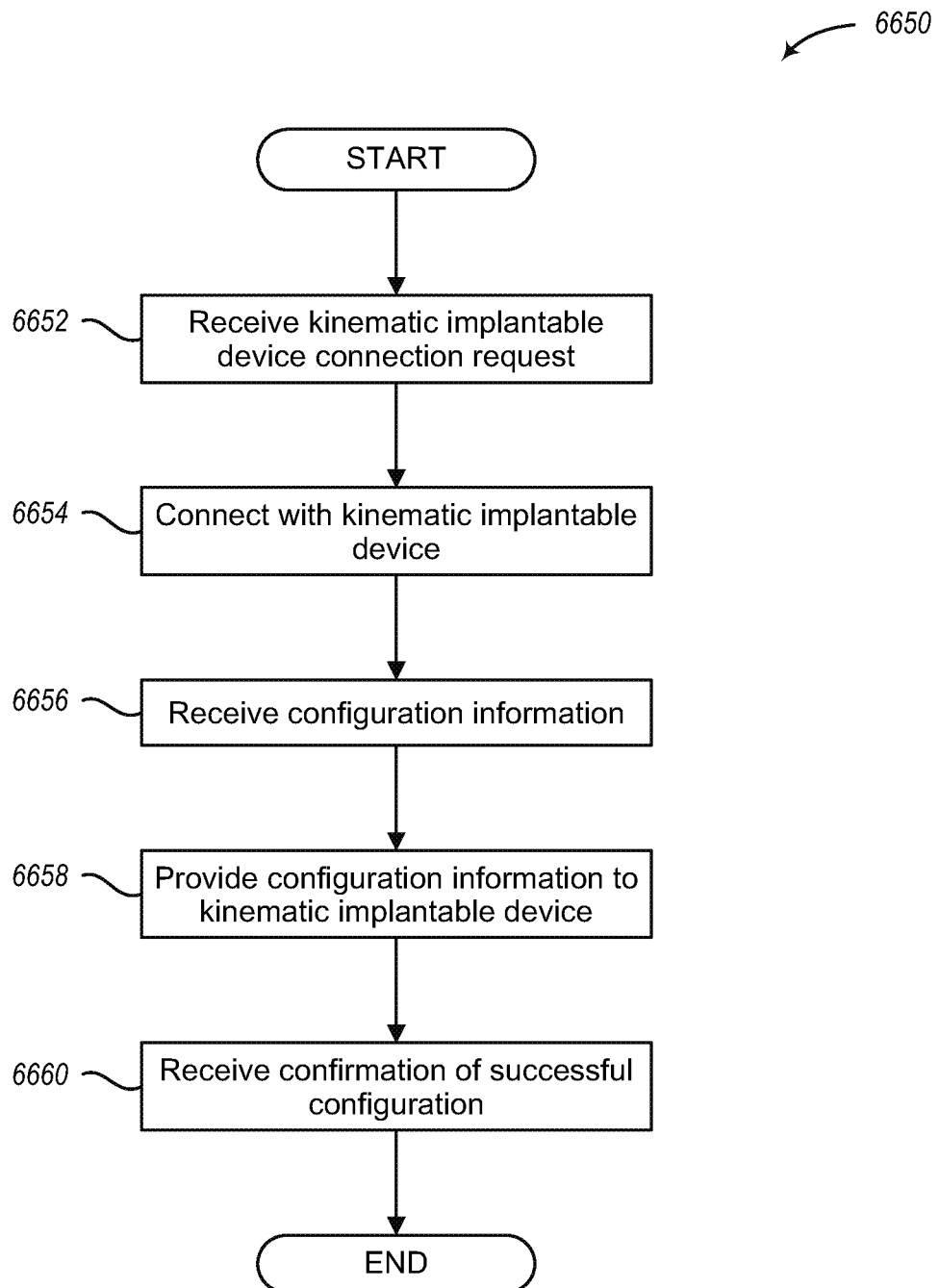
FIG. 40 is a logical flow diagram generally showing one embodiment of a process for configuring a kinematic implantable device from an operating room base station.

FIG. 40 illustrates a logical flow diagram generally showing one embodiment of a process for configuring a kinematic implantable device from an operating room base station. Process 6650 begins at a start block.

At block 6652, the operating room base station receives a request to connect to a kinematic implantable device (e.g., kinematic implantable device 6602 in FIG. 34). In some embodiments, a surgeon or another medical practitioner in the operating room may initiate the connection request by pushing a connection or configuration button on the operating room base station. In other embodiments, the operating room base station may receive the connection request from an operating room configuration computer (e.g., operating room configuration computer 6606 in FIG. 34).

Process 6650 proceeds to block 6654, where the operating room base station connects with the kinematic implantable device. In various embodiments, the operating room base station may provide a wake-up command to the kinematic implantable device. The wake-up command may include identification information of the operating room base station so that the kinematic implantable device can establish a connection with the operating room base station. In some embodiments, the operating room base station and the kinematic implantable device may establish a dedicated connection between the devices. In other embodiments, the devices may be connected through a broadcast scheme without a dedicated network connection.

In various embodiments, the operating room base station may connect to the kinematic implantable device prior to the medical practitioner (e.g., surgeon) implanting the kinematic implantable device into the patient. In this way, the operating room base station or the kinematic implantable device can detect a problem with the kinematic implantable device before it is implanted into the patient. In some embodiments, once the kinematic implantable device wakes up, it can perform a self-test to determine if it is functioning properly. And if so, the operating room base station may receive a confirmation message from the kinematic implantable device indicating that it is functioning properly.

Process 6650 continues at block 6656, where the operating room base station receives configuration information for the kinematic implantable device. In some embodiments, some or all of the configuration information may be received from the operating room configuration computer. In other embodiments, some or all of the configuration information may be predetermined and stored in the memory of the operating room base station. In yet other embodiments, the operating room base station may receive the configuration from the medical practitioner (e.g., surgeon) through a user interface on the operating room base station (or the operating room configuration computer). The configuration information may be identification information or information that defines one or more parameters associated with the collection of kinematic data by the kinematic implantable device, or some other information. Examples of configuration information include, but are not limited to, a time, day, identification of the body part in which the kinematic implantable device is associated, identification of associated implanted devices, medical practitioner information, patient identification (e.g., encoded or otherwise obfuscated information), operating room information, an initial mode of operation of the kinematic implantable device, settings for one or more sensors on the kinematic implantable device for one or more different modes of operation, specification of a particular movement that triggers a change in the mode of operation, radio settings, data collection information, home base station identification information, and the like.

Process 6650 proceeds next to block 6658, where the operating room base station provides the configuration information to the kinematic implantable device for the kinematic implantable device to store the configuration information and begin operation. In some embodiments, some or all of the configuration information may be provided to the kinematic implantable device prior to or after the implantation of the device into the patient.

Process 6650 continues next at block 6660, where the operating room base station receives a confirmation of a successful configuration of the kinematic implantable device. If unsuccessful, the operating room base station may receive an error message from the kinematic implantable device or it may not receive any response, which would be interpreted by the operating room base station as a failure to properly configure the kinematic implantable device.

After block 6660, process 6650 terminates or returns to a calling process to perform other actions.

Figure 41:
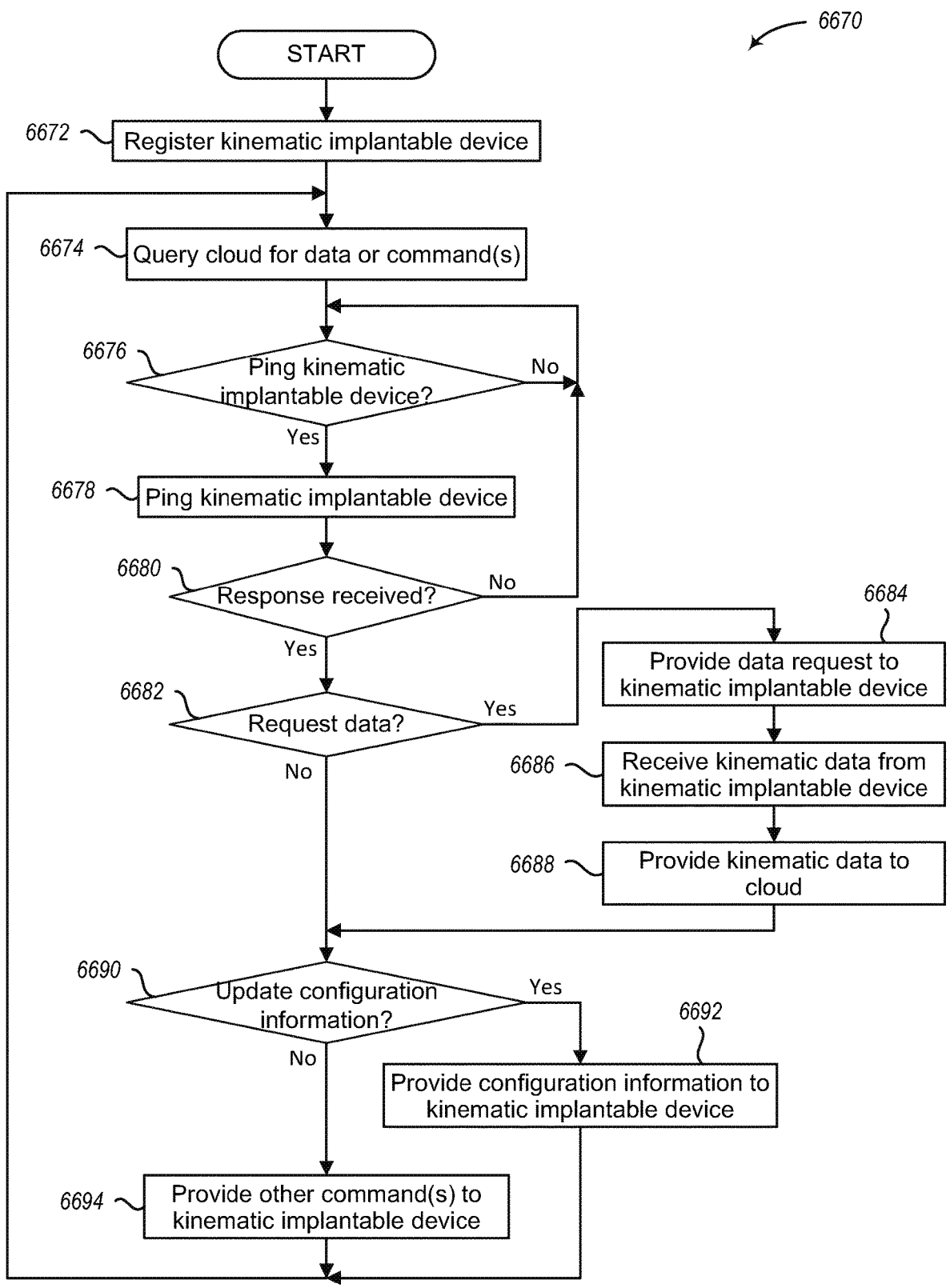
FIG. 41 is a logical flow diagram generally showing one embodiment of a process for receiving kinematic data at a home base station from a kinematic implantable device that collected the kinematic data.

FIG. 41 is a logical flow diagram generally showing one embodiment of a process for receiving kinematic data at a home base station from a kinematic implantable device that collected the kinematic data. Process 6670 begins at a start block.

At block 6672, the home base station (e.g., home base station 6608 in FIG. 34) registers a kinematic implantable device. In some embodiments, the home base station periodically transmits a message requesting that a kinematic implantable device respond with registration information. If the kinematic implantable device is within communication range of the home base station, then the home base station can receive a response message from the kinematic implantable device. In some embodiments, the response may include identifier of the kinematic implantable device that sent the response. In other embodiments, the home base station may receive the kinematic implantable device identifier from another computing device, such as from the cloud (e.g., cloud 6616 in FIG. 34), or it may be manually input by the medical practitioner of the patient.

Process 6670 proceeds to block 6674, where the home base station queries the cloud for data or commands that the home base station can forward to the kinematic implantable device. The data, commands, or other information that is received may include updated configuration information (e.g., a change in the mode of operation, a change in the timing or rate at which kinematic data is collected, the type of kinematic data that is collected, and the like), a request to transmit kinematic data stored by the kinematic implantable device to the home base station, a request to perform a self-test or other diagnostic procedure, and the like.

Process 6670 continues at decision block 6676, where a determination is made whether the home base station is permitted to ping the kinematic implantable device to see if the kinematic implantable device is within communication range. In various embodiments, this determination is based on a communication window that defines when the home base station is permitted to attempt to contact the kinematic implantable device. For example, the communication window may be scheduled in the middle of the night. In this way, if the home base station is positioned in the patient's bedroom as the patient sleeps, then there is a higher likelihood in the middle of the night that the kinematic implantable device will be within range of the home base station and respond to the ping. If the home base station is within the communication window, then process 6670 flows to block 6678; otherwise, process 6670 loops to decision block 6676 to wait until it is within the communication window.

At block 6678, the home base station transmits a ping or other message requesting a response from any kinematic implantable device that receives the ping. In various embodiments, this message may be the same or similar to the message sent in block 6672 to attempt to register the kinematic implantable device.

Process 6670 continues at decision block 6680, where a determination is made whether the home base station receives a response to the ping. If the kinematic implantable device is within communication range of the home base station, then it sends a response to the home base station. If the home base station receives a response from the kinematic implantable device, then process 6670 proceeds to decision block 6682; otherwise, process 6670 loops to decision block 6676 to continue to ping the kinematic implantable device while within the communication window.

At decision block 6682, a determination is made whether the received data or commands at block 6674 include a request for kinematic data that was collected and stored by the kinematic implantable device. If the command is a request for data, then process 6670 flows to block 6684; otherwise, process 6670 flows to decision block 6690.

At block 6684, the home base station provides a data request to the kinematic implantable device. This request indicates that the home base station is ready to receive stored data from the kinematic implantable device. In some embodiments, this request is a message instructing the kinematic implantable device to begin communicating some or all the data that it collected and stored.

Process 6670 continues at block 6686, where the home base station receives the stored data from the kinematic implantable device. The data that is communicated may include, but is not limited to, log data, the collected and stored kinematic data (e.g., step count, accelerometer data, gyroscope data, and the like), self-test results (if performed), battery voltage, and the like.

In some embodiments, if the transfer of data was successful, home base station may send an acknowledgment message to the kinematic implantable device indicating the successful transfer. This message allows the kinematic implantable device to purge the stored data once it is successfully transferred. However, if the transfer was unsuccessful, the home base station may send a message to the kinematic implantable device requesting the kinematic implantable device to retransmit the data. Since retransmission of data from the kinematic implantable device to the home base station would use up additional power, the kinematic implantable device may, in some embodiments, discard the data and not retransmit it to the home base station, regardless of whether the transmission was successful or not.

Process 6670 proceeds to block 6688, where the home base station provides the data to the cloud (e.g., cloud 6616 in FIG. 34). In various embodiments, the data is stored in a database for aggregation with other kinematic data that was previously collected from the kinematic implantable device or from other kinematic implantable devices.

After block 6688, or if, at decision block 6684, the received data or commands are not a request for the transfer of the collected data, then process 6670 flows to decision block 6690. At decision block 6690, a determination is made whether the received data or commands includes updated configuration information. If the data includes updated configuration data, then process 6670 flows to block 6692 to provide the updated configuration information to the kinematic implantable device similar to block 6658 in FIG. 41; otherwise, process 6670 flows to block 6694 to provide other commands to the kinematic implantable device. Examples, of the other commands may include a request for the kinematic implantable device to perform a self-test, reboot, and the like.

After blocks 6692 and 6694, process 6670 loops to block 6674 to continue to query the cloud for additional data or commands and continue to collect data from the kinematic implantable device if the kinematic implantable device is within communication range of the home base station during the communication window.

Process 6670 may continue to loop until the home base station is powered down, until the kinematic implantable device fails, or until the kinematic implantable device is put into a non-collection mode of operation, such as when the patient is no longer being monitored. In various embodiments, the kinematic implantable device may be put into a non-collection mode of operation based on an update to the configuration information or an elapse of a predetermined lifetime of the kinematic implantable device. In at least one embodiment, the kinematic implantable device may send a notification to the home base station indicating that it will no longer be collecting data and the home base station can stop pinging the kinematic implantable device.

Although FIG. 41 is described as the home base station communicating with a single kinematic implantable device, embodiments are not so limited. Since a patient (or multiple patients in a single home) may have multiple kinematic implantable devices implanted in their body—for the same or different monitoring purposes—the home base station can communicate with each of the kinematic implantable devices when such devices are within communication range of the home base station.

In some embodiments, the home base station may communicate simultaneously with each of the plurality of kinematic implantable devices. In other embodiments, the home base station communicates with one kinematic implantable device at a given point in time until that communication session has ended. For example if the home base station receives a ping response from kinematic_implantable_device_1, then the home base station communicates with that device until the kinematic data is successfully transmitted from that device to the home base station, until the updated configuration information is provided to the kinematic_implantable_device_1, until the kinematic_implantable_device_1 executes the other provided commands, or the home base station has not received a communication from the kinematic_implantable_device_1 for a predetermined amount of time. Once the home base station is finished communicating with the kinematic_implantable_device_1, then it may transmit another ping to determine if there is another kinematic implantable device within communication range of the home base station. At that point, the home base station may receive a ping response from kinematic_i- mplantable_device_2, and may begin communicating with this other device. One of the purposes of communicating with a single kinematic implantable device at a time is to reduce the possibility of missed transmissions and resent communications, since every retransmission uses additional battery power of the kinematic implantable devices.

Figure 42:
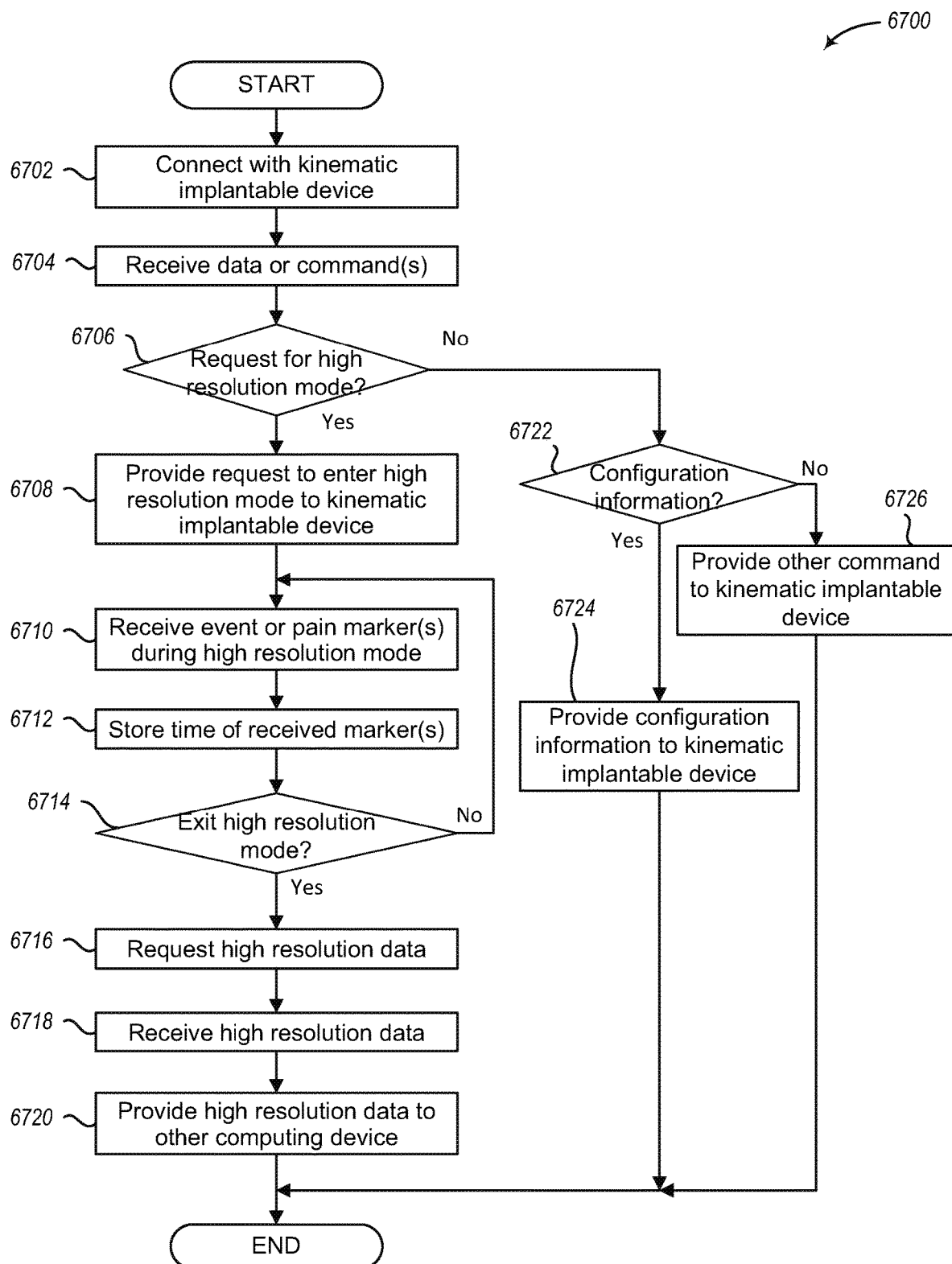
FIG. 42 is a logical flow diagram generally showing one embodiment of a process for receiving, at a doctor office base station and from a kinematic implantable device, kinematic data that was collected by the kinematic implantable device.

FIG. 42 is a logical flow diagram generally showing one embodiment of a process for receiving, at a doctor office base station and from a kinematic implantable device, kinematic data that was collected by the kinematic implantable device. Process 6700 begins at a start block.

At block 6702, the doctor office base station (e.g., doctor office base station 6612 in FIG. 34) connects with a kinematic implantable device associated with a patient. In various embodiments, the doctor office base station may send a connection request to the kinematic implantable device, similar to what is described in conjunction with block 6654 in FIG. 41. A connection between the doctor office base station and the kinematic implantable device may be established in response to the doctor office base station receiving a response from the kinematic implantable device.

Process 6700 proceeds next to block 6704, where the doctor office base station receives data, commands, or other information from the medical practitioner. In some embodiments, the medical practitioner may utilize a doctor office computing device (e.g., doctor office configuration computing device 6614 in FIG. 34) to input the information. In other embodiments, the medical practitioner may provide the information directly to the doctor office base station, such as through a user interface on the doctor office base station. The data, commands, or other information may include updated configuration information (e.g., a change in the mode of operation, a change in the timing or rate at which kinematic data is collected, the type of data that is collected, and the like.), a request to enter a high-resolution mode, a request to perform a self-test, or some other procedure.

Process 6700 proceeds next to decision block 6706, where a determination is made whether the received data, commands, or other information includes a request to put the kinematic implantable device into a high-resolution mode. If a request to put the kinematic implantable device into the high-resolution mode is received, then process 6700 flows to block 6708; otherwise, process 6700 flows to decision block 6722.

At block 6708, the doctor office base station communicates the high resolution mode request to the kinematic implantable device. In response to receiving the request, the kinematic implantable device begins to collect data, such as kinematic data, in a high-resolution mode. As described herein, the high-resolution mode may be a mode of operation where the kinematic implantable device collects a large amount of data for a predetermined period of time while the medical practitioner is observing the patient perform a given movement or activity.

Process 6700 proceeds to block 6710 while the kinematic implantable device is in the high-resolution mode. At block 6710, the doctor office base station receives event or pain markers from the medical practitioner. In some embodiments, the medical practitioner can input event or pain markers through a user interface on the doctor office base station (or through an interface on the doctor office configuration computing device). The medical practitioner can use these markers to indicate the patient's discomfort in performing the given movement or activity while the high-resolution mode is active.

Process 6700 continues at block 6712, where a time is recorded for the received marker. In various embodiments, the doctor office base station stores a time stamp associated with the medical practitioner's input of the event or pain marker. These time stamps can be synchronized with the high-resolution data collected by the kinematic implantable device.

Process 6700 proceeds next to decision block 6714, where a determination is made whether to exit the high-resolution mode. In some embodiments, the medical practitioner can activate a button on the doctor office base station (or on the doctor office configuration computing device) to exit the high-resolution mode. Upon activation of the button, the doctor office base station sends a command to the kinematic implantable device to halt the high-resolution mode. In other embodiments, the kinematic implantable device may itself terminate the high-resolution mode if it reaches a maximum determined time or amount of collected data for that high-resolution mode session. If the high-resolution mode exits, then process 6700 flows to block 6716; otherwise, process 6700 loops to block 6710 to continue to wait for and receive event or pain markers from the medical practitioner.

At block 6716, the doctor office base station provides a request to the kinematic implantable device for the stored collected high-resolution data. This command indicates that the doctor office base station is ready to receive the high-resolution data from the kinematic implantable device.

Process 6700 continues at block 6718, where the doctor office base station receives the stored high-resolution data from the kinematic implantable device. In various embodiments, block 6718 employs embodiments similar to those described in block 6686 in FIG. 41, but the data is received at the doctor office base station rather than the home base station.

Process 6700 proceeds to block 6720, where the doctor office base station provides the data to another computing device. In some embodiments, the doctor office base station provides the received high-resolution data to the cloud (e.g., cloud 6616 in FIG. 34). In various embodiments, block 6720 may employ embodiments similar to those described in block 6688 in FIG. 41 to provide the data to the cloud.

In other embodiments, the doctor office base station may provide the high-resolution data to the doctor office configuration computing device for display to the medical practitioner. In at least one embodiment, the doctor office base station (or the doctor office configuration computing device) may synchronize the event or pain markers with the received data prior to displaying the data to the medical practitioner. In this way, the medical practitioner can observe the data collected by the kinematic implantable device at the same time that the marker was input. In some other embodiments, the doctor office base station may display the received data to the medical practitioner without the use of the doctor office configuration computing device.

After block 6720, process 6700 terminates or returns to a calling process to perform other actions.

If, at decision block 6706, the received information is not a request for the kinematic implantable device to enter the high-resolution mode, then process 6700 flows from decision block 6706 to decision block 6722. At decision block 6722, a determination is made whether the received information includes updated configuration information. If the information includes updated configuration information, then process 6700 flows to block 6724 to provide the updated configuration information to the kinematic implantable device similar to block 6692 in FIG. 41; otherwise, process 6700 flows to block 6726 to provide other commands to the kinematic implantable device. In various embodiments, block 6724 may employ embodiments similar to those described in conjunction with block 6694 in FIG. 41. After blocks 6724 and 6726, process 6700 terminates or returns to another process to perform other actions.

Although FIG. 42 describes the doctor office base station as connecting to a single kinematic implantable device, embodiments are not so limited. In various other embodiments, process 6700 may be employed by a doctor office base station to concurrently connect to and receive data from a plurality of separate or different kinematic implantable devices. In this way, a single doctor office base station can communicate with a plurality of different kinematic implantable devices, similar to how the home base station can communicate with a plurality of kinematic implantable devices. The plurality of kinematic implantable devices can be associated with a single patient or a plurality of patients.

For example, the doctor office base station may be used in a physical therapy office. At any point during normal business hours, there may be multiple patients in the physical therapy office being seen by one or more medical practitioners. Each medical practitioner can utilize the doctor office base station to put each separate kinematic implantable device into its own high-resolution mode. In this way, each medical practitioner can monitor their respective patients as they perform some movement (e.g., stretching, walking on a treadmill, or receiving other types of physical therapy) associated their respectively associated kinematic implantable device.

In some embodiments, each medical practitioner can utilize a separate doctor office configuration computing device to communicate with one or more respective kinematic implantable devices via the doctor office base station. For example, each of a plurality of doctor office configuration computing devices can establish a Wi-Fi connection (or other wired or wireless connection) with a doctor office base station. The doctor office base station can forward data, commands, or other information (e.g., requests to enter a high-resolution mode or updated configuration information) from the doctor office configuration computing device to a respective kinematic implantable device. Similarly, the doctor office base station can receive data (e.g., high-resolution data) from the plurality of kinematic implantable devices of patients in the physical therapy office and forward it to each respective medical practitioner's doctor office configuration computing device.

Figure 43:
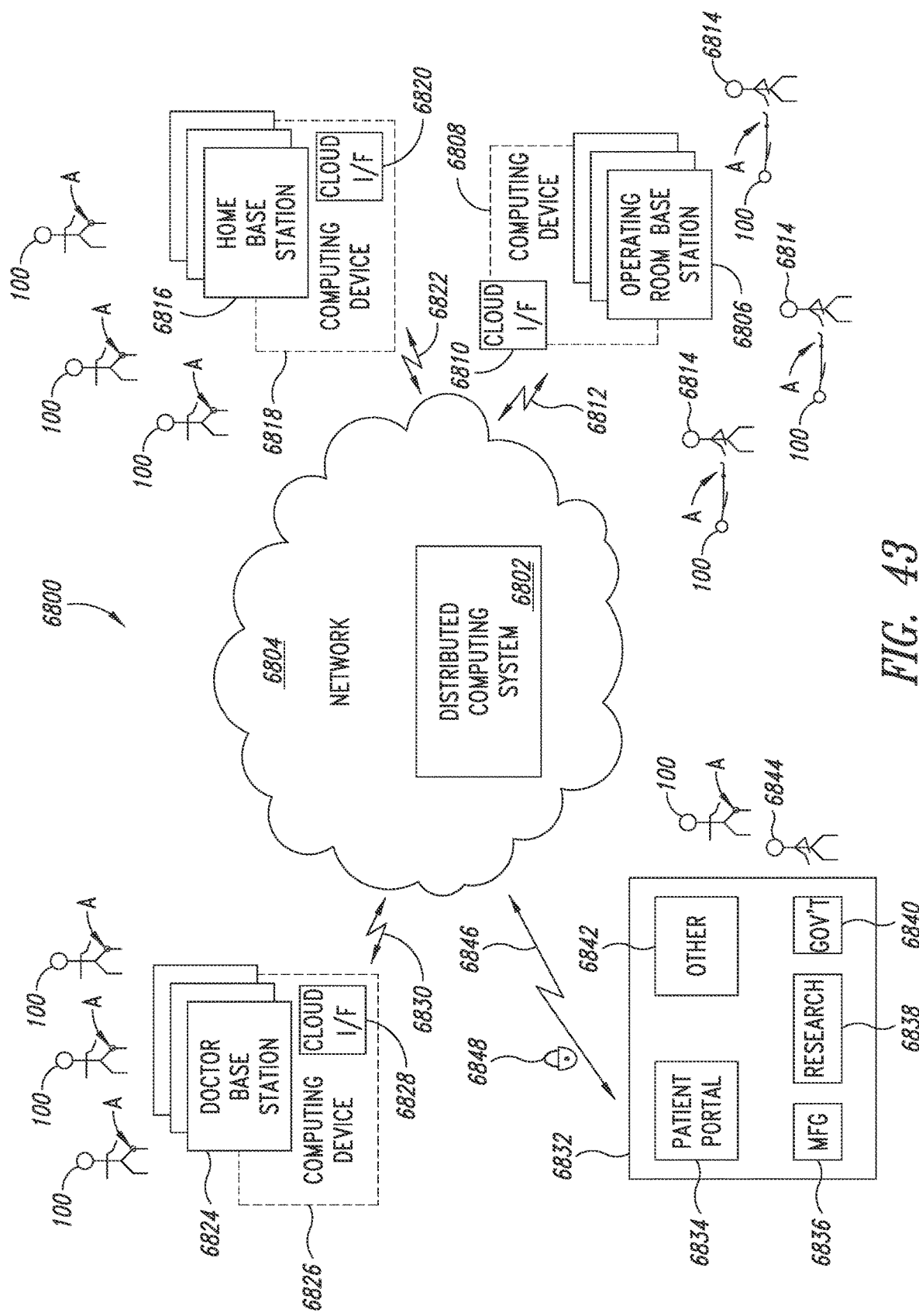
FIG. 43 is an exemplary distributed computing system for alert implantable medical devices.

FIG. 43 is an exemplary distributed computing system for alert implantable medical devices 6800. A network of computing server devices 6802, which may also be referred to as a distributed computing system or simply a "computing server," is arranged to communicatively access a plurality of remote computing devices via a network 6804. The network 6804 may comprise one or more complete or portions of a wide area network (WAN) such as the internet, a cellular telecommunications network, a satellite network or the like. The network 6804 may further comprise one or more complete or portions of a local area network (LAN) such as Ethernet, WiFi, powerline communications, or the like and one or more complete or portions of a personal area network (PAN) such as BLUETOOTH, USB, or the like.

The computing server 6802 includes one or more computing server devices arranged to concurrently communicate information between the computing server 6802 and a plurality of remote devices.

Some of the remote devices are operating room base stations 6806. Each operating room base station 6806 may be associated with an operating room computing device 6808. The operating room base station 6806 may communicate with a computing server 6802 via a cloud interface 6810. As represented by the dashed lines, the operating room base station 6806, the operating room computing device 6808, and the cloud interface 6810 may be integrated into a single device, formed as separate devices, formed or some combination thereof, or formed in another manner.

A medical practitioner 6814, which may be a surgeon, nurse, technician, or some other person, is performing or assisting in the performance of a medical procedure on a patient 100. The medical procedure is performed to implant a kinematic implantable device such as an alert knee prosthesis "A" into the patient 100. During the course of the medical procedure, information 6812 generated by the kinematic implantable device is wirelessly communicated to the operating room base station 6806. During or after the course of the medical procedure, at least some of the information 6812 is communicated from the operating room base station 6806 to the computing server 6802 via the cloud interface 6810.

As shown in FIG. 43, a plurality of medical practitioners 6814 may be performing medical procedures to implement kinematic implantable devices into a plurality of patients 100. In some cases, a single kinematic implantable device is in communication with an associated operating room base station 6806. In other cases, a plurality of kinematic implantable devices associated with a same patient 100 are in communication with a same operating room base station 6806. Once implanted, a single home or doctor's office base station may communicate with multiple implants in a single patient or multiple implants across multiple patients. The computing server 6802 is formed with robust communication logic such that a large number (e.g., tens, hundreds, thousands, or more) of communication operations between the computing server 6802 and any number of base stations may be concurrently conducted.

Some others of the remote devices are home base stations 6816. Each home base station 6816 may be associated with a home computing device 6818. The home base station 6816 may communicate with a computing server 6802 via a cloud interface 6820. As represented by the dashed lines, the home base station 6816, the home computing device 6818, and the cloud interface 6820 may be integrated into a single device, formed as separate devices, formed or some combination thereof, or formed in another manner.

One or more home base stations 6816 are located in a residence of a patient 100. Occasionally, periodically, on a schedule, or at some other times, a kinematic implantable device implanted into the patient 100 wirelessly communicates information 6822 to the home base station 6816. In some cases, information 6822 also includes personally descriptive information provided by the patient 100 or some other user associated with the patient 100. Occasionally, periodically, on a schedule, in conjunction with receiving information 6822, or at some other times, the home base station 6816 will communicate some or all of the information 6822 from or otherwise associated with the kinematic implantable device to the computing server 6802 via the cloud interface 6820. In some cases, a plurality of patients 100 will share a residence. In this case, the home base station 6816 may communicatively couple to a plurality of kinematic implantable devices implanted in the plurality of patients 100. In these or other cases, a single patient 100 will have a plurality of kinematic implantable devices implanted in their body. The home base station 6816 is arranged to distinguish information 6822 generated by or otherwise associated with one kinematic implantable device from information 6822 generated by or otherwise associated with any other kinematic implantable device.

Still others of the remote devices are doctor office base stations 6824. Each doctor office base station 6824 may be associated with a doctor office computing device 6826. The doctor office base station 6824 may communicate with a computing server 6802 via a cloud interface 6828. As represented by the dashed lines, the doctor office base station 6824, the doctor office computing device 6826, and the cloud interface 6828 may be integrated into a single device, formed as separate devices, formed or some combination thereof, or formed in another manner.

After having a medical procedure to implant a kinematic implantable device, patients 100 will sometimes see a medical professional, e.g., a doctor, physician's assistant, nurse, and/or physical therapist. In some cases, a plurality of patients 100 will be in a doctor office at the same time. When a patient 100 is in the doctor office, their kinematic implantable device may occasionally communicate with the doctor office base station 6824. A plurality of kinematic implantable devices in one or many patients 100 may concurrently communicate information to the doctor office base station 6824.

In some cases, a medical practitioner will interact with the doctor office base station 6824 to direct a particular communication event with a particular kinematic implantable device. For example, the medical practitioner may direct a particular kinematic implantable device to enter a high resolution data collection mode. During or after the high resolution data collection mode, collected data is communicated from the kinematic implantable device to the doctor office base station 6824. Occasionally, periodically, on command, on schedule, or on some other basis, the doctor office base station 6824 communicates information 6830 to the computing server 6802.

Various non-base station remote devices 6832 may also communicate with the computing server 6802. The non-base station remote devices 6832 may be any type of computing device such as a personal computer, laptop computer, tablet computer, mobile device, or some other type of computing device. For example, the non-base station remote devices 6832 include patient portal devices 6834, manufacturer computing devices 6836, research entity computing devices 6838, government agency computing devices 6840, and other computing devices 6842. In some cases, the non-base station remote devices 6832 are operated by patients 100, and in other cases, the non-base station remote devices 6832 are operated by non-patient users 6844. In some cases, the non-base station remote devices 6832 are used to communicate information such as personally descriptive information.

The non-base station remote devices 6832 may be used to communicate information 6846 between the particular non-base station remote devices 6832 and the computing server 6802. In some cases, the communicated information 6846 is secure information 6848.

Figure 44:
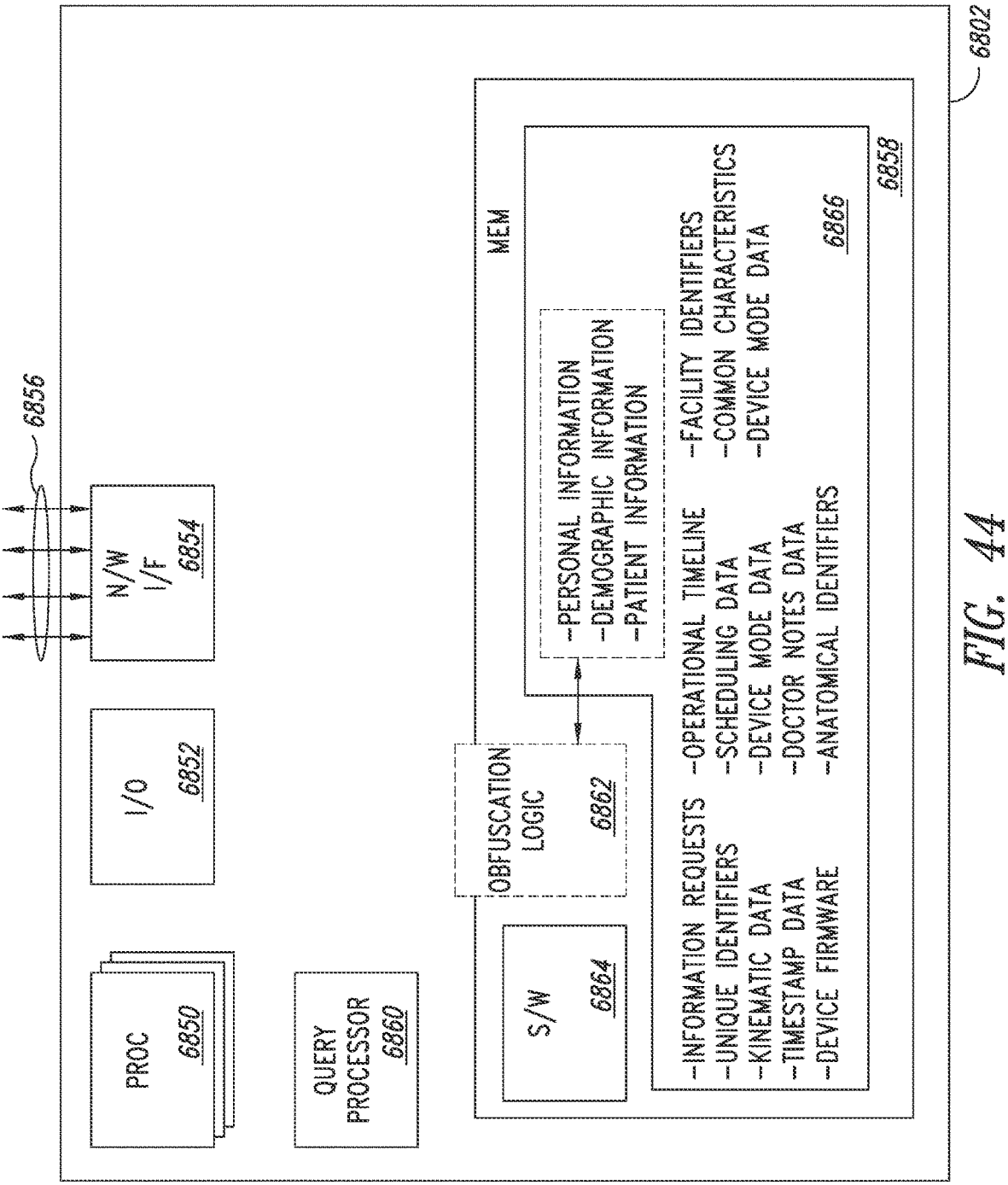
FIG. 44 is exemplary computing server embodiment.

FIG. 44 is exemplary computing server 6802 embodiment. The computing server 6802 is arranged as a single computing server, a network of computing server devices, a distributed computing system, or in some other in arrangement. The computing server 6802 may be referred to as a "cloud device," a "cloud computer," the "cloud," or by some other like name that identifies a remote scalable set of computing resources. In some cases, the computing server 6802 may be implemented in a commercial cloud computing environment such as AMAZON WEB SERVICES (AWS), AZURE, or some other like environment.

An exemplary computing server 6802 includes at least one processor 6850, input/output logic 6852, a network interface 6854 including logic arranged to implement a plurality of communication channels 6856. Each of the plurality of communication channels 6856 may form a physical, virtual, logical, or another type of peer-to-peer communication channel between the computing server 6802 and a remote computing device such as a base station (e.g., operating room base station 6806, home base station 6816, doctor office base station 6824, or some other base station) or another non-base station remote device 6832.

Computing server 6802 further includes at least one memory 6858 and query processor logic 6860, and obfuscation logic 6862. The query processor logic 6860 is arranged to receive and fulfill incoming requests from remote computing devices. The obfuscation logic 6862, which may be formed wholly or partially in hardware, software, or a combination of hardware and software, is arranged to obfuscate particular information that is meant to be kept secret (e.g., personally identifying patient information, payment information, security keys for encrypting, security keys for decrypting, and other such information).

Memory 6858 is arranged to store executable software instructions 6864, which may be executed by a processor 6850. Memory 6858 is also arranged to include a database 6866. The database 6866 is arranged to store records associated with a plurality of kinematic implantable devices. Generally speaking, the incoming information requests received and fulfilled by the query processor 6860 are associated with kinematic implantable devices. More specifically the incoming information requests often include or request specific kinematic data information collected by a kinematic implantable device.

Each kinematic implantable device has a unique identifier that is different from each other kinematic implantable device. In cases where a single kinematic implantable device comprises several individually distinguishable components, two or more of the individually distinguishable components may each have a unique identifier. Additionally, each patient 100 may have a unique identifier, each medical practitioner 6814 may have a unique identifier, each medical facility may have a unique identifier, each operating room may have a unique identifier, each base station may have a unique identifier, and other unique identifiers may be assigned to other individuals, devices, entities, or the like. Accordingly, records in the database 6866 may be stored, searched, retrieved, or otherwise processed based on any number of unique identifiers.

In one exemplary case, the query processor 6860 receives a first request from a remote computing device. The remote computing device is an operating room base station 6806. A medical practitioner 6814 is assisting in a medical procedure to implant a first kinematic implantable device into a patient 100. The operating room base station 6806 includes input logic to register at least one unique identifier of the first kinematic implantable device that will be implanted into the patient 100. The input logic may be a barcode reader, scanner, keyboard, a mechanism within the first kinematic implantable device to automatically provide certain data, or some other input device.

In addition to the at least one unique identifier, the medical practitioner 6814 may also direct or cause the input of further information such as a medical facility identifier that identifies the, hospital, clinic, operating room, surgical suite, or other such data; one or more medical practitioner identifiers that uniquely identify one or more individuals who participate in the medical procedure to implant the first kinematic implantable device; information identifying roles that one or more medical practitioners fulfill during the medical procedure; time and date information (e.g., a timestamp) associated with the medical procedure to implant the first kinematic implantable device; an anatomical identifier associated with a body part that the kinematic implantable device will replace or otherwise supplement; a patient identifier associated with the kinematic implantable device; notes provided by a medical practitioner associated with the medical procedure to implant the first kinematic implantable device; scheduling, mode, data-type, or other operational control information associated with the first kinematic implantable device; status information associated with a self-test, calibration, communications, data storage, or other operation of the first kinematic implantable device; and other such information. After collecting such information, the operating room base station 6806 may then communicate the some or all of information to the computing server 6802. The communication of such information performs an act of registering the first kinematic implantable device with the exemplary distributed computing system for alert implantable medical devices 6800.

Upon receiving the information provided by the operating room base station 6806, the query processor may cause the creation of one or more records in the database 6866. Some of the records, such as the patient information or other data that personally identifies a patient 100, will be passed through obfuscation logic 6862 prior to storage in the database 6866.

In some optional cases, the computing server 6802 processes the data received from the operating room base station 6806. The processing may include one or more validation checks of the unique identifiers associated with the first kinematic implantable device, the medical practitioner, the medical facility, and the like. The processing may also include validation checks to determine if the first kinematic implantable device is determined to be safe for implantation in the patient 100. The validation checks may include verifying government information or a lack thereof, verifying manufacturer information, analyzing status information (e.g., battery level) associated with the first kinematic implantable device, and other information.

Upon completion of database updates, optional validation checks, and certain other procedures, the computing server 6802 may provide a suitable response to the operating room base station 6806. The suitable response, which may be an acknowledgment, directs a particular output indication via the operating room base station 6806 to inform the medical practitioner that the first kinematic implantable device has been registered, approved, and may be implanted into the patient 100.

Before, during, and after the medical procedure is performed, the first kinematic implantable device may wirelessly communicate data to the operating room base station 6806. The data may include kinematic data, operational data, status data, or any other data. In some cases, the information is high resolution kinematic data from one, many, or all of the sensors of the kinematic implantable device. The operating room base station 6806 may communicate the data to the computing server 6802 occasionally, periodically, on a schedule, on a triggered event, or based on some other characteristic.

Each collection and communication of data by the kinematic implantable device is associated with one or more timestamps. In some cases, timestamps are based on actual time of day based on a particular reference time such as Zulu. In other cases, timestamps are based on a "time-zero" value.

The kinematic implantable device may have stored thereon one or more "time-zero" values. A time-zero value is a timestamp associated with a particular initial event. Future events are given a timestamp that is retrieved from a counter that has been operating at a known rate since the time-zero value was first set. For example, when a kinematic implantable device is powered for the very first time at manufacture, an initial time-zero value may be set. The initial time-zero value may be based on a certain clock that was started when the kinematic implantable device was first powered. If the certain clock counts at a known rate, then all future events during the life of the kinematic implantable device (i.e., while the kinematic implantable device has sufficient power) may be measured from the initial time-zero value. Other time-zero values are also contemplated, such as when the kinematic implantable device is woken from a deepest sleep mode after manufacture for implantation into a patient, or some other notable event.

After the medical procedure to implant the kinematic implantable device into the patient 100 is complete, the patient may return home. At home, the kinematic implantable device will communicate with a home base station 6816 occasionally, periodically, on a schedule, on a triggered event, or based on some other characteristic. During the communication, the kinematic implantable device will deliver information associated with the kinematic implantable device to the home base station 6816. The information may include a unique identifier of the kinematic implantable device or some portion thereof, a patient identifier, one or more timestamps associated with data from one or more sensors, the data from the one or more sensors, status information, operational information, control information, and any other such information. Occasionally, periodically, on a schedule, on a triggered event, or based on some other characteristic, the home base station 6816 will send an information request to the computing server 6802. The information request may ask or otherwise direct the computing server 6802 to store particular data in its database 6866.

In some cases, a patient will live with a kinematic implantable device in their body for a long period of time (e.g., months, years, or decades). In these cases, the kinematic implantable device may provide substantial quantities of kinematic data over time to the computing server 6802. In these cases, the computing server 6802 continues to collect and store the kinematic data in database 6866.

In some cases, such as when a fault is detected, when a manufacturer updates firmware, or for some other reason, the kinematic implantable device may request updated firmware or the computing server 6802 may direct an update of firmware. In such cases, the computing server 6802 will provide said firmware via a base station (e.g., operating room base station 6806, home base station 6816, doctor office base station 6824, or some other base station) to the kinematic implantable device.

After a kinematic implantable device is implanted in the patient 100, the patient 100 will in some cases see a medical practitioner for treatment. In these cases, the patient 100 will typically travel to a medical practitioner's office (e.g., doctor's office, physical therapy facility, and the like), a medical clinic, a hospital, or some other location where medical service will be provided. In these cases the kinematic implantable device of the patient will begin to communicate with a doctor office base station 6824. The doctor office base station 6824 may automatically or via a direction from a medical practitioner direct the kinematic implantable device to operate in a particular mode, collect particular data, deliver particular data, or take some other action.

For example, in some cases, the medical practitioner will direct the patient 100 to perform a particular exercise, move in a particular way, or take some other action to operate the kinematic implantable device in a particular way. The kinematic implantable device may collect kinematic data, high resolution kinematic data, or some other data. The medical practitioner may apply particular markers, notes, or some other input or identifying information in association with the collected kinematic data. Subsequently, after the kinematic data is delivered to the doctor office base station 6824, the doctor office base station 6824 will communicate the kinematic data, high resolution kinematic data, or other data to the computing server 6802 along with a request that the computing server 680 to store the particular data in database 6866. In these cases, as with all other cases where kinematic data is delivered to the computing server 6802, the kinematic data will include and associated unique identifier of the kinematic implantable device or some portion thereof along with an associated timestamp.

In some cases, one or more non-base station remote devices 6832 may also communicate with the computing server 6802. In these cases, the non-base station remote devices 6832 may be operated by a patient 100, a non-patient user 6844, or some other user. The non-base station remote devices 6832 may be a patient portal computing device 6834, a manufacturer computing device 6836, a research entity computing device 6838, a government agency computing device 6840, or some other computing device 6842. In these cases, the non-base station remote device 6832 may pass a request to the computing server 6802 to receive specific or aggregated information from the database 6866. For example, the request may ask for particular data from one or more records that share a common characteristic.

The specific or aggregated request may specify, for example, a common characteristic that is a unique identifier of a particular kinematic implantable device. In this way all of the collected data stored in the database 6866 that is associated with the particular kinematic implantable device having the unique identifier will be retrieved. In another example, the common characteristic may be a same type of kinematic implantable device, such as an alert knee prosthesis, an alert hip prosthesis, an alert shoulder prosthesis, an alert ankle prosthesis, or some other type of kinematic implantable device. In another example, the common characteristic is a same anatomical identifier (e.g., left knee, right shoulder, and the like). In such cases, particular research can be done focused on particular devices. In still other examples, the common characteristic may be same medical practitioner identifier, a same medical facility identifier, a same manufacturer identifier, a same manufacturing lot number identifier, or some other information that may permit desirable research. Other common characteristics are also contemplated, including demographic information, chronological information, particular notes taken by a doctor or medical practitioner, firmware version numbers, kinematic data (e.g., when particular thresholds are crossed such as angle of motion, velocity, stress, and others), and many others.

Figure 45:
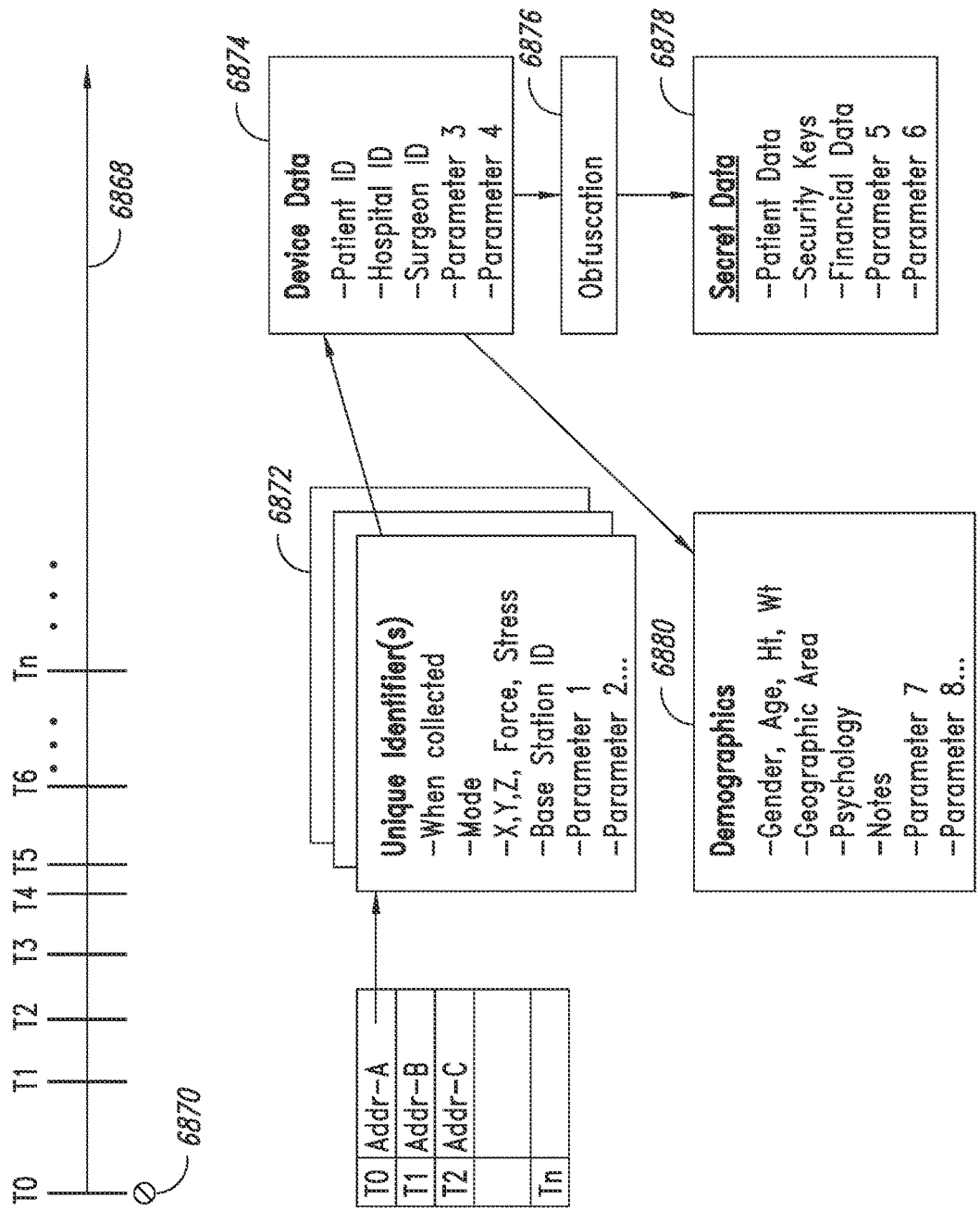
FIG. 45 is a data flow diagram of a timeline associated with a particular kinematic implantable device embodiment.

FIG. 45 is a data flow diagram of a timeline 6868 associated with a particular kinematic implantable device embodiment. The timeline 6868 may be logical, virtual, or formed in another way for example, by a linked list, a database query, or in some other way. Generally speaking, the timeline 6868 permits reconstruction of all data collected for a particular kinematic implantable device. In some cases, the computing server 6802 constructs a timeline 6868 as data is collected. For example, the computing server 6802 may create one or more new database records each time kinematic data associated with a particular kinematic implantable device is received, and the one or more new database records may be linked to one or more existing database records.

The timeline 6868 begins at time-zero 6870. Time-zero 6870 may be a point in time associated with a first power-on of the particular kinematic implantable device. Alternatively, time-zero 6870 may be a point in time associated with the particular kinematic implantable device waking from a deep sleep mode which was entered after the device was manufactured and exited during the medical procedure when the kinematic implantable device was being implant in the patient 100. Alternatively still, time-zero 6870 may be a point in time associated with a particular time reference (e.g., Greenwich Mean Time). Time-zero 6870 may also be some other time.

Occasionally, periodically, on a schedule, or at some other times after time-zero 6870, additional data associated with the kinematic implantable device is collected by a base station and communicated to the computing server 6802. As illustrated in the timeline 6868, data is collected at times T1 to Tn, where "n" is an integer, and the collection of data continues beyond time Tn. In some cases, such as between times T1 and T4, the collection of data is periodic based on a particular schedule stored and acted on by the kinematic implantable device. At other times, kinematic data may be collected frequently or in frequently. Each timestamp of kinematic data (e.g., T0 to Tn) may be identified as corresponding to one or more records that associate the timestamp with a kinematic implantable device unique identifier.

Each timestamp T0 to Tn is linked to one or more per device records 6872, which store timing information kinematic implantable device operational mode, sensor data, a unique identifier of a base station that communicated the data, and a plurality of other data identified as Parameter 1 and Parameter 2. In this way, during or after the lifetime of each kinematic implantable device, an operational timeline specific to each particular kinematic implantable device can be constructed, and all of the device specific data can be collected, retrieved, analyzed, and the like. If a device has failed, or caused pain, a medical practitioner, researcher, or some other person, can determined when particular stresses, forces, motion, or other parameters associated with the device occurred.

The one or more per device records 6872 are linked to one or more device data records 6874. The one or more device data records 6874 may be collected one time, such as when the kinematic implantable device is registered via the operating room base station 6806. Alternatively, or in addition, the one or more device data records 6874 may be collected or supplemented at other times of data collection. The device data records 6874 may include patient identifier information, medical facility (e.g., hospital, clinic, surgical suite, and the like) identifier information, medical practitioner (e.g., surgeon, nurse, technician, and the like) identifier information, and a plurality of other device data identified as Parameter 3 and Parameter 4.

At least some of the device data may be obfuscated at 6876 and stored in one or more obfuscated data records 6878. In some cases, in a manufacturer's recall, for example, a patient may need to be contacted. In this way, a particular query by an authorized party having specific authorization information 6848 may be able to find the name, contact information, address, or other personal information associated with a particular patient 100 who received a specific kinematic implantable device.

Certain other data may also be stored in one or more demographics data records 6880. The data stored in the one or more demographics data records may be collected one time, many times, or when particular kinematic implantable device data is collected. The demographic data may include gender, age, height, weight, geographic area, a particular state of mind or personality assessment, medical practitioner notes, and any other demographic data which is so identified as Parameter 7 and Parameter 8.

In some cases, as described with respect to the non-base station remote devices 6832, for example, the query processor 6860 of computing server 6802 may receive requests for particular data. The requests may be for specific items of data, or aggregated items of data. One researcher may search for information collected by a plurality of kinematic implantable devices having a same model number, manufacturer, date of manufacture, timeframe of implantation, or any other such criteria. Another researcher may search for information collected by a different plurality of kinematic implantable devices implanted in a particular anatomical location. Yet another researcher may search for information to learn why certain kinematic implantable devices have different failure rates than other kinematic implantable devices.

Figure 46:
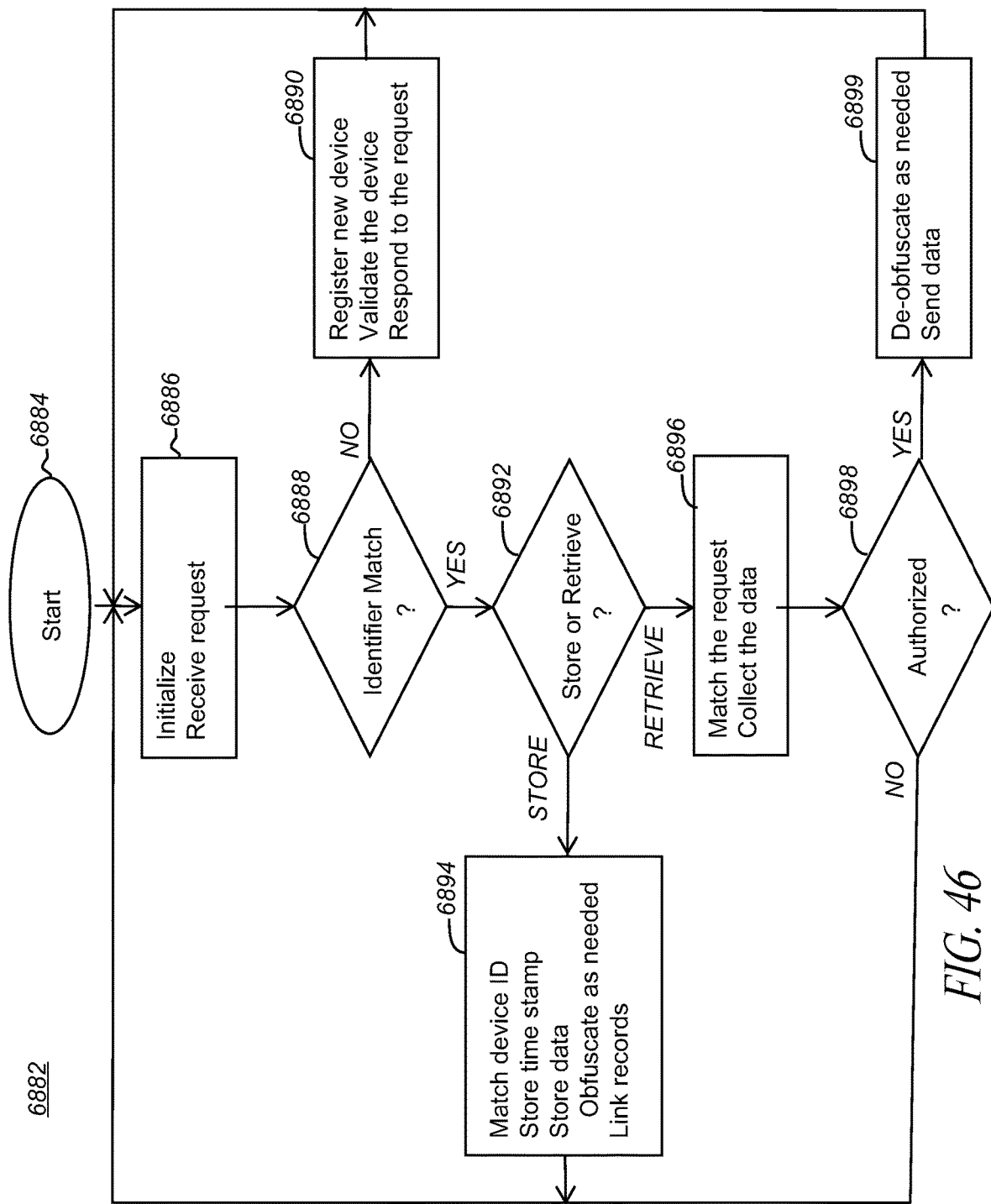
FIG. 46 is a data flow diagram representing information passing into and out of a computing server.

FIG. 46 is a data flow diagram 6882 representing information passing into and out of a computing server 6802. Processing begins at 6884.

At 6886, various portions of the computing server 6802 are initialized. If the computing server 6802 is being initialized for the first time, memory is cleared communications are initialized and various other conventional tasks associated with initializing a computing server are executed. If the computing server 6802 is not being initialized for the first time, memory buffers are cleared, timers are initialized, and the computing server 6802 weights for a request from a remote computing device such as a base station (e.g., operating room base station 6806, home base station 6816, doctor office base station 6824, or some other base station) or another non-base station remote device 6832. When a request is received, processing advances to 6888.

At 6888, a query processor 6860 parses the received request. One or more identifiers in the request payload are interrogated. The computing server 6802 may determine if the sender of the request is identifiable. The computing server 6802 may determine if a unique identifier of the kinematic implantable device is recognized. Other identifiers, such as a user identifier, or some other identifiers may also be verified.

If the unique identifier of the kinematic implantable device is not recognized at 6888, processing advances to 6890. At 6890, the computing server 6802 attempts to register the kinematic implantable device is a new device in the database 6866. The computing server 6802 may perform any number of validation checks to determine whether the kinematic implantable device is known, and fit for implantation. The computing server 6802 may interactively request information from the sender. Alternatively, or in addition, the computing server 6802 may analyze data in the payload of the original message. The computing server 6802 may interrogate other databases internal to the computing server 6802 or external to the computing server 6802 (e.g., via the internet), such as manufacturing databases, government databases, consumer databases, or other databases. Based on the suitability of the kinematic implantable device for implantation, the computing server 6802 will respond to the request. The response may inform a medical practitioner that the kinematic implantable device is suitable for implantation and registered, not suitable for implantation, or the computing server 6802 may provide different information. Processing from 6890 returns to 6886 for re-initialization and to await another request.

If the computing server 6802 determined at 6888 that an identifier matched and the kinematic implantable device was recognized, processing advances to 6892.

At 6892, the query processor 6860 determines whether the request is attempting to provide data for storage in the database 6886 or retrieve data from the database 6886. If the received request is attempting to provide data, processing advances to 6894. At 6894, the computing server 6802 will validate the data, store the data, and perform other housekeeping tasks. The unique identifier of the kinematic implantable device is used as an index or other inquiry term for the database 6866. One or more timestamps in the request message payload are retrieved and stored. Other payload data, such as kinematic data collected by the kinematic implantable device is stored. If any of the data is personal data, secure data, or the like, such data may be obfuscated prior to storage. The computing server 6802 may link particular records or perform actions to support the building of a particular time line 6868. After the data is stored, processing from 6894 returns to 6886.

If at 6892 the computing server 6802 determined that the received request is attempting to retrieve data, processing advances to 6896. At 6896, the request payload is interrogated by the query processor 6860 and particular data request information is identified. Data may also be collected or otherwise identified in the database 6866. At 6898, the computing server 6802 determines if the requester is authorized to retrieve the requested data. If the requester is not authorized, processing advances back to 6886 for re-initialization and to await another request. On the other hand, if the requester is authorized, processing advances to 6899 where the data is de-obfuscated if necessary, appropriately packaged, and communicated to the requester's remote computing device.

Processing advances back to 6886 for re-initialization and to await another request.

As used in the present disclosure, the term "module" and "logic" refer to an application specific integrated circuit (ASIC), an electronic circuit, a processor and a memory operative to execute one or more software or firmware programs, combinational logic circuitry, or other suitable components (hardware, software, or hardware and software) that provide the functionality described with respect to the module or logic as the case may be.

A processor (i.e., a processing unit), as used in the present disclosure, refers to one or more processing units individually, shared, or in a group, having one or more processing cores (e.g., execution units), including central processing units (CPUs), digital signal processors (DSPs), microprocessors, micro controllers, state machines, and the like that execute instructions.

In the present disclosure, memory may be used in one configuration or another. The memory may be configured to store data. In the alternative or in addition, the memory may be a non-transitory computer readable medium (CRM) wherein the CRM is configured to store instructions executable by a processor. The instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of the systems, methods, and apparatus described in the present disclosure.

As known by one skilled in the art, a computing device such as computing server 6802 has one or more memories 6858, and each memory comprises any combination of transitory and non-transitory, volatile and non-volatile computer-readable media for reading and writing. Volatile computer-readable media includes, for example, random access memory (RAM). Non-volatile computer-readable media includes, for example, read only memory (ROM), magnetic media such as a hard-disk, an optical disk drive, a flash memory device, a CD-ROM, and/or the like. In some cases, a particular memory is separated virtually or physically into separate areas, such as a first memory, a second memory, a third memory, etc. In these cases, it is understood that the different divisions of memory may be in different devices or embodied in a single memory. Some or all of the stored contents of a memory may include software instructions executable by a processing device to carry out one or more particular acts.

The terms, "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds, milliseconds, seconds, or minutes), and that the activity may be performed on an ongoing basis (e.g., transmission of the kinematic data being triggered by a schedule, an event, or the detection of a fault or anomaly). An example of an activity that is not real-time is one that occurs over an extended period of time (e.g., hours or days) or that occurs based on intervention or direction by a person.

FIG. 44 illustrates portions of a non-limiting embodiment of a computing server 6802. Computing server 6802 is a computing server that includes operative hardware found in a conventional computing server apparatus such as one or more central processing units (CPU's), volatile and non-volatile memory, serial and parallel input/output (I/O) circuitry compliant with various standards and protocols, wired and/or wireless networking circuitry (e.g., a communications transceiver).

Computing server 6802 further includes operative software found in a conventional computing server such as an operating system, software drivers to direct operations through the I/O circuitry, networking circuitry, and other peripheral component circuitry. In addition, computing server 6802 includes operative application software such as network software for communicating with other computing devices, database software for building and maintaining databases, and task management software for distributing the communication and/or operational workload amongst various processors. In some cases, computing server 6802 is a single hardware machine having the hardware and software listed herein, and in other cases, computing server 6802 is a networked collection of hardware and software machines working together in a server farm to execute the functions of the exemplary distributed computing system for alert implantable medical devices 6800. The conventional hardware and software of computing server 6802 is not shown in FIG. 44 for simplicity.

FIG. 46 is a flowchart 6882 illustrating processes that may be used by embodiments of the computing server 6802 for directing the collection and retrieval of particular kinematic data. In this regard, each described process may represent a module, segment, or portion of code, which comprises one or more executable instructions for implementing the specified logical function(s). In some implementations, the functions noted in the process may occur in a different order, may include additional functions, may occur concurrently, and/or may be omitted.

The present disclosure has provided implantable reporting processors and alert implants comprising the same. The information obtained from the alert implant is sent to a recipient to review/interpret. That information may provide a detailed view of the status of the implant over a period of time. That information may be conveniently viewed by the recipient on a display. That display may be incorporated into a virtual reality headset.

In one embodiment the present disclosure provides that the alert implant may be visualized by virtual reality techniques. Virtual reality techniques provide electronic input to a viewing screen, typically worn by the user as a headset or headgear, where that viewing screen provides the user with an apparent 3-dimension "real" image. This technology can be used to provide a 3-dimensional view of the alert implants of the present disclosure. The user may operate controls that shift the vantage point utilized in the virtual reality representation, so that the user can see the visualized features from different points of view.

Virtual reality techniques are being actively developed by the video game industry and their partners. Examples from the gaming industry include Sulon Q, a VR and augmented reality headset offered by Sulon Technologies (Markham, Ontario, Canada), the PlayStation VR headset offered by Sony (Japan), Gear VR developed by Samsung (South Korea), Rift, developed by Oculus (a division of Facebook, California, USA), and Vive, developed by HTC (Bellevue, Washington, USA). See also US Patent Publication Nos. US2016025978; US2016019720; 20160011422; 20160011425; 20150253574; 20080214903; and 20070271301.

In a further embodiment, the present invention relates generally to a mechanical tool, and more specifically to a tool that may be used to join two pieces together. In general, pressure may be used to force to complementary pieces together, where pressure develops a so-called force-fit between the pieces, whereby the pieces are held together by frictional forces. When at least one of the pieces has a fragile portion, such that the portion is too fragile to withstand the force being exerted to achieve a force-fit between the pieces, a way must be found to exert the necessary force without damaging the fragile portion. This situation occurs, for example, when an IRP is being inserted into a medical implant to provide an alert implant as described herein. The present disclosure provides a solution to this problem.

Figure 47A:
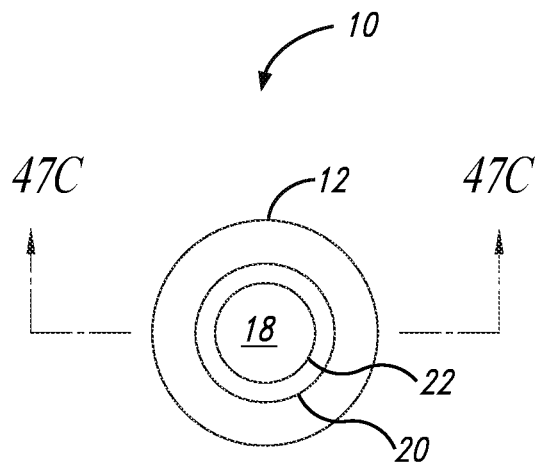
FIG. 47A is a top perspective view of an embodiment of a tool of the present disclosure.
Figure 47B:
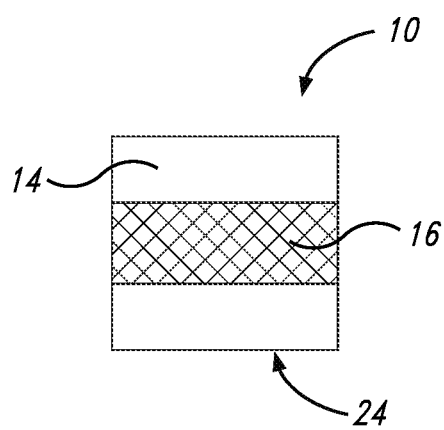
FIG. 47B is a side perspective view of the tool embodiment of FIG. 47A.
Figure 47C:
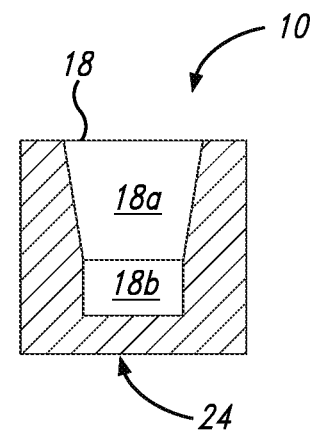
FIG. 47C is a cross-sectional view corresponding to the side perspective view of FIG. 47B.

FIGS. 47A, 47B and 47C provide three different views of a tool 10 of the present disclosure. In FIG. 47A, the tool 10 has an outer perimeter 12, which is shown as being circular. The outer perimeter need not be circular, but can be any shape, e.g., oval, square, or rectangular. The outer perimeter 12 of the tool 10 will have a surface 14, shown in FIG. 47B, where some or all of that surface 14 may optionally be textured for ease of handling, as shown by textured surface 16 in FIG. 47B. The tool 10 will also have a central inner cavity 18, shown in FIG. 47A. That central cavity 18 may be visualized as being divided into sections based upon the cross section of the cavity. For example, as shown in FIG. 47C, the central cavity 18 may be divided into a cavity 18A have a constantly varying cross-sectional distance, and a cavity 18B having a constant cross-sectional distance. FIG.

47A shows the circumference 20 of a cylinder having a constantly varying cross-sectional distance from 20, which is the largest circumference and corresponds to the longest cross sectional distance in central cavity 18, to 22, which is the smallest circumference and corresponds to the shortest cross sectional distance in central cavity 18. Cavity 18B has a constant cross sectional distance bounded by circumference 22. Cavity 18A has a varying cross sectional distance. The tool 10 has a surface 24 as shown in FIGS. 47B and 47C, against which force may be applied, as discussed further in reference to FIGS. 48 and 49.

Figure 48:
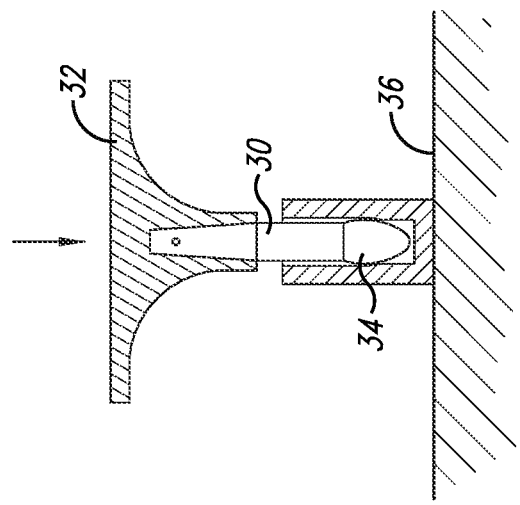
FIG. 48 illustrates the use of a tool of the present disclosure to achieve a tight fit between two pieces.
Figure 49:
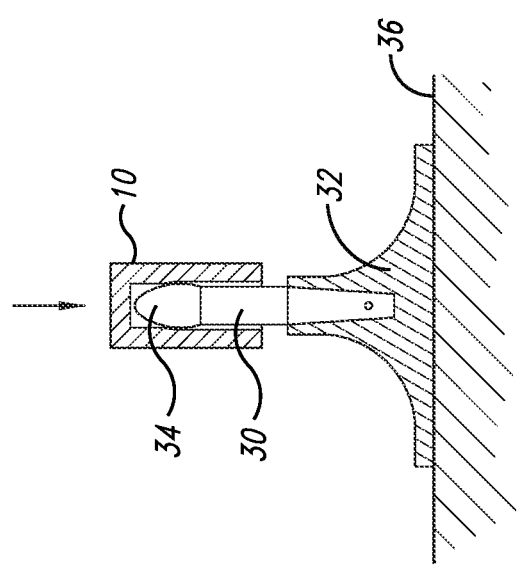
FIG. 49 illustrates the use of a tool of the present disclosure to achieve a tight fit between two pieces.

A use of the tool 10 is illustrated in FIGS. 48 and 49. In FIGS. 48 and 49, a first piece 30 is being fitted into a second piece 32, by use of the tool 10. In FIG. 48, force is applied downward against the tool 10, where tool 10 fits around the first piece 30, although does not come into contact with a fragile portion 34 of first piece 30. In FIG. 48, the second piece 32 is held stationary against a table or other non-movable surface 36. In FIG. 48, force is exerted downward onto tool 10, where that force is transmitted onto and through the first piece 30, thereby forcing first piece 30 into a complementarily sized cavity in second piece 32.

FIG. 49 illustrates an alternative way to use tool 10. In FIG. 49, the tool 10 is placed on the non-movable surface 36, and the first piece is fitted into the tool 10. The second piece 32 is then placed into contact with the first piece 30, and force is exerted downwards onto second piece 32. That force is transmitted to the first piece 30, where first piece 30 is held in place with tool 10.

In each of FIG. 48 and FIG. 49, sufficient force is applied such that first piece 30 and second piece 32 come into contact with one another, and that contact is under sufficient force that a frictional force is created between first piece 30 and second piece 32. That frictional force keeps the two pieces together. After the two pieces have been coupled or mated together, the tool 10 can be readily removed. In this way, first piece 30 is inserted into second piece 32, in a manner that allows for a fragile portion of first piece 30 to extend out of and not be damaged during the impaction process.

In FIGS. 48 and 49, the second piece is a tibial plate. More generally, the second piece may be a prosthesis that will be placed into a subject, where the first piece is added to the prosthesis prior to the combined first and second pieces being placed into a subject.

Some commercial tibial inserts for a total knee arthroscopy (TKA) prostheses are attached to the tibial plate component using an impact force delivered from a hammer or by other forceful means. The tibial insert is the affixed further by means of a secondary retaining structure such as a setscrew contained within the tibial plate which interfaces to the tibial insert to insure that it cannot be removed from the tibial plate once implanted. When it is desired to have a tibial insert with a fragile surface, there are limitations on where such force may be applied, so as not to damage the surface and what may lie underneath that surface. The present disclosure provides a tibial plate impaction tool whereby an ancillary piece may be added to the tibial plate without causing damage to the ancillary piece. In one embodiment, the tool facilitates the joining together of a tibial plate and a tibial extension, where the tibial extension has a fragile surface due, for example, to the presence of an IRP (implantable reporting processor) on the tibial extension. The tool has an internal cavity which engages with the tibial extension, and which has a maximum cross-sectional distance suited for connecting with a tibial extension of less than 100 mm, or less than 50 mm, or less than 25 mm, or about 5 mm.

Because the combined first and second pieces may be implanted into a living subject, e.g., a human, the material selected are capable of terminal sterilization by, e.g., sterilizing radiation. The materials may be, for example, metal, ceramic or polymeric.

Figure 50:
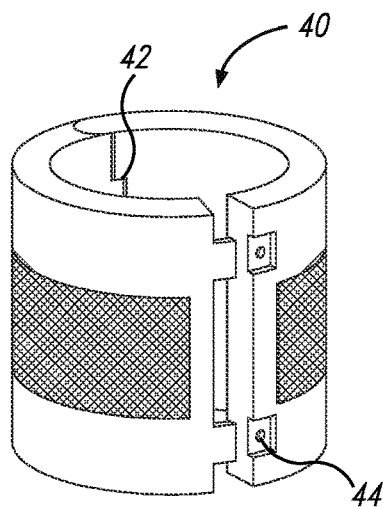
FIG. 50 shows a perspective view of a tool embodiment of the present disclosure, having a hinge.

FIG. 50 shows an alternative tool 40 of the present disclosure, which is similar to tool 10 except that tool 40 is hinged so as to allow the tool 40 to open. This is particularly useful after the tool 40 has been used to mate first and second pieces together, since after the mating process the tool 40 may be opened up via the hinged mechanism, to allow the tool 40 to be more easily separated from the joined pieces. In FIG. 50, the hinge is shown as feature 42, and feature 44 shows a locking or clasping mechanism to hold the hinged piece together during the use of tool 40.

Figure 51A:
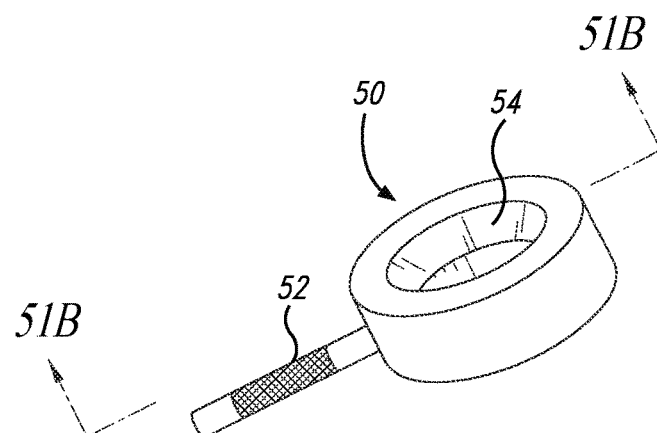
FIG. 51A shows a perspective view of a tool embodiment of the present disclosure, having a handle.

FIG. 51A shows an alternative tool 50 of the present disclosure, which is similar to tool 10 except that tool 50 has a handle 52.

Figure 51B:
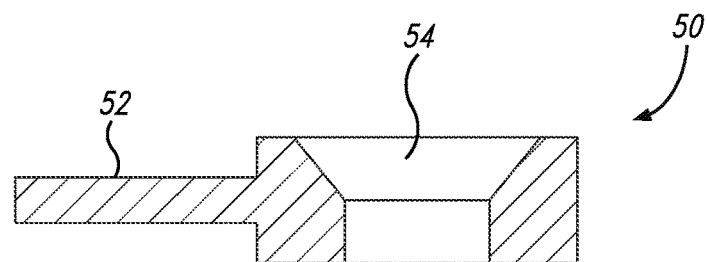
FIG. 51B is a cross-sectional view of the tool of FIG. 51A.

FIG. 51B is a cross-sectional view of the tool 50 also shown in FIG. 5A. In FIG. 5B, the tool 50 has a handle 52, and a cavity 54, in analogy to cavity 18 of tool 10.

Figure 52:
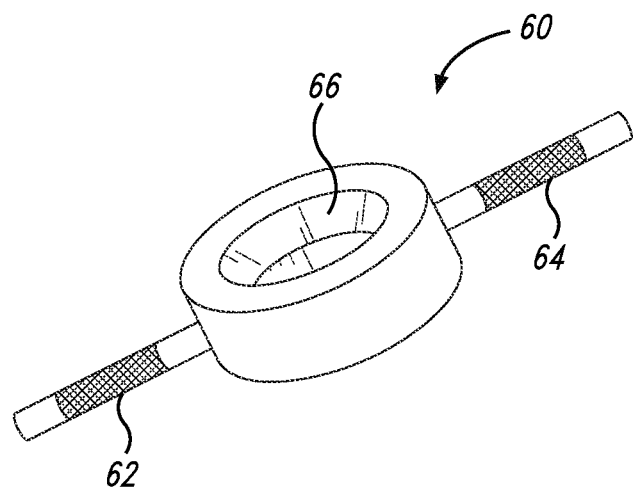
FIG. 52 is a perspective view of a tool of the present disclosure, having two handles.

FIG. 52 shows an alternative tool 60 of the present disclosure, which is similar to tool 50 except that tool 60 has two handles 62 and 64, in addition to a cavity 66.

Figure 53:
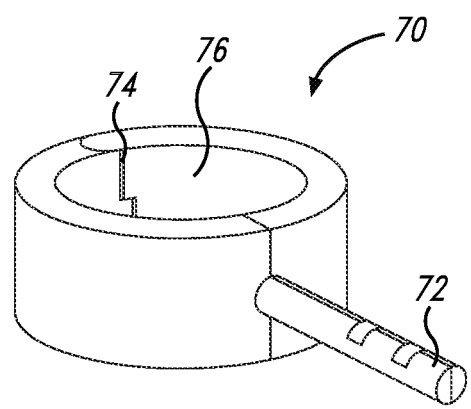
FIG. 53 is a perspective view of a tool of the present disclosure, having one handle and a hinged opening mechanism.

FIG. 53 shows an alternative tool 70 of the present disclosure which has both a handle 72 to hold and apply force, and a hinge 74 to allow the cavity 76 to be expanded to assist in opening the tool when it is desired to separate the tool 70 from the compacted first and second pieces.

In general, a cylindrical tool, e.g., 10 as shown in FIG. 47A, may contain an internal cavity having dimensions that include a tapered section designed to mate with a first piece. The internal mating surface may be smooth or contains ribs and/or other structural features (not shown) designed to decrease surface area to facilitate removal of the tool from the piece after force has been applied. The tool, e.g., 10, contains a surface, e.g., 24 in FIG. 47B, which can be used to impart an axial load sufficient to engage the first piece to the second piece, as illustrated in FIGS. 48 and 49. The tool 10 may or may not have features such as surface texturing on the outer casing which facilitate griping by hand and removal to the tool. In the alternative of surface texturing, a hinge/clasp mechanism as shown in FIG. 50 may be used.

Figure 54:
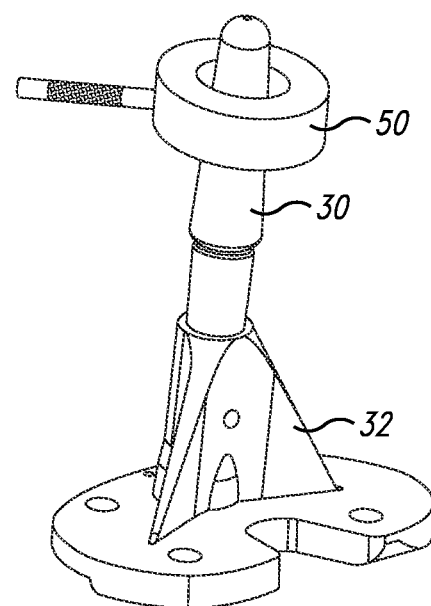
FIG. 54 shows an embodiment of a tool of the present disclosure being used to force together a tibial extension having a fragile surface, and a tibial plate.

FIG. 54 shows an embodiment of a tool 50 of the present disclosure being used to force together a tibial extension having a fragile surface 30, and a tibial plate 32.

Accordingly, the present disclosure provides an impaction tool comprising an internal cavity exposed to the surroundings via an opening in the cavity, the internal cavity partially enclosed by an outer casing. Optionally, the tool may be described by one or more, e.g., all, of the following features: the internal cavity is complementary in size and shape to a tibial insert; the tool further comprises a hinge that allows the internal cavity to expand; the tool further comprises a handle extending from the outer casing; the tool further comprises an outer casing comprising a textured surface; the internal cavity of the tool has a maximum cross-sectional distance for connecting with a tibial extension, and that distance is about 5 mm. In addition, the present disclosure provides a method of inserting a tibial extension into a complementarily sized and shaped opening in a tibial plate, where the method comprises inserting a portion of the tibial extension into a tool as described above; inserting another portion of the tibial extension into a tibial plate, and applying force through the tool to push the extension into the plate.

The following are additional exemplary embodiments of the invention provided in the present disclosure:

1. An implantable medical device, comprising:
   an electronics assembly;
   a power component coupled to the electronics assembly; and
   an antenna component coupled to the electronics assembly, wherein the electronics assembly includes a space-efficient printed circuit assembly.

2. The implantable medical device of embodiment 1, wherein the electronics assembly is a folded multi-board printed circuit assembly.

3. The implantable medical device of embodiment 1, wherein the electronics assembly is a folded three board printed circuit assembly.

4. The implantable medical device of embodiment 1, wherein the electronics assembly is a folded two board printed circuit assembly.

5. The implantable medical device of embodiment 1, wherein the electronics assembly is a single board printed circuit assembly.

6. The implantable medical device of embodiment 1, wherein the electronics assembly is a multi-board circular-stacked printed circuit assembly.

7. The implantable medical device of embodiment 1, wherein the electronics assembly is a single board circular printed circuit assembly.

8. The implantable medical device of each of embodiments 1-7, wherein at least one of the electronics assembly, power component, and antenna component is enclosed in a hermetically sealable casing.

9. The implantable medical device of each of embodiments 1-8, wherein the electronics assembly includes a plurality of sensors configured to monitor a plurality of kinematic parameters.

10. The implantable medical device of each of embodiments 1-9, wherein the electronics assembly includes at least one sensor configured to monitor pressure.

11. The implantable medical device of each of embodiments 1-10, wherein the electronics assembly includes a plurality of sensors configured to monitor biologic parameters associated with at least one of temperature, pH, and biomarkers associated with infection.

12. An implantable medical device, comprising:
   a reporting processor configured to be fixedly attached to an implantable prosthetic device, wherein the reporting processor includes an implantable casing configured to enclose a power component, an electronics assembly electrically coupled and physically attached to the power component, and an antenna component electrically coupled and physical attached to the electronics assembly.

13. The implantable medical device of embodiment 12, wherein the casing is configured to be hermetically sealed and/or the casing is configured to include material capable of allowing the implantable reporting processor to transmit and receive information.

14. The implantable medical device of embodiments 12 and 13, wherein the implantable prosthetic device comprises a tibial extension affixed to a tibial plate.

15. The implantable medical device of embodiments 12-14, wherein the power component comprises a battery.

16. The implantable medical device of embodiments 12-15, wherein the antenna component comprises a transmission antenna.

17. The implantable medical device of embodiments 12-16, wherein the electronics assembly includes a memory integrated circuit or chip configured to receive and store unique identification information for the implantable medical device during a surgical procedure.

18. A method of manufacture of an implantable medical device, comprising:
   forming an electronics assembly;
   forming a power component;
   electrically coupling and fixedly attaching the power component to the electronics assembly;
   forming an antenna component;
   electrically coupling and fixedly attaching the antenna component to the electronics assembly; and
   enclosing the electronics assembly, power component and antenna component in a hermetically sealable outer casing.

19. The method of manufacture of embodiment 18, wherein the forming the electronics assembly comprises forming at least one of a single board printed circuit assembly, a two-board printed circuit assembly, or a three board printed circuit assembly.

20. The method of manufacture of embodiment 18, wherein the forming the electronics assembly comprises forming a circular stacked printed circuit assembly.

21. An implantable medical device, comprising:
   a printed circuit assembly;
   a power component coupled to the printed circuit assembly; and
   an antenna component coupled to the printed circuit assembly, wherein the antenna component is configured internally or externally to the implantable medical device.

22. The implantable medical device of embodiment 21, wherein the antenna component comprises a ceramic chip antenna configured internally to the implantable medical device.

23. The implantable medical device of embodiment 21, wherein the antenna component comprises a first whip antenna configured externally to the implantable medical device.

24. The implantable medical device of embodiment 21, wherein the antenna component comprises a second whip antenna configured externally to the implantable medical device.

25. The implantable medical device of embodiment 21, wherein the antenna component comprises a patch antenna configured externally to the implantable medical device.

26. The implantable medical device of embodiment 21, wherein the antenna component comprises a patch antenna configured internally to the implantable medical device.

27. The implantable medical device of embodiment 21, wherein the antenna component comprises a near field communication (NFC) coil antenna configured internally to the implantable medical device.

28. The implantable medical device of embodiment 21, wherein the antenna component is a metal case enclosure for the printed circuit assembly.

29. The implantable medical device of embodiment 21, wherein the antenna component comprises a metal component of a tibial plate.

30. The implantable medical device of embodiment 21, wherein the antenna component comprises a metal component of a tibial plate electrically coupled to the implantable medical device.

31. The implantable medical device of embodiment 21, wherein the antenna component comprises a tibial plate, and the implantable medical device is a reporting processor in a tibial extension.

32. An implantable medical device, comprising:
a reporting processor configured to be fixedly attached to an implantable prosthetic device, wherein the reporting processor includes an implantable casing configured to enclose a power component, an electronics assembly electrically coupled and physically attached to the power component, and an antenna component electrically coupled and physically attached internally or externally to the reporting processor.

33. The implantable medical device of embodiment 32, wherein the reporting processor comprises a tibial extension.

34. The implantable medical device of embodiment 32, wherein the implantable prosthetic device comprises a tibial extension affixed to a tibial plate.

35. The implantable medical device of embodiments 32-34, wherein the power component comprises a battery.

36. The implantable medical device of embodiments 32-35, wherein the antenna component comprises a transmission antenna.

37. The implantable medical device of embodiments 32-36, wherein the electronics assembly includes a memory integrated circuit or chip configured to receive and store unique identification information for the implantable medical device during a surgical procedure.

38. A method of manufacture of an implantable medical device, comprising:
forming an electronics assembly;
forming a power component;
electrically coupling and fixedly attaching the power component to the electronics assembly;
forming an antenna component; and
electrically coupling and fixedly attaching the antenna component to the electronics assembly.

39. The method of manufacture of embodiment 38, wherein the electrically coupling and fixedly attaching the antenna component to the electronics assembly comprises attaching the antenna component externally to the implantable medical device.

40. The method of manufacture of embodiment 38, wherein the wherein the electrically coupling and fixedly attaching the antenna component to the electronics assembly comprises attaching the antenna component internally in the implantable medical device.

41. A battery, comprising:
a container sized to fit inside of a bone;
an anode disposed in the container;
a cathode disposed in the container;
a cathode terminal coupled to the cathode and exposed outside of the container; and
an anode terminal coupled to the anode and exposed outside of the container.

42. The battery of embodiment 41 wherein the container includes a metal.

43. The battery of embodiment 41 wherein the container is rigid.

44. The battery of embodiments 41-43 wherein the container is sized to fit inside of a bone of a living subject.

45. The battery of embodiments 41-44 wherein the container is sized to fit inside of a femur of a living subject.

46. The battery of embodiments 41-44 wherein the container is sized to fit inside of a cavity in a tibia of a living subject.

47. The battery of embodiments 41-46 wherein the container is sized to fit inside of a device that is at least partially implanted in the bone.

48. The battery of embodiment 41 wherein:
the container is sized to fit in a tibial extension of a knee prosthesis; and
the tibial extension is sized to fit in a tibia of a living subject.

49. The battery of embodiment 41 wherein:
the container is sized to fit in a femoral stem of a hip prosthesis; and
the femoral stem is sized to fit in a femur of a living subject.

50. The battery of embodiments 41-49 wherein the anode includes lithium.

51. The battery of embodiments 41-50 wherein the cathode includes carbon monofluoride.

52. The battery of embodiments 41-51 wherein the anode and the cathode are configured to provide power for at least one year without recharging or replacement.

53. The battery of embodiments 41-51 wherein the anode and the cathode are configured to provide power for at least one year, for at least ten years, for at least fifteen years, for at least eighteen years, or for over eighteen years, without recharging or replacement.

54. An assembly, comprising:
a cylindrical container having a diameter and an end, sized to fit inside of a bone, and housing electronic circuitry; and
a cylindrical battery having approximately the diameter, sized to fit inside of the bone, and having an end attached to the end of the container.

55. The assembly of embodiment 54 wherein the battery includes a lithium-carbon-monofluoride battery.

56. The assembly of embodiment 54 wherein the battery includes a nickel-cadmium, zinc-mercury, or Lithium iodine (Li/SO2, Li/SOCl2, and Li/MNO2) battery.

57. The assembly of embodiment 54 wherein the battery is a rechargeable battery.

58. The assembly of embodiment 54 wherein the battery is a rechargeable battery configured for recharging in response to kinetic motion.

59. The assembly of embodiment 54 wherein the battery is a rechargeable battery configured for recharging in response to inductive coupling.

60. An implantable reporter processor, comprising:
a housing sized to fit in a prosthesis;
electronic circuitry disposed in the housing and configured to provide information related to the prosthesis; and
a battery disposed in the housing and coupled to the electronic circuitry.

61. The implantable reporter processor of embodiment 60 wherein the housing is sized to fit in a tibial extension of a knee prosthesis.

62. The implantable reporter processor of embodiment 60 wherein the housing is sized to fit in a location selected from a femoral stem of a hip prosthesis, a humeral stem of a shoulder prosthesis, and a shaft of a intramedullary rod for stabilization of a fracture of a bone selected from a femur, tibia, and a fibula.

63. The implantable reporter processor of embodiment 60, further comprising:
a cylindrical casing having a diameter and an end;
wherein the electronic circuitry is disposed in the casing; and
wherein the battery is cylindrical, has approximately the diameter, and has an end coupled to the end of the casing.

64. A prosthesis, comprising:
a receptacle; and
an implantable reporting processor having a coupling section disposed in the receptacle and including
electronic circuitry; and
a battery coupled to the electronic circuitry.

65. The prosthesis of embodiment 64 wherein the implantable reporting processor is configured to be disposed in a bone of a living subject.

66. The prosthesis of embodiment 64, further comprising:
a tibial plate; and
a tibial extension attached to the tibial plate and including the receptacle and the implantable reporting processor.

67. The prosthesis of embodiment 64, further comprising:
a femoral head; and
a femoral stem attached to the femoral head and including the receptacle and the implantable reporting processor.

68. A method, comprising:
forming a cavity in a bone of a living subject; and
inserting at least a portion of a prosthesis in the cavity, the prosthesis including an implantable reporting processor having
electronic circuitry; and
a battery coupled to the electronic circuitry.

69. The method of embodiment 68 wherein forming the cavity includes forming the cavity in a tibia of the living subject.

70. The method of embodiment 68 wherein forming the cavity includes forming the cavity in a femur of the living subject.

71. The method of embodiments 68-70 wherein the implantable reporting processor is disposed in the cavity.

72. The method of embodiments 68-71, further comprising configuring the electronic circuitry such that the battery has a projected lifetime of at least one year.

73. The method of embodiments 68-71, further comprising configuring the electronic circuitry such that the battery has a projected lifetime of at least ten years.

74. A prosthesis, comprising:
a hollow region; and
an implantable reporting processor disposed in the hollow region and including
electronic circuitry; and
a battery coupled to the electronic circuitry.

75. The prosthesis of embodiment 74, further comprising a member that includes the hollow region and that is configured to be disposed in a bone of a living subject.

76. The prosthesis of embodiment 74, further comprising:
a tibial plate; and
a tibial extension attached to the tibial plate and including the hollow region.

77. The prosthesis of embodiment 74, further comprising:
a femoral head; and
a femoral stem attached to the femoral head and including the hollow region.

78. A method, comprising:
forming a cavity in a bone of a living subject; and
inserting at least a portion of a prosthesis in the cavity, the prosthesis including
a hollow region, and
a reporting processor disposed in the hollow region and including
electronic circuitry; and
a battery coupled to the electronic circuitry.

79. The method of embodiment 78 wherein forming the cavity includes forming the cavity in a tibia of the living subject.

80. The method of embodiment 78 wherein forming the cavity includes forming the cavity in a femur of the living subject.

81. The method of embodiments 78-80 wherein the hollow region is disposed in the at least a portion of the prosthesis.

82. The method of embodiments 78-81, further comprising configuring the electronic circuitry such that the battery has a projected lifetime of at least one year.

83. The method of embodiments 78-81, further comprising configuring the electronic circuitry such that the battery has a projected lifetime of at least ten years.

84. A prosthesis, comprising:
a hollow region; and
an implantable reporting processor disposed in the hollow region and including
electronic circuitry; and
a battery coupled to the electronic circuitry.

85. The prosthesis of embodiment 84, further comprising a member that includes the hollow region and that is configured to be disposed in a breast implant.

86. The prosthesis of embodiment 84, further comprising:
multiple prostheses each contained in a sealed compartment of a breast implant 87. A method, comprising:
forming a cavity in the breast tissue of a living subject; and
inserting at least a portion of a prosthesis in the cavity, the prosthesis including
a hollow region, and
a reporting processor disposed in the hollow region and including
electronic circuitry; and
a battery coupled to the electronic circuitry.

88. The method of embodiment 87 wherein forming the cavity includes forming the cavity in the breast tissue of the living subject.

89. The method of embodiments 87-88, further comprising configuring the electronic circuitry such that the battery has a projected lifetime of at least one year.

90. The method of embodiments 87-88, further comprising configuring the electronic circuitry such that the battery has a projected lifetime of at least fifteen years.

91. Electronic circuitry, comprising:
a supply node configured to be coupled to a battery;
at least one peripheral circuit;
a processing circuit coupled to the supply node and configured to couple the at least one peripheral circuit to the supply node; and
a timing circuit coupled to the supply node and configured to activate the processing circuit at at least one set time.

92. The electronic circuitry of embodiment 91 wherein the at least one peripheral circuit comprises an inertial measurement circuit.

93. The electronic circuitry of embodiments 91-92 wherein the at least one peripheral circuit comprises a memory circuit.

94. The electronic circuitry of embodiments 91-93 wherein the processing circuit comprises a microprocessor.

95. The electronic circuitry of embodiments 91-93 wherein the processing circuit comprises a microcontroller.

96. The electronic circuitry of embodiments 91-95 wherein the timing circuit comprises a real-time clock.

97. The electronic circuitry of embodiments 91-96, further comprising:
a switch coupled between the supply node and the at least one peripheral circuit; and
wherein the processing circuit is configured to close the switch to couple the at least one peripheral circuit to the supply node.

98. The electronic circuitry of embodiments 91-97 wherein the timing circuit is configured to activate the processing circuit at set intervals by causing the processing circuit to exit a lower-power mode at at least one set time.

99. The electronic circuitry of embodiments 91-98 wherein the timing circuit is configured to activate the processing circuit at least at one set time by awakening the processing circuit at the at least one set time.

100. The electronic circuitry of embodiments 91-99, further comprising:
a radio circuit coupled to the supply node and to the processing circuit; and
wherein the timing circuit is configured to activate the radio circuit at at least one set time.

101. An assembly, comprising:
a container implantable in a living subject; and
electronic circuitry disposed in the container and comprising
a supply node;
at least one peripheral circuit;
a processing circuit coupled to the supply node and configured to couple the at least one peripheral circuit to the supply node; and
a timing circuit coupled to the supply node and configured to activate the processing circuit at at least one set time.

102. The assembly of embodiment 101 wherein the container is implantable in a bone of the living subject.

103. The assembly of embodiment 101 wherein the container is implantable in the proximity of a bone of a living subject.

104. The assembly of embodiment 101 wherein the container is implantable within a breast implant located in a living subject.

105. The assembly of embodiments 101-104, further comprising a battery implantable in the living subject and coupled to the supply node.

106. The assembly of embodiments 101-105, further comprising a battery implantable in a bone of the living subject and coupled to the supply node.

107. The assembly of embodiments 101-105, further comprising a battery implantable in the proximity of a bone of the living subject and coupled to the supply node.

108. The assembly of embodiments 101-105, further comprising a battery implantable within a breast of a living subject and coupled to the supply node.

109. The assembly of embodiments 101-105, further comprising a battery coupled to the supply node and implantable within a breast implant that is implanted in a living subject.

110. An implantable reporting processor, comprising:
a housing configured to fit in a prosthesis;
electronic circuitry disposed in the housing and comprising
a supply node;
at least one peripheral circuit;
a processing circuit coupled to the supply node and configured to couple the at least one peripheral circuit to the supply node; and
a timing circuit coupled to the supply node and configured to activate the processing circuit at at least one set time; and
a battery disposed in the housing and coupled to the supply node.

111. The implantable reporting processor of embodiment 110 wherein the housing is configured to fit in a tibial extension of a knee prosthesis.

112. The implantable reporting processor of embodiment 110 wherein the housing is configured to fit in a femoral stem of a hip prosthesis.

113. The implantable reporting processor of embodiment 110 wherein the housing is configured to fit in a breast-implant prosthesis.

114. The implantable reporting processor of embodiments 110-113, further comprising:
a cylindrical casing having a diameter and an end;
wherein the electronic circuitry is disposed in the casing; and
wherein the battery is cylindrical, has approximately the diameter, and has an end coupled to the end of the casing.

115. An implantable reporting processor, comprising:
a housing configured to fit in a prosthesis and having a discoid shape;
electronic circuitry disposed in the housing and comprising
a supply node;
at least one peripheral circuit;
a processing circuit coupled to the supply node and configured to couple the at least one peripheral circuit to the supply node; and
a timing circuit coupled to the supply node and configured to activate the processing circuit at at least one set time; and
a battery having a discoid shape, having a surface coupled to the surface of the housing, and coupled to the supply node.

116. A prosthesis, comprising:
a receptacle; and
an implantable reporting processor having a coupling section disposed in the receptacle and including
electronic circuitry comprising
a supply node;
at least one peripheral circuit;
a processing circuit coupled to the supply node and configured to couple the at least one peripheral circuit to the supply node; and
a timing circuit coupled to the supply node and configured to activate the processing circuit at at least one set time; and
a battery coupled to the supply node.

117. The prosthesis of embodiment 116 wherein the implantable reporting processor is configured to be disposed in a bone of a living subject.

118. The prosthesis of embodiment 116 wherein the implantable reporting processor is configured to be disposed in proximity to a bone of a living subject.

119. The prosthesis of embodiment 116 wherein the implantable reporting processor is configured to be disposed in a breast prosthesis of a living subject.

120. The prosthesis of embodiments 116-119, further comprising:
  a tibial plate; and
  a tibial extension attached to the tibial plate and including the receptacle and the implantable reporting processor.

121. The prosthesis of embodiments 116-119, further comprising:
  a femoral head; and
  a femoral stem attached to the femoral head and including the receptacle and the implantable reporting processor.

122. The prosthesis of embodiments 116-119, further comprising a breast implant with an internal integrated fixation receptacle for an implantable reportable processor.

123. A method, comprising:
  forming a cavity in a bone of a living subject; and
  inserting at least a portion of a prosthesis in the cavity, the prosthesis including an implantable reporting processor having
  electronic circuitry comprising
  a supply node;
  at least one peripheral;
  a processing circuit coupled to the supply node and configured to couple the at least one peripheral circuit to the supply node; and
  a timing circuit coupled to the supply node and configured to activate the processing circuit at at least one set time; and
  a battery coupled to the supply node.

124. The method of embodiment 123 wherein forming the cavity includes forming the cavity in a tibia of the living subject.

125. The method of embodiment 123 wherein forming the cavity includes forming the cavity in a femur of the living subject.

126. The method of embodiment 123 wherein the implantable reporting processor is disposed in the cavity.

127. The method of embodiments 123-126, further comprising configuring the timing circuitry or the processing circuitry such that the battery has a projected lifetime of at least one year.

128. The method of embodiments 123-126, further comprising configuring the timing circuitry or the processing circuit such that the battery has a projected lifetime of at least ten years.

129. A prosthesis, comprising:
  a hollow region; and
  an implantable reporting processor disposed in the hollow region and including
  electronic circuitry comprising
  a supply node;
  at least one peripheral;
  a processing circuit coupled to the supply node and configured to couple the at least one peripheral circuit to the supply node; and
  a timing circuit coupled to the supply node and configured to activate the processing circuit at at least one set time; and
  a battery coupled to the supply node.

130. The prosthesis of embodiment 129, further comprising a member that includes the hollow region and that is configured to be disposed in a bone of a living subject.

131. The prosthesis of embodiment 129, further comprising:
  a tibial plate; and
  a tibial extension attached to the tibial plate and including the hollow region.

132. The prosthesis of embodiment 129, further comprising:
  a femoral head; and
  a femoral stem attached to the femoral head and including the hollow region.

133. A method, comprising:
  forming a cavity in a bone of a living subject; and
  inserting at least a portion of a prosthesis in the cavity, the prosthesis including
  a hollow region, and
  an implantable reporting processor disposed in the hollow region and including
  electronic circuitry comprising
  a supply node;
  at least one peripheral circuit;
  a processing circuit coupled to the supply node and configured to couple the at least one peripheral circuit to the supply node; and
  a timing circuit coupled to the supply node and configured to activate the processing circuit at at least one set time; and
  a battery coupled to the supply node.

134. The method of embodiment 133 wherein forming the cavity includes forming the cavity in a tibia of the living subject.

135. The method of embodiment 133 wherein forming the cavity includes forming the cavity in a femur of the living subject.

136. The method of embodiment 133 wherein the hollow region is disposed in the at least a portion of the prosthesis.

137. The method of embodiments 133-136, further comprising configuring the timing circuit or the processing circuit such that the battery has a projected lifetime of at least one year.

138. The method of embodiments 133-136, further comprising configuring the timing circuit or the processing circuit such that the battery has a projected lifetime of at least ten years.

139. Electronic circuitry, comprising:
  a sensing circuit configured to generate data in response to an implantable prosthesis; and
  a processing circuit coupled to the sensing circuit and configured to process data from the sensing circuit such that energy consumed during each of a plurality of periods does not exceed a respective energy consumption for that period.

140. The electronic circuitry of embodiment 139 wherein the sensing circuit includes at least one of:
  an accelerometer configured to generate data indicative of linear acceleration along a corresponding axis;
  a gyroscope configured to generate data indicative of rotational acceleration about a corresponding axis;
  a pedometer configure to generate data indicative of a number of steps taken by a subject in which the prosthesis is implanted;
  a temperature sensor disposed in a location and configured to generate data indicative of a temperature of the location;
  a pressure sensor disposed in a location and configured to generate data indicative of a pressure at the location.

141. The electronic circuitry of embodiments 139-140 wherein the processing circuit is configured to activate the sensing circuit such that energy consumed during each of the plurality of periods does not exceed a respective energy consumption for that period.

142. The electronic circuitry of embodiments 139-142 wherein each period corresponds to a respective time from an implanting of the prosthesis.

143. The electronic circuitry of embodiments 139-143 wherein the processing circuit comprises a microprocessor.

144. The electronic circuitry of embodiments 139-143 wherein the processing circuit comprises a microcontroller.

145. The electronic circuit of embodiments 139-144, further comprising a timing circuit coupled to the processing circuit and configured to activate the processing circuit such that energy consumed during each of the plurality of periods does not exceed a respective energy consumption for that period.

146. The electronic circuitry of embodiment 145 wherein the timing circuit comprises a real-time clock.

147. The electronic circuitry of embodiments 145-146, further comprising:
a radio circuit coupled to the timing circuit and to the processing circuit; and
wherein the timing circuit is configured to activate the processing circuit such that energy consumed during each of the plurality of periods does not exceed a respective energy consumption for that period.

148. The electronic circuitry of embodiments 145-147 wherein a respective energy-consumption rate during each of the periods is a function of the period and the energy anticipated to be consumed by the electronic circuitry during the period.

149. An assembly, comprising:
a container implantable in a living subject and corresponding to an implantable prosthesis; and
electronic circuitry disposed in the container and comprising
a sensing circuit configured to generate data in response to the implantable prosthesis; and
a processing circuit coupled to the sensing circuit and configured to process data from the sensing circuit such that energy consumed during each of a plurality of periods does not exceed a respective energy consumption for that period.

150. The assembly of embodiment 149 wherein the container is implantable in a bone of the living subject.

151. The assembly of embodiment 149, further comprising a battery implantable in the living subject and coupled to the electronic circuitry.

152. The assembly of embodiment 149, further comprising a battery implantable in a bone of the living subject and coupled to the electronic circuitry.

153. An implantable reporting processor, comprising:
a housing configured to fit in a prosthesis;
electronic circuitry disposed in the housing and comprising
a sensing circuit configured to generate data in response to the prosthesis; and
a processing circuit coupled to the sensing circuit and configured to process data from the sensing circuit such that energy consumed during each of a plurality of periods does not exceed a respective energy consumption for that period; and
a battery disposed in the housing and coupled to the electronic circuitry.

154. The implantable reporting processor of embodiment 153 wherein the housing is configured to fit in a tibial extension of a knee prosthesis.

155. The implantable reporting processor of embodiment 153 wherein the housing is configured to fit in a femoral stem of a hip prosthesis.

156. The implantable reporting processor of embodiment 153, further comprising:
a cylindrical casing having a diameter and an end;
wherein the electronic circuitry is disposed in the casing; and
wherein the battery is cylindrical, has approximately the diameter, and has an end coupled to the end of the casing.

157. A prosthesis, comprising:
a receptacle; and
an implantable reporting processor having a coupling section disposed in the receptacle and including
electronic circuitry comprising
a sensing circuit configured to generate data in response to the prosthesis; and
a processing circuit coupled to the sensing circuit and configured to process data from the sensing circuit such that energy consumed during each of a plurality of periods does not exceed a respective energy consumption for that period; and
a battery coupled to the electronic circuitry.

158. The prosthesis of embodiment 157 wherein the implantable reporting processor is configured to be disposed in a bone of a living subject.

159. The prosthesis of embodiment 157, further comprising:
a tibial plate; and
a tibial extension attached to the tibial plate and including the receptacle and the implantable reporting processor.

160. The prosthesis of embodiment 157, further comprising:
a femoral head; and
a femoral stem attached to the femoral head and including the receptacle and the implantable reporting processor.

161. A method, comprising:
forming a cavity in a bone of a living subject; and
inserting at least a portion of a prosthesis in the cavity, the prosthesis including an implantable reporting processor having
electronic circuitry comprising
a sensing circuit configured to generate data in response to an implanted prosthesis; and
a processing circuit coupled to the sensing circuit and configured to process data from the sensing circuit such that energy consumed during each of a plurality of periods does not exceed a respective energy consumption for that period; and
a battery coupled to the electronic circuitry.

162. The method of embodiment 161 wherein forming the cavity includes forming the cavity in a tibia of the living subject.

163. The method of embodiment 161 wherein forming the cavity includes forming the cavity in a femur of the living subject.

164. The method of embodiment 161 wherein the implantable reporting processor is disposed in the cavity.

165. The method of embodiments 161-164, further comprising configuring the processing circuitry such that the battery has a projected lifetime of at least one year.

166. The method of embodiments 161-164, further comprising configuring the processing circuit such that the battery has a projected lifetime of at least ten years.

167. A prosthesis, comprising:
a hollow region; and
an implantable reporting processor disposed in the hollow region and including
electronic circuitry comprising
a sensing circuit configured to generate data in response to an implanted prosthesis; and
a processing circuit coupled to the sensing circuit and configured to process data from the sensing circuit such that energy consumed during each of a plurality of periods does not exceed a respective energy consumption for that period; and
a battery coupled to the electronic circuitry.

168. The prosthesis of embodiment 167, further comprising a member that includes the hollow region and that is configured to be disposed in a bone of a living subject.

169. The prosthesis of embodiment 167, further comprising:
a tibial plate; and
a tibial extension attached to the tibial plate and including the hollow region.

170. The prosthesis of embodiment 167, further comprising:
a femoral head; and
a femoral stem attached to the femoral head and including the hollow region.

171. A method, comprising:
forming a cavity in a bone of a living subject; and
inserting at least a portion of a prosthesis in the cavity, the prosthesis including
a hollow region, and
an implantable reporting processor disposed in the hollow region and including
electronic circuitry comprising
a sensing circuit configured to generate data in response to an implanted prosthesis; and
a processing circuit coupled to the sensing circuit and configured to process data from the sensing circuit such that energy consumed during each of a plurality of periods does not exceed a respective energy consumption for that period; and
a battery coupled to the electronic circuitry.

172. The method of embodiment 171 wherein forming the cavity includes forming the cavity in a tibia of the living subject.

173. The method of embodiment 171 wherein forming the cavity includes forming the cavity in a femur of the living subject.

174. The method of embodiment 171 wherein the hollow region is disposed in the at least a portion of the prosthesis.

175. The method of embodiments 171-174, further comprising configuring the processing circuit such that the battery has a projected lifetime of at least one year.

176. The method of embodiments 171-174, further comprising configuring the processing circuit such that the battery has a projected lifetime of at least ten years.

177. An assembly, comprising:
a container implantable in a living subject and corresponding to an implantable prosthesis; and
electronic circuitry disposed in the container and configured such that energy consumed during each of a plurality of periods does not exceed a respective energy consumption for that period.

178. An implantable reporting processor, comprising:
a housing configured to fit in a prosthesis;
electronic circuitry disposed in the housing configured such that energy consumed during each of a plurality of periods does not exceed a respective energy consumption for that period; and
a battery disposed in the housing and coupled to the electronic circuitry.

179. A prosthesis, comprising:
a receptacle; and
an implantable reporting processor having a coupling section disposed in the receptacle and including
electronic circuitry configured such that energy consumed during each of a plurality of periods does not exceed a respective energy consumption for that period; and
a battery coupled to the electronic circuitry.

180. A method, comprising:
forming a cavity in a bone of a living subject; and
inserting at least a portion of a prosthesis in the cavity, the prosthesis including an implantable reporting processor having
electronic circuitry configured such that energy consumed during each of a plurality of periods does not exceed a respective energy consumption for that period; and
a battery coupled to the electronic circuitry.

181. A prosthesis, comprising:
a hollow region; and
an implantable reporting processor disposed in the hollow region and including
electronic circuitry configured such that energy consumed during each of a plurality of periods does not exceed a respective energy consumption for that period; and
a battery coupled to the electronic circuitry.

182. A method, comprising:
forming a cavity in a bone of a living subject; and
inserting at least a portion of a prosthesis in the cavity, the prosthesis including
a hollow region, and
an implantable reporting processor disposed in the hollow region and including
electronic circuitry configured such that energy consumed during each of a plurality of periods does not exceed a respective energy consumption for that period; and
a battery coupled to the electronic circuitry.

183. A base station, comprising:
a first circuit configured to communicate with an implantable reporting processor; and
a second circuit configured to communicate with a computing system.

184. The base station of embodiment 183 wherein the first circuit comprises a first antenna and a first radio circuit.

185. The base station of embodiment 183 wherein the second circuit comprises a second antenna and a second radio circuit.

186. The base station of embodiment 183 wherein the second circuit comprises a universal-serial-bus circuit.

187. The base station of embodiments 183-186, further comprising a processing circuit configured to control the first and second circuits.

188. The base station of embodiment 187 wherein the processing circuit comprises a microprocessor.

189. The base station of embodiment 187 wherein the processing circuit comprises a microcontroller.

190. The base station of embodiment 187 wherein the processing circuit is configured to generate and to send control information to the implantable reporting processor via the first circuit.

191. The base station of embodiment 187 wherein the processing circuit is configured to generate and to send configuration information to the implantable reporting processor via the first circuit.

192. The base station of embodiment 187 wherein the processing circuit is configured to receive control information from the computing system via the second circuit and to send the control information to the implantable reporting processor via the first circuit.

193. The base station of embodiment 187 wherein the processing circuit is configured to receive configuration information form the computing system via the second circuit and to send the configuration information to the implantable reporting processor via the first circuit.

194. The base station of embodiment 187 wherein the processing circuit is configured to receive information from the implantable reporting processor via the first circuit and to send the information to the computing system via the second circuit.

195. The base station of embodiment 187 wherein the processing circuit is configured to receive, from the implantable reporting processor via the first circuit, information related to an implanted prosthesis, and to send the information to the computing system via the second circuit.

196. The base station of embodiment 187 wherein the processing circuit is configured to request information from the implantable reporting processor via the first circuit and to receive the requested information from the implantable reporting processor via the first circuit.

197. The base station of embodiment 187 wherein the processing circuit is configured to receive, from the computing system via the second circuit, a request for information, to send a request for the information to the implantable reporting processor via the first circuit, to receive the requested information from the implantable reporting processor via the first circuit, and to send the received information to the computing system via the second circuit.

198. The base station of embodiments 183-197 wherein the computing system comprises a personal computer.

199. The base station of embodiments 183-197 wherein the computing system comprises a smart phone.

200. The base station of embodiments 183-197 wherein the computing system comprises a tablet computer.

201. The base station of embodiments 183-197 wherein the computing system comprises a server computer.

202. The base station of embodiments 183-197 wherein the computing system comprises a cloud-based server.

203. A system, comprising:
an implantable reporting processor; and
a base station configured to communicate with the implantable reporting processor and with a computing system.

204. The system of embodiment 203 wherein the implantable reporting processor is disposed in a prosthesis.

205. The system of embodiment 203 wherein the implantable reporting processor forms part of a prosthesis.

206. The system of embodiment 203 wherein the implantable reporting processor is related to a prosthesis.

207. The system of embodiments 203-206, further comprising:
an implantable prosthesis; and
wherein the implantable reporting processor is disposed in the implantable prosthesis.

208. The system of embodiments 203-206, further comprising:
an implantable prosthesis; and
wherein the implantable reporting processor forms part of the implantable prosthesis.

209. The system of embodiments 203-206, further comprising:
an implantable prosthesis; and
wherein the implantable reporting processor is related to the implantable prosthesis.

210. The system of embodiments 203-209, further comprising:
a voice-command device configured to communicate with the base station and to receive from a patient in which the implantable reporting processor is implanted information regarding a health status of the patient.

211. The system of embodiments 203-209, further comprising:
a voice-command device configured to communicate with the base station and to receive from a patient in which the implantable reporting processor is implanted voice information regarding a health status of the patient.

212. The system of embodiments 203-209, further comprising:
a voice-command configured to communicate with the base station and to provide to a patient information regarding the implantable reporting processor.

213. The system of embodiments 203-209, further comprising:
a voice-command configured to communicate with the base station and to provide to a patient voice information regarding the implantable reporting processor.

214. The system of embodiments 203-209, further comprising:
a voice-command configured to communicate with the base station and to provide to a patient information regarding a prosthetic including the implantable reporting processor.

215. The system of embodiments 203-209, further comprising:
a voice-command configured to communicate with the base station and to provide to a patient voice information regarding a prosthetic including the implantable reporting processor.

216. The system of embodiments 203-209, further comprising:
a voice-command configured to communicate with the base station and to provide to a patient voice information regarding a prosthetic including the implantable reporting processor and implanted in the patient.

217. A method, comprising:
establishing a communication channel between a base station and an implantable reporting processor; and
transferring information over the channel between the base station and the implantable reporting processor.

218. The method of embodiment 217 wherein establishing a communication channel comprises:
polling the implantable reporting processor with the base station; and
responding to the base station with the implantable reporting processor.

219. The method of embodiment 217 wherein establishing a communication channel comprises:
polling the implantable reporting processor with the base station; and responding to the base station with the implantable reporting processor only during a window during which the implantable reporting processor is configured to respond.

220. The method of embodiment 217 wherein transferring information comprises sending configuration data from the base station to the implantable reporting processor to configure the implantable reporting processor.

221. The method of embodiment 217 wherein transferring information comprises sending configuration data from the base station to the implantable reporting processor to change a configuration of the implantable reporting processor.

222. The method of embodiment 217 wherein transferring information comprises sending, with the base station, control information to the implantable reporting processor.

223. The method of embodiment 217 wherein transferring information comprises receiving, with the base station, control information from a computing system and sending, with the base station, the control information to the implantable reporting processor.

224. The method of embodiment 217 wherein transferring information comprises receiving, with the base station, configuration information from a computing system, and sending, with the base station, the configuration information to the implantable reporting processor.

225. The method of embodiment 217 wherein transferring information comprises receiving, with the base station, information from the implantable reporting processor, and sending, with the base station, the information to a computing system.

226. The method of embodiment 217 wherein transferring information comprises receiving, with the base station from the implantable reporting processor, information related to an implanted prosthesis, and sending, with the base station, the information to a computing system.

227. A kinematic implantable device, comprising:
an inertial measurement unit to measure a plurality of kinematic characteristics associated with a movement of a body part of a human, the kinematic implantable device being associated with the body part;
a radio to communicate with a base station that is outside of the human;
a memory arranged to store instructions, configuration information, and data produced by the inertial measurement unit;
a processor that executes the stored instructions to perform actions, the actions including:
receiving the configuration information from the base station via the radio, the configuration information defining at least one parameter associated with collection of data by the inertial measurement unit;
storing the configuration information in the memory;
occasionally collecting, from the inertial measurement unit, data for at least one of the plurality of kinematic characteristics, the collecting occurring based on the configuration information;
storing the collected data in the memory;
receiving a request for the stored collected data from the base station when the kinematic implantable device is in communication range of the base station;
in response to receiving the request for the stored collected data, communicating the stored collected data to the base station via the radio; and
when not collecting data from the inertial measurement unit, disabling at least a portion of the inertial measurement unit to save power;
a power supply to provide power to the memory, the inertial measurement unit, the radio, and the processor; and
a shell to house the power supply, the memory, the processor, the inertial measurement unit, and the radio to enable substantially permanent implantation of the kinematic implantable device into the body part.

228. The kinematic implantable device of embodiment 227, wherein the processor executes the instructions to perform further actions, including:
receiving a request from a doctor office base station via the radio to enter a high-resolution mode to temporarily increase an amount of data collected by the kinematic implantable device;
collecting, from the inertial measurement unit, high-resolution data associated with at least some of the plurality of kinematic characteristics;
storing the high-resolution data in the memory; and
after termination of the high-resolution mode, communicating the high-resolution data to the doctor office base station via the radio.

229. The kinematic implantable device of embodiment 227, wherein the processor executes the instructions to perform further actions, including:
collecting, from the inertial measurement unit, high-resolution data associated with at least some of the plurality of kinematic characteristics; and
communicating, via the radio, the high-resolution data to a doctor office base station wherein the doctor office base station is different from the base station.

230. The kinematic implantable device of embodiment 227, wherein the processor executes the instructions to perform further actions, including:
purging at least some of the stored collected data from the memory after the stored collected data is communicated from the kinematic implantable device.

231. The kinematic implantable device of embodiment 227, wherein the processor executes the instructions to perform further actions, including:
receiving updated configuration information from a home base station; and
storing the updated configuration information in the memory.

232. The kinematic implantable device of embodiment 227, wherein receiving the configuration information includes receiving the configuration information from an operating room base station via the radio and wherein receiving the request for the stored collected data includes receiving the request from a home base station that is different from the operating room base station.

233. The kinematic implantable device of embodiment 227, wherein the inertial measurement unit includes an accelerometer and a gyroscope.

234. The kinematic implantable device of embodiment 227, wherein the processor executes the instructions to perform further actions, including:
transitioning between different modes of operation to collect data from the inertial measurement unit at different rates.

235. A method, comprising:
receiving, at a kinematic implantable device, configuration information from a base station, the configuration information defining at least one parameter associated with collection of data by an inertial measurement unit of the kinematic implantable device;
storing the configuration information in a memory of the kinematic implantable device;

occasionally collecting, from the inertial measurement unit, data for at least one of the plurality of kinematic characteristics, the collecting occurring based on the configuration information;

storing the collected data in the memory;

receiving a request for the stored collected data from the base station when the kinematic implantable device is in communication range of the base station;

in response to receiving the request for the stored collected data, transmitting the stored collected data to the base station via the radio; and when not collecting data from the inertial measurement unit, reducing power consumption of the kinematic implantable device by disabling at least a portion of the inertial measurement unit.

236. The method of embodiment 235, further comprising:

receiving a request from a doctor office base station via the radio to enter a high-resolution mode to temporarily increase an amount of data collected by the kinematic implantable device;

collecting, from the inertial measurement unit, high-resolution data for the plurality of kinematic characteristics;

storing the high-resolution data in the memory; and after termination of the high-resolution mode, communicating the high-resolution data to the doctor office base station via the radio.

237. The method of embodiment 235, further comprising:

purging the stored collected data from the memory after the stored collected data is communicated to the base station.

238. The method of embodiment 235, further comprising:

receiving updated configuration information from a home base station; and storing the updated configuration information in the memory.

239. The method of embodiment 235, wherein receiving the configuration information includes receiving the configuration information from an operating room base station via the radio and wherein receiving the request for the stored collected data includes receiving the request from a home base station that is separate from the operating room base station.

240. The method of embodiment 235, further comprising:

transitioning between different modes of operation to collect data from the inertial measurement unit at different rates.

241. A processor-readable non-transitory storage media having stored contents that cause a kinematic implantable device to perform actions, the actions comprising:

receiving, at the kinematic implantable device, configuration information from a base station, the configuration information defining at least one parameter associated with collection of data by an inertial measurement unit of the kinematic implantable device;

storing the configuration information in a memory of the kinematic implantable device;

collecting, from the inertial measurement unit at a determined time, data for at least one of the plurality of kinematic characteristics, the collecting occurring based on at least some of the configuration information;

storing the collected data in the memory;

receiving a request for the stored collected data from the base station when the kinematic implantable device is in communication range of the base station;

in response to receiving the request for the stored collected data, communicating the stored collected data to the base station via the radio; and when not collecting data from the inertial measurement unit, disabling at least a portion of the inertial measurement unit to save power.

242. The processor-readable non-transitory storage media of embodiment 241, wherein the stored contents further cause the kinematic implantable device to perform further actions, comprising:

receiving a request from a doctor office base station via the radio to enter a high-resolution mode to temporarily increase an amount of data collected by the kinematic implantable device;

collecting, from the inertial measurement unit, high-resolution data for the plurality of kinematic characteristics;

storing the high-resolution data in the memory; and after termination of the high-resolution mode, transmitting the high-resolution data to the doctor office base station via the radio.

243. The processor-readable non-transitory storage media of embodiment 241, wherein the stored contents further cause the kinematic implantable device to perform further actions, comprising:

purging the stored collected data from the memory after the stored collected data is communicated from the kinematic implantable device.

244. The processor-readable non-transitory storage media of embodiment 241, wherein the stored contents further cause the kinematic implantable device to perform further actions, comprising:

receiving updated configuration information from a home base station; and storing the updated configuration information in the memory.

245. The processor-readable non-transitory storage media of embodiment 241, wherein receiving the configuration information includes receiving the configuration information from an operating room base station via the radio and wherein receiving the request for the stored collected data includes receiving the request from a home base station that is remote from the operating room base station.

246. The processor-readable non-transitory storage media of embodiment 241, wherein the stored contents further cause the kinematic implantable device to perform further actions, comprising:

transitioning between different modes of operation to collect data from the inertial measurement unit at different rates.

247. A base station for use in an operating room, comprising:

a radio to communicate with a kinematic implantable device that is associated with a body part of a patient;

a memory arranged to store instructions and configuration information for the kinematic implantable device;

a processor that executes the stored instructions to perform actions, the actions including:

receiving the configuration information, the configuration information setting at least one parameter that defines the kinematic implantable device collection of data on a movement of the body part in which the kinematic implantable device is associated;

establishing a connection with the kinematic implantable device via the radio; and providing the configuration information to the kinematic implantable device via the radio, the configuration information is stored on the kinematic implantable device to initialize the kinematic implantable device;

a power supply to provide power to the memory, the radio, and the processor; and a housing to encase the memory, the processor, and the radio.

248. The base station of embodiment 247, further comprising:

a communication interface to communicate with another computing device;

wherein the configuration information is received from the other computing device via the communication interface;

249. The base station of embodiment 247, further comprising:

a communication interface to communicate with another computing device; and wherein the processor executes the instructions to perform further actions, including:

receiving a confirmation message from the kinematic implantable device indicating that the kinematic implantable device is initialized; and providing the confirmation message to the other computing device via the communication interface.

250. The base station of embodiment 247, wherein the processor executes the instructions to perform further actions, including:

receiving information from a medical practitioner to indicate a rate at which the kinematic implantable device collects data; and providing the information to the kinematic implantable device.

251. A base station for use in a patient's medical practitioner's office, comprising:

a radio to communicate with a kinematic implantable device that is associated with a body part of the patient;

a memory arranged to store instructions and data received from the kinematic implantable device;

a processor that executes the stored instructions to perform actions, the actions including:

establishing a connection with the kinematic implantable device via the radio;

providing a request, via the radio, to the kinematic implantable device to temporarily modify at least one parameter associated with collection of data by the kinematic implantable device;

receiving the collected data from the kinematic implantable device via the radio; and enabling display of the collected data to a medical practitioner;

a power supply to provide power to the memory, the radio, and the processor; and a housing to encase the memory, the processor, and the radio.

252. The base station of embodiment 251, wherein providing the request to the kinematic implantable device to temporarily modify the at least one parameter associated with the collection of data by the kinematic implantable device, includes:

providing a request to the kinematic implantable device to enter a high-resolution mode to temporarily increase an amount of data collected by the kinematic implantable device during the high-resolution mode.

253. The base station of embodiment 251, wherein providing the request to the kinematic implantable device to temporarily modify the at least one parameter associated with the collection of data by the kinematic implantable device, includes:

providing a request to the kinematic implantable device to enter a high-resolution mode to temporarily change a type of data collected by the kinematic implantable device during the high-resolution mode.

254. The base station of embodiment 251, wherein the processor executes the instructions to perform further actions, including:

in response to termination of the temporary modification to the at least one parameter, providing another request, via the radio, to the kinematic implantable device for the kinematic implantable device to communicate the collected data to the base station.

255. The base station of embodiment 251, further comprising:

a communication interface to communicate with another computing device;

wherein the processor executes the instructions to perform further actions, including:

receiving the request from the other computing device via the communication interface; and providing the collected data to the other computing device via the communication interface.

256. The base station of embodiment 251, wherein the processor executes the instructions to perform further actions, including:

providing the collected data to a cloud database;

257. The base station of embodiment 251, wherein the processor executes the instructions to perform further actions, including:

receiving at least one event marker from the medical practitioner;

storing a timestamp for each of the at least one received event marker; and synchronizing the stored timestamps with the collected data.

258. The base station of embodiment 251, wherein the processor executes the instructions to perform further actions, including:

receiving configuration information, the configuration information defining the at least one parameter associated with the collection of data by the kinematic; and providing the configuration information to the kinematic implantable device via the radio.

259. The base station of embodiment 251, wherein the processor executes the instructions to perform further actions, including:

receiving information from another computing device, the information modifying a rate at which the kinematic implantable device collects data; and providing the information to the kinematic implantable device.

260. The base station of embodiment 251, wherein the processor executes the instructions to perform further actions, including:

receiving information from another computing device, the information modifying a type of data collected by the kinematic implantable device; and providing the information to the kinematic implantable device.

261. A base station for use in a patient's home, comprising:

a radio to communicate with a kinematic implantable device that is associated with a body part of the patient;

a network communication interface to communicate with a cloud database;

a memory arranged to store instructions and data collected by the kinematic implantable device;

a processor that executes the stored instructions to perform actions, the actions including:

registering the kinematic implantable device with the base station via the radio;

broadcasting a first request for registered kinematic implantable devices within communication range of the radio to respond to the base station;

in response to receiving a response from the kinematic implantable device, providing a second request, to the kinematic implantable device via the radio, to transmit the collected data from the kinematic implantable device to the base station;

receiving the collected data from the kinematic implantable device via the radio; and providing the collected data to the cloud database via the network communication interface;

a power supply to provide power to the memory, the radio, the communication interface, and the processor; and a housing to encase the memory, the processor, the communication interface, and the radio.

262. The base station of embodiment 261, wherein the processor executes the instructions to perform further actions, including:

receiving configuration information from another computing device via the network communication interface, the configuration information defining at least one parameter for the kinematic implantable device to collect data on a movement of the body part in which the kinematic implantable device is associated; and providing the configuration information to the kinematic implantable device via the radio.

263. The base station of embodiment 261, wherein the processor executes the instructions to perform further actions, including:

receiving information from another computing device via the network communication interface, the information modifying a rate at which the kinematic implantable device collects data; and providing the information to the kinematic implantable device.

264. The base station of embodiment 261, wherein the processor executes the instructions to perform further actions, including:

receiving information from another computing device via the network communication interface, the information modifying a type of data collected by the kinematic implantable device; and providing the information to the kinematic implantable device.

265. The base station of embodiment 261, wherein transmitting the first request includes:

determining that a current time of the base station is within a predetermined communication window; and in response to the current time being within the communication window, broadcasting the first request.

266. The base station of embodiment 261, wherein the processor executes the instructions to perform further actions, including:

determining if a current time of the base station is within a communication window;

in response to the current time being within the communication window, broadcasting the first request; and in response to the current time being outside the communication window, waiting for the current time to be within the communication window.

267. A distributed computing system, comprising:

a network of computing server devices having at least one computing server;

a network interface coupled to the network of computing server devices and arranged to concurrently maintain a plurality of communicative channels, each communicative channel providing a peer-to-peer channel to communicate information between the network of computing server devices and a remote computing device;

a database to store records associated with a plurality of implantable reporting processors (IRPs), each implantable reporting processor (IRP) having a unique identifier different from each other IRP; and a query processor arranged to receive and fulfill information requests, including a first information request, wherein the first information request includes:

a request from a first remote computing device to send first information to the network of computing server devices for storage in the database, the first information including:

a first unique identifier of a first IRP;

first data, e.g., first kinematic data, collected by the first IRP; and a timestamp associated with the first data.

268. A distributed computing system according to embodiment 267, further comprising:

at least one memory to store executable software instructions;

at least one processor to execute at least some of the executable software instructions, where at least some of the executable software instructions are arranged to obfuscate personal information associated with patients who have at least one IRP.

269. A distributed computing system according to embodiment 267, wherein a firmware information request received and fulfilled by the query processor includes:

a request from the first remote computing device to receive firmware information from the network of computing server devices, the firmware information including:

the first unique identifier of the first IRP, e.g., an IRP associated with a first kinematic implantable device; and updated firmware for the first kinematic implantable device.

270. A distributed computing system according to embodiment 267, wherein the first remote computing device is a base station device arranged to wirelessly communicate with the at least the first IRP, e.g., an IRP associated with a first kinematic implantable device.

271. A distributed computing system according to embodiment 270, wherein the first remote computing device is a home base station device arranged to wirelessly communicate with only a single IRP, e.g., a single IRP associated with a kinematic implantable device.

272. A distributed computing system according to embodiment 270, wherein the first remote computing device is a doctor office base station device arranged to wirelessly communicate with a plurality of IRPs, e.g., a plurality of IRPs associated with a plurality of kinematic implantable devices.

273. A distributed computing system according to embodiment 270, wherein the first remote computing device is an operating room base station device arranged to wirelessly communicate with the first IRP, e.g., a first IRP in a first kinematic implantable device, before the first IRP is implanted and after the first IRP is implanted.

274. A distributed computing system according to embodiment 267, wherein one or more records stored in the database are linkable together to form an operational timeline for the first IRP, e.g., a first IRP associated with a first kinematic implantable device, the operational timeline for the first IRP including a plurality of records that together include all of the data, e.g., all of the kinematic data, associated with the first IRP that is stored in the database, the operational timeline for the first IRP.

275. A distributed computing system according to embodiment 274, wherein the operational timeline for the first IRP, where the first IRP may be associated with a first kinematic implantable device, is organizable based at least in part on a timestamp associated with each element of data, e.g., kinematic data, that was collected by the first IRP or the first kinematic implantable device.

276. A distributed computing system according to embodiment 274, wherein the operational timeline for the first IRP, e.g., a first IRP associated with a first kinematic implantable device, is organizable based at least in part on a type of data, e.g., kinematic data, collected by the first IRP, e.g., the first IRP associated with a first kinematic implantable device.

277. A distributed computing system according to embodiment 271, wherein the information requests received and fulfilled by the query processor include:
a plurality of requests sent on a substantially periodic schedule from the first remote computing device to send additional data, e.g., additional kinematic data, to the network of computing server devices for storage in the database, each of the plurality of requests sent on the substantially periodic schedule including:
the first unique identifier of the first IRP, e.g., the first IRP associated with a first kinematic implantable device;
updated data, e.g., updated kinematic data, collected by the first IRP, e.g., the first IRP associated with the first kinematic implantable device; and
an updated timestamp associated with the updated data, e.g., updated kinematic data.

278. A distributed computing system according to embodiment 272, wherein the information requests received and fulfilled by the query processor include:
a request from the first remote computing device to send high-resolution data, e.g., high resolution kinematic data, to the network of computing server devices for storage in the database, the request to send high-resolution data including:
the first unique identifier of the first IRP, e.g., the first IRP associated with a first kinematic implantable device;
high-resolution data, e.g., high-resolution kinematic data, collected by the IRP, e.g., the first IRP associated with a first kinematic implantable device; and
a timestamp associated with the high-resolution data, e.g., the high-solution kinematic data.

279. A distributed computing system according to embodiment 278, wherein the first information includes notes provided by a medical practitioner.

280. A distributed computing system according to embodiment 273, wherein the information requests received and fulfilled by the query processor include:
a request from the first remote computing device to send implantation data, e.g., implantation kinematic data, to the network of computing server devices for storage in the database, the request to send implantation data, e.g., implantation kinematic data, including:
the first unique identifier of the first IRP, e.g., the first IRP associated with a first kinematic implantable device;
a patient identifier associated with the first IRP;
an anatomical identifier associated with the first IRP;
a medical practitioner identifier associated with a medical procedure to implant the first IRP;
a medical facility identifier associated with a medical procedure to implant the first IRP; and
a timestamp associated with the medical procedure to implant the first IRP, e.g., the first IRP associated with the first kinematic implantable device.

281. A distributed computing system according to embodiment 267, wherein a second information request received and fulfilled by the query processor includes:
a request from a second remote computing device to receive aggregated information from the database, the aggregated information including:
a plurality of records wherein each of the plurality of records shares a common characteristic.

282. A distributed computing system according to embodiment 281, wherein the common characteristic is the first unique identifier of the first IRP or a first kinematic implantable device which is associated with the first IRP.

283. A distributed computing system according to embodiment 281, wherein the common characteristic is a same type of IRP or kinematic implantable device.

284. A distributed computing system according to embodiment 281, wherein the common characteristic is a same anatomical identifier.

285. A distributed computing system according to embodiment 281, wherein the common characteristic is a same medical practitioner identifier.

286. A distributed computing system according to embodiment 281, wherein the common characteristic is a same medical facility identifier.

In embodiments, the base station has voice-command (also known as voice controlled) capability. In other words, a person such as the patient or a health care professional may speak to the base station and the base station will respond appropriately. For instance, the person may say to the base station that the implant feels uncomfortable, and in response the base station will record that information along with a record of when that statement was made. The base station may be programmed to query the implantable reporting processor in response to certain verbal information provided by a person, so as to obtain and store additional information about the implant from the IRP to thereby be in a position to provide supplemental information to the patient, health care professional, etc. In addition, or alternatively, a person may be able to command the voice-command feature to verbally report information about the status of the prosthesis or IRP.

For example, in one embodiment the present disclosure provides a base station comprising a first circuit configured to communicate with an implantable reporting processor; a second circuit configured to communicate with a computing system; and additional circuitry as needed to provide the base station with voice-command (also known as voice controlled) capability, where a third circuit may optionally be employed and configured to communicate with the patient in a voice controlled manner. Optionally, the third circuit comprises an antenna and a radio circuit, e.g., a third antenna and a third radio circuit, and the base station has a processing circuit configured to control the first, second and third circuits. The processing circuit may be configured to receive input from the patient and send information to the first and/or the second circuits.

The base station of each of embodiments 183-202 may incorporate the voice-command feature, or equivalently, a device having voice-command features may be modified or supplemented to incorporate the features of the base stations of any of embodiments 183-202. In either event, the patient is able to verbally communicate with a voice-command device in order to place additional information into the record that is being generated by the IRP interacting with the base station. For example, the computing system may comprise a voice-command device.

As another example, in one embodiment the present disclosure provides a system comprising an implantable reporting processor and a base station, where the base station is configured to communicate with the implantable reporting processor, with a computing system, and with a voice-command device. Optionally, the voice-command device is incorporated into the base station so that the patient sees a single device.

The base station in each of embodiments 203-216 may incorporate the voice-command feature, or the system of each of embodiments 203-216 may additionally comprise a voice-command device that is able to communication with the patient and with the base station. In either event, the patient is able to verbally communicate with a voice-command device present in the system of embodiments 203-216 in order to place additional information into the record that is being generated by the IRP interacting with the base station. For example, the present disclosure provides a system, such as the system of embodiments 203-209, further comprising a voice-command device configured to communicate with the base station and to receive from a patient in which the implantable reporting processor is implanted information regarding a health status of the patient. As another example, the present disclosure provides the system of embodiments 203-209, further comprising a voice-command feature configured to communicate with the base station and to provide to a patient voice information regarding a prosthetic including the implantable reporting processor and the prosthesis implanted in the patient.

As another example, the present disclosure provides a method comprising establishing a communication channel between a base station and an implantable reporting processor; and transferring information over the channel between the base station and the implantable reporting processor, where the method further comprises having the base station respond to a verbal command from a person, such as the patient or a health care professional.

The base station in each of the methods of embodiments 217-226 may incorporate the voice-command feature, or equivalently, a device having voice-command features may be modified or supplemented to incorporate the features of the base stations of any of the methods of embodiments 221-226. In either event, the patient is able to verbally communicate with a voice-command device in order to place additional information into the record that is being generated by the IRP interacting with the base station, and the methods of the present disclosure include this feature.

The base stations of each of embodiments 247-266 may incorporate the voice-command feature, or equivalently, a device having voice-command features may be modified or supplemented to incorporate the features of the base stations of any of embodiments 247-266. In either event, a person is able to verbally communicate with a voice-command device in order to place additional information into the record that is being generated by the IRP interacting with the base station and/or in order to obtain information concerning the prosthesis.

For example, a base station for use in an operating room, comprises: a radio to communicate with a kinematic implantable device that is associated with a body part of a patient; a memory arranged to store instructions and configuration information for the kinematic implantable device; a processor that executes the stored instructions to perform actions, the actions including: receiving the configuration information, the configuration information setting at least one parameter that defines the kinematic implantable device collection of data on a movement of the body part in which the kinematic implantable device is associated; establishing a connection with the kinematic implantable device via the radio; and providing the configuration information to the kinematic implantable device via the radio, the configuration information is stored on the kinematic implantable device to initialize the kinematic implantable device; a power supply to provide power to the memory, the radio, and the processor; and a housing to encase the memory, the processor, and the radio, and may additionally comprise a voice-command feature whereby a person in the operating room may verbally input information into the record being generated, or may query the voice-command feature to obtain information about the state of the prosthesis.

As another example, a base station for use in a patient's medical practitioner's office, comprises: a radio to communicate with a kinematic implantable device that is associated with a body part of the patient; a memory arranged to store instructions and data received from the kinematic implantable device; a processor that executes the stored instructions to perform actions, the actions including: establishing a connection with the kinematic implantable device via the radio; providing a request, via the radio, to the kinematic implantable device to temporarily modify at least one parameter associated with collection of data by the kinematic implantable device; receiving the collected data from the kinematic implantable device via the radio; and enabling display of the collected data to a medical practitioner; a power supply to provide power to the memory, the radio, and the processor; and a housing to encase the memory, the processor, and the radio, and may additionally comprise a voice-command feature whereby a person in the patient's medical practitioner's office may verbally input information into the record being generated, or may query the voice-command feature to obtain information about the state of the prosthesis at the present time or at a past time.

As another example, a base station for use in a patient's home, comprises: a radio to communicate with a kinematic implantable device that is associated with a body part of the patient; a network communication interface to communicate with a cloud database; a memory arranged to store instructions and data collected by the kinematic implantable device; a processor that executes the stored instructions to perform actions, the actions including: registering the kinematic implantable device with the base station via the radio; broadcasting a first request for registered kinematic implantable devices within communication range of the radio to respond to the base station; in response to receiving a response from the kinematic implantable device, providing a second request, to the kinematic implantable device via the radio, to transmit the collected data from the kinematic implantable device to the base station; receiving the collected data from the kinematic implantable device via the radio; and providing the collected data to the cloud database via the network communication interface; a power supply to provide power to the memory, the radio, the communication interface, and the processor; and a housing to encase the memory, the processor, the communication interface, and the radio, and may additionally comprise a voice-command feature whereby the patient may verbally input information into the record being generated, or may query the voice-command feature to obtain information about the state of the prosthesis at the present time or at a past time.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

As described herein, for simplicity, a patient, clinician, or another human may in some cases be described in the context of the male gender. It is understood that a medical practitioner can be of any gender, and the terms "he," "his," "himself," and the like as used herein are to be interpreted broadly inclusive of all known gender definitions.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

In the foregoing description, certain specific details are set forth to provide a thorough understanding of various disclosed embodiments. However, one skilled in the relevant art will recognize that embodiments may be practiced without one or more of these specific details, or with other methods, components, materials, etc. In other instances, well-known structures associated with electronic and computing systems including client and server computing systems, as well as networks have not been shown or described in detail to avoid unnecessarily obscuring descriptions of the embodiments.

Although any methods and materials similar or equivalent to those described herein can also be used in the practice or testing of the present invention, a limited number of the exemplary methods and materials are described herein. Generally, unless otherwise indicated, the materials for making the invention and/or its components may be selected from appropriate materials such as metal, metallic alloys, ceramics, plastics, etc.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet are incorporated herein by reference, in their entireties. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A base station comprising:
   a radio configured to communicate with a kinematic implantable device associated with a body part of a patient and configured to collect data in accordance with configuration information comprising parameters for each of 1) a high-resolution mode during which a first plurality of kinematic sensors are active and a processing circuit samples signals generated by the first plurality of kinematic sensors at a first sampling rate and a first bit resolution to collect high-resolution kinematic data, and 2) a non-high-resolution mode during which a second plurality of kinematic sensors are active and the processing circuit samples signals generated by the second plurality of kinematic sensors at a second sampling rate less than the first sampling rate and a second bit resolution less than the first bit resolution to collect non-high-resolution kinematic data;
a network communication interface configured to communicate with a cloud database and a network server;
a memory configured to store instructions and data; and
a processor configured to execute the instructions to perform actions, the actions including:
transmitting a request to the kinematic implantable device to temporarily enter the high-resolution mode and collect high-resolution kinematic data;
providing a request to the kinematic implantable device to transmit high-resolution kinematic data collected by the kinematic implantable device to the base station;
receiving the high-resolution kinematic data from the kinematic implantable device; and
providing the high-resolution kinematic data to the cloud database;
wherein the base station further comprises a user interface; and the processor executes the instructions to perform further actions, including:
receiving, via the user interface, the request for the kinematic implantable device to enter the high-resolution mode;
implementing an office mode during which the kinematic implantable device is permitted to be in the high-resolution mode for a duration that does not exceed a maximum duration; and
limiting the number of times the office mode can be implemented during a period.

2. The base station of claim 1, wherein the processor executes the instructions to perform further actions, including:
receiving at least one event marker via the user interface while the kinematic implantable device is in the high-resolution mode;
storing a timestamp for each of the at least one event marker;
receiving the high-resolution kinematic data from the kinematic implantable device; and
synchronizing the timestamps with the high-resolution kinematic data.

3. The base station of claim 1, wherein:
parameters for the high-resolution mode identify each of: the first plurality of kinematic sensors, the first sampling rate and the first bit resolution, and at least one type of kinematic measurement to be generated based on the high-resolution kinematic data; and
parameters for the non-high-resolution mode identify each of: the second plurality of kinematic sensors, the second sampling rate and the second bit resolution, and at least one type of kinematic measurement to be generated based on the non-high-resolution kinematic data.

4. The base station of claim 1, wherein the configuration information comprises an identification of a type of the kinematic implantable device and an implant location of the kinematic implantable device.

5. The base station of claim 1, wherein:
a plurality of additional kinematic implantable devices are associated with the patient; and
the memory is configured to associate a single patient identifier of the patient with each of the kinematic implantable device and the plurality of additional kinematic implantable devices, together with a unique identifier for each of the kinematic implantable device and the plurality of additional kinematic implantable devices.

6. The base station of claim 1, wherein the processor executes the instructions to perform further actions, including:
periodically querying the cloud database for updated configuration information for the kinematic implantable device;
receiving updated configuration information;
storing the updated configuration information in the memory; and
providing the updated configuration information to the kinematic implantable device during a next communication between the base station and the kinematic implantable device.

7. The base station of claim 1, wherein the number of kinematic sensors in the first plurality of kinematic sensors is greater than the number of kinematic sensors in the second plurality of kinematic sensors.

8. The base station of claim 1, wherein the first plurality of kinematic sensors comprises at least three accelerometers and at least three gyroscopes, and the second plurality of kinematic sensors comprises less than three accelerometers and less than three gyroscopes.

9. A method of controlling operation of a kinematic implantable device that replaces or supplements a natural body part of a patient and configured to collect data in accordance with configuration information comprising parameters for each of 1) a high-resolution mode during which a first plurality of kinematic sensors are active and a processing circuit samples signals generated by the first plurality of kinematic sensors at a first sampling rate and a first bit resolution to collect high-resolution kinematic data, and 2) a non-high-resolution mode during which a second plurality of kinematic sensors are active and the processing circuit samples signals generated by the second plurality of kinematic sensors at a second sampling rate less than the first sampling rate and a second bit resolution less than the first bit resolution to collect non-high-resolution kinematic data:
transmitting, from a base station, a request to the kinematic implantable device to temporarily enter the high-resolution mode and collect high-resolution kinematic data;
providing, from the base station, a request to the kinematic implantable device to transmit high-resolution kinematic data collected by the kinematic implantable device to the base station;
receiving, at the base station, the high-resolution kinematic data from the kinematic implantable device;
providing, from the base station, the high-resolution kinematic data to a cloud database;
receiving, via a user interface of the base station, the request for the kinematic implantable device to enter the high-resolution mode;
implementing an office mode during which the kinematic implantable device is permitted to be in the high-resolution mode for a duration that does not exceed a maximum duration; and limiting the number of times the office mode can be implemented during a period.

10. The method of claim 9, further comprising:
receiving at least one event marker via the user interface while the kinematic implantable device is in the high-resolution mode;
storing a timestamp for each of the at least one event marker;
receiving the high-resolution kinematic data from the kinematic implantable device; and
synchronizing the timestamps with the high-resolution kinematic data.

11. The method of claim 9, wherein:
parameters for the high-resolution mode identify each of: the first plurality of kinematic sensors, the first sampling rate and the first bit resolution, and at least one type of kinematic measurement to be generated based on the high-resolution kinematic data; and
parameters for the non-high-resolution mode identify each of: the second plurality of kinematic sensors, the second sampling rate and the second bit resolution, and at least one type of kinematic measurement to be generated based on the non-high-resolution kinematic data.

12. The method of claim 9, wherein the configuration information comprises an identification of a type of the kinematic implantable device and an implant location of the kinematic implantable device.

13. The method of claim 9, further comprising:
periodically querying the cloud database for updated configuration information for the kinematic implantable device;
receiving updated configuration information;
storing the updated configuration information in a memory; and
providing the updated configuration information to the kinematic implantable device during a next communication between the base station and the kinematic implantable device.

14. A non-transitory computer-readable storage medium storing instructions that when executed by a processor of a base station, cause the base station to:
transmit a request to a radio configured to communicate with a kinematic implantable device that replaces or supplements a natural body part of a patient and configured to collect data in accordance with configuration information comprising parameters for each of 1) a high-resolution mode during which a first plurality of kinematic sensors are active and a processing circuit samples signals generated by the first plurality of kinematic sensors at a first sampling rate and a first bit resolution to collect high-resolution kinematic data, and 2) a non-high-resolution mode during which a second plurality of kinematic sensors are active and the processing circuit samples signals generated by the second plurality of kinematic sensors at a second sampling rate less than the first sampling rate and a second bit resolution less than the first bit resolution to collect non-high-resolution kinematic data, the request being to temporarily enter the high-resolution mode and collect high-resolution kinematic data;
provide a request to the kinematic implantable device to transmit high-resolution data collected by the kinematic implantable device to the base station;
receive the high-resolution kinematic data from the kinematic implantable device;
provide the high-resolution kinematic data to a cloud database;
receive, via a user interface of the base station, the request for the kinematic implantable device to enter the high-resolution mode;
implement an office mode during which the kinematic implantable device is permitted to be in the high-resolution mode for a duration that does not exceed a maximum duration; and
limit the number of times the office mode can be implemented during a period.

15. The non-transitory computer-readable storage medium of claim 14 storing further instructions that when executed by the processor of the base station, cause the base station to:
receive at least one event marker via the user interface while the kinematic implantable device is in the high-resolution mode;
store a timestamp for each of the at least one event marker;
receive the high-resolution kinematic data from the kinematic implantable device; and
synchronize the timestamps with the high-resolution kinematic data.

* * * * *